US011465991B2

(12) United States Patent
Jorgensen et al.

(10) Patent No.: US 11,465,991 B2
(45) Date of Patent: Oct. 11, 2022

(54) PYRAZOLE-CONTAINING MACROPHAGE MIGRATION INHIBITORY FACTOR INHIBITORS

(71) Applicant: YALE UNIVERSITY, New Haven, CT (US)

(72) Inventors: William L. Jorgensen, Deep River, CT (US); Vinay Trivedi-Parmar, Boston, MA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/979,306

(22) PCT Filed: Mar. 15, 2019

(86) PCT No.: PCT/US2019/022476
§ 371 (c)(1),
(2) Date: Sep. 9, 2020

(87) PCT Pub. No.: WO2019/178480
PCT Pub. Date: Sep. 19, 2019

(65) Prior Publication Data
US 2021/0002264 A1  Jan. 7, 2021

Related U.S. Application Data

(60) Provisional application No. 62/643,332, filed on Mar. 15, 2018.

(51) Int. Cl.
*C07D 405/12* (2006.01)
*C07D 231/12* (2006.01)
*C07D 231/16* (2006.01)

(52) U.S. Cl.
CPC ......... *C07D 405/12* (2013.01); *C07D 231/12* (2013.01); *C07D 231/16* (2013.01)

(58) Field of Classification Search
CPC .................................................. C07D 405/12
See application file for complete search history.

(56) References Cited

U.S. PATENT DOCUMENTS

| | | | |
|---|---|---|---|
| 2007/0010563 A1 | 1/2007 | Morand et al. | |
| 2010/0267714 A1 | 10/2010 | Jorgensen et al. | |
| 2014/0288111 A1 | 9/2014 | Bagley et al. | |
| 2016/0145251 A1 | 8/2016 | Jorgensen et al. | |

FOREIGN PATENT DOCUMENTS

| WO | 2006045505 A1 | 5/2006 |
|---|---|---|
| WO | 2016130968 A1 | 8/2016 |

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Chen, et al. Document No. 165:274560, retrieved from STN; Aug. 11, 2016.*
Schindler, et al. (Document No. 164:314918, retrieved from STN; Feb. 18, 2016.*
Al-Abed, Yousef, "ISO-1 Binding to the Tautomerase Active Site of MIF Inhibits Its Pro-inflammatory Activity and Increases Survival in Severe Sepsis", J. Biol. Chem. Nov. 4, 2005, vol. 280, No. 44, pp. 36541-36544.
Asare, Yaw et al. "The vascular biology of macrophage migration inhibitory factor (MIF)", Thromb. Haemost., Jan. 17, 2013, vol. 109, No. 3, pp. 391-398.
Babu, Spoorthy N. et al., "Macrophage Migration Inhibitory Factor: a Potential Marker for Cancer Diagnosis and Therapy", J. Cancer Prev., May 30, 2012, vol. 13, No. 5 pp. 1737-1744.
Chapman, Eli et al., "Sulfotransferases: Structure, Mechanism, Biological Activity, Inhibition, and Synthetic Utility", Angew. Chem. Int. Ed. Jun. 29, 2004, vol. 43, pp. 3526-3548.
Cisneros, Jose et al., "A Fluorescence Polarization Assay for Binding to Macrophage Migration Inhibitory Factor and Crystal Structures for Complexes of Two Potent Inhibitors", J. Am. Chem. Soc., Jun. 14, 2016, vol. 138, No. 27, pp. 3630-8638.
Conroy, H. et al., "Article Navigation Inflammation and cancer: macrophage migration inhibitory factor (MIF)—the potential missing link", Q. J. Med., Aug. 30, 2010, vol. 103, pp. 831-836.
Dziedzic, Pawel, et al., "Design, Synthesis, and Protein Crystallography of Biaryltriazoles as Potent Tautomerase Inhibitors of Macrophage Migration Inhibitory Factor", J. Am. Chem. Soc., Mar. 4, 2015, vol. 137, No. 8, pp. 2996-3003.
Garai, Janos et al., "Macrophage migration inhibitory factor (MIF) tautomerase inhibitors as potential novel anti-inflammatory agents: current developments", Curr. Med. Chem. Mar. 1, 2009, vol. 16, No. 9, pp. 1091-1114.
Guimaraes Nobre, Camilla et al. "Macrophage Migration Inhibitory Factor (MIF): Biological Activities and Relation with Cancer", Pathol. Oncol Res , Oct. 23, 2016, vol. 23, pp. 235-24.
Hare, Alissa et al., "Optimization of N-benzyl-benzaxazol-2-ones as receptor antagonists of macrophage migration inhibitory factor (MIF)", Bioorg. Med. Chem. Lett., Aug. 3, 2010, vol. 20, No. 19, pp. 5811-5814.
International Search Report and Written Opinion dated Jul. 16, 2019 for International Patent Application No. PCT/JS2019/022476 by the International Search Authority of the U.S.
International Preliminary Report on Patentability dated Sep. 24, 2020 for International Patent Application No. PCT/US2019/022476 by the Internatinoal Bureau of WIPO.

(Continued)

*Primary Examiner* — Shawquia Jackson
(74) *Attorney, Agent, or Firm* — Saul Ewing Arnstein & Lehr LLP; Kathryn Doyle; Domingos J. Silva

(57) ABSTRACT

In one aspect, the invention comprises compounds that bind and inhibit macrophage migration inhibitory factor. In another aspect, the invention provides methods of treating inflammatory disease, neurological disorders and cancer using the compounds of the invention.

17 Claims, 7 Drawing Sheets

(56) References Cited

OTHER PUBLICATIONS

Leyton-Jaimes, Marcel F., et al., "Macrophage migration inhibitory factor: A multifaceted cytokine implicated in multiple neurological diseases", Exp. Neurol., vol. 301, Jul. 2, 2017, pp. 82-896.

Meinig, J. Matthew et al., "Targeting fatty-acid amide hydrolase with prodrugs for CNS-selective therapy", ACS Chem. Neurosci. Aug. 18, 2017, vol. 8, No. 11, pp. 2468-2476.

Ouertatani-Sakouhi, Hajer et al., "Identification and Characterization of Novel Classes of Macrophage Migration nhibitory Factor (MIF) Inhibitors with Distinct Mechanisms of Action", J. Biol. Chem., Aug. 20, 2010, vol. 285, No. 34, pp. 26581-26598.

PubChem Compound Summary for CID 122445333, Methyl 3-(1H-pyrazol-4-yl)benzoate, National Center for Biotechnology Information, Retrieved Nov. 15, 2021 from https://pubchem.ncbi.nlm.nih.gov/compound/Methyl-3-_1H-pyrazol-4-yl_benzoate, 10 pages.

Rakers, Christin et al., "In Silico Prediction of Human Sulfotransferase 1E1 Activity Guided by Pharmacophores from Molecular Dynamics Simulations", J. Biol. Chem., Jan. 1, 2016, vol. 291, No. 1, 291, pp. 58-71.

Senter, Peter D., et al.,"Inhibition of macrophage migration inhibitory factor (MIF) tautomerase and biological activities by acetaminophen metabolites", Natl. Acad. Sci. U.S.A. Jan. 8, 2002, vol. 99, No. 1, pp. 144-149.

Tsai, Tsung-Lin et al., "Virtual Screening of Some Active Human Macrophage Migration Inhibitory Factor Antagonists", J. Biomol. Screen, Feb. 19, 2014, vol. 19, No. 7, pp. 1116-1123.

Wilkening, R. R. et al., "Estrogen receptor p. subtype selective tetrahydrofluorenones: Use of a fused pyrazole as a phenol bioisostere", Bioorg. Med. Chem. Lett., Aug. 1, 2006, vol. 16, No. 15, pp. 3896-3901.

Wu, Baojian et al., "First-pass metabolism via UDP-glucuronosyltransferase: a barrier to oral bioavailability of phenolics", Jrl. Pharm. Sci, Apr. 11, 2011, vol. 100, No. 9, pp. 3655-3681.

Greven, Dorothee et al., "Autoimmune diseases: MIF as a therapeutic target", Expert Opin. Ther.Targets, Feb. 12, 2010, vol. 4, No. 9, pp. 253-264.

Jarconcyk, Malgorzata et al., "Theoretical studies on tautomerism and IR spectra of pyrazole derivatives". J. Mol. Struct (Theochem) Mar. 19, 2004, vol. 673, Nos. 1-3, pp. 17-28.

O'Reilly, Ciaran et al., "Targeting MIF in Cancer: Therapeutic Strategies, Current Developments, and Future Dpportunities", Med. Res. Rev., Jan. 18, 2016, vol. 36, No. 3, pp. 440-460.

* cited by examiner

FIG. 5B

NaH, MeI
DMF, 80 °C, 3 h

10a; R$^1$ = Ph
10b; R$^1$ = 1-Np
10c; R$^1$ = 2-Np
11a; R$^1$ = Ph, R$^2$ = H
11b'; R$^1$ = 2-Np, R$^2$ = H
11b; R$^1$ = 2-Np, R$^2$ = Me
12a; R$^1$ = Ph
12b; R$^1$ = o-MePh
12c; R$^1$ = m-MePh
12d; R$^1$ = p-MePh
12e; R$^1$ = m-FPh
12f; R$^1$ = p-FPh
12g; R$^1$ = 2-Np
12j; R$^1$ = 9-phenanthryl
12k; R$^1$ = 2-adamantyl
12l; R$^1$ = 4-acen
12m; R$^1$ = 1-Np
12o; R$^1$ = 4-Et-2-Np
12p; R$^1$ = 5-Et-2-Np
12q; R$^1$ = 7-Et-2-Np
12r; R$^1$ = 4-c-Pr-2-Np
12s; R$^1$ = 4-c-Pr,7-Et-2-Np
12t; R$^1$ = p-Bp
12u; R$^1$ = m-Bp
12v; R$^1$ = 3,5-diMe-m-Bp
12w; R$^1$ = 4-OEt-m-Bp
12x; R$^1$ = 4-MrPrO-m-Bp

FIG. 5C

13a; R = Ph, X = H
13b; R = 1-Np, X = H
13c; R = 2-Np, X = H
14a; R = NHPh, X = H
14b; R = N(Me)-2-Np, X = H
15a; R = PhO, X = H
15b; R = o-MePhO, X = H
15c; R = m-MePhO, X = H
15d; R = p-MePhO, X = H
15e; R = m-FPhO, X = H
15f; R = p-FPhO, X = H
15g; R = 2-NpO, X = H
15j; R = 9-phenanthrylO, X = H
15k; R = 2-adamantylO, X = H
15l; R = 4-acenO, X = H
15m; R = 1-NpO, X = F
15n; R = 2-NpO, X = F
15o; R = 4-Et-2-NpO, X = F
15p; R = 5-Et-2-NpO, X = F
15q; R = 7-Et-2-NpO, X = F
15r; R = 4-c-Pr-2-NpO, X = F
15s; R = 4-c-Pr,7-Et-2-NpO, X = F
15t; R = p-BpO, X = F
15u; R = m-BpO, X = F
15v; R = 3,5-diMe-m-BpO, X = F
15w; R = 4-OEt-m-BpO, X = F
15x; R = 4-MrPrO-m-BpO, X = F 6a; R = Ph, X = H
6b; R = 1-Np, X = H
6c; R = 2-Np, X = H
7a; R = NHPh, X = H
7b; R = N(Me)-2-Np, X = H
8a; R = PhO, X = H
8b; R = o-MePhO, X = H
8c; R = m-MePhO, X = H
8d; R = p-MePhO, X = H
8e; R = m-FPhO, X = H
8f; R = p-FPhO, X = H
8g; R = 2-NpO, X = H
8j; R = 9-phenanthrylO, X = H
8k; R = 2-adamantylO, X = H
8l; R = 4-acenO, X = H
8m; R = 1-NpO, X = F
8n; R = 2-NpO, X = F
8o; R = 4-Et-2-NpO, X = F
8p; R = 5-Et-2-NpO, X = F
8q; R = 7-Et-2-NpO, X = F
8r; R = 4-c-Pr-2-NpO, X = F
8s; R = 4-c-Pr,7-Et-2-NpO, X = F
8t; R = p-BpO, X = F
8u; R = m-BpO, X = F
8v; R = 3,5-diMe-m-BpO, X = F
8w; R = 4-OEt-m-BpO, X = F
8x; R = 4-MrPrO-m-BpO, X = F

PYRAZOLE-CONTAINING MACROPHAGE MIGRATION INHIBITORY FACTOR INHIBITORS

CROSS-REFERENCE TO RELATED APPLICATIONS

The present application is a 35 U.S.C. § 371 national phase application from, and claiming priority to, International Application No. PCT/US2019/022476, filed Mar. 15, 2019, which claims priority under 35 U.S.C. § 119(e) to U.S. Provisional Patent Application No. 62/643,332, filed Mar. 15, 2018, all of which applications are incorporated herein by reference in their entireties.

STATEMENT REGARDING FEDERALLY SPONSORED RESEARCH OR DEVELOPMENT

This invention was made with government support under GM032136 awarded by National Institutes of Health. The government has certain rights in the invention.

BACKGROUND OF THE INVENTION

Human macrophage migration inhibitory factor (MIF) is a proinflammatory cytokine that is implicated in the pathogenesis of numerous inflammatory diseases, neurological disorders, and cancer. MIF is expressed in various cell types, and its tissue distribution is widespread. Upon activation of cells such as macrophages, monocytes and T-cells, expression of MIF in turn activates release of inflammatory cytokines including interleukins, interferon, and TNFα. Complex signaling pathways are invoked when MIF binds to its membrane-bound receptors CD74 and CXCR4, leading to leukocyte chemotaxis, inflammatory response, and potential tissue damage. There is strong correlation between MIF expression and the severity of many inflammatory and autoimmune diseases including asthma, sepsis, lupus, and rheumatoid arthritis. For cancer, the AKT pathway may be activated by MIF binding causing suppression of apoptosis by inhibition of the normal action of BAD, BAX, and p53. However, MIF's role in cancer is multifaceted with undesirable effects also on cell proliferation, angiogenesis, and metastasis; MIF is over-expressed in most human cancer cells.

Interestingly, MIF also shows enzymatic activity as a keto-enol tautomerase. MIF is a toroid-shaped, trimeric protein consisting of 342 amino acid residues with three identical active sites occurring at the interfaces of the monomer subunits. The active sites are relatively cylindrical and open to the surface of the protein in the vicinity of Prol, which serves as the catalytic base.

There is a need in the art for potent and specific inhibitors of MIF. Such compounds should be useful in the treatment of diseases and disorders, such as but not limited to, inflammatory diseases, neurological disorders, and/or cancer. The present invention addresses this need.

SUMMARY OF THE INVENTION

In one aspect the invention provides a compound of formula (I), or a salt, solvate, stereoisomer, or tautomer thereof, or any mixtures thereof:

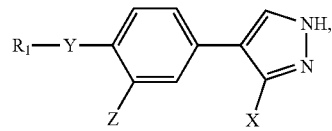

(I)

wherein in (I): Y is selected from the group consisting of a bond, —$CH_2$—, —O—, —S—, —S(=O)—, —S(=O)$_2$, and —N($R_2$)—; $R_1$ is selected from the group consisting of H, $C_1$-$C_6$ alkyl, phenyl, naphthyl, tetrahydronaphthyl, phenanthryl, bicyclic heteroaryl, 1,2-dihydroacenaphthyl, acenaphthyl, adamantyl, (heteroaryl)-phenyl, and biphenyl; $R_2$ is selected from the group consisting of H and $C_1$-$C_6$ alkyl; Z is selected from the group consisting of —COOR, —S(=O)R, —S(=O)$_2$R, and $SO_2$NRR; X is selected from the group consisting of H, $C_1$-$C_3$ alkyl, and halogen; wherein the phenyl, naphthyl, tetrahydronaphthyl, phenanthryl, bicyclic heteroaryl, 1,2-dihydroacenaphthyl, acenaphthyl, adamantyl, (heteroaryl)-phenyl, or biphenyl is independently optionally substituted with at least one group independently selected from the group consisting of halogen, —OH, —C(=O)OR, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_3$-$C_6$ halocycloalkyl, $C_3$-$C_6$ halocycloalkoxy, —($CH_2$)$_{1-6}$NRR, —O($CH_2$)$_{1-6}$NRR, —($CH_2$)$_{1-6}$NR($C_1$-$C_6$ acyl), —O($CH_2$)$_{1-6}$NR($C_1$-$C_6$ acyl), —($CH_2$)$_{1-6}$OR, —O($CH_2$)$_{1-6}$OR, —($CH_2$)$_{1-6}$C(=O)OR, —O($CH_2$)$_{1-6}$C(=O)OR, —($CH_2$)$_{1-6}$OR, —O($CH_2$)$_{1-6}$OR, —(O$CH_2$$CH_2$)$_{1-6}$NRR, and —(O$CH_2$$CH_2$)$_{1-6}$C(=O)OR; wherein each occurrence of R is independently selected from the group consisting of H and $C_1$-$C_6$ alkyl, or two R groups combine with the N atom to which they are both bound to form a 3-8 membered heterocyclyl or heteroaryl group (such as, but not limited to, piperidinyl, morpholinyl, pyrrolidinyl, pyridinyl, imidazolyl, and the like); and wherein if $R_1$—Y is H, then Z cannot be —COOH.

In various embodiments, the compound of formula (I) is a compound of formula (6):

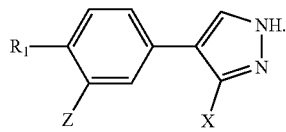

6

In various embodiments, $R_1$ is selected from the group consisting of phenyl and naphthyl.

In various embodiments, the compound is selected from the group consisting of: 6a, 4-(1H-pyrazol-4-yl)-[1,1'-biphenyl]-2-carboxylic acid; 6b, 2-(Naphthalen-1-yl)-5-(1H-pyrazol-4-yl)benzoic acid; 6c, 2-(Naphthalen-2-yl)-5-(1H-pyrazol-4-yl)benzoic acid; 9a, methyl 3-(1H-pyrazol-4-yl)benzoate; 9b, 4-(3-(methylsulfonyl)phenyl)-1H-pyrazole; 9c, 4-(3-(methylsulfonyl)phenyl)-1H-pyrazole; 9d, N-methyl-3-(1H-pyrazol-4-yl)benzenesulfonamide; 9e, 2-methyl-5-(1H-pyrazol-4-yl)benzoic acid.

In various embodiments, the compound of formula (I) is a compound of formula (7):

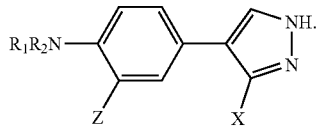

In various embodiments, $R_1$ is selected from the group consisting of phenyl and naphthyl.

In various embodiments, $R_2$ is methyl.

In various embodiments, the compound of formula 7 is selected from the group consisting of: 7a, 2-(Phenylamino)-5-(1H-pyrazol-4-yl)benzoic acid; 7b, 2-(Methyl(naphthalen-2-yl)amino)-5-(1H-pyrazol-4-yl)benzoic acid.

In various embodiments, the compound of formula (I) is a compound of formula (8):

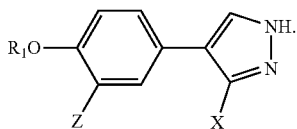

In various embodiments, $R_1$ is selected from the group consisting of methylphenyl, methoxyphenyl, fluorophenyl, ethylnapthyl, cyclopropylnaphthyl, methylbiphenyl, ethoxybiphenyl and N-morpholinopropoxybiphenyl.

In various embodiments, X is fluorine.

In various embodiments, the compound of formula 8 is selected from the group consisting of: 8a, 2-Phenoxy-5-(1H-pyrazol-4-yl)benzoic acid; 8b, 5-(1H-Pyrazol-4-yl)-2-(o-tolyloxy)benzoic acid; 8c, 5-(1H-Pyrazol-4-yl)-2-(m-tolyloxy)benzoic acid; 8d, 5-(1H-Pyrazol-4-yl)-2-(p-tolyloxy)benzoic acid; 8e, 2-(3-Fluorophenoxy)-5-(1H-pyrazol-4-yl)benzoic acid; 8f, 2-(4-Fluorophenoxy)-5-(1H-pyrazol-4-yl)benzoic acid; 8g, 2-(Naphthalen-2-yloxy)-5-(1H-pyrazol-4-yl)benzoic acid; 8h, 4-(3-(Methylsulfonyl)-4-(naphthalen-2-yloxy)phenyl)-1H-pyrazole; 8i, 2-(Naphthalen-2-yloxy)-5-(1H-pyrazol-4-yl)benzenesulfonamide; 8j, 2-(Phenanthren-9-yloxy)-5-(1H-pyrazol-4-yl)benzoic acid; 8k, 2-((Adamantan-2-yl)oxy)-5-(1H-pyrazol-4-yl)benzoic acid; 8l, 2-((1,2-Dihydroacenaphthylen-4-yl)oxy)-5-(1H-pyrazol-4-yl)benzoic acid; 8m, 5-(3-Fluoro-1H-pyrazol-4-yl)-2-(naphthalen-1-yloxy)benzoic acid; 8n, 5-(3-Fluoro-1H-pyrazol-4-yl)-2-(naphthalen-2-yloxy)benzoic acid; 8o, 2-((4-Ethylnaphthalen-2-yl)oxy)-5-(3-fluoro-1H-pyrazol-4-yl)benzoic acid; 8p, 2-((5-Ethylnaphthalen-2-yl)oxy)-5-(3-fluoro-1H-pyrazol-4-yl)benzoic acid; 8q, 2-((7-Ethylnaphthalen-2-yl)oxy)-5-(3-fluoro-1H-pyrazol-4-yl)benzoic acid; 8r, 2-((4-Cyclopropylnaphthalen-2-yl)oxy)-5-(3-fluoro-1H-pyrazol-4-yl)benzoic acid; 8s, 2-((4-Cyclopropyl-7-ethylnaphthalen-2-yl)oxy)-5-(3-fluoro-1H-pyrazol-4-yl)benzoic acid; 8t, 2-([1,1'-Biphenyl]-4-yloxy)-5-(3-fluoro-1H-pyrazol-4-yl)benzoic acid; 8u, 2-([1,1'-Biphenyl]-3-yloxy)-5-(3-fluoro-1H-pyrazol-4-yl)benzoic acid; 8v, 2-((3',5'-Dimethyl-[1,1'-biphenyl]-3-yl)oxy)-5-(3-fluoro-1H-pyrazol-4-yl)benzoic acid; 8w, 2-((4'-Ethoxy-[1,1'-biphenyl]-3-yl)oxy)-5-(3-fluoro-1H-pyrazol-4-yl)benzoic acid; 8x, 5-(3-Fluoro-1H-pyrazol-4-yl)-2-((4'-(3-morpholinopropoxy)-[1,1'-biphenyl]-3-yl)oxy)benzoic acid; 9f, 2-(3-chlorophenoxy)-5-(1H-pyrazol-4-yl)benzoic acid; 9g, 2-(4-chlorophenoxy)-5-(1H-pyrazol-4-yl)benzoic acid; 9h, 2-(4-methoxyphenoxy)-5-(1H-pyrazol-4-yl)benzoic acid; 9i, 2-(3-methoxyphenoxy)-5-(1H-pyrazol-4-yl)benzoic acid; 9j, 2-(4-(aminomethyl)phenoxy)-5-(1H-pyrazol-4-yl)benzoic acid; 9k, 2-(3-(aminomethyl)phenoxy)-5-(1H-pyrazol-4-yl)benzoic; 9l, 2-(4-(2-acetamidoethyl)phenoxy)-5-(1H-pyrazol-4-yl)benzoic acid; 9m, 2-(benzofuran-7-yloxy)-5-(1H-pyrazol-4-yl)benzoic acid; 9n, 2-(3-carboxyphenoxy)-5-(1H-pyrazol-4-yl)benzoic acid; 9o, 2-(benzofuran-5-yloxy)-5-(1H-pyrazol-4-yl)benzoic acid; 9p, 2-(benzofuran-6-yloxy)-5-(1H-pyrazol-4-yl)benzoic acid; 9q, 2-(acenaphthylene-4-yloxy)-5-(1H-pyrazol-4-yl)benzoic acid; 9r, 2-(phenylsulfinyl)-5-(1H-pyrazol-4-yl)benzoic acid; 9s, 2-(benzofuran-6-yloxy)-5-(3-fluoro-1H-pyrazol-4-yl)benzoic acid; 9t, 5-(3-fluoro-1H-pyrazol-4-yl)-2-(3-fluorophenoxy)benzoic acid; 9u, 2-((7-methylnaphthalen-2-yl)oxy)-5-(1H-pyrazol-4-yl)benzoic acid; 9v, 2-((1,2-dihydroacenaphthylen-4-yl)oxy)-5-(3-fluoro-1H-pyrazol-4-yl)benzoic acid; 9w, 5-(3-fluoro-1H-pyrazol-4-yl)-2-(3-(trifluoromethyl)phenoxy) benzoic acid; 9x, 2-((7-cyclopropylnaphthalen-2-yl)oxy)-5-(3-fluoro-1H-pyrazol-4-yl)benzoic acid; 9y, 5-(3-fluoro-1H-pyrazol-4-yl)-2-((5,6,7,8-tetrahydronaphthalen-2-yl)oxy)benzoic acid; 9z, 2-((5-cyclopropylnaphthalen-2-yl)oxy)-5-(3-fluoro-1H-pyrazol-4-yl)benzoic acid; 9aa, 5-(3-fluoro-1H-pyrazol-4-yl)-2-(3-(pyrimidin-2-yl)phenoxy)benzoic acid; 9bb, 5-(3-fluoro-1H-pyrazol-4-yl)-2-44'-(2-morpholinoethyl)-[1,1'-biphenyl]-3-yl)oxy)benzoic acid; 9cc, 5-(3-methyl-1H-pyrazol-4-yl)-2-(naphthalen-2-yloxy)benzoic acid.

In various embodiments, the invention provides a pharmaceutical composition comprising at least one compound of the invention and at least one pharmaceutically acceptable excipient.

In various embodiments, the invention provides a method of treating an inflammatory disease, a neurological disorder, and/or cancer in a subject in need thereof, the method comprising administering to the subject an effective amount of the compounds and/or the pharmaceutical compositions of the invention.

In various embodiments, the inflammatory disease is rheumatoid arthritis, Crohn's disease, or inflammatory bowel syndrome.

In various embodiments, the neurological disorder is schizophrenia.

In various embodiments, the cancer is colorectal, lung, breast, or prostate.

In another aspect, the invention provides a method of inhibiting macrophage migration inhibitory factor in a subject in need thereof, the method comprising administering to the subject an effective amount of the compounds and/or the pharmaceutical compositions of the invention.

In another aspect, the invention provides a method of treating a disease or disorder associated with upregulated and/or dysregulated macrophage migration inhibitory factor expression in a subject in need thereof, the method comprising administering to the subject an effective amount of the compound of any of the compounds and/or the pharmaceutical compositions of the invention.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIGS. 5A-5C depict schemes for the synthesis of inhibitors 6ac, 7a, 7b, and 8ax.

DETAILED DESCRIPTION OF THE INVENTION

Figure 1:
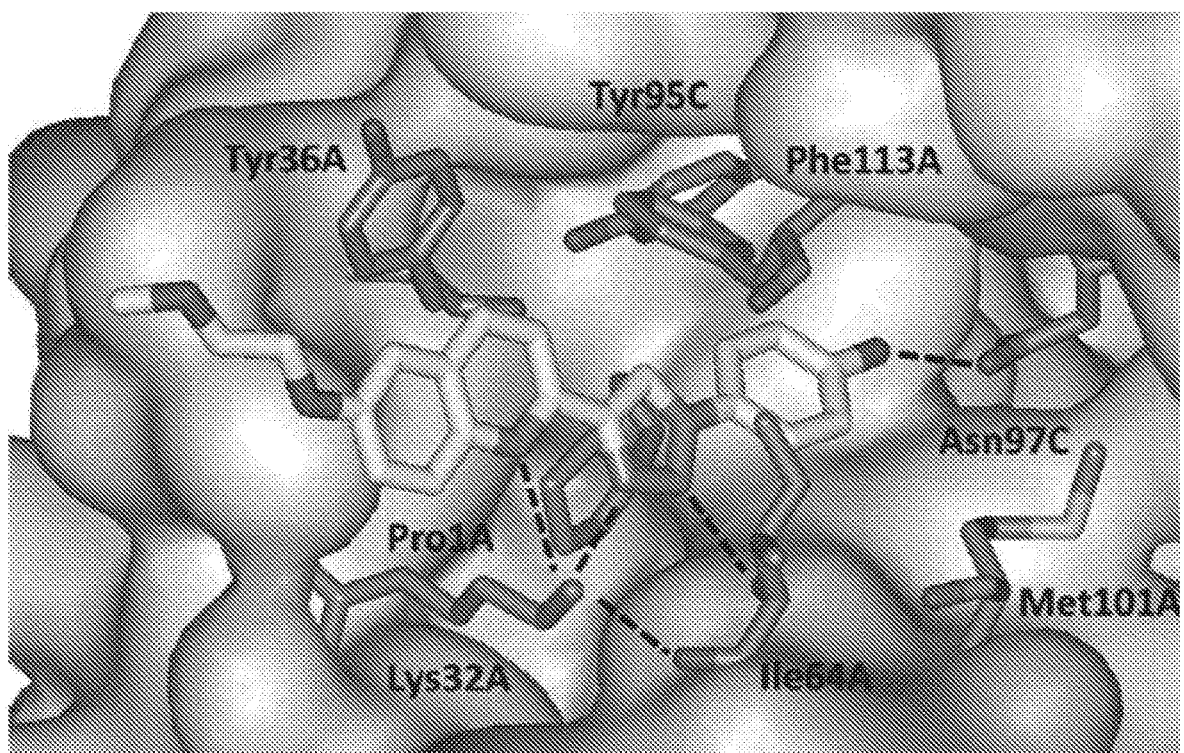
FIG. 1 is a rendering from an 1.8-Å crystal structure of an analog of 2 bound to MIF. Carbon atoms of the inhibitor are colored yellow. Hydrogen bonds are indicated with dashed lines.

In one aspect, the invention provides novel compounds that, in various embodiments, act as inhibitors of MIF. In various aspects and embodiments, the invention provides methods of treating disease associated with upregulated and/or dysregulated MIF expression, such as but not limited to inflammatory diseases or disorder, neurological diseases or disorders, and/or cancer in a subject by administering to the subject a pharmaceutical composition containing an effective amount of at least one of the compounds of the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

Generally, the nomenclature used herein and the laboratory procedures in cell culture, molecular genetics, pharmacology, and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "analog," "analogue," or "derivative" are meant to refer to a chemical compound or molecule made from a parent compound or molecule by one or more chemical reactions. As such, an analog can be a structure having a structure similar to that of the small molecules described herein or can be based on a scaffold of a small molecule described herein, but differing from it in respect to certain components or structural makeup, which may have a similar or opposite action metabolically.

As used herein, the term "binding" refers to the adherence of molecules to one another, such as, but not limited to, enzymes or any other proteins to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

A "disease" is a state of health of an animal, such as a human subject, wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "disease or disorder associated with high MIF expression" as used herein, refers to any disease or disorder where high levels of MIF expression at the level of transcription or translation or high levels of MIF activity play a role in the pathogenesis or contribute in any way to the progression or maintenance of the disease. By way of non-limiting example, a disease or disorder associated with high MIF expression may include bacterial, viral or fungal infection, asthma, arthritis, autism spectrum disorder, schizophrenia, cancer, anemia of chronic disease, malaria, Crohn's disease and lupus.

An "effective amount" of a compound, as used herein, is that amount of compound which is sufficient to achieve the intended effect, typically, treatment or prevention of a disease or disorder, when provided to the patient by a particular method of administration. An appropriate effective amount in any individual case may be determined by one of ordinary skill in the art using routine experimentation and the material disclosed herein.

As used herein, the phrase "a first compound is essentially free of a second compound" in a composition indicates that the ratio of the second compound to the first second compound in the composition is about 10:90, 5:95, 4:96, 3:97, 2:98, 1:99, 0.5:99.5, 0.25:99.75, 0.1:99.9, 0.05:99.95, 0.025:99.975, 0.01:99.99 or 0:100.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "pharmaceutically acceptable carrier" and "pharmaceutically acceptable excient" are used interchangeably and mean a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids or bases, organic acids or bases, solvates, hydrates, or clathrates thereof.

By the term "specifically binds," as used herein, is meant a molecule, such as an antibody, which recognizes and binds to another molecule or feature, but does not substantially recognize or bind other molecules or features in a sample.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$)alkyl, such as, but not limited to, ethyl, methyl, isopropyl, isobutyl, n-pentyl, n-hexyl and cyclopropylmethyl.

As used herein, the term "aromatic" refers to a carbocycle or heterocycle with one or more polyunsaturated rings and having aromatic character, i.e., having (4n+2) delocalized 7E (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-($C_1$-$C_6$)alkyl" refers to a functional group wherein a one to six carbon alkanediyl chain is attached to an aryl group, e.g., —$CH_2CH_2$-phenyl or —$CH_2$-phenyl (or benzyl). Specific examples are aryl-$CH_2$— and aryl-$CH(CH_3)$—. The term "substituted aryl-($C_1$-$C_6$)alkyl" refers to an aryl-($C_1$-$C_6$)alkyl functional group in which the aryl group is substituted. A specific example is substituted aryl($CH_2$)—. Similarly, the term "heteroaryl-($C_1$-$C_6$)alkyl" refers to a functional group wherein a one to three carbon alkanediyl chain is attached to a heteroaryl group, e.g., —$CH_2CH_2$-pyridyl. A specific example is heteroaryl-($CH_2$)—. The term "substituted heteroaryl-($C_1$-$C_6$)alkyl" refers to a heteroaryl-($C_1$-$C_6$)alkyl functional group in which the heteroaryl group is substituted. A specific example is substituted heteroaryl-($CH_2$)—.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1] heptanyl, bicyclo[3.1.1]heptanyl, 1,3-dimethyl[2.2.1] heptan-2-yl, bicyclo[2.2.2]octanyl, and bicyclo[3.3.3]undecanyl.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —OCH$_2$CH$_2$CH$_3$, —CH$_2$CH$_2$CH$_2$OH, —CH$_2$CH$_2$NHCH$_3$, —CH$_2$SCH$_2$CH$_3$, and —CH$_2$CH$_2$S(=O)CH$_3$. Up to two heteroatoms may be consecutive, such as, for example, —CH$_2$NH—OCH$_3$, or —CH$_2$CH$_2$SSCH$_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined elsewhere herein, substituted by one, two or three substituents independently selected from the group consisting of halogen, —OH, alkoxy, tetrahydro-2-H-pyranyl, —NH$_2$, —NH(C$_1$-C$_6$ alkyl), —N(C$_1$-C$_6$ alkyl)$_2$, 1-methyl-imidazol-2-yl, pyridin-2-yl, pyridin-3-yl, pyridin-4-yl, —C(=O)OH, —C(=O)O(C$_1$-C$_6$)alkyl, trifluoromethyl, —C(=O)NH$_2$, —C(=O)NH(C$_1$-C$_6$)alkyl, —C(=O)N((C$_1$-C$_6$)alkyl)$_2$, —SO$_2$NH$_2$, —SO$_2$NH(C$_1$-C$_6$ alkyl), —SO$_2$N(C$_1$-C$_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of C$_1$-C$_6$ alkyl, —OH, C$_1$-C$_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., two groups taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and so forth, as well as individual numbers within that range, for example, 1, 2, 2.7, 3, 4, 5, 5.3, and 6. This applies regardless of the breadth of the range.

Compounds

In one aspect, the invention provides compounds according to formula (I) or a salt, solvate, stereoisomer (such as, in a non-limiting example, an enantiomer or diastereoisomer, and any mixtures thereof, such as, in a non-limiting example, mixtures in any proportion of enantiomers and/or diastereoisomers thereof), tautomer and any mixtures thereof, and/or geometric isomer and any mixtures thereof:

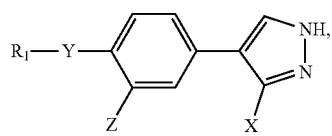

(I)

wherein in (I):

Y is selected from the group consisting of a bond, —CH$_2$—, —O—, —S—, —S(=O)—, —S(=O)$_2$, and —N(R$_2$)—;

R$_1$ is selected from the group consisting of H, C$_1$-C$_6$ alkyl, phenyl, naphthyl, tetrahydronaphthyl, phenanthryl, bicyclic heteroaryl (such as, but not limited to, benzofuranyl, benzothiophenyl, and indolyl), 1,2-dihydroacenaphthyl, acenaphthyl, adamantyl, (heteroaryl)-phenyl, and biphenyl;

R$_2$ is selected from the group consisting of H and C$_1$-C$_6$ alkyl;

Z is selected from the group consisting of —COOR, —S(=O)R, —S(=O)$_2$R, and SO$_2$NRR;

X is selected from the group consisting of H, C$_1$-C$_3$ alkyl, and a halogen (such as, for example, F or Cl);

wherein the phenyl, naphthyl, tetrahydronaphthyl, phenanthryl, bicyclic heteroaryl, 1,2-dihydroacenaphthyl, acenaphthyl, adamantyl, (heteroaryl)-phenyl, or biphenyl is independently optionally substituted with at least one group independently selected from the group consisting of halogen, —OH, —C(=O)OR, C$_1$-C$_6$ alkyl, C$_1$-C$_6$ haloalkyl, C$_1$-C$_6$ alkoxy, C$_1$-C$_6$ haloalkoxy, C$_3$-C$_6$ cycloalkyl, C$_3$-C$_6$ cycloalkoxy, C$_3$-C$_6$ halocycloalkyl, C$_3$-C$_6$ halocycloalkoxy, —(CH$_2$)$_{1-6}$NRR, —O(CH$_2$)$_{1-6}$NRR, —(CH$_2$)$_{1-6}$NR(C$_1$-C$_6$ acyl), —O(CH$_2$)$_{1-6}$NR(C$_1$-C$_6$ acyl), —(CH$_2$)$_{1-6}$OR, —O(CH$_2$)$_{1-6}$OR, —(CH$_2$)$_{1-6}$C(=O)OR, —O(CH$_2$)$_{1-6}$C(=O)OR, —(CH$_2$)$_{1-6}$OR, —O(CH$_2$)$_{1-6}$OR, —(OCH$_2$CH$_2$)$_{1-6}$NRR, and —(OCH$_2$CH$_2$)$_{1-6}$C(=O)OR;

wherein each occurrence of R is independently selected from the group consisting of H and C$_1$-C$_6$ alkyl, or two R groups combine with the N atom to which they are both bound to form a 3-8 membered heterocyclyl or heteroaryl group (such as, but not limited to, piperidinyl, morpholinyl, pyrrolidinyl, pyridinyl, imidazolyl, and the like).

In certain embodiments, if R$_1$—Y is H, then Z is not —COOH. In certain embodiments, if R$_1$—Y is H and Z is —COOR, then X is not H. In certain embodiments, if R$_1$—Y is H and Z is —COOH, then X is not H.

In certain embodiments, the (heteroaryl)-phenyl is selected from the group consisting of (pyrimidinyl)-phenyl, (pyridinyl)-phenyl, (thiophenyl)-phenyl, and the like.

In certain embodiments, the compound of formula (I) is a compound of formula (6):

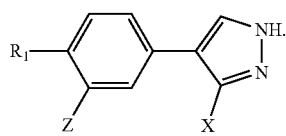

6

In various embodiments, R$_1$ is selected from the group consisting of phenyl and naphthyl. In various embodiments, the compound is selected from the group consisting of:

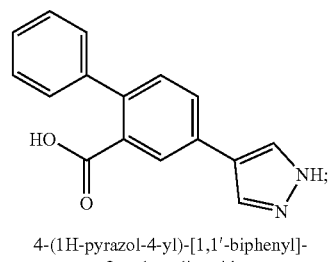

6a 4-(1H-pyrazol-4-yl)-[1,1'-biphenyl]-2-carboxylic acid

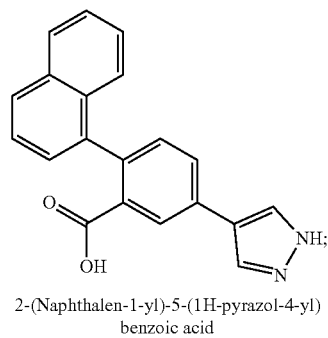

6b 2-(Naphthalen-1-yl)-5-(1H-pyrazol-4-yl) benzoic acid

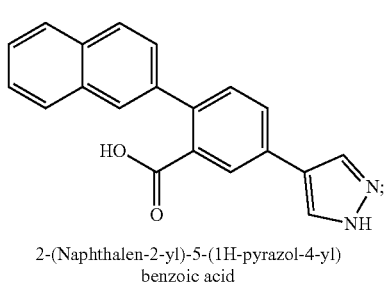

6c 2-(Naphthalen-2-yl)-5-(1H-pyrazol-4-yl) benzoic acid

-continued

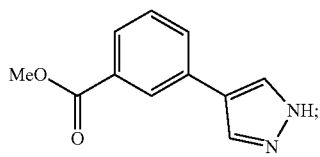

methyl 3-(1H-pyrazol-4-yl)
benzoate

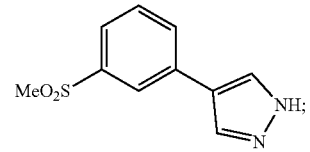

4-(3-(methysulfonyl)phenyl)-
1H-pyrazole

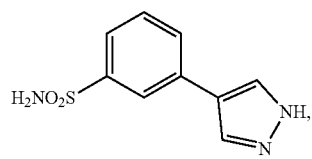

4-(3-(methysulfonyl)phenyl)-
1H-pyrazole

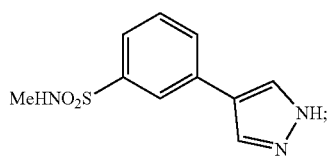

N-methyl-3-(1H-pyrazol-4-yl)
benzenesulfonamide

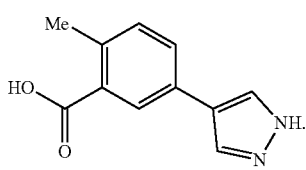

2-methyl-5-(1H-pyrazol-4-yl)
benzoic acid

In certain embodiments, the compound of formula (I) is a compound of formula (7):

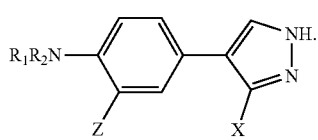

In various embodiments, $R_1$ is selected from the group consisting of phenyl and naphthyl. In various embodiments, $R_2$ is methyl. In various embodiments, the compound is selected from the group consisting of:

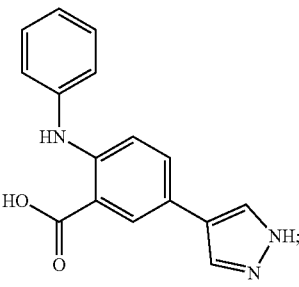

2-(Phenylamino)-5-(1H-pyrazol-
4-yl)benzoic acid

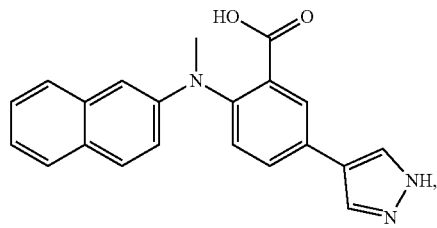

2-(Methyl(naphthalen-2-yl)amino)-5-
(1H-pyrazol-4-yl)benzoic acid

In certain embodiments, the compound of formula (I) is a compound of formula (8):

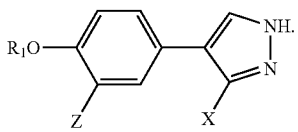

In various embodiments, $R_1$ is selected from the group consisting of methylphenyl, methoxyphenyl, fluorophenyl, ethylnapthyl, cyclopropylnaphthyl, methylbiphenyl, ethoxybiphenyl, and N-morpholinopropoxybiphenyl. In various embodiments, X is fluorine. In various embodiments, the compound is selected from the group consisting of:

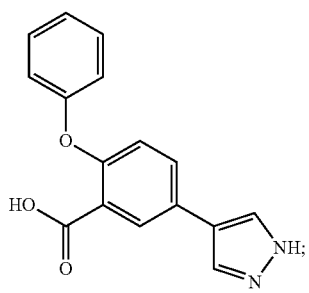

2-Phenoxy-5-(1H-pyrazol-4-yl)
benzoic acid

| | |
|---|---|
| 8b 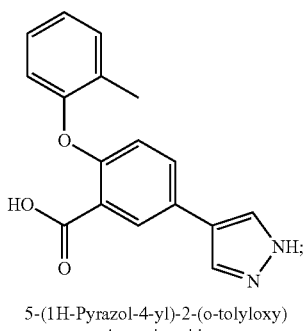5-(1H-Pyrazol-4-yl)-2-(o-tolyloxy) benzoic acid | 8f 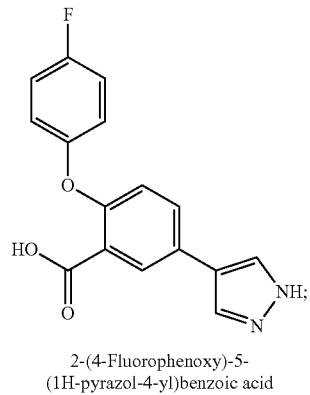2-(4-Fluorophenoxy)-5-(1H-pyrazol-4-yl)benzoic acid |
| 8c 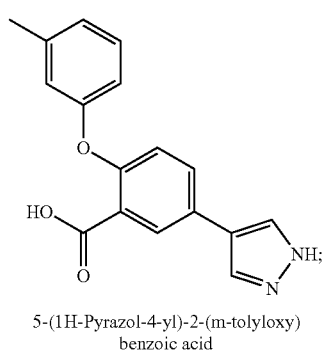5-(1H-Pyrazol-4-yl)-2-(m-tolyloxy) benzoic acid | 8g 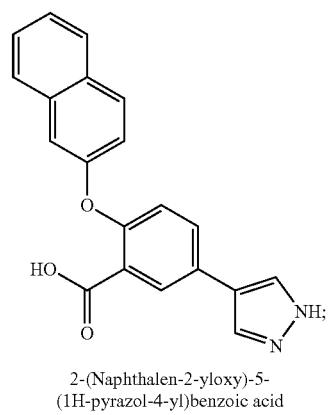2-(Naphthalen-2-yloxy)-5-(1H-pyrazol-4-yl)benzoic acid |
| 8d 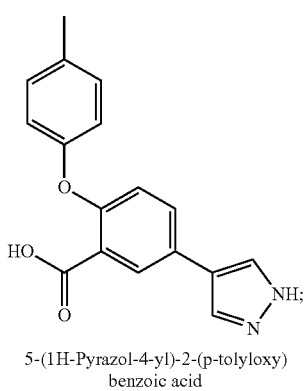5-(1H-Pyrazol-4-yl)-2-(p-tolyloxy) benzoic acid | 8h 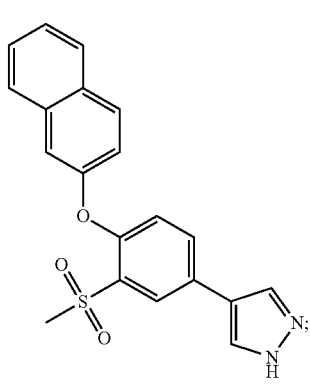4-(3-(Methylsulfonyl)-4-(naphthalen-2-yloxy)phenyl)-1H-pyrazole |
| 8e 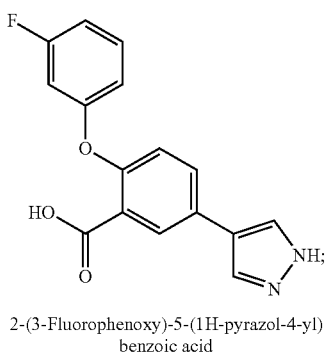2-(3-Fluorophenoxy)-5-(1H-pyrazol-4-yl) benzoic acid | 8i 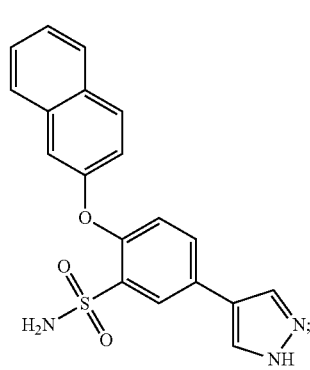2-(Naphthalen-2-yloxy)-5-1H-pyrazol-4-yl)benzenesulfonamide |

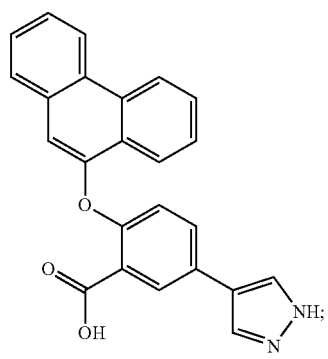
2-(Phenanthren-9-yloxy)-5-
(1H-pyrazol-4-yl)benzoic acid
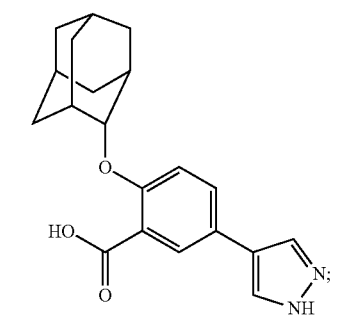
2-((Adamantan-2-yl)oxy)-5-(1H-pyrazol-4-yl)
benzoic acid
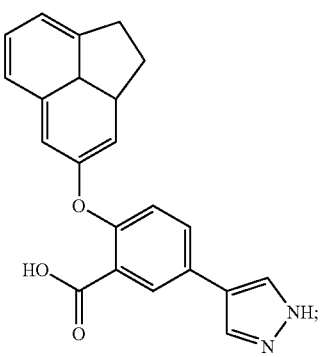
2-((1,2-Dihydroacenaphthylen-4-yl)
oxy)-5-(1H-pyrazol-4-yl)
benzoic acid
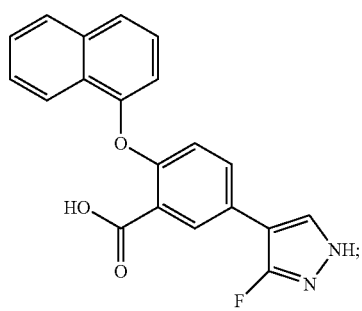
5-(3-Fluoro-1H-pyrazol-4-yl)-2-
(naphthalen-1-yloxy)benzoic acid
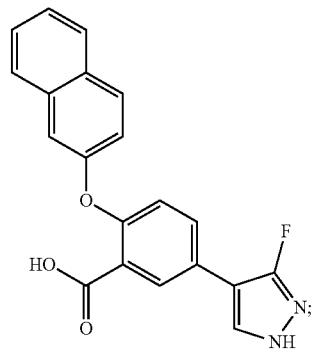
5-(3-Fluoro-1H-pyrazol-4-yl)-2-
(naphthalen-2-yloxy)benzoic acid
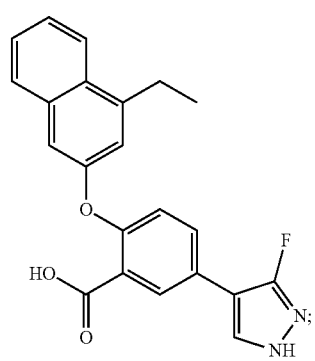
2-((4-Ethylnaphthalen-2-yl)oxy)-5-
(3-fluoro-1H-pyrazol-4-yl)benzoic acid
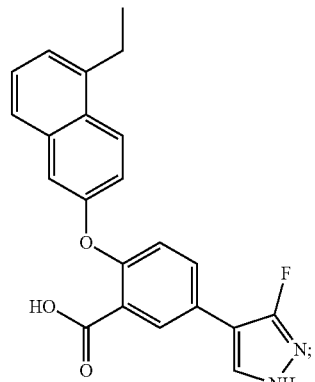
2-((5-Ethylnaphthalen-2-yl)oxy)-5-
(3-fluoro-1H-pyrazol-4-yl)benzoic acid

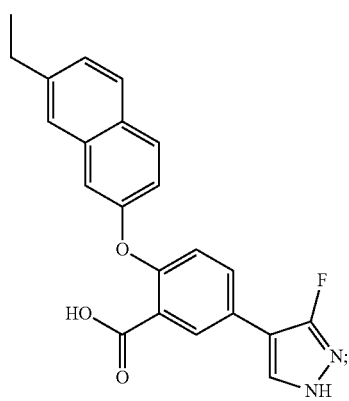
2-((7-Ethylnaphthalen-2-yl)oxy)-5-
(3-fluoro-1H-pyrazol-4-yl)benzoic acid
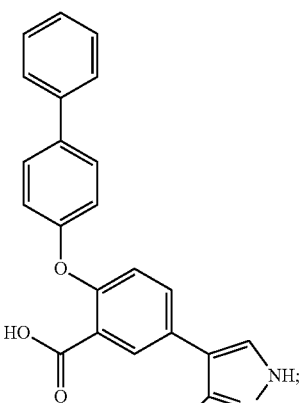
2-([1,1'-Biphenyl]-4-yloxy)-5-
(3-fluoro-1H-pyrazol-4-yl)benzoic acid
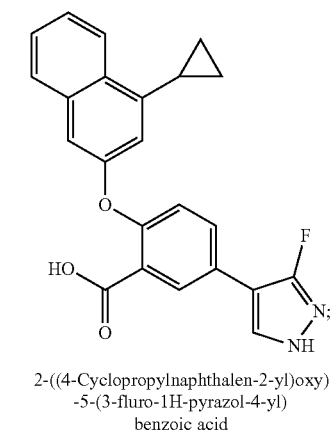
2-((4-Cyclopropylnaphthalen-2-yl)oxy)
-5-(3-fluoro-1H-pyrazol-4-yl)
benzoic acid
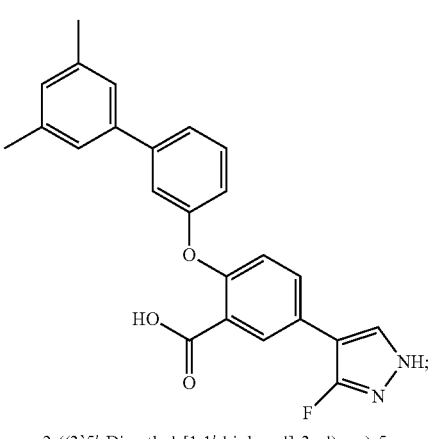
2-([1,1'-Biphenyl]-3-yloxy)-5-
(3-fluoro-1H-pyrazol-4-yl)benzoic acid
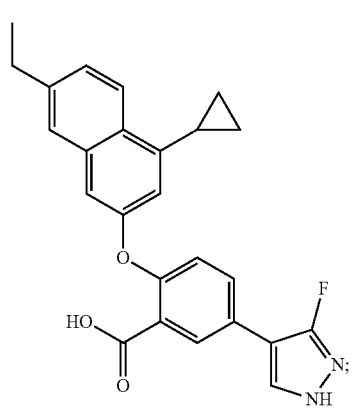
2-((4-Cyclopropyl-7-ethylnaphthalen-2-yl)
oxy)-5-(3-fluoro-1H-pyrazol-4-yl)benzoic acid
2-((3'5'-Dimethyl-[1,1'-biphenyl]-3-yl)oxy)-5-
(3-fluoro-1H-pyrazol-4-yl)
benzoic acid

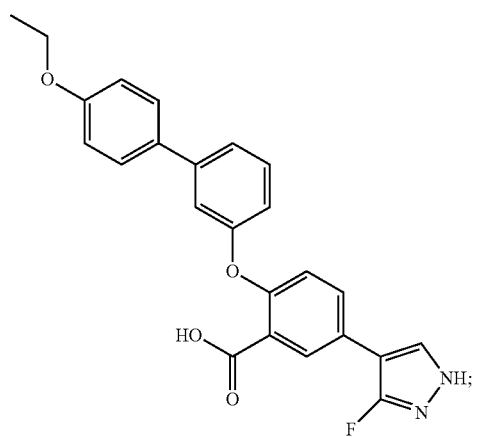
2-((4'-Ethoxy-[1,1'-biphenyl]-3-yl)oxy)-5-
(3-fluoro-1H-pyrazol-4yl)
benzoic acid
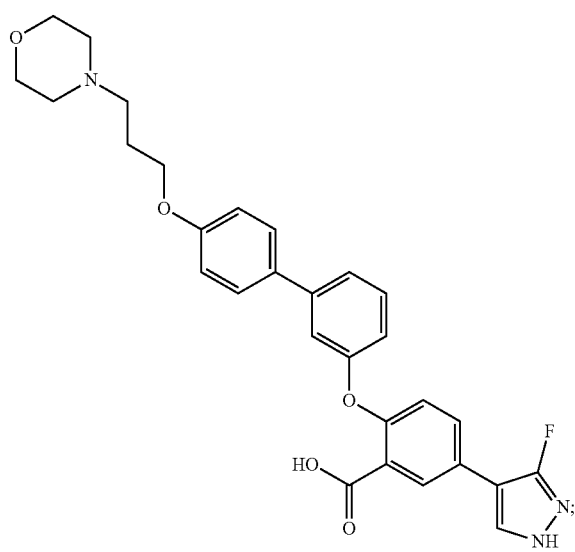
5-(3-Fluoro-1H-pyrazol-4-yl)-2-((4'-(3-morpholinopropoxy)-[1,1'-biphenyl]-3-yl)oxy)benzoic acid
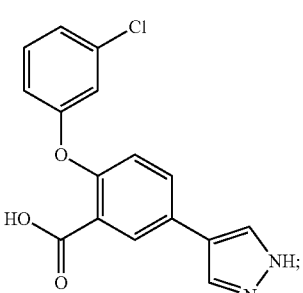
2-(3-chlorophenoxy)-5-
(1H-pyrazol-4-yl)benzoic acid
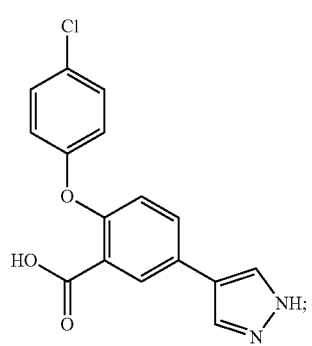
2-(4-chlorophenoxy)-5-
(1H-pyrazol-4-yl)benzoic acid
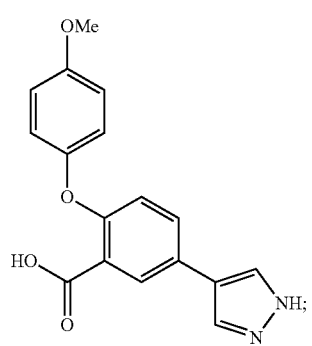
2-(4-methoxyphenoxy)-5-
(1H-pyrazol-4-yl)benzoic acid
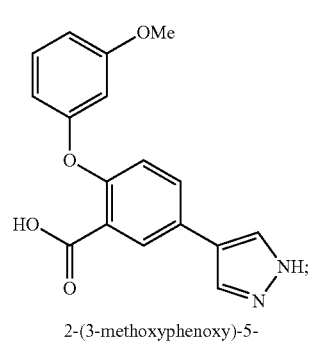
2-(3-methoxyphenoxy)-5-
(1H-pyrazol-4-yl)benzoic acid
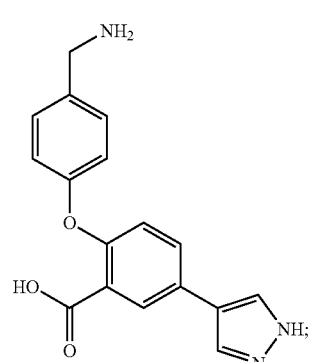
2-(4-(aminomethyl)phenoxy)-5-
(1H-pyrazol-4-yl)benzoic acid

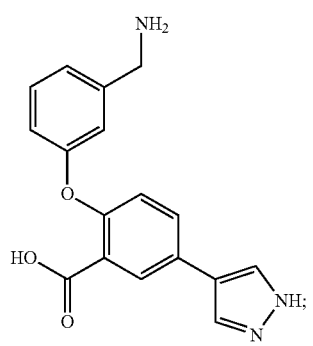
2-(3-(aminomethyl)phenoxy)-5-
(1H-pyrazol-4-yl)benzoic acid
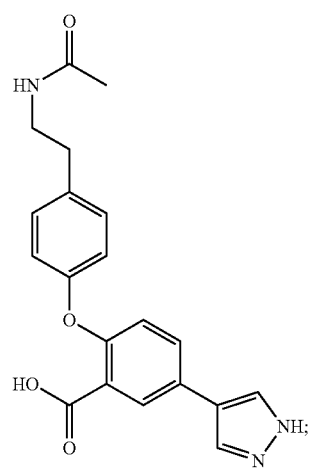
2-(4-(2-acetamidoethyl)phenoxy)-5-
(1H-pyrazol-4-yl)benzoic acid
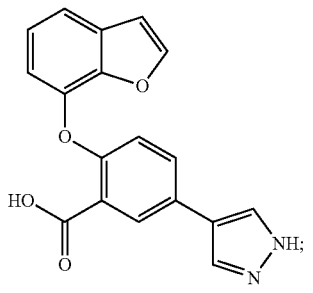
2-(benzofuran-7-yloxy)-5-
(1H-pyrazol-4-yl)benzoic acid
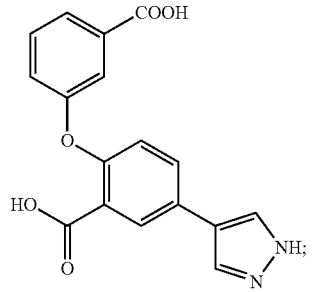
2-(3-carboxyphenoxy)-5-
(1H-pyrazol-4-yl)benzoic acid
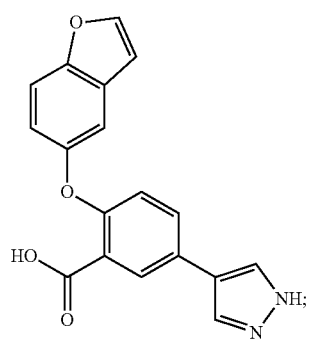
2-(benzofuran-5-yloxy)-5-
(1H-pyrazol-4-yl)benzoic acid
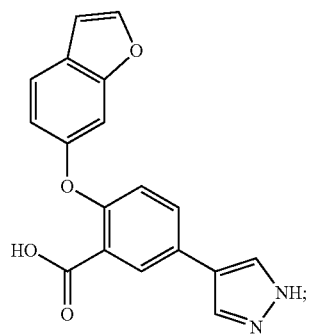
2-(benzofuran-6-yloxy)-5-
(1H-pyrazol-4-yl)benzoic acid
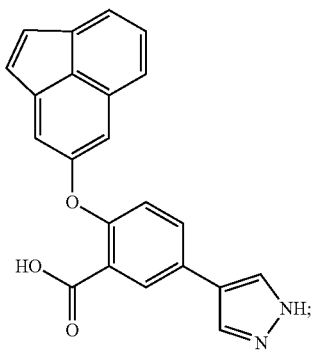
2-(acenaphthylen-4-yloxy)-5-
(1H-pyrazol-4-yl)benzoic acid
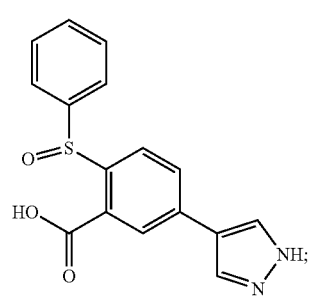
2-(phenylsulfinyl)-5-
(1H-pyrazol-4-yl)benzoic acid

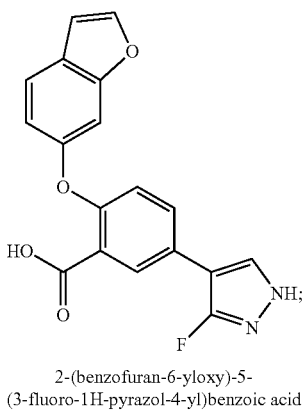

2-(benzofuran-6-yloxy)-5-
(3-fluoro-1H-pyrazol-4-yl)benzoic acid

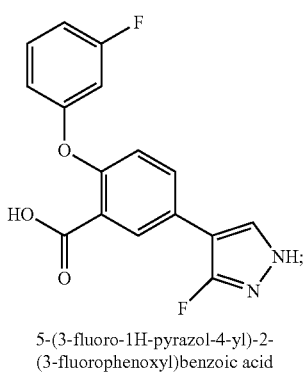

5-(3-fluoro-1H-pyrazol-4-yl)-2-
(3-fluorophenoxyl)benzoic acid

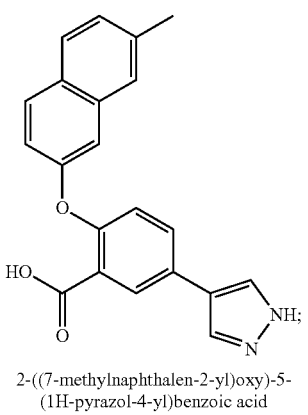

2-((7-methylnaphthalen-2-yl)oxy)-5-
(1H-pyrazol-4-yl)benzoic acid

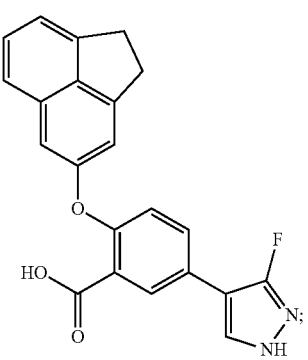

2-((1,2-dihydroacenaphthylen-4-yl)
oxy)-5-(3-flouro-1H-pyrazol-4-yl)
benzoic acid

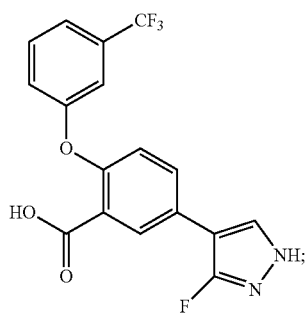

5(3-fluoro-1H-pyrazol-4-yl)-2-(3-
(trifluoromethyl)phenoxy)
benzoic acid

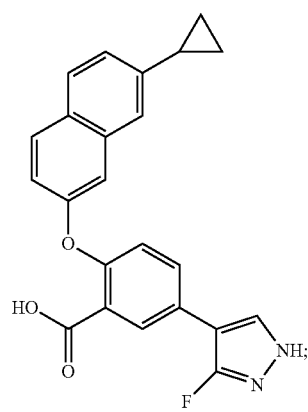

2-((7-cyclopropylnaphthalen-2-yl)
oxy)-5-(3-fluoro-1H-pyrazol-4-yl)
benzoic acid

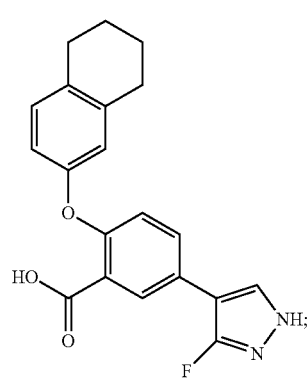

5(3-fluoro-1H-pyrazol-4-yl)-2-
((5,6,7,8-tetrahydronaphthalen-2-
yl)oxy)benzoic acid

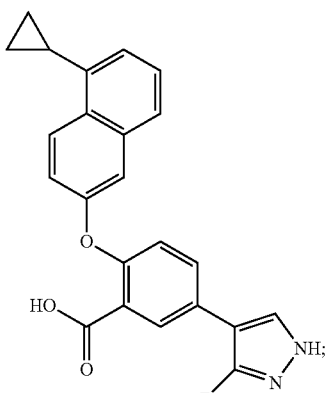

2-((5-cyclopropylnaphthalen-2-yl)oxy)-5-(3-fluoro-1H-pyrazol-4-yl)benzoic acid

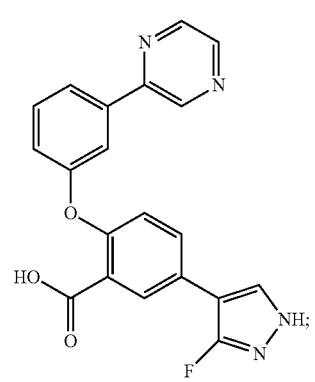

5-(3-fluoro-1H-pyrazol-4-yl)-2-(3-pyrimidin-2-yl)phenoxy)benzoic acid

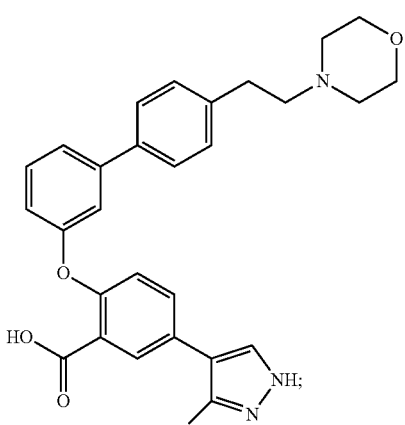

5(3-fluoro-1H-pyrazol-4-yl)-2-((4'-(2-morpholinoethyl)-[1,1'-biphenyl]-3-yl)oxy)benzoic acid

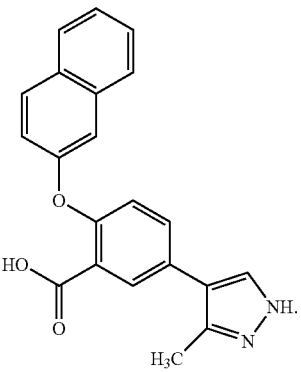

5(3-methyl-1H-pyrazol-4-yl)-2-(naphthalen-2-yloxy)benzoic acid

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature.

Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}F$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

In various embodiments, the compounds of the invention may be incorporated into a pharmaceutical composition comprising at least one pharmaceutically acceptable excipient. Dosage, administration and formulation is discussed elsewhere herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Methods

In one aspect, the invention provides a method of inhibiting MIF activity in a subject. In certain embodiments, the method comprises administering to a subject at least one compound of the invention, or a composition comprising the same. In other embodiments, the compound is administered to the subject by any known means of administration, and optionally in a pharmaceutical composition further comprising at least one excipient as appropriate to administer the compound to the subject.

In one aspect, the invention provides a method of treating a disease or disorder associated with upregulated and/or dysregulated MIF expression in a subject. In certain embodiments, the method comprises administering to a subject at least one compound of the invention, or a composition comprising the same. In other embodiments, the compound is administered to the subject by any known means of administration, and optionally in a pharmaceutical composition further comprising at least one excipient as appropriate to administer the compound to the subject.

In one aspect, the invention provides a method of treating an inflammatory disease, neurological disorders or cancer in a subject. In certain embodiments, the method comprises administering to a subject at least one compound of the invention, or a composition comprising the same. In other embodiments, the compound is administered to the subject by any known means of administration, and optionally in a pharmaceutical composition further comprising at least one excipient as appropriate to administer the compound to the subject.

In various embodiments, the subject has or is at risk of developing the disease or disorder. Diseases associated with upregulated and/or dysregulated MIF expression include, by way of non-limiting example, diseases caused by infection by a protozoan (for example malaria) fungus, bacteria and viruses, including flavivirus, such as West Nile, Dengue, Japanese encephalitis, St Louis encephalitis, or equine encepahalitis viruses; anemia of chronic disease; asthma and autism spectrum disorder (ASD). In various embodiments, the inflammatory disease is rheumatoid arthritis, Crohn's disease, or inflammatory bowel syndrome. In various embodiments, the neurological disorder is schizophrenia. In various embodiments, the cancer is colorectal, lung, breast, or prostate.

Administration/Dosage/Formulations

Administration of the compounds and/or compositions of the present invention to a patient, preferably a mammal, more preferably a human, may be carried out using known procedures, at dosages and for periods of time effective to perform the methods contemplated in the invention. An effective amount of the compound necessary may vary according to factors such as the state of a disease or disorder in the patient; the age, sex, and weight of the patient. One of ordinary skill in the art would be able to study the relevant factors and make the determination regarding the effective amount of the compound without undue experimentation.

Actual dosage levels of the active ingredients in the pharmaceutical compositions of this invention may be varied so as to obtain an amount of the active ingredient that is effective to achieve successful treatment for a particular patient, composition, and mode of administration, without being toxic to the patient.

In certain embodiments, the compositions of the invention are formulated using one or more pharmaceutically acceptable excipients or carriers. In certain embodiments, the pharmaceutical compositions of the invention comprise an effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound of the invention is from about 1 mg and about 2,500 mg. In certain embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-fibrotic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 2003/0147952; 2003/0104062; 2003/0104053; 2003/0044466; 2003/0039688; and 2002/0051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

The materials and methods used in the following illustrative examples are here described. Reagents and solvents were obtained from commercial suppliers and used without further purification. Compound 5 was purchased from Sigma Aldrich for use in MIF activity and solubility assays. Reactions requiring microwave irradiation were performed on either a BIOTAGE® Initiator Classic or a BIOTAGE® Initiator+. Reactions were monitored by thin-layer chromatography (TLC) using Merck pre-coated silica gel plates (analytical, $SiO_2$-60, $F_{254}$). TLC plates were visualized under UV light (254 nm) and/or by staining with a solution of potassium permanganate (7.5 g/L), potassium carbonate (50 g/L), and sodium hydroxide (0.63 g/L) in water. Flash column chromatography was performed on a COMBI-FLASH® Rf+ (Teledyne Isco, Lincoln, Nebr.) with either Grace REVELERIS™ (silica gel, particle size 40 µm), REDISEP® (silica gel, particle size 40-63 µm), or REDISEP RF GOLD® (silica gel, particle size 20-40 µm) prepacked cartridges. The purity of final compounds (>95%) was determined by high performance liquid chromatography (HPLC), which was performed on a Waters Acquity UPLC® column ($C_{18}$ 1.7 µm, 2.1×50 mm) using a Waters Acquity UPLC® system equipped with a Waters Acquity UPLC® Photodiode Array (PDA) eλ Detector (detection from 210-700 nm). Chromatography was performed at a flow rate of 0.6 mL/min using mobile phases A (water with 0.1% formic acid) and B (acetonitrile with 0.1% formic acid) for 0.4 minutes at 95% A, then in a linear gradient from 5% to 95% of B for 1.6 minutes, and held at 95% B for 1 minute. Nuclear magnetic resonance (NMR) spectra were recorded on either an Agilent $DD_2$ 400 NMR, $^{13}C$ NMR, and $^{19}F$ NMR recorded at 400, 101, and 376 MHz, respectively), an Agilent $DD_2$ 500 NMR, $^{13}C$ NMR, and $^{19}F$ NMR recorded at 500, 126, and 470 MHz, respectively), or an Agilent $DD_2$ 600 CH NMR and $^{13}C$ NMR recorded at 600 and 151 MHz, respectively). All spectra were recorded at room temperature. Chemical shifts are reported in ppm relative to deuterated solvent as an internal standard ($\delta_H$ $CDCl_3$ 7.26 ppm; $\delta_C$ $CDCl_3$ 77.16 ppm; $\delta_H$ DMSO-$d_6$ 2.50 ppm; $\delta_C$ DMSO-$d_6$ 39.52 ppm; $\delta_H$ $CD_3OD$ 4.87 ppm; $\delta_C$ $CD_3OD$ 49.00 ppm) with the following convention for describing multiplicity: s=singlet, d=doublet, t=triplet, q=quartet, quint=quintet, app=apparent, br=broad signal, m=multiplet, dd=doublet of doublets, etc. Low resolution mass spectrometry (MS) measurements for intermediate compounds were performed using an Agilent 1290 UHPLC equipped with an Agilent 6120 quadrupole time-of-flight (TOF) mass spectrometer operated in both positive and negative electrospray ionization (ESI). High-resolution mass spectrometry (HRMS) measurements of assayed compounds were recorded using a Waters ACQUITY UPLC® coupled to a Waters XEVO® QTOF mass spectrometer equipped with a Waters ZSpray™ electrospray ionization source.

Recombinant expression and purification of human MIF was carried out as previously reported. Crystallization of MIF in complex with 5 and 8g was achieved by soaking with apo-MIF crystals, while for the complexes of 8a and 8n, co-crystallization was performed via sitting drop vapor diffusion at 20° C. The structures were determined in-house using a Rigaku 007 HF+ diffractometer and Saturn 944+ CCD detector at T=100 K. The crystal structures have been deposited in the RSC Protein Data Bank with IDs 6CBG (5), 6CBF (8a), 6CB5 (8g), and 6CBH (8n).

HPP Tautomerase Assay

Inhibition of the tautomerase activity of MIF was measured using the substrate 4-hydroxyphenyl pyruvic acid (HPP) in a procedure largely adapted from previous reports. A solution of HPP (10 mM) in acetate buffer (0.5 M ammonium acetate, pH adjusted to 6.0) was prepared and allowed to incubate overnight in the dark at room temperature to allow for equilibration of the keto and enol forms. Following the incubation period, the HPP solution was stored at 4° C. and used for no more than a week. For $K_i$ determination, MIF protein (final concentration: ca. 50 nm) and inhibitor (multiple concentrations in DMSO, maintaining a final DMSO concentration of 1%) were incubated in borate buffer (0.5 M boric acid, pH 6.2) in a U-bottom 96-well plate (Falcon) for 20 minutes. A negative control (containing water and DMSO in lieu of protein and inhibitor, respectively) and a positive control (containing DMSO in lieu of inhibitor) were also prepared. The reaction began upon the addition of HPP solution (final concentration: 1.0 mM and 2.5 mM). The absorbance was monitored at 305 nm for the formation of the borateenol complex using a Tecan INFINITE® F500 plate reader over 175 seconds. Absorbance was measured three times for each [inhibitor]-[HPP] combination. Calculation of initial velocities and the non-linear regression analyses for the enzyme kinetics were performed using the program Prism 6 (GraphPad), setting the Michaelis-Menten constant ($K_m$) to 2.4. Reported $K_i$ values represent the average value obtained from two assays performed on different days. (R)-ISO-1 (purchased from Santa Cruz Biotechnology) was used as a control.

Solubility Assay

Aqueous solubility values of selected compounds were obtained via the shake-flask method. The solid sample (1-4 mg) was suspended in 1.5-2.0 mL Britton-Robinson (BR) buffer (0.04 M acetic acid, 0.04 M phosphoric acid, 0.04 M boric acid, pH 6.5). The mixture, containing excess undissolved compound, was stirred at 30° C. for 48 hours. The saturated solution was separated from the precipitate by filtration through a 0.45 µm polyethersulfone membrane (VWR International). The filtrate was diluted with BR buffer if necessary, then cut with an equal volume of DMSO. UV-vis absorbance was measured with an Agilent 8453 UV-visible Spectroscopy System (200-900 nm). Calibration curves were prepared with sample concentrations ranging from 0.24 µg/mL-0.25 mg/mL in 50:50 DMSO/BR buffer. Reported solubility results are the average values of two shake-flask experiments run in parallel. Piroxicam (purchased from Sigma-Aldrich) was used as a control, using BR buffer at pH 3.73.

Protein Expression and Purification

Recombinant human MIF was expressed and purified according to published protocols. Briefly, for the purification of MIF, *E. coli* cell pellets were suspended in lysis buffer (20 mM Tris, pH 7.5; 20 mM sodium chloride; 10% glycerol; 2 mM magnesium chloride; 1 cOmplete mini protease inhibitor cocktail tablet per 250 mL of buffer). The solution was sonicated and centrifuged at 27,000G for 30 mins. The supernatant was filtered through a 0.22 µm syringe filter and loaded on a GE Healthcare Hi-Trap SP HP column in sequence with a GE Healthcare Hi-Trap Q SP column equilibrated with a buffer composed of 20 mM NaCl and 20 mM Tris, pH 7.5. MIF bound to neither of the columns. To achieve highest purity, the flow-through was further purified with a GE Healthcare Superdex 200 column. The purified protein was concentrated with a 10 kDa centrifugal filter unit to 30 mg/mL, flash-frozen in liquid nitrogen, and stored at −80° C.

Crystallization of MIF in Complex with 5, 8a, 8g and 8n

Reservoir buffer for 5, 8a, and 8n: 0.1 M Tris, pH 7; 3% isopropyl alcohol; 2.4 M $(NH_4)SO_4$ Reservoir buffer for 8g:

0.1 M Tris, pH 7; 3% isopropyl alcohol; 2.0 M $(NR_4)SO_4$ Crystal structures of MIF in complex with 5 and 8g were prepared by crystal soaking. Apo MIF was crystallized by sitting drop vapor diffusion. To crystallize MIF, 1.0 µL of protein (20 mg/mL) in a buffer composed of 20 mM NaCl and 20 mM Tris at pH 7.5 was added to 1.0 µL of reservoir buffer. Crystal trays were incubated at 20° C. for one week. A 100 mM DMSO stock solution of 5 was diluted to 10 mM with reservoir buffer, and 0.5 µL of this dilution were added to a drop containing apo MIF crystals. After a 24-hour incubation period, crystals were cryo-protected in reservoir buffer cut with 25% glycerol and flash-frozen in liquid nitrogen. Soaking of 8g was performed by transferring apo crystals into a 0.5 µL drop of reservoir buffer containing 5% of a 200 mM DMSO stock of 8g. After incubation for 24 hours, crystals were cryo-protected in reservoir buffer cut with 20% glycerol and 5% of a 200 nM DMSO stock solution of 8g. Crystals were flash-frozen in liquid nitrogen.

Crystal structures of MIF in complex with 8a and 8n were prepared by co-crystallization. A solution of inhibitor (25 mM), DMSO (25% v/v) and MIF (11.25 mg/mL) was prepared and incubated for 1 hour. Co-crystallization was performed by incubating 1.0 µL of this solution with 1.0 µL of reservoir buffer for 1 week. Crystals were cryo-protected in reservoir buffer cut with 25% glycerol and flash-frozen in liquid nitrogen.

Diffraction Data Collection, Processing and Refinement

Diffraction data were collected in-house on a Rigaku 007 HF+X-ray diffractometer equipped with a Cu rotating anode ($\lambda$=1.54178 Å) and a Saturn 944+ CCD detector at T=100 K. Data processing was performed with HKL2000. Crystallographic statistics are given in Table 1. Phases of 5, 8a and 8n were obtained by molecular replacement with PDB file 3U18 using the CCP4i and Phaser programs. Model building was performed in Coot with iterative restrained refinement (XYZ coordinates, occupancies, isotropic B factors) with Refmac5. Restraints for inhibitors 5, 8a and 8n were generated with JLigand. Phases of 8g were obtained by molecular replacement with PDB file 6CB5 using CCP4i and Phaser, and model building was performed in Coot with iterative restrained refinement (XYZ coordinates, occupancies, isotropic B factors, riding hydrogen atoms) with Phenix. refine. Restraints for inhibitor 8g were created with Phenix. elbow. From all datasets, a randomly chosen subset (5%) of the reflections was excluded from refinement and used for the computation of $R_{free}$.

TABLE 1

| | MIF-ligand complex (PDB code) | | | |
|---|---|---|---|---|
| | 5 (6CBG) | 8a (6CBF) | 8g (6CB5) | 8n (6CBH) |
| (A) Data collection and processing | | | | |
| Space group | $P2_12_12_1$ | $P2_12_12_1$ | $P2_12_12_1$ | $P2_12_12_1$ |
| Unit cell parameters: a, b, c (Å) | 68.3, 68.3, 86.8 | 68.3, 68.3, 83.3 | 68.3, 69.1, 89.2 | 68.1, 68.5, 88.7 |
| (B) Diffraction data | | | | |
| Resolution range (Å) | 53.68-2.00 | 52.82-2.30 | 50.00-1.78 | 54.20-2.00 |
| | (2.05-2.00) | (2.34-2.30) | (1.81-1.78) | (2.03-2.00) |
| Unique reflections | 24739 | 17430 | 40550 | 28209 |
| $R(I)_{merge}$ (%) | | 10.3 (56.3) | 8.0 (65.7) | 4.0 (11.2) |
| Completeness (%) | 97.92 (93.07) | 97.0 (95.0) | 98.3 (78.7) | 98.3 (93.2) |
| Multiplicity | 3.1 (2.0) | 6.4 (4.8) | 6.5 (2.2) | 5.8 (3.8) |
| $<I/\sigma(I)>$ | 49.2 (5.8) | 16.2 (2.4) | 21.7 (1.3) | 39.8 (10.8) |
| (C) Refinement | | | | |
| Resolution range (Å) | 53.68-2.00 | 52.82-2.30 | 37.49-1.78 | 54.20-2.00 |
| Reflections used in refinement (work/free) | 24739/2764 | 14279/1608 | 38476/2011 | 25311/1709 |
| Final R value for all reflections (work/free) (%) | 17.2/20.5 | 23.7/28.2 | 17.8/21.3 | 17.7/21.5 |
| Protein residues | 342 | 342 | 342 | 342 |
| Inhibitor atoms | 28 | 42 | 56 | 78 |
| Water molecules | 194 | 18 | 256 | 317 |
| RMSD, bond lengths (Å) | 0.009 | 0.009 | 0.010 | 0.008 |
| RMSD, bond angles (°) | 1.4 | 1.5 | 1.0 | 1.5 |
| Ramachandran plot[b] | | | | |
| Ramachandran favored (%) | 98.5 | 97.6 | 98.2 | 97.4 |
| Ramachandran allowed (%) | 1.5 | 1.8 | 1.4 | 2.6 |
| Ramachandran outliers (%) | 0.0 | 0.6 | 0.4 | 0.0 |
| Mean B factors (Å2): | | | | |
| Protein non-hydrogen atoms | 14.9 | 34.8 | 21.5 | 24.3 |
| Inhibitor | 20.2 | 38.2 | 34.6 | 33.0 |
| Water molecules | 26.6 | 28.9 | 29.5 | 35.2 |

[a] Values in parenthesis refer to the highest resolution shell.
[b] Calculated with MolProbity.[26]

Example 1

The strategy for interference with the binding of MIF to its receptor CD74 is to find tautomerase inhibitors that change the surface characteristics of MIF. Indeed, numerous studies have shown a correlation between inhibition of the enzymatic and biological activities of MIF by measuring tautomerase activity, and, for example, MIF/CD74 binding, protein phosphorylation in inflamed cells, production of interleukins, and glucocorticoid overriding ability. Though many MIF tautomerase inhibitors have been discovered through screening of compound libraries, lead optimization to give inhibitors with nanomolar potency has been limited. The most promising compounds from the literature have been tested in a tautomerase inhibition assay and only few compounds have sub-micromolar $K_i$ values. The results were confirmed by measurement of $K_d$ values in a fluorescence polarization assay. Exemplary potent compounds are 1 (NVS-2) and 2 with $K_i$ values of ca. 0.03 μM, which are ca. 1000-fold lower than for well-known MIF inhibitors such as 3 ((R)-ISO-1) and the chromen-4-one 4 (Scheme 1).

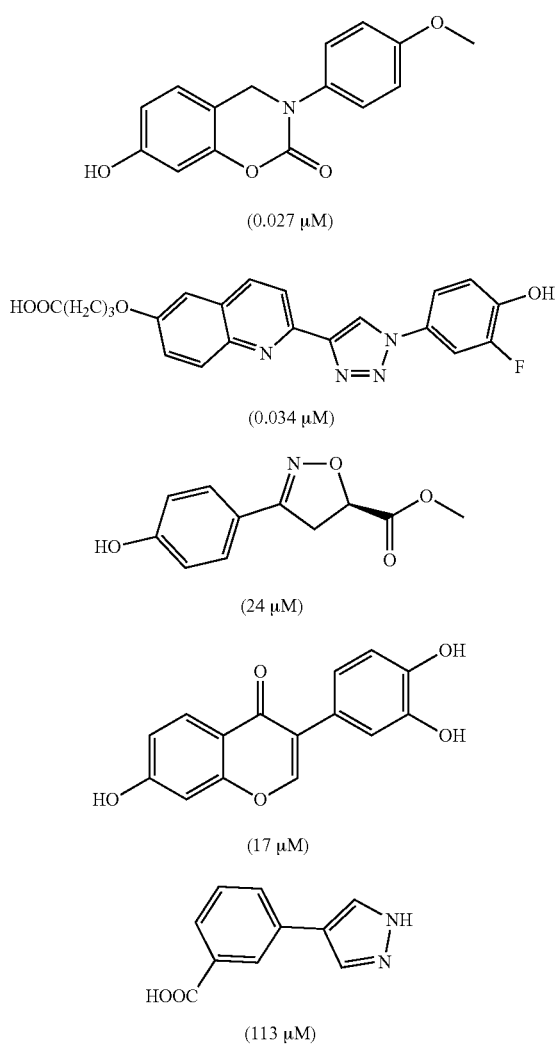

Scheme 1. Examples of MIF tautomerase inhibitors with Ki data.

A feature, which is addressed here, is that 1-4 and many other non-covalent MIF tautomerase inhibitors and substrates contain a phenol subunit, which lodges in the back of the active site and forms hydrogen bonds with the sidechain of Asn97 (FIG. 1). Though there are more than 125 approved drugs that contain a phenolic group including, for example, acetaminophen, albuterol, amoxicillin, raloxifene, and doxycycline, the oral bioavailability of phenols is well-known to often be unacceptably low owing to metabolic glucoronidation and/or sulfation. Thus, a phenol-free series of MIF tautomerase inhibitors with low-nanomolar potencies was sought.

Success in the past has come from exchange of the phenol for a 6:5 fused heteroaromatic incorporating a pyrrole or pyrazole that retains the hydrogen-bond donating character of phenol. However, the MIF active site is too constricted near Asn97 for this approach to be viable; addition of a methyl group ortho to the hydroxyl group for the compound in FIG. 1 leads to a ca. 100-fold loss in activity. Instead, interest has focused on direct replacement of the phenol by a pyrazole. In fact, in the initial virtual screening study 11 compounds were found to be active in an assay that measured interference of binding between MIF and immobilized CD74 ectodomain; and, one contained a pyrazole with the expected hydrogen bonds to Asn97 in the docked structure. This compound, 5, gave an IC50 of 15 μM in the binding assay; however, it showed little activity in a tautomerase assay using 4-hydroxyphenylpyruvate (HPP) as the substrate with a maximum of 30% inhibition at 50 μM. Thus, an alternative series from the virtual screening and from de novo design was pursued, which provided the biaryltriazoles including 2. However, interest in 5 was renewed since in another phenol-containing inhibitor series rapid metabolic glucoronidation and sulfation were observed. It was decided to retest 5 in an HPP tautomerase assay using optimized protocols. Though the $K_i$ for 5 from this assay was only 113 μM, in view of its low molecular weight and possibilities for substitution in the phenyl ring, therefore structure-based, computer-aided lead optimization was performed. As detailed here, this has been successful in providing pyrazole derivatives with ca. 2000-fold greater potency.

Figure 2:
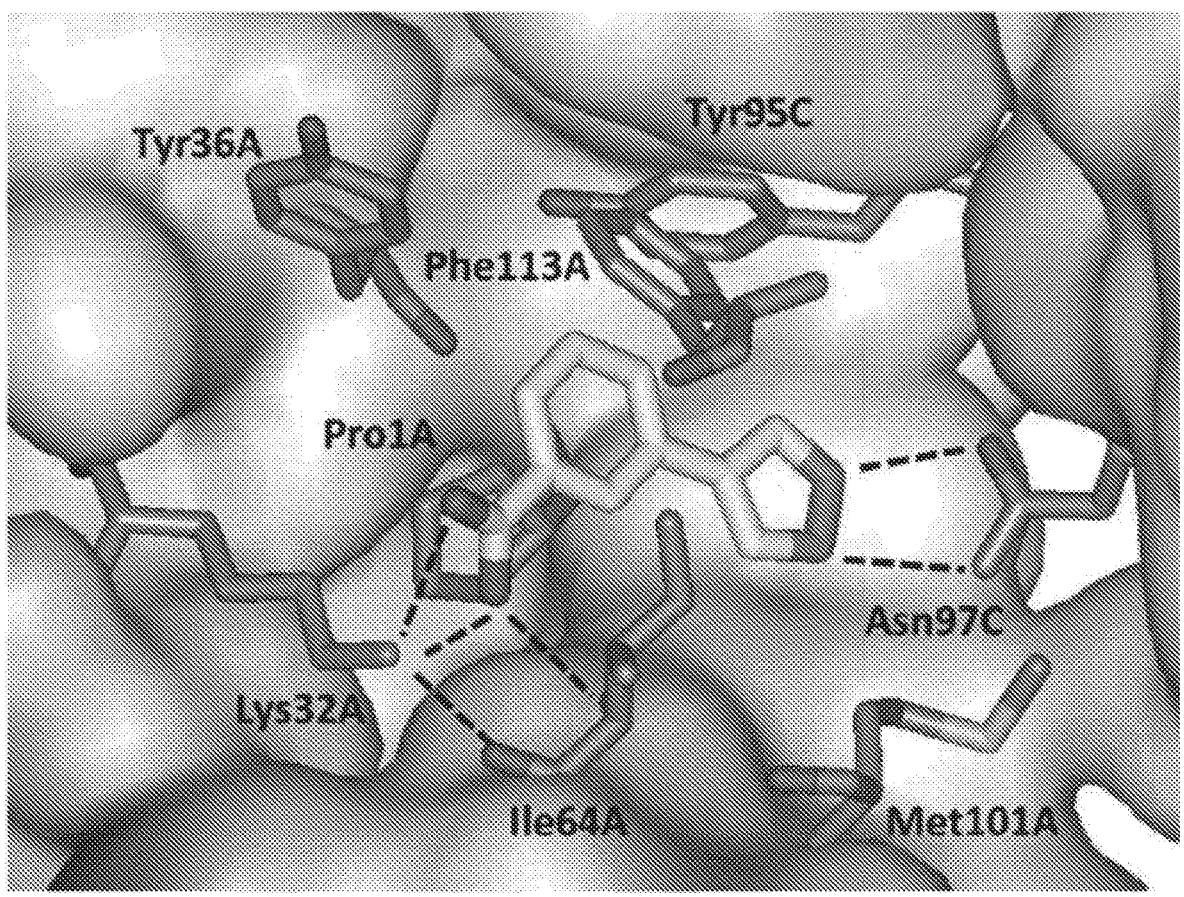
FIG. 2 is a rendering from the 2.0-Å crystal structure of 5 bound to MIF. Details as in FIG. 1.

In working with 5, it was noted that it had high solubility in polar media. This motivated successful pursuit of a crystal structure with MIF in spite of the modest $K_i$ (FIG. 2). There are two copies of 5 in each MIF trimer. The expected hydrogen bonds with Asn97 have average N—O and N—N lengths of 3.0 and 3.1 Å, while Lys32 has hydrogen bonds with the carboxylate group of 5 (3.0 and 2.7 Å) and the oxygen atom of Ile64 (2.7 Å). The NH of Ile64 also forms one with the carboxylate (2.9 Å), and the phenyl ring of 5 is well packed between Pro1, Tyr95, and Phe113. From this structure and model building with the BOMB program, substitution para to the pyrazolyl group seemed likely to yield beneficial interactions with Tyr36 and possibly Phe113. Thus, constructs 6-8 were pursued where $R_1$ was mostly an aryl group.

Scheme 2.

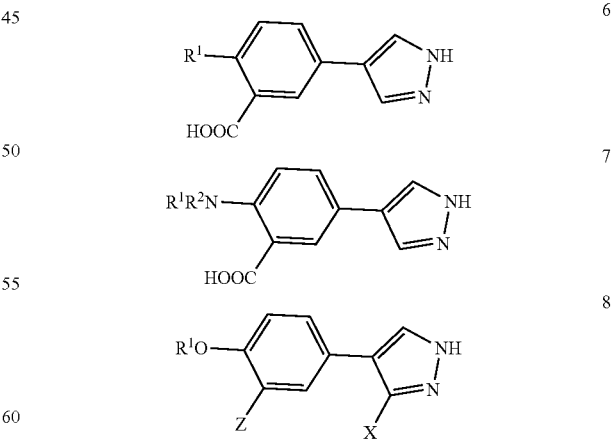

The syntheses of 6-8 are detailed below. As summarized in Scheme 3, the key steps started from the commercially available phenyl iodide 9, which underwent Pd- or Cu-mediated coupling to yield phenylaryl, arylanilinyl, or biaryl ether derivatives 10-12. Installation of the pyrazole was then achieved by a Suzuki coupling to yield esters 13-15, which were hydrolyzed under mild conditions to provide the desired carboxylic acids.

Scheme 3. Synthesis of pyrazole-based MIF inhibitors.

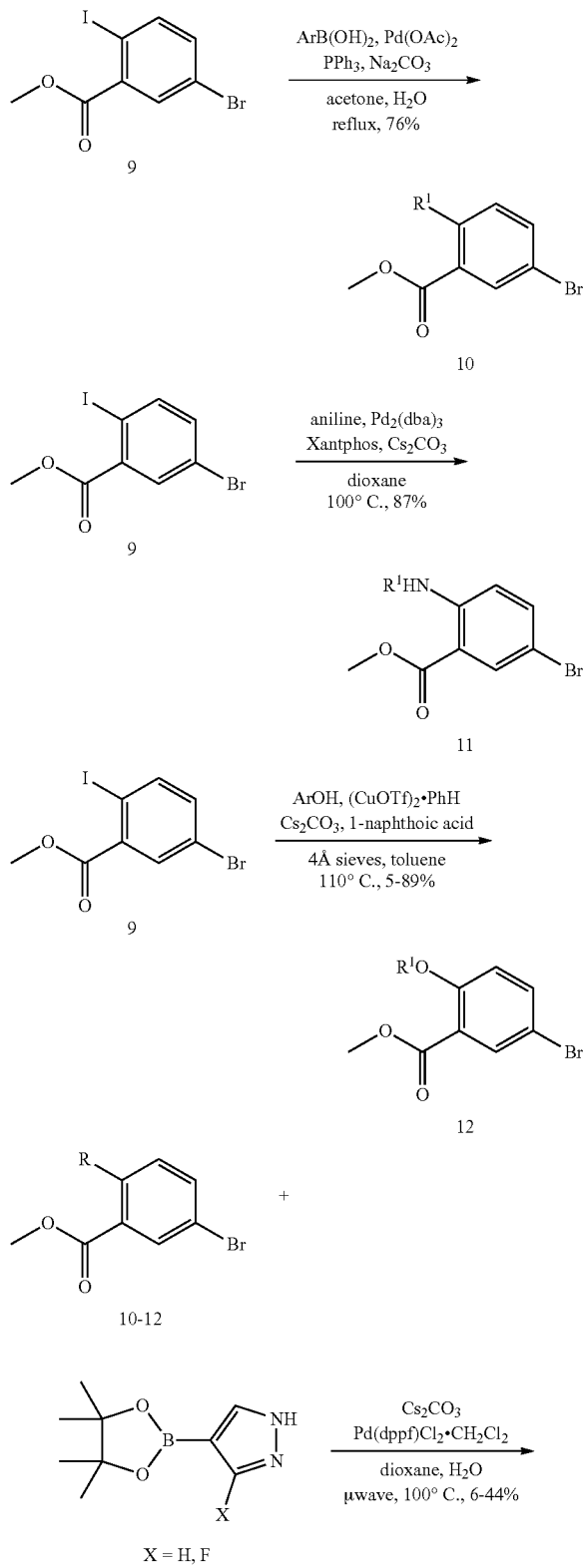

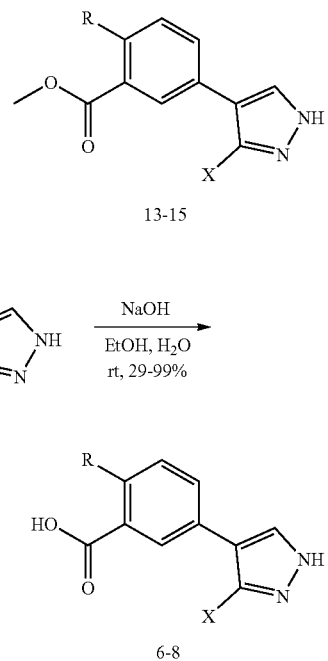

The compounds reported here are listed in Table 2 along with the results from the tautomerase assay. The identity of assayed compounds was confirmed by $^1$H and $^{13}$C NMR and high-resolution mass spectrometry; HPLC analyses established purity as >95%. As in prior studies, the inhibition constants $K_i$ were determined using HPP as the substrate. Inhibitory activity is monitored by measuring formation of the borate complex of the enol product at 305 nm using a Tecan Infinite F500 plate reader. In addition, the aqueous solubilities of several compounds were measured with a shake-flask procedure. Saturated solutions are filtered (polyethersulfone syringe, 0.2 μm pore) and analyzed by UV-vis spectroscopy (Agilent 8453).

TABLE 2

Experimental inhibition constants, $K_i$

| Cmpd | $R^{1[a]}$ | $R^2$ | Z | X | $K_i$ (μM) |
|---|---|---|---|---|---|
| 5 | H | — | — | — | 113 |
| 6a | Ph | — | — | — | 20.6 |
| 6b | 1-Np | — | — | — | 19.5 |
| 6c | 2-Np | — | — | — | 5.4 |
| 7a | Ph | H | — | — | 12.7 |
| 7b | 2-Np | Me | — | — | 4.2 |
| 8a | Ph | — | COOH | H | 6.8 |
| 8b | o-MePh | — | COOH | H | 4.3 |
| 8c | m-MePh | — | COOH | H | 3.8 |
| 8d | p-MePh | — | COOH | H | 7.0 |
| 8e | m-FPh | — | COOH | H | 1.7 |
| 8f | p-FPh | — | COOH | H | 4.6 |
| 8g | 2-Np | — | COOH | H | 4.3 |
| 8h | 2-Np | — | $SO_2Me$ | H | 6.4 |
| 8i | 2-Np | — | $SO_2NH_2$ | H | 5.6 |
| 8j | 9-Phenanthryl | — | COOH | H | 2.3 |
| 8k | 2-Adamantyl | — | COOH | H | 2.6 |
| 8l | 4-Acen | — | COOH | H | 1.1 |
| 8m | 1-Np | — | COOH | F | 0.48 |
| 8n | 2-Np | — | COOH | F | 0.51 |
| 8o | 4-Et-2-Np | — | COOH | F | 0.15 |
| 8p | 5-Et-2-Np | — | COOH | F | 0.17 |
| 8q | 7-Et-2-Np | — | COOH | F | 0.14 |
| 8r | 4-Cp-2-Np | — | COOH | F | 0.11 |

TABLE 2-continued

Experimental inhibition constants, $K_i$

| Cmpd | R$^{1[a]}$ | R$^2$ | Z | X | $K_i$ (µM) |
|---|---|---|---|---|---|
| 8s | 4-Cp,7-Et-2-Np | — | COOH | F | 0.066 |
| 8t | p-Bp | — | COOH | F | 0.35 |
| 8u | m-Bp | — | COOH | F | 0.13 |
| 8v | 3,5-diMe-m-Bp | — | COOH | F | 0.24 |
| 8w | 4-OEt-m-Bp | — | COOH | F | 0.075 |
| 8x | 4-MrPrO-m-Bp | — | COOH | F | 0.067 |

[a] Np = naphthyl;
Acen = 1,2-dihydroacenaphthyl;
Cp = cyclopropyl;
Bp = biphenyl;
MrPrO = N-morpholinylpropoxy Further experimental data are provided in Table 3:

TABLE 3

Experimental inhibition constants, $K_i$

| No. | Z | R$_1$-Y- | X | HPP Ki |
|---|---|---|---|---|
| 9a | COOMe | H | | |
| 9b | SO$_2$Me | H | | |
| 9c | SO$_2$NH$_2$ | H | | |
| 9d | SO$_2$NHMe | H | | |
| 9e | COOH | Me | | 60 |
| 9f | COOH | 3-ClPhO- | | 20 |
| 9g | COOH | 4-ClPhO- | | 8.4 |
| 9h | COOH | 4-MeOPhO- | | 2.3 |
| 9i | COOH | 3-MeOPhO- | | 2.5 |
| 9j | COOH | 4-NH$_2$CH$_2$PhO- | | |
| 9k | COOH | 3-NH$_2$CH$_2$PhO- | | |
| 9l | COOH | pMeCONHCH$_2$CH$_2$PhO- | | 11 |
| 9m | COOH | 7-benzofuranyl-O- | | 3.7 |
| 9n | COOH | m-COOHPhO- | | 9.4 |
| 9o | COOH | 5-benzofuranyl-O- | | 3.8 |
| 9p | COOH | 6-benzofuranyl-O- | | 1.5 |
| 9q | COOH | 4-acenaphthylenyl-O- | | 1.5 |
| 9r | COOH | Ph-S(=O)- | | 13 |
| 9s | COOH | 6-benzofuranyl-O- | fluoro | 0.57 |
| 9t | COOH | m-FPh-O- | fluoro | 2.1 |
| 9u | COOH | 7-Me-2-Np-O- | | 1.9 |
| 9v | COOH | 1,2-dihydro-4-acenaphthyl-O- | fluoro | 0.10 |
| 9w | COOH | m-CF$_3$-PhO- | fluoro | 0.71 |
| 9x | COOH | 7-cPr-2-Np-O- | fluoro | 0.15 |
| 9y | COOH | 2-tetrahydroNp-O- | fluoro | 0.26 |
| 9z | COOH | 5-cPr-2-Np-O- | fluoro | 0.11 |
| 9aa | COOH | 2-pyrimidinyl-3-Ph-O- | fluoro | 0.23 |
| 9bb | COOH | 4-morpholinyl-CH$_2$CH$_2$-3-biphenyl-O | fluoro | 0.33 |
| 9cc | COOH | 2-NpO- | methyl | 15 |

Figure 3:
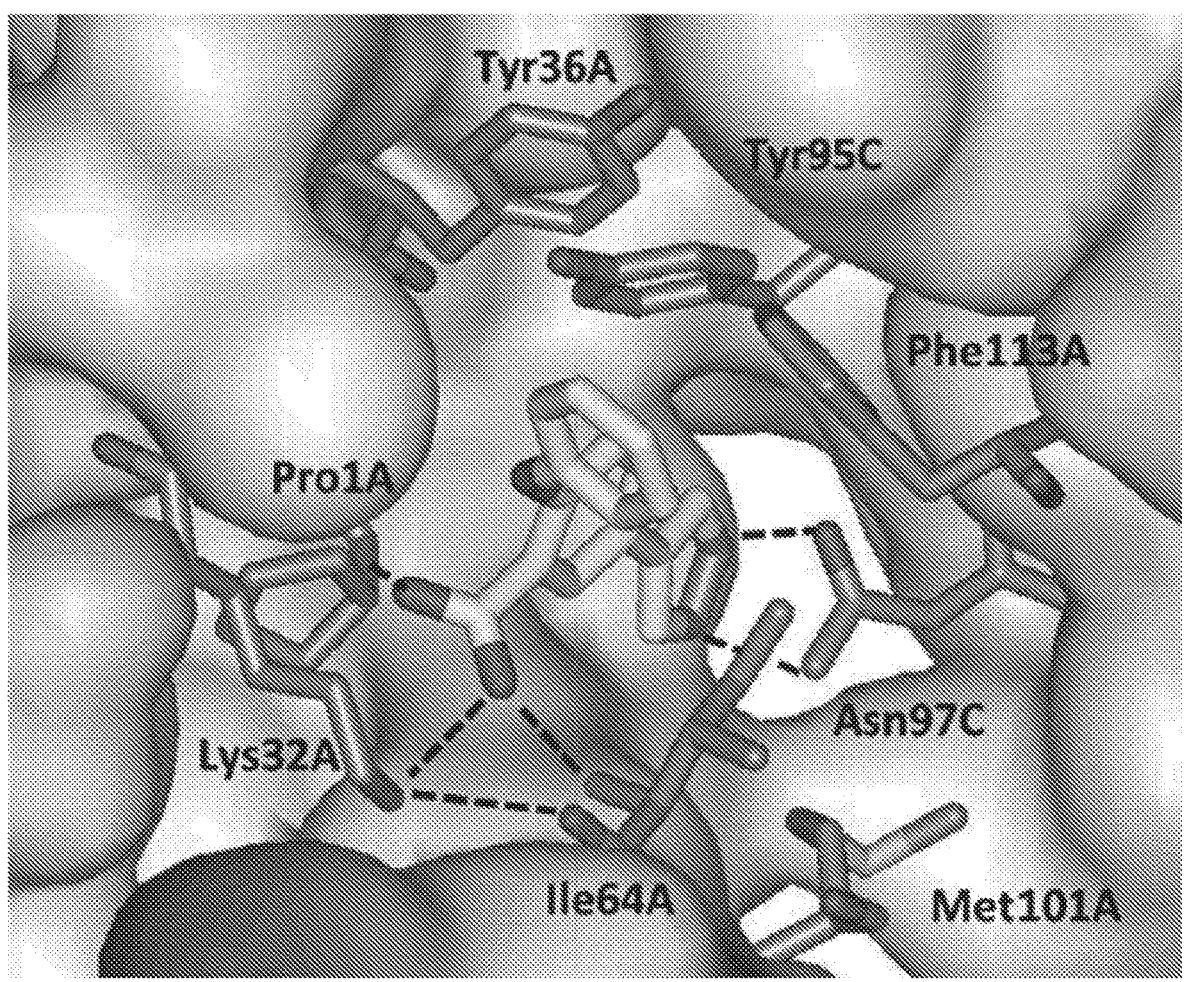
FIG. 3 is a rendering from the 2.3-Å crystal structure of 8a bound to MIF. Details as in FIG. 1.

Consistent with the modeling, addition of an aryl group in 6 did provide a significant boost over 5, bringing the $K_i$ values down to ca. 20 µM for a phenyl or 1-naphthyl group and to 5 µM for 2-naphthyl (6c). The analogous anilinyl and phenoxy compounds, 7a and 8a, were prepared, and the greater activity for the complex of 8a with MIF was also obtained (FIG. 3), which does show aryl-aryl contacts between the phenoxy phenyl group and both Tyr36 and Phe113. A basic SAR (structure-activity relationship) study was then carried out with 8b-8f, which revealed a small activity range for addition of a methyl or fluoro substituent, with para-substitution the least favored. Consistent with this guidance, the 2-naphthyl analog 8g was found to show good activity at 4.3 µM; the BOMB modeling indicated increased contact with Phe113 projecting to the right in FIG. 3. Modeling further indicated that still larger hydrophobic groups could be accommodated in this region at the entrance of the MIF active site. This was borne out by $K_i$ values of 1-3 µM obtained for phenanthryl, adamantyl, and acenaphthyl analogs, 8j-8l (Scheme 4). However, the project seemed stalled at this point without reaching the desired low-nanomolar range and with increasing concerns about solubility.

Scheme 4. Some pyrazole-based MIF inhibitors.

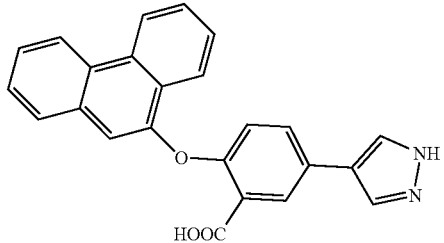

8j

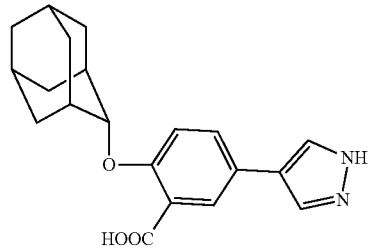

8k

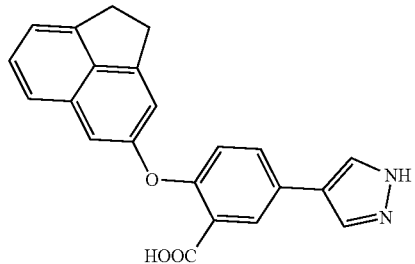

8l

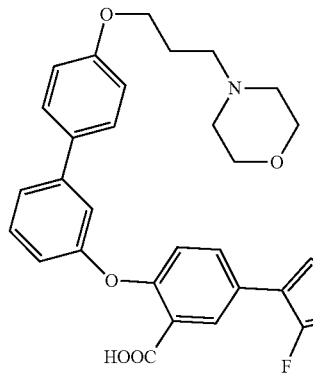

8x

For the biaryltriazoles series, it was recalled that placement of a fluorine adjacent to the hydroxyl group in compounds like 2 provided a ca. 3-fold increase in activity. The effect was attributed to enhancing the acidity of the phenol, which increases the strength of the hydrogen bond with Asn97, and also to hydrophobic contact of the fluorine with the side chain of Met 101 (FIG. 1). For the pyrazoles, the enhanced hydrogen bonding could be envisioned for a fluorine at the 3-position; however, the fluorine would project more towards the side chain of Ile64 rather than Met101 with uncertain outcome (FIG. 2). Still, a potential additional benefit might arise from the influence of the fluorine on the tautomeric equilibrium for the pyrazole. Reliable quantum mechanical calculations (MP2/6-311++G) show that the N1-H tautomer is favored by 3.6 kcal/mol over the N2-H tautomer with a fluorine in the 3-position (Scheme 5).[19] From the present crystal structures the hydrogen bonds are expected to be more linear for the N1-H tautomer as implied by the alignment of the side-chain oxygen atom of Asn97 and N1 in FIGS. 2 and 3**.

Scheme 5. Shift in the tautomeric equilibrium with a fluorine.

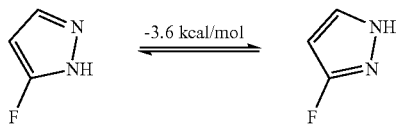

Preparation of the fluorinated pyrazole for the Suzuki coupling in Scheme 3 proved difficult. Multiple routes were attempted, but success was only achieved using a SEM [2-(trimethylsilyl)ethoxymethyl] protecting group; the yield was still low, but sufficient to proceed (Scheme 6).

Scheme 6. Synthesis of fluorinated pyrazoles.

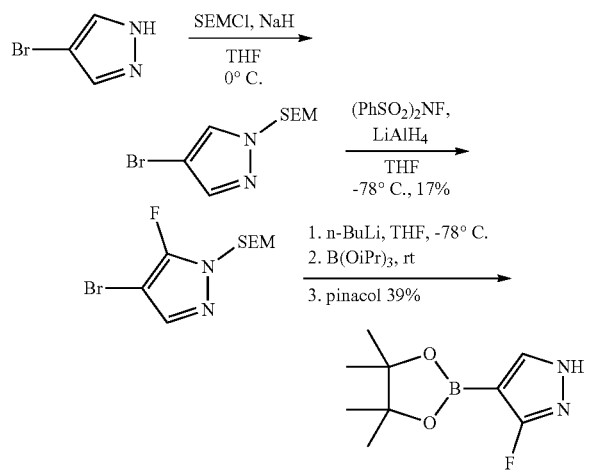

Figure 4:
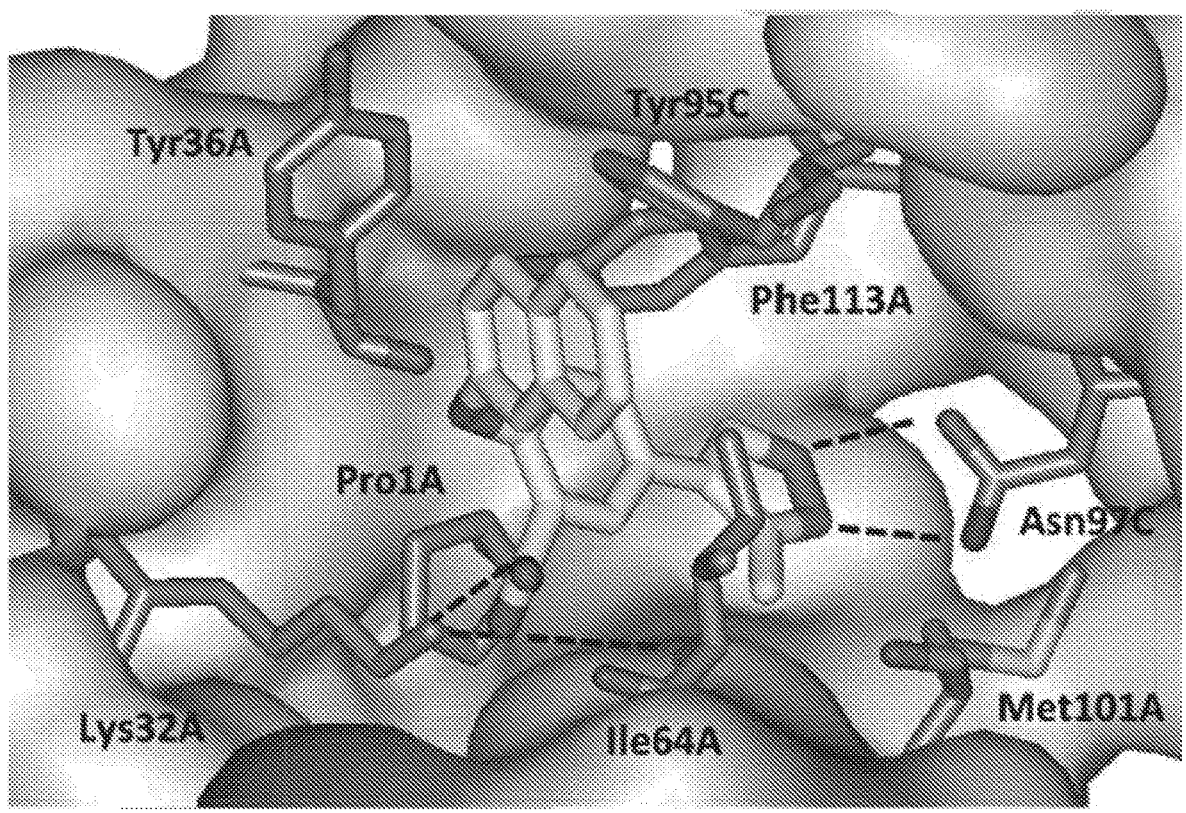
FIG. 4 is a rendering from the 2.0-Å crystal structure of 8n bound to MIF. Details as in FIG. 1.
Figure 5A:
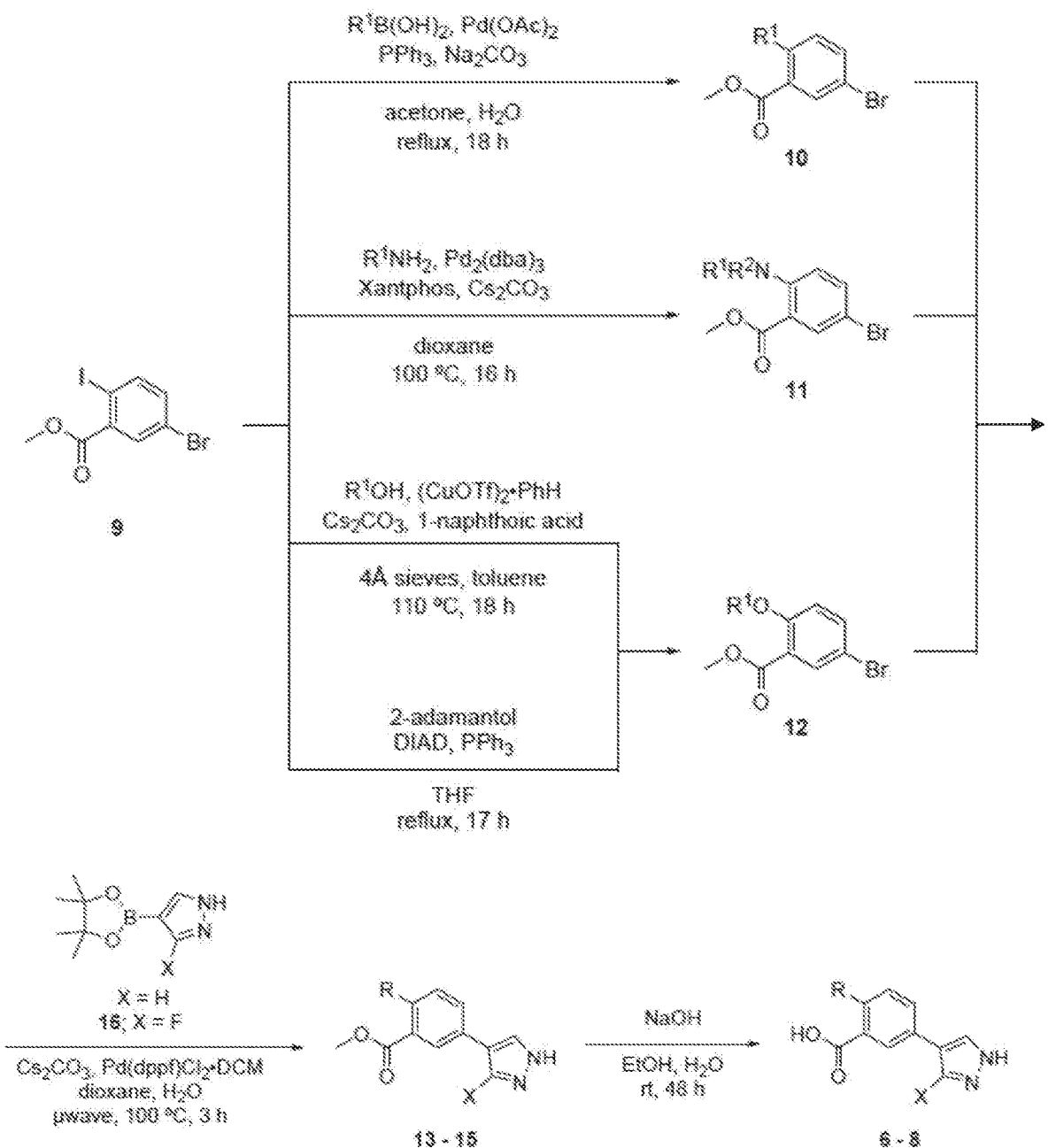

The effort was highly fruitful yielding a nearly 10-fold increase in potency in progressing from the parent 2-naphthyl inhibitor 8g (4.3 µM) to its fluorinated analog 8n (0.51 µM). It was also possible to obtain a crystal structure for this compound in complex with MIF at 2.0-Å resolution (FIG. 4). The structure confirmed the positioning of the fluorine between the sidechains of Ile64 and Met101. There is one copy of the inhibitor in each MIF trimer in this case; the N—O and N—N hydrogen bond lengths with Asn97 are 2.87 and 3.12 Å. There are also close-packed Though the exact positioning of the naphthyl group may be influenced by crystal packing, the structure and BOMB modeling indicated that additional gains in activity could arise from alkyl-substitution at the 4-, and 5-positions of the naphthyl group to achieve further contact with Phe113 or at the 7-position for contact with Ile64. This was shown to be correct with the ethyl analogs 8o, 8p, and 8q, which each provided a 3-fold lowering of the $K_i$ relative to 8n. Addition of a cyclopropyl group at the 4-position also appeared promising for interaction with the front edge of Phe113; this was realized with 8r bringing the $K_i$ to 0.11 µM. Combining this with the 7-ethyl substitution provided the very potent 8s with a $K_i$ of 0.066 µM. From the structures for 8a and 8n (FIGS. 3 and 4) and modeling, it was also clear that it should be possible to expand to a biphenyl at either the para or meta position of 8a. Thus, 8t and 8u were synthesized and provided significantly lower $K_i$ values (0.35 and 0.13 µM) than the unsubstituted naphthyl analogs, 8m and 8n. Substantial activity gains could be expected by judicious substitution for the biphenyls; however, only a few derivatives were prepared with 8w and 8x (Scheme 4) demonstrating ca. 0.07 µM potency and that large groups can be extended into the solvent from the terminal 4-position.

Two additional items are worth noting. First, the results for 8g, 8h, and 8i show that the carboxylic acid group may be replaced by a methylsulfone or sulfonamide with little impact on potency. This is relevant if one wished to explore these compounds as potential neurological agents, since sulfones are expected to exhibit better penetration of the blood-brain barrier than carboxylic acids or sulfonamides. Secondly, it is always important to monitor aqueous solubilities for compounds of interest for oral administration. Most oral drugs are observed to have aqueous solubilities of 4 to 4000 µg/mL, which translates to 10 µM to 10 mM for a drug with a molecular weight of 400. [21] The solubilities of several of the present compounds were measured in Britton-Robinson buffer at pH 6.5. As noted, the solubility of the starting compound 5 is very high (927±88 µg/mL). The solubility of the parent 2-naphthyl analog 8g is also high (739±32 µg/mL); it is affected little by addition of the fluorine in 8n (681±59 µg/mL), while switch to the sulfonamide 8i yields a significant reduction (55.2±4.8 µg/mL). Given these results, it was surprising to find in the biphenyl series that the solubility of 8w is only 1.7±0.7 µg/mL. However, this is readily remedied by attachment of solvent-exposed, solubilizing groups as in 8x (34.6±4.8 µg/mL, or 67 µM).

Synthesis of 10a-c

Methyl 4-bromo-[1,1'-biphenyl]-2-carboxylate (10a)

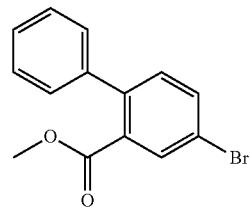 [SMILES: COC(=O)c1cc(Br)ccc1-c1ccccc1]

Methyl 5-bromo-2-iodobenzoate (500 mg, 1.47 mmol), phenylboronic acid (197 mg, 1.61 mmol), Pd(OAc)$_2$ (16.5 mg, 0.0733 mmol), and triphenylphosphine (38.5 mg, 0.147 mmol) were dissolved in a solution of 2M aqueous Na$_2$SO$_4$ (2.5 mL) and acetone (6 mL). The mixture was degassed with N$_2$ for 7 minutes then heated at reflux for 18 hours. The reaction mixture was diluted with EtOAc (100 mL) and washed with brine (100 mL). The organic phase was dried over anhydrous Na$_2$SO$_4$ and concentrated under reduced pressure. Purification by flash column chromatography (hexanes to 90:10 hexanes/EtOAc) afforded 10a as a clear oil (326 mg, 76% yield). R$_f$=0.47 (hexanes/EtOAc 90:10 v/v). $^1$H NMR (400 MHz, CDCl$_3$) δ 7.99 (d, J=2.1 Hz, 1H), 7.67 (dd; J=8.2, 2.1 Hz; 1H), 7.45-7.38 (m, 3H), 7.32-7.27 (m, 3H), 3.67 (s, 3H). $^{13}$C NMR (101 MHz, CDCl$_3$) δ 167.8, 141.5, 140.2, 134.3, 132.8, 132.5, 132.4, 132.4, 128.3, 127.7, 121.2, 52.4. MS (ESI$^+$) calcd for [C$_{14}$H$_{12}$BrO$_2$]$^+$ [M+H]$^+$, 291.0; found 290.9.

Methyl 5-bromo-2-(naphthalen-1-yl)benzoate (10b)

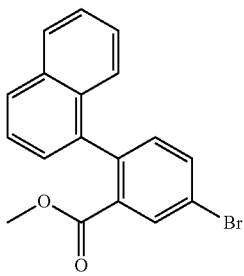 [SMILES: COC(=O)c1cc(Br)ccc1-c1cccc2ccccc12]

Phenyl bromide 10b was prepared according to the procedure for 10a using methyl 5-bromo-2-iodobenzoate (500 mg, 1.47 mmol), naphthalene-1-boronic acid (252 mg, 1.47 mmol), Pd(OAc)$_2$ (16.5 mg, 0.0733 mmol), and triphenylphosphine (38.5 mg, 0.147 mmol) in 2M aqueous Na$_2$SO$_4$ (2.5 mL) and acetone (6 mL). Purification by flash column chromatography (hexanes to 85:15 hexanes/EtOAc) afforded 10b as a white solid (442 mg, 88% yield). R$_f$=0.50 (hexanes/EtOAc 90:10 v/v). $^1$H NMR (400 MHz, CDCl$_3$) δ 8.18 (d, J=2.0 Hz, 1H), 7.88 (app t, J=8.7 Hz, 2H), 7.74 (dd, J=8.2, 2.1 Hz, 1H), 7.54-7.43 (m, 3H), 7.41-7.35 (m, 1H), 7.31-7.27 (m, 2H), 3.39 (s, 3H). $^{13}$C NMR (101 MHz, CDCl$_3$) δ 166.6, 140.4, 138.5, 134.7, 133.6, 133.4, 133.2, 133.1, 131.9, 128.4, 128.1, 126.3, 126.1, 125.9, 125.3, 125.2, 121.6, 52.2. MS (ESI$^+$) calculated for [C$_{18}$H$_{13}$BrNaO$_2$]$^+$ [M+Na]$^+$, 363.0; found 363.0.

Methyl 5-bromo-2-(naphthalen-2-yl)benzoate (10c)

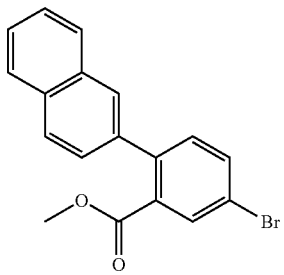 [SMILES: COC(=O)c1cc(Br)ccc1-c1ccc2ccccc2c1]

Phenyl bromide 10c was prepared according to the procedure for 10a using methyl 5-bromo-2-iodobenzoate (500 mg, 1.47 mmol), 2-naphthylboronic acid (252 mg, 1.47 mmol), Pd(OAc)$_2$ (16.5 mg, 0.0733 mmol), and triphenylphosphine (38.5 mg, 0.147 mmol) in 2M aqueous Na$_2$SO$_4$ (2.5 mL) and acetone (6 mL). Purification by flash column chromatography (hexanes to 85:15 hexanes/EtOAc) afforded 10c as a white solid (391 mg, 78% yield). R$_f$=0.42 (hexanes/EtOAc 90:10 v/v). $^1$H NMR (400 MHz, CDCl$_3$) δ 8.03 (d, J=2.0 Hz, 1H), 7.90-7.83 (m, 3H), 7.77 (s, 1H), 7.69 (dd, J=8.2, 2.1 Hz, 1H), 7.55-7.48 (m, 2H), 7.39 (dd, J=8.5, 1.7 Hz, 1H), 7.35 (d, J=8.2 Hz, 1H), 3.62 (s, 3H). $^{13}$C NMR (101 MHz, CDCl$_3$) δ 167.8, 141.5, 137.8, 134.5, 133.3, 132.9, 132.8, 132.7, 132.6, 128.2, 127.9, 127.7, 127.0, 126.8, 126.5, 126.4, 121.4, 52.4. MS (ESI$^+$) calculated for [C$_{18}$H$_{14}$BrO$_2$]$^+$ [M+H]$^+$, 341.0; found 341.0.

Synthesis of 11a and 11b

Methyl 5-bromo-2-(phenylamino)benzoate (11a)

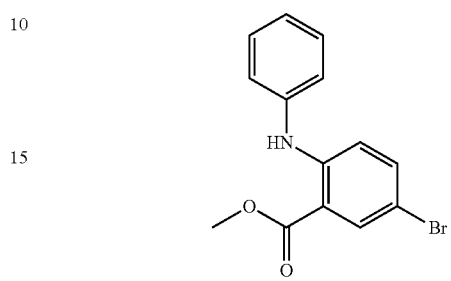

A mixture of methyl 5-bromo-2-iodobenzoate (300 mg, 0.880 mmol), aniline (115 mg, 1.23 mmol), Pd$_2$(dba)$_3$ (8.1 mg, 0.0088 mmol), Xantphos (10.2 mg, 0.0176 mmol), and Cs$_2$CO$_3$ (401 mg, 1.23 mmol) suspended in anhydrous dioxane (1.5 mL) was heated at 100° C. under N$_2$ atmosphere for 16 hours. The reaction mixture was diluted with EtOAc (100 mL) and washed with brine (100 mL). The organic phase was dried over anhydrous Na$_2$SO$_4$ and concentrated under reduced pressure. Purification by flash column chromatography (hexanes to 80:20 hexanes/EtOAc) afforded 11a as a yellow oil (234 mg, 87% yield). R$_f$=0.63 (hexanes/EtOAc 90:10 v/v). $^1$H NMR (400 MHz, CDCl$_3$) δ 9.42 (br s, 1H), 8.07 (d, J=2.3 Hz, 1H), 7.39-7.32 (m, 3H), 7.22 (d, J=7.8 Hz, 2H), 7.12 (t, J=8.4 Hz, 2H), 3.91 (s, 3H). $^{13}$C NMR (101 MHz, CDCl$_3$) δ 168.0, 147.2, 140.3, 136.9, 134.0, 129.6, 124.3, 123.0, 115.9, 113.3, 108.4, 52.2. MS (ESI$^+$) calculated for [C$_{14}$H$_{13}$BrNO$_2$]$^+$ [M+H]$^+$, 306.0; found 306.1.

Methyl 5-bromo-2-(naphthalen-2-ylamino)benzoate (11b')

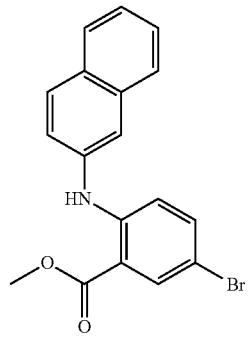 [SMILES: COC(=O)c1cc(Br)ccc1Nc1ccc2ccccc2c1]

Amine 11b' was prepared according to the procedure for 11a using methyl 5-bromo-2-iodobenzoate (667 mg, 1.96 mmol), 2-naphthylamine (200 mg, 1.40 mmol), Pd$_2$(dba)$_3$ (12.8 mg, 0.0140 mmol), Xantphos (16.2 mg, 0.0279 mmol), and Cs$_2$CO$_3$ (637 mg, 1.96 mmol) in anhydrous dioxane (2.5 mL). Purification by flash column chromatography (hexanes to 80:20 hexanes/EtOAc) afforded 11b' as a yellow oil (484 mg, 97% yield). R$_f$=0.29 (hexanes/EtOAc 90:10 v/v). $^1$H NMR (600 MHz, CDCl$_3$) δ 9.60 (s, 1H), 8.10 (app t, J=1.8 Hz, 1H), 7.84-7.79 (m, 2H), 7.74 (d, J=8.1 Hz, 1H), 7.64 (s, 1H), 7.47 (t, J=7.5 Hz, 1H), 7.42 (d, J=7.5 Hz, 1H), 7.41 (app t, J=7.5 Hz, 1H), 7.41-7.38 (m, 1H), 7.36-7.33 (m, 1H), 7.23 (d, J=9.0 Hz, 1H), 3.93 (s, 3H). $^{13}$C NMR (151 MHz, CDCl$_3$) δ 168.0, 147.0, 137.9, 137.0, 134.3, 134.0, 130.8, 129.5, 127.8, 127.2, 126.7, 125.1, 123.1, 118.7, 116.2, 113.6, 108.7, 52.2. MS (ESI$^+$) calculated for [C$_{18}$H$_{15}$BrNO$_2$]$^+$ [M+H]$^+$, 356.0; found 356.0.

Methyl 5-bromo-2-(methyl(naphthalen-2-yl)amino) benzoate (11b)

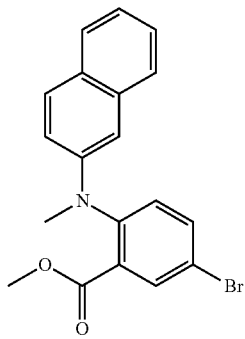 [SMILES: COC(=O)c1cc(Br)ccc1N(C)c1ccc2ccccc2c1]

To a suspension of NaH (60% dispersion in mineral oil, 29.7 mg, 0.737 mmol) in anhydrous DMF (1.5 mL) at 0° C. was added amine 11b' (dissolved in 1.5 mL DMF, 150 mg, 0.421 mmol) dropwise. After 15 minutes, methyl iodide (0.10 mL, 1.7 mmol) was added, and the contents were stirred at 80° C. for 3 hours. The reaction mixture was diluted with EtOAc (90 mL) and washed with brine (90 mL). The organic phase was dried over anhydrous Na$_2$SO$_4$ and concentrated under reduced pressure. Purification by flash column chromatography (hexanes to 85:15 hexanes/EtOAc) afforded 11b as a yellow oil (37.6 mg, 24% yield). R$_f$=0.43 (hexanes/EtOAc 90:10 v/v). $^{1H}$ NMR (600 MHz, CDCl$_3$) δ 7.95 (d, J=2.4 Hz, 1H), 7.69-7.62 (m, 3H), 7.58 (d, J=9.0 Hz, 1H), 7.37 (app t, J=7.5 Hz, 1H), 7.24 (app t, J=7.4 Hz, 1H), 7.19 (d, J=8.5 Hz, 1H), 7.01 (d, J=2.2 Hz, 1H), 6.85 (dd, J=9.0, 2.4 Hz, 1H), 3.53 (s, 3H), 3.37 (s, 3H). $^{13}$C NMR (151 MHz, CDCl$_3$) δ 166.1, 147.4, 146.6, 136.3, 134.8, 134.5, 130.7, 130.6, 128.7, 128.0, 127.6, 126.6, 126.5, 123.0, 118.2, 118.0, 109.1, 52.5, 40.9. MS (ESI$^+$) calculated for [C$_{19}$H$_{17}$BrNO$_2$]$^+$ [M+H]$^+$, 370.0; found 370.0.

Synthesis of 12a-g, 12j, and 12l-x

Methyl 5-bromo-2-phenoxybenzoate (12a)

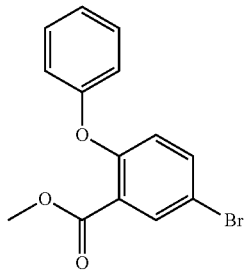 [SMILES: COC(=O)c1cc(Br)ccc1Oc1ccccc1]

This procedure was adapted from Marcoux et al.[1] Methyl 5-bromo-2-iodobenzoate (750 mg, 2.20 mmol), phenol (104 mg, 1.10 mmol), Cs$_2$CO$_3$ (717 mg, 2.20 mmol), (CuOTf)$_2$.PhH (27.7 mg, 0.0550 mmol), 1-naphthoic acid (284 mg, 1.65 mmol), and 4 Å molecular sieves (625 mg) were suspended in anhydrous toluene (2.5 mL) in a vial. The vial was sealed, and the mixture was degassed with N$_2$ for 7 minutes and heated at 110° C. for 18 hours. The reaction mixture was filtered through a pad of celite, and the filtrate was diluted with EtOAc (100 mL) and washed with brine (100 mL). The organic phase was dried over anhydrous Na$_2$SO$_4$ and concentrated under reduced pressure. Purification by flash column chromatography (hexanes to 85:15 hexanes/EtOAc) afforded 12a as a yellow oil (300 mg, 89% yield). R$_f$=0.46 (hexanes/EtOAc 90:10 v/v). NMR (400 MHz, CDCl$_3$) δ 8.03 (d, J=2.3 Hz, 1H), 7.54 (dd, J=8.8, 2.4 Hz, 1H), 7.34 (t, J=7.5 Hz, 2H), 7.11 (t, J=7.4 Hz, 1H), 6.96 (d, J=8.5 Hz, 2H), 6.85 (d, J=8.8 Hz, 1H), 3.82 (s, 3H). $^{13}$C NMR (101 MHz, CDCl$_3$) δ 165.0, 157.2, 155.7, 136.5, 134.6, 130.0, 124.7, 123.8, 122.4, 118.5, 115.9, 52.6. MS (ESI$^+$) calculated for [C$_{14}$H$_{12}$BrO$_3$]$^+$ [M+H]$^+$, 307.0; found 307.0.

Methyl 5-bromo-2-(o-tolyloxy)benzoate (12b)

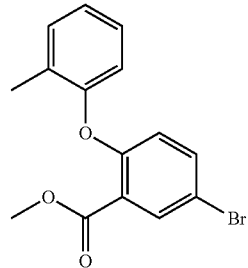 [SMILES: COC(=O)c1cc(Br)ccc1Oc1ccccc1C]

Phenyl bromide 12b was prepared according to the procedure for 12a using methyl 5-bromo-2-iodobenzoate (600 mg, 1.76 mmol), o-cresol (95.2 mg, 0.880 mmol), Cs$_2$CO$_3$ (573 mg, 1.76 mmol), (CuOTf)$_2$.PhH (22.1 mg, 0.0440 mmol), 1-naphthoic acid (277 mg, 1.32 mmol), and 4 Å molecular sieves (500 mg) in anhydrous toluene (2.5 mL). Purification by flash column chromatography (hexanes to 80:20 hexanes/EtOAc) afforded 12b as a pale yellow solid (130 mg, 46% yield). R$_f$=0.34 (hexanes/EtOAc 95:5 v/v). $^1$H NMR (600 MHz, CDCl$_3$) δ 8.01 (d, J=2.5 Hz, 1H), 7.47 (dd, J=8.8, 2.5 Hz, 1H), 7.27-7.24 (m, 1H), 7.16 (app t, J=7.5 Hz, 1H), 7.08 (app t, J=7.4 Hz, 1H), 6.83 (d, J=8.0 Hz, 1H), 6.64 (d, J=8.8 Hz, 1H), 3.86 (s, 3H), 2.24 (s, 3H). $^{13}$C NMR (101 MHz, CDCl$_3$) δ 165.2, 156.3, 154.3, 136.3, 134.6, 131.7, 129.8, 127.4, 124.6, 123.4, 120.0, 119.2, 114.7, 52.5, 16.2. MS (ESI$^+$) calculated for [C$_{15}$H$_{14}$BrO$_3$]$^+$ [M+H]$^+$, 321.0; found 321.1.

Methyl 5-bromo-2-(m-tolyloxy)benzoate (12c)

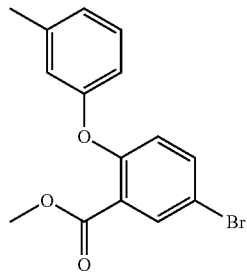 [SMILES: COC(=O)c1cc(Br)ccc1Oc1cccc(C)c1]

Phenyl bromide 12c was prepared according to the procedure for 12a using methyl 5-bromo-2-iodobenzoate (600 mg, 1.76 mmol), m-cresol (95.2 mg, 0.880 mmol), $Cs_2CO_3$ (573 mg, 1.76 mmol), $(CuOTf)_2PhH$ (22.1 mg, 0.0440 mmol), 1-naphthoic acid (227 mg, 1.32 mmol), and 4 Å molecular sieves (500 mg) in anhydrous toluene (2.5 mL). Purification by flash column chromatography (hexanes to 90:10 hexanes/EtOAc) afforded 12c as a clear oil (199 mg, 70% yield). $R_f$=0.54 (hexanes/EtOAc 90:10 v/v). $^1$H NMR (400 MHz, CDCl$_3$) δ 8.02 (d, J=2.5 Hz, 1H), 7.53 (dd, J=8.8, 2.5 Hz, 1H), 7.21 (app t, J=7.8 Hz, 1H), 6.93 (d, J=7.5 Hz, 1H), 6.84 (d, J=8.8 Hz, 1H), 6.81-6.73 (m, 2H), 3.83 (s, 3H), 2.33 (s, 3H). $^{13}$C NMR (101 MHz, CDCl$_3$) δ 165.0, 157.1, 155.9, 140.3, 136.4, 134.5, 129.7, 124.6, 124.6, 122.3, 119.3, 115.7, 115.6, 52.6, 21.5. MS (ESI$^+$) calculated for $[C_{15}H_{14}BrO_3]^+$ [M+H]$^+$, 321.0; found 321.1.

Methyl 5-bromo-2-(p-tolyloxy)benzoate (12d)

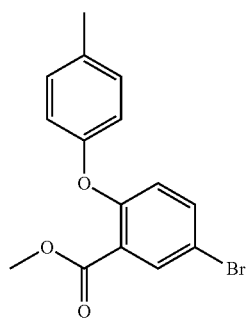 [SMILES: COC(=O)c1cc(Br)ccc1Oc1ccc(C)cc1]

Phenyl bromide 12d was prepared according to the procedure for 12a using methyl 5-bromo-2-iodobenzoate (600 mg, 1.76 mmol), p-cresol (95.2 mg, 0.880 mmol), $Cs_2CO_3$ (573 mg, 1.76 mmol), $(CuOTf)_2PhH$ (22.1 mg, 0.0440 mmol), 1-naphthoic acid (227 mg, 1.32 mmol), and 4 Å molecular sieves (500 mg) in anhydrous toluene (2.5 mL). Purification by flash column chromatography (hexanes to 90:10 hexanes/EtOAc) afforded 12d as a white solid (224 mg, 79% yield). $R_f$=0.49 (hexanes/EtOAc 90:10 v/v). $^1$H NMR (400 MHz, CDCl$_3$) δ 8.01 (d, J=2.5 Hz, 1H), 7.50 (dd, J=8.8, 2.5 Hz, 1H), 7.14 (d, J=8.3 Hz, 2H), 6.87 (d, J=8.5 Hz, 2H), 6.80 (d, J=8.8 Hz, 1H), 3.84 (s, 3H), 2.33 (s, 3H). $^{13}$C NMR (101 MHz, CDCl$_3$) δ 165.1, 156.3, 154.7, 136.3, 134.5, 133.5, 130.5, 124.3, 121.7, 118.8, 115.3, 52.6, 20.8. MS (ESI$^+$) calculated for $[C_{15}H_{14}BrO_3]^+$ [M+H]$^+$, 321.0; found 321.1.

Methyl 5-bromo-2-(3-fluorophenoxy)benzoate (12e)

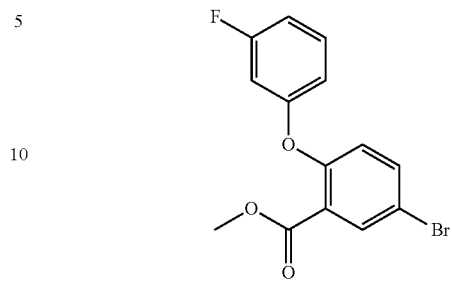

Phenyl bromide 12e was prepared according to the procedure for 12a using methyl 5-bromo-2-iodobenzoate (600 mg, 1.76 mmol), 3-fluorophenol (98.6 mg, 0.880 mmol), $Cs_2CO_3$ (573 mg, 1.76 mmol), $(CuOTf)_2PhH$ (22.1 mg, 0.0440 mmol), 1-naphthoic acid (227 mg, 1.32 mmol), and 4 Å molecular sieves (500 mg) in anhydrous toluene (2.5 mL). Purification by flash column chromatography (hexanes to 95:5 hexanes/EtOAc) afforded 12e as a clear oil (91.0 mg, 32% yield). $R_f$=0.23 (hexanes/EtOAc 95:5 v/v). $^1$H NMR (400 MHz, CDCl$_3$) δ 8.06 (d, J=2.5 Hz, 1H), 7.60 (dd, J=8.7, 2.5 Hz, 1H), 7.31-7.23 (m, 1H), 6.93 (d, J=8.7 Hz, 1H), 6.83-6.77 (m, 1H), 6.71 (dd, J=8.3, 1.6 Hz, 1H), 6.65 (app dt, J=10.1, 2.1 Hz, 1H), 3.81 (s, 3H). $^{13}$C NMR (101 MHz, CDCl$_3$) δ 164.6, 163.7 (d, J=246.9 Hz), 158.8 (d, J=10.5 Hz), 154.5, 136.7, 134.9, 130.7 (d, J=9.7 Hz), 125.2, 123.4, 117.1, 113.4 (d, J=3.1 Hz), 110.3 (d, J=21.2 Hz), 105.7 (d, J=25.0 Hz), 52.6. MS (ESI$^+$) calculated for $[C_{14}H_{11}BrFO_3]^+$ [M+H]$^+$, 325.0; found 325.0.

Methyl 5-bromo-2-(4-fluorophenoxy)benzoate (12f)

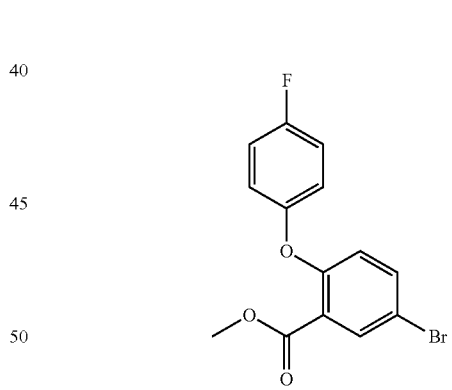

Phenyl bromide 12f was prepared according to the procedure for 12a using methyl 5-bromo-2-iodobenzoate (600 mg, 1.76 mmol), 4-fluorophenol (98.6 mg, 0.880 mmol), $Cs_2CO_3$ (573 mg, 1.76 mmol), $(CuOTf)_2PhH$ (22.1 mg, 0.0440 mmol), 1-naphthoic acid (227 mg, 1.32 mmol), and 4 Å molecular sieves (500 mg) in anhydrous toluene (2.5 mL). Purification by flash column chromatography (hexanes to 95:5 hexanes/EtOAc) afforded 12f as a yellow oil (186 mg, 65% yield). $R_f$=0.29 (hexanes/EtOAc 95:5 v/v). $^1$H NMR (400 MHz, CDCl$_3$) δ 8.02 (d, J=2.0 Hz, 1H), 7.53 (dd, J=8.8, 2.2 Hz, 1H), 7.03 (t, J=8.5 Hz, 2H), 6.97-6.90 (m, 2H), 6.80 (d, J=8.8 Hz, 1H), 3.84 (s, 3H). $^{13}$C NMR (101 MHz, CDCl$_3$) δ 164.8, 159.1 (d, J=242.3 Hz), 156.0, 152.9 (d, J=2.6 Hz), 136.5, 134.7, 124.5, 121.7, 120.1 (d, J=8.3

Hz), 116.6 (d, J=23.5 Hz), 115.9, 52.6. MS (ESI⁺) calculated for [C₁₄H₁₁BrFO₃]⁺ [M+H]⁺, 325.0; found 325.0.

Methyl 5-bromo-2-(naphthalen-2-yloxy)benzoate (12g)

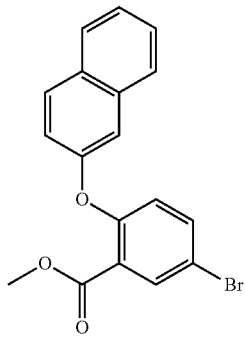 [SMILES: COC(=O)c1cc(Br)ccc1Oc1ccc2ccccc2c1]

Phenyl bromide 12g was prepared according to the procedure for 12a using methyl 5-bromo-2-iodobenzoate (750 mg, 2.20 mmol), 2-naphthol (159 mg, 1.10 mmol), Cs₂CO₃ (717 mg, 2.20 mmol), (CuOTf)₂·PhH (27.7 mg, 0.0550 mmol), 1-naphthoic acid (284 mg, 1.65 mmol), and 4 Å molecular sieves (625 mg) in anhydrous toluene (2.5 mL). Purification by flash column chromatography (hexanes to 85:15 hexanes/EtOAc) afforded 12g as a lemon yellow oil (86.9 mg, 22% yield). R_f=0.42 (hexanes/EtOAc 90:10 v/v). ¹H NMR (400 MHz, CDCl₃) δ 8.09 (d, J=2.4 Hz, 1H), 7.87-7.80 (m, 2H), 7.69 (d, J=8.0 Hz, 1H), 7.57 (dd, J=8.8, 2.5 Hz, 1H), 7.49-7.39 (m, 2H), 7.28-7.23 (m, 1H), 7.22 (s, 1H), 6.92 (d, J=8.8 Hz, 1H), 3.81 (s, 3H). ¹³C NMR (101 MHz, CDCl₃) δ 164.9, 155.5, 155.1, 136.6, 134.8, 134.3, 130.4, 130.2, 127.9, 127.3, 126.8, 125.1, 124.8, 122.8, 119.5, 116.2, 113.6, 52.6. MS (ESI⁺) calculated for [C₁₈H₁₄BrO₃]⁺ [M+H]⁺, 357.0; found 357.1.

Methyl 5-bromo-2-(phenanthren-9-yloxy)benzoate (12j)

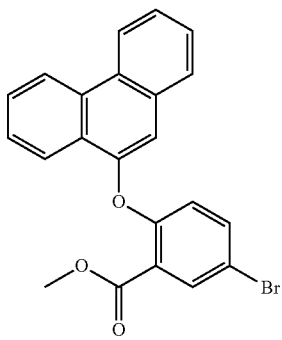 [SMILES: COC(=O)c1cc(Br)ccc1Oc1cc2ccccc2c2ccccc12]

Phenyl bromide 12j was prepared according to the procedure for 12a using methyl 5-bromo-2-iodobenzoate (600 mg, 1.76 mmol), 9-phenanthrol (171 mg, 0.880 mmol), Cs₂CO₃ (573 mg, 1.76 mmol), (CuOTf)₂·PhH (22.1 mg, 0.0440 mmol), 1-naphthoic acid (227 mg, 1.32 mmol), and 4 Å molecular sieves (500 mg) in anhydrous toluene (2.5 mL). Purification by flash column chromatography (hexanes to 90:10 hexanes/EtOAc) afforded 12j as a yellow solid (29.7 mg, 8% yield). R_f=0.44 (hexanes/EtOAc 90:10 v/v). ¹H NMR (600 MHz, CDCl₃) δ 8.72 (d, J=8.3 Hz, 1H), 8.65 (d, J=8.2 Hz, 1H), 8.36 (d, J=8.1 Hz, 1H), 8.15 (s, 1H), 7.74 (app t, J=7.6 Hz, 1H), 7.69 (d, J=7.8 Hz, 1H), 7.66 (app t, J=7.6 Hz, 1H), 7.61-7.52 (m, 3H), 6.99 (s, 1H), 6.95 (d, J=8.7 Hz, 1H), 3.72 (s, 3H). ¹³C NMR (151 MHz, CDCl₃) δ 165.0, 155.6, 151.8, 136.6, 134.9, 132.1, 131.9, 128.0, 127.9, 127.7, 127.2, 127.1, 126.5, 125.8, 124.7, 122.9, 122.8, 122.7, 122.7, 116.3, 110.9, 52.6. MS (ESI⁺) calculated for [C₂₂H₁₆BrO₃]⁺ [M+H]⁺, 407.0; found 407.0.

Methyl 5-bromo-2-((1,2-dihydroacenaphthylen-4-yl)oxy)benzoate (12l)

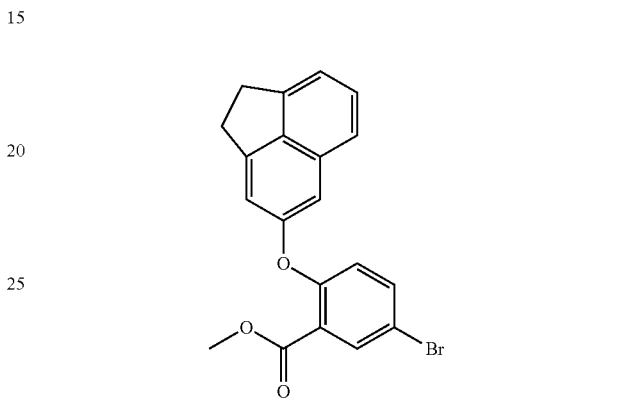

Phenyl bromide 12l was prepared according to the procedure for 12a using methyl 5-bromo-2-iodobenzoate (1.86 g, 5.45 mmol), alcohol 28 (619 mg, 3.63 mmol), Cs₂CO₃ (2.37 g, 7.27 mmol), (CuOTf)₂·PhH (91.5 mg, 0.182 mmol), 1-naphthoic acid (939 mg, 5.45 mmol), and 4 Å molecular sieves (1.00 g) in anhydrous toluene (10 mL). Purification by flash column chromatography (hexanes to 90:10 hexanes/EtOAc) afforded 12l as an olive-colored solid (180 mg, 13% yield). R_f=0.46 (hexanes/EtOAc 90:10 v/v). ¹H NMR (400 MHz, CDCl₃) δ 8.06 (d, J=2.5 Hz, 1H), 7.54 (dd, J=8.8, 2.6 Hz, 1H), 7.46-7.40 (m, 2H), 7.22 (d, J=6.0 Hz, 1H), 7.03-7.00 (m, 2H), 6.89 (d, J=8.8 Hz, 1H), 3.83 (s, 3H), 3.45-3.40 (m, 2H), 3.40-3.35 (m, 2H). ¹³C NMR (101 MHz, CDCl₃) δ 165.0, 157.5, 156.2, 148.8, 145.9, 136.5, 134.6, 131.8, 128.9, 125.0, 124.6, 122.5, 121.8, 118.6, 115.8, 113.3, 109.4, 52.6, 30.8, 30.4. MS (ESI⁺) calculated for [C₂₀H₁₆BrO₃]⁺ [M+H]⁺, 383.1; found 383.1.

Methyl 5-bromo-2-(naphthalen-1-yloxy)benzoate (12m)

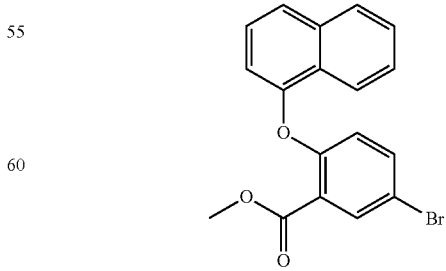

Phenyl bromide 12m was prepared according to the procedure for 12a using methyl 5-bromo-2-iodobenzoate (710 mg, 2.08 mmol), 1-naphthol (250 mg, 1.73 mmol), Cs$_2$CO$_3$ (1.13 g, 3.47 mmol), (CuOTf)$_2$PhH (65.5 mg, 0.130 mmol), 1-naphthoic acid (448 mg, 2.60 mmol), and 4 Å molecular sieves (1.00 g) in anhydrous toluene (5 mL). Purification by flash column chromatography (hexanes to 95:5 hexanes/EtOAc; then hexanes to 65:35 hexanes/DCM) afforded 12m as a cream-colored solid (30.5 mg, 5% yield). R$_f$=0.26 (hexanes/EtOAc 95:5 v/v). $^1$H NMR (400 MHz, CDCl$_3$) δ 8.22-8.18 (m, 1H), 8.08 (d, J=2.5 Hz, 1H), 7.90-7.86 (m, 1H), 7.64 (d, J=8.3 Hz, 1H), 7.57-7.48 (m, 3H), 7.37 (app t, J=7.9 Hz, 1H), 6.86 (dd, J=7.5, 0.6 Hz, 1H), 6.79 (d, J=8.8 Hz, 1H), 3.75 (s, 3H). $^{13}$C NMR (101 MHz, CDCl$_3$) δ 165.2, 156.2, 152.9, 136.5, 135.1, 134.7, 127.9, 126.9, 126.6, 126.4, 125.8, 124.3, 124.0, 122.1, 121.7, 115.7, 113.1, 52.6. MS (ESI$^+$) calculated for [C$_{18}$H$_{13}$BrNaO$_3$]$^+$ [M+Na]$^+$, 379.0; found 379.0.

Methyl 5-bromo-2-((4-ethylnaphthalen-2-yl)oxy)benzoate (12o)

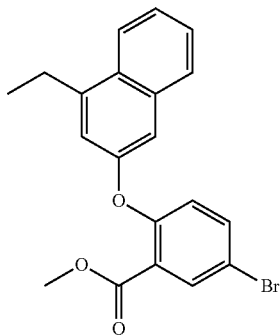 [SMILES: CCc1cc(Oc2ccc(Br)cc2C(=O)OC)cc2ccccc12]

Phenyl bromide 12o was prepared according to the procedure for 12a using methyl 5-bromo-2-iodobenzoate (404 mg, 1.18 mmol), naphthol 34o (170 mg, 0.987 mmol), Cs$_2$CO$_3$ (643 mg, 1.97 mmol), (CuOTf)$_2$PhH (37.3 mg, 0.0740 mmol), 1-naphthoic acid (255 mg, 1.48 mmol), and 4 Å molecular sieves (500 mg) in anhydrous toluene (2.5 mL). Purification by flash column chromatography (hexanes to 95:5 hexanes/EtOAc) afforded 12o as a brownish-yellow oil (90.3 mg, 24% yield). R$_f$=0.29 (hexanes/EtOAc 95:5 v/v). $^1$H NMR (400 MHz, CDCl$_3$) δ 8.09 (d, J=2.5 Hz, 1H), 8.04-8.00 (m, 1H), 7.71-7.67 (m, 1H), 7.56 (dd, J=8.8, 2.6 Hz, 1H), 7.47-7.43 (m, 2H), 7.15 (d, J=2.4 Hz, 1H), 7.07 (d, J=2.3 Hz, 1H), 6.92 (d, J=8.8 Hz, 1H), 3.83 (s, 3H), 3.11 (q, J=7.5 Hz, 2H), 1.39 (t, J=7.5 Hz, 3H). $^{13}$C NMR (101 MHz, CDCl$_3$) δ 164.9, 155.7, 154.7, 143.4, 136.5, 134.9, 134.7, 128.9, 128.2, 126.5, 124.9, 124.7, 123.9, 122.6, 118.5, 116.0, 111.9, 52.6, 25.9, 14.8. MS (ESI$^+$) calculated for [C$_{20}$H$_{18}$BrO$_3$]$^+$ [M+H]$^+$, 385.0; found 385.0.

Methyl 5-bromo-2-((5-ethylnaphthalen-2-yl)oxy)benzoate (12p)

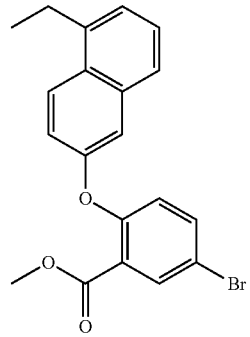 [SMILES: CCc1cccc2cc(Oc3ccc(Br)cc3C(=O)OC)ccc12]

Phenyl bromide 12p was prepared according to the procedure for 12a using methyl 5-bromo-2-iodobenzoate (409 mg, 1.20 mmol), naphthol 34p (172 mg, 1.00 mmol), Cs$_2$CO$_3$ (651 mg, 2.00 mmol), (CuOTO$_2$PhH (37.7 mg, 0.0750 mmol), 1-naphthoic acid (258 mg, 1.50 mmol), and 4 Å molecular sieves (500 mg) in anhydrous toluene (2.5 mL). Purification by flash column chromatography (hexanes to 95:5 hexanes/EtOAc) afforded 12p as a yellow oil (79.2 mg, 21% yield). R$_f$=0.24 (hexanes/EtOAc 95:5 v/v). $^1$H NMR (400 MHz, CDCl$_3$) δ 8.09-8.04 (m, 2H), 7.59-7.53 (m, 2H), 7.41-7.36 (m, 1H), 7.30-7.22 (m, 3H), 6.92 (d, J=8.8 Hz, 1H), 3.82 (s, 3H), 3.10 (q, J=7.5 Hz, 2H), 1.38 (t, J=7.5 Hz, 3H). $^{13}$C NMR (151 MHz, CDCl$_3$) δ 165.0, 155.6, 154.7, 140.6, 136.6, 134.9, 134.7, 128.7, 126.8, 126.3, 125.8, 124.8, 124.2, 122.7, 119.2, 116.1, 114.5, 52.6, 26.1, 15.2. MS (ESI$^+$) calculated for [C$_{20}$H$_{18}$BrO$_3$]$^+$ [M+H]$^+$, 385.0; found 385.0.

Methyl 5-bromo-2-((7-ethylnaphthalen-2-yl)oxy)benzoate (12q)

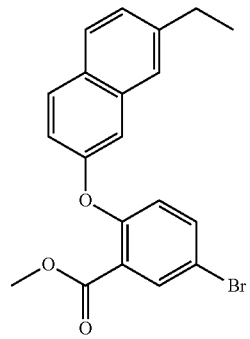 [SMILES: CCc1ccc2ccc(Oc3ccc(Br)cc3C(=O)OC)cc2c1]

Phenyl bromide 12q was prepared according to the procedure for 12a using methyl 5-bromo-2-iodobenzoate (470 mg, 1.38 mmol), naphthol 34q (198 mg, 1.15 mmol), Cs$_2$CO$_3$ (749 mg, 2.30 mmol), (CuOTf)$_2$.PhH (43.4 mg, 0.0863 mmol), 1-naphthoic acid (297 mg, 1.72 mmol), and 4 Å molecular sieves (550 mg) in anhydrous toluene (2.5 mL). Purification by flash column chromatography (hexanes to 95:5 hexanes/EtOAc) afforded 12q as an amber oil (96.0 mg, 20% yield). R$_f$=0.33 (hexanes/EtOAc 95:5 v/v). $^1$H NMR (400 MHz, CDCl$_3$) δ 8.08 (d, J=2.5 Hz, 1H), 7.80 (d, J=8.6 Hz, 1H), 7.74 (d, J=8.4 Hz, 1H), 7.56 (dd, J=8.8, 2.5

Hz, 1H), 7.48 (s, 1H), 7.29 (dd, J=8.4, 1.2 Hz, 1H), 7.20-7.15 (m, 2H), 6.91 (d, J=8.8 Hz, 1H), 3.81 (s, 3H), 2.78 (q, J=7.6 Hz, 2H), 1.30 (t, J=7.6 Hz, 3H). $^{13}$C NMR (101 MHz, CDCl$_3$) δ 165.0, 155.7, 155.2, 142.9, 136.5, 134.7, 134.6, 129.9, 128.9, 127.8, 126.4, 125.1, 124.8, 122.7, 118.7, 116.1, 113.4, 52.6, 29.2, 15.6. MS (ESI$^+$) calculated for [C$_{20}$H$_{17}$BrNaO$_3$]$^+$ [M+Na]$^+$, 407.0; found 407.0.

Methyl 5-bromo-2-((4-cyclopropylnaphthalen-2-yl)oxy)benzoate (12r)

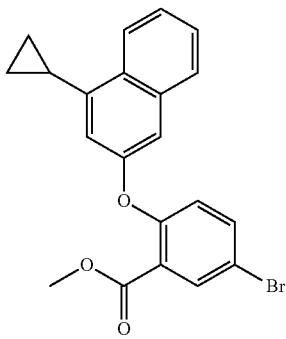 [SMILES: COC(=O)c1cc(Br)ccc1Oc1cc(C2CC2)c2ccccc2c1]

Phenyl bromide 12r was prepared according to the procedure for 12a using methyl 5-bromo-2-iodobenzoate (517 mg, 1.52 mmol), naphthol 40r (233 mg, 1.26 mmol), Cs$_2$CO$_3$ (824 mg, 2.53 mmol), (CuOTf)$_2$.PhH (47.7 mg, 0.0948 mmol), 1-naphthoic acid (327 mg, 1.90 mmol), and 4 Å molecular sieves (1.00 g) in anhydrous toluene (5 mL). Purification by flash column chromatography (hexanes to 95:5 hexanes/EtOAc) afforded 12r as a brown solid (62.1 mg, 12% yield). R$_f$=0.23 (hexanes/EtOAc 95:5 v/v). $^1$H NMR (400 MHz, CDCl$_3$) δ 8.38-8.34 (m, 1H), 8.07 (d, J=2.5 Hz, 1H), 7.71-7.66 (m, 1H), 7.55 (dd, J=8.8, 2.6 Hz, 1H), 7.50-7.45 (m, 2H), 7.07-7.04 (m, 2H), 6.88 (d, J=8.8 Hz, 1H), 3.82 (s, 3H), 2.41-2.32 (m, 1H), 1.12-1.05 (m, 2H), 0.81-0.73 (m, 2H). $^{13}$C NMR (101 MHz, CDCl$_3$) δ 165.0, 155.7, 154.7, 142.5, 136.5, 134.7, 134.6, 133.8, 130.7, 128.0, 126.7, 124.9, 124.6, 122.5, 117.6, 116.0, 112.2, 52.6, 13.4, 6.9. MS (ESI$^+$) calculated for [C$_{21}$H$_{17}$BrNaO$_3$]$^+$ [M+Na]$^+$, 419.0; found 419.0.

Methyl 5-bromo-2-((4-cyclopropyl-7-ethylnaphthalen-2-yl)oxy)benzoate (12s)

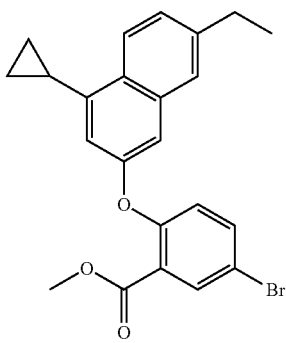 [SMILES: CCc1ccc2c(C3CC3)cc(Oc3ccc(Br)cc3C(=O)OC)cc2c1]

Phenyl bromide 12s was prepared according to the procedure for 12a using methyl 5-bromo-2-iodobenzoate (345 mg, 1.01 mmol), naphthol 40s (179 mg, 0.842 mmol), Cs$_2$CO$_3$ (549 mg, 1.68 mmol), (CuOTf)$_2$.PhH (31.8 mg, 0.0632 mmol), 1-naphthoic acid (218 mg, 1.26 mmol), and 4 Å molecular sieves (900 mg) in anhydrous toluene (5 mL). Purification by flash column chromatography (hexanes to 95:5 hexanes/EtOAc) afforded 12s as a yellow solid (48.4 mg, 14% yield). R$_f$=0.32 (hexanes/EtOAc 95:5 v/v). $^1$H NMR (400 MHz, CDCl$_3$) δ 8.27 (d, J=8.6 Hz, 1H), 8.06 (d, J=2.5 Hz, 1H), 7.54 (dd, J=8.8, 2.5 Hz, 1H), 7.47 (s, 1H), 7.34 (dd, J=8.5, 1.3 Hz, 1H), 7.00 (d, J=2.1 Hz, 1H), 6.98 (d, J=2.1 Hz, 1H), 6.87 (d, J=8.8 Hz, 1H), 3.82 (s, 3H), 2.78 (q, J=7.6 Hz, 2H), 2.39-2.30 (m, 1H), 1.31 (t, J=7.6 Hz, 3H), 1.10-1.03 (m, 2H), 0.79-0.73 (m, 2H). $^{13}$C NMR (126 MHz, CDCl$_3$) δ 165.0, 155.9, 154.7, 142.7, 142.3, 136.5, 134.9, 134.7, 129.1, 126.1, 125.8, 124.6, 124.5, 122.4, 116.7, 115.8, 112.0, 52.6, 29.0, 15.6, 13.4, 6.9. MS (ESI$^+$) calculated for [C$_{23}$H$_{22}$BrO$_3$]$^+$ [M+H]$^+$, 425.1; found 425.0.

Methyl 2-([1,1'-biphenyl]-4-yloxy)-5-bromobenzoate (12t)

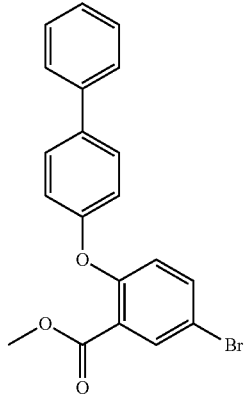 [SMILES: COC(=O)c1cc(Br)ccc1Oc1ccc(-c2ccccc2)cc1]

Phenyl bromide 12t was prepared according to the procedure for 12a using methyl 5-bromo-2-iodobenzoate (481 mg, 1.41 mmol), 4-phenylphenol (200 mg, 1.18 mmol), Cs$_2$CO$_3$ (766 mg, 2.35 mmol), (CuOTf)$_2$.PhH (44.4 mg, 0.0881 mmol), 1-naphthoic acid (304 mg, 1.76 mmol), and 4 Å molecular sieves (1.00 g) in anhydrous toluene (5 mL). Purification by flash column chromatography (hexanes to 95:5 hexanes/EtOAc) afforded 12t as a bright yellow solid (127 mg, 28% yield). R$_f$=0.23 (hexanes/EtOAc 95:5 v/v). $^1$H NMR (400 MHz, CDCl$_3$) δ 8.06 (d, J=2.5 Hz, 1H), 7.60-7.53 (m, 5H), 7.43 (t, J=7.6 Hz, 2H), 7.34 (t, J=7.3 Hz, 1H), 7.03 (d, J=8.6 Hz, 2H), 6.93 (d, J=8.8 Hz, 1H), 3.84 (s, 3H). $^{13}$C NMR (101 MHz, CDCl$_3$) δ 164.9, 156.8, 155.6, 140.5, 136.8, 136.5, 134.7, 129.0, 128.7, 127.3, 127.1, 124.9, 122.6, 118.7, 116.1, 52.6. MS (ESI$^+$) calculated for [C$_{20}$H$_{15}$BrNaO$_3$]$^+$ [M+Na]$^+$, 405.0; found 405.0.

Methyl 2-([1,1'-biphenyl]-3-yloxy)-5-bromobenzoate (12u)

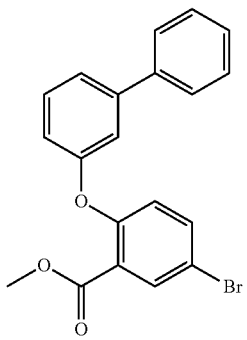 [SMILES: COC(=O)c1cc(Br)ccc1Oc1cccc(-c2ccccc2)c1]

Phenyl bromide 12u was prepared according to the procedure for 12a using methyl 5-bromo-2-iodobenzoate (481 mg, 1.41 mmol), 3-phenylphenol (200 mg, 1.18 mmol), Cs$_2$CO$_3$ (766 mg, 2.35 mmol), (CuOTf)$_2$·PhH (44.4 mg, 0.0881 mmol), 1-naphthoic acid (304 mg, 1.76 mmol), and 4 Å molecular sieves (1.00 g) in anhydrous toluene (5 mL). Purification by flash column chromatography (hexanes to 95:5 hexanes/EtOAc) afforded 12u as a pale yellow oil (161 mg, 36% yield). R$_f$=0.23 (hexanes/EtOAc 95:5 v/v). $^1$H NMR (400 MHz, CDCl$_3$) δ 8.05 (d, J=2.4 Hz, 1H), 7.59-7.52 (m, 3H), 7.47-7.39 (m, 3H), 7.39-7.32 (m, 2H), 7.21 (app t, J=1.7 Hz, 1H), 6.97-6.89 (m, 2H), 3.84 (s, 3H). $^{13}$C NMR (101 MHz, CDCl$_3$) δ 165.0, 157.6, 155.7, 143.4, 140.4, 136.5, 134.7, 130.3, 129.0, 128.7, 127.9, 127.2, 122.6, 122.4, 118.7, 117.3, 116.0, 52.6. MS (ESI$^+$) calculated for [C$_{20}$H$_{15}$BrNaO$_3$]$^+$ [M+Na]$^+$, 405.0; found 405.0.

Methyl 5-bromo-2-((3',5'-dimethyl-[1,1'-biphenyl]-3-yl)oxy)benzoate (12v)

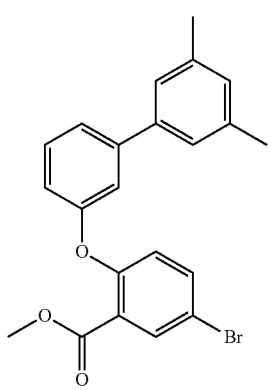

Phenyl bromide 12v was prepared according to the procedure for 12a using methyl 5-bromo-2-iodobenzoate (298 mg, 1.22 mmol), phenol 45v (202 mg, 1.02 mmol), Cs$_2$CO$_3$ (664 mg, 2.04 mmol), (CuOTf)$_2$·PhH (38.5 mg, 0.0764 mmol), 1-naphthoic acid (263 mg, 1.53 mmol), and 4 Å molecular sieves (1.00 g) in anhydrous toluene (6 mL). Purification by flash column chromatography (hexanes to 95:5 hexanes/EtOAc) afforded 12v as a clear oil (55.8 mg, 13% yield). R$_f$=0.50 (hexanes/EtOAc 95:5 v/v). $^1$H NMR (400 MHz, CDCl$_3$) δ 8.04 (d, J=2.4 Hz, 1H), 7.54 (dd, J=8.8, 2.5 Hz, 1H), 7.41-7.32 (m, 2H), 7.20 (app t, J=2.0 Hz, 1H), 7.17 (s, 2H), 7.00 (s, 1H), 6.94-6.91 (m, 1H), 6.89 (d, J=8.8 Hz, 1H), 3.85 (s, 3H), 2.37 (s, 6H). $^{13}$C NMR (101 MHz, CDCl$_3$) δ 165.1, 157.3, 155.9, 143.7, 140.4, 138.5, 136.5, 134.6, 130.2, 129.5, 125.1, 124.6, 122.8, 122.1, 117.6, 117.3, 115.7, 52.6, 21.5. MS (ESI$^+$) calculated for [C$_{22}$H$_{19}$BrNaO$_3$]$^+$ [M+Na]$^+$, 433.0; found 433.0.

Methyl 5-bromo-2-((4'-ethoxy-[1,1'-biphenyl]-3-yl)oxy)benzoate (12w)

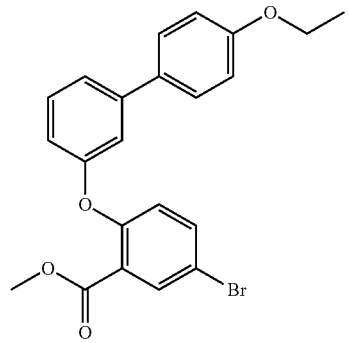 [SMILES: CCOc1ccc(-c2cccc(Oc3ccc(Br)cc3C(=O)OC)c2)cc1]

Phenyl bromide 12w was prepared according to the procedure for 12a using methyl 5-bromo-2-iodobenzoate (361 mg, 1.06 mmol), phenol 45w (189 mg, 0.883 mmol), Cs$_2$CO$_3$ (575 mg, 1.77 mmol), (CuOTf)$_2$·PhH (33.3 mg, 0.0662 mmol), 1-naphthoic acid (228 mg, 1.32 mmol), and 4 Å molecular sieves (1.00 g) in anhydrous toluene (5 mL). Purification by flash column chromatography (hexanes to 95:5 hexanes/EtOAc) afforded 12w as a yellow solid (85.5 mg, 23% yield). R$_f$=0.18 (hexanes/EtOAc 95:5 v/v). $^1$H NMR (400 MHz, CDCl$_3$) δ 8.04 (d, J=2.5 Hz, 1H), 7.54 (dd, J=8.8, 2.5 Hz, 1H), 7.47 (d, J=8.7 Hz, 2H), 7.37 (app t, J=7.8 Hz, 1H), 7.31 (d, J=7.8 Hz, 1H), 7.17 (app t, J=1.9 Hz, 1H), 6.94 (d, J=8.7 Hz, 2H), 6.92-6.86 (m, 2H), 4.07 (q, J=7.0 Hz, 2H), 3.84 (s, 3H), 1.43 (t, J=7.0 Hz, 3H). $^{13}$C NMR (151 MHz, CDCl$_3$) δ 165.0, 159.0, 157.5, 155.8, 143.0, 136.5, 134.6, 132.7, 130.2, 128.2, 124.6, 122.3, 122.2, 116.9, 116.8, 115.8, 114.9, 63.7, 52.6, 15.0. MS (ESI$^+$) calculated for [C$_{22}$H$_{20}$BrO$_4$]$^+$ [M+H]$^+$, 427.0; found 426.9.

Methyl 5-bromo-2-((4'-(3-morpholinopropoxy)-[1,1'-biphenyl]-3-yl)oxy)benzoate (12x)

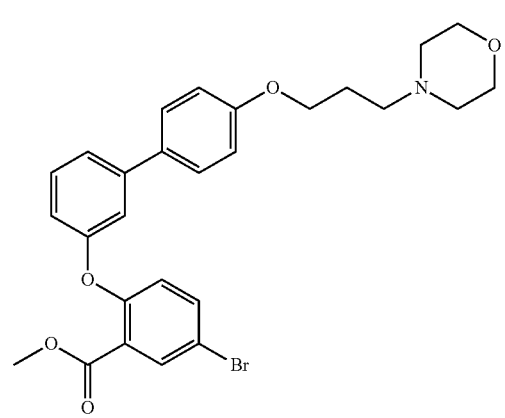 [SMILES: COC(=O)c1cc(Br)ccc1Oc1cccc(-c2ccc(OCCCN3CCOCC3)cc2)c1]

Phenyl bromide 12x was prepared according to the procedure for 12a using methyl 5-bromo-2-iodobenzoate (872 mg, 2.56 mmol), phenol 48 (668 mg, 2.13 mmol), Cs$_2$CO$_3$ (1.39 g, 4.26 mmol), (CuOTf)$_2$.PhH (80.5 mg, 0.180 mmol), 1-naphthoic acid (551 mg, 3.20 mmol), and 4 Å molecular sieves (1.00 g) in anhydrous toluene (7 mL). Purification by flash column chromatography (DCM to EtOAc with 2% MeOH throughout) afforded 12x as a brown solid (166 mg, 15% yield). R$_f$=0.42 (DCM/EtOAc/MeOH 47.5:47.5:5 v/v/v). $^1$H NMR (400 MHz, CDCl$_3$) δ 8.04 (d, J=2.5 Hz, 1H), 7.54 (dd, J=8.8, 2.5 Hz, 1H), 7.47 (d, J=8.7 Hz, 2H), 7.37 (app t, J=7.9 Hz, 1H), 7.30 (d, J=7.8 Hz, 1H), 7.16 (t, J=2.0 Hz, 1H), 6.95 (d, J=8.7 Hz, 2H), 6.92-6.86 (m, 2H), 4.06 (t, J=6.3 Hz, 2H), 3.84 (s, 3H), 3.74 (t, J=4.7 Hz, 4H), 2.57 (t, J=7.1 Hz, 2H), 2.54-2.47 (m, 4H), 2.01 (app quint, J=6.7 Hz, 2H). $^{13}$C NMR (101 MHz, CDCl$_3$) δ 165.0, 159.0, 157.5, 155.8, 143.0, 136.5, 134.6, 132.8, 130.3, 128.3, 124.7, 122.3, 122.2, 116.9, 116.8, 115.9, 115.0, 67.0, 66.3, 55.7, 53.8, 52.6, 26.5. MS (ESI$^+$) calculated for [C$_{27}$H$_{29}$BrNO$_5$]$^+$ [M+H]$^+$, 526.1; found 526.1.

Synthesis of 12k

Methyl 2-((adamantan-2-yl)oxy)-5-bromobenzoate (12k)

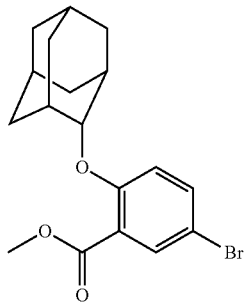 [SMILES: COC(=O)c1cc(Br)ccc1OC1C2CC3CC(C2)CC1C3]

To a solution of methyl 5-bromosalicylate (500 mg, 2.16 mmol) and triphenylphosphine (681 mg, 2.60 mmol) in anhydrous THF (10 mL) was added 2-adamantol (395 mg, 2.60 mmol). The solution was brought to reflux and diisopropyl azodicarboxylate (dissolved in 1.5 mL THF, 525 mg, 2.60 mmol) was added over 45 minutes. After 17 hours at reflux, the reaction mixture was concentrated under vacuum. The residue was dissolved in EtOAc (100 mL) and washed with brine (100 mL). The organic phase was dried over anhydrous Na$_2$SO$_4$ and concentrated under reduced pressure. Purification by flash column chromatography (hexanes to 95:5 hexanes/EtOAc) afforded 12k as a foggy white oil (613 mg, 78% yield). R$_f$=0.51 (hexanes/EtOAc 90:10 v/v). $^1$H NMR (400 MHz, CDCl$_3$) δ 7.89 (d, J=2.6 Hz, 1H), 7.47 (dd, J=8.9, 2.6 Hz, 1H), 6.84 (d, J=8.9 Hz, 1H), 4.48 (app t, J=3.1 Hz, 1H), 3.89 (s, 3H), 2.25-2.13 (m, 4H), 1.96-1.85 (m, 4H), 1.80-1.71 (m, 4H), 1.53 (d, J=12.1 Hz, 2H). $^{13}$C NMR (101 MHz, CDCl$_3$) δ 166.0, 156.3, 135.8, 134.5, 123.0, 116.4, 111.7, 80.8, 52.3, 37.5, 36.4, 31.5, 31.5, 27.4, 27.2. MS (ESI$^+$) calculated for [C$_{18}$H$_{21}$BrNaO$_3$]$^+$ [M+Na]$^+$, 387.0; found 387.1.

Synthesis of 13a-c, 14a, 14b, 15a-g, and 15i-15x

Methyl 4-(1H-pyrazol-4-yl)-[1,1'-biphenyl]-2-carboxylate (13a)

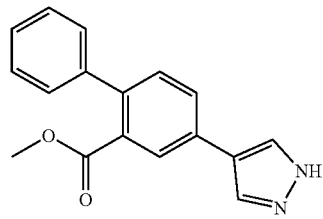 [SMILES: COC(=O)c1cc(-c2cn[nH]c2)ccc1-c1ccccc1]

To a microwave vial were added phenyl bromide 10a (75.3 mg, 0.259 mmol) and 4-pyrazoleboronic acid pincol ester (50.2 mg, 0.259 mmol). The starting materials were fully dissolved in dioxane (2.5 mL) and water (1 mL) before the addition of Cs$_2$CO$_3$ (253 mg, 0.776 mmol) and Pd(dppf)Cl$_2$.DCM (21.1 mg, 0.0259 mmol). The mixture was degassed with N$_2$ for 7 minutes and heated with microwave irradiation at 100° C. for 3 hours. The reaction mixture was diluted with EtOAc (100 mL) and washed with brine (100 mL). The organic phase was dried over anhydrous Na$_2$SO$_4$ and concentrated under reduced pressure. Purification by flash column chromatography (DCM to EtOAc) afforded 13a as a white solid (18.8 mg. 26% yield). R$_f$=0.38 (DCM/EtOAc 50:50 v/v). $^1$H NMR (400 MHz, DMSO-d$_6$) δ 13.06 (br s, 1H), 8.35 (s, 1H), 8.03 (s, 1H), 7.92 (s, 1H), 7.85 (d, J=8.0 Hz, 1H), 7.46-7.33 (m, 4H), 7.30 (d, J=7.5 Hz, 2H), 3.60 (s, 3H). $^{13}$C NMR (101 MHz, DMSO-d$_6$) δ 168.9, 140.2, 138.1, 132.3, 131.7, 130.9, 128.3, 128.0, 127.8, 127.3, 126.1, 125.4, 119.9, 52.0. MS (ESI$^+$) calculated for [C$_{17}$H$_{18}$N$_2$O$_2$]$^+$ [M+H]$^+$, 279.1; found 279.1.

Methyl 2-(naphthalen-1-yl)-5-(1H-pyrazol-4-yl)benzoate (13b)

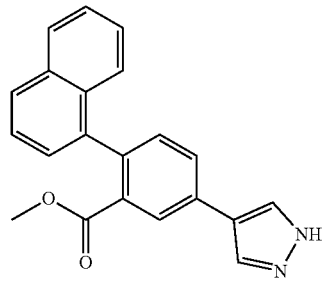

Methyl ester 13b was prepared according to the procedure for 13a using phenyl bromide 10b (100 mg, 0.293 mmol), 4-pyrazoleboronic acid pincol ester (56.9 mg, 0.293 mmol), Cs$_2$CO$_3$ (287 mg, 0.879 mmol), and Pd(dppf)Cl$_2$.DCM (23.9 mg, 0.0293 mmol) in dioxane (2.5 mL) and water (1 mL). Purification by flash column chromatography (DCM to EtOAc) afforded 13b as a white solid (23.5 mg, 24% yield). R$_f$=0.40 (DCM/EtOAc 50:50 v/v). $^1$H NMR (400 MHz, DMSO-d$_6$) δ 13.09 (br s, 1H), 8.39 (s, 1H), 8.12 (s, 1H), 8.07 (s, 1H), 7.98 (d, J=8.1 Hz, 1H), 7.93 (d, J=8.0 Hz, 2H), 7.58-7.38 (m, 5H), 7.32 (d, J=6.9 Hz, 1H), 3.33 (s, 3H). $^{13}$C NMR (101 MHz, DMSO-d$_6$) δ 167.4, 138.8, 137.4, 136.5, 133.0, 132.7, 132.2, 132.1, 131.5, 128.2, 127.4, 127.4, 126.1, 126.1, 125.7, 125.7, 125.3, 125.0, 120.0, 51.7. MS (ESI⁺) calculated for [C$_{21}$H$_{17}$N$_2$O$_2$]⁺ [M+H]⁺, 329.1; found 329.1.

Methyl 2-(naphthalen-2-yl)-5-(1H-pyrazol-4-yl)benzoate (13c)

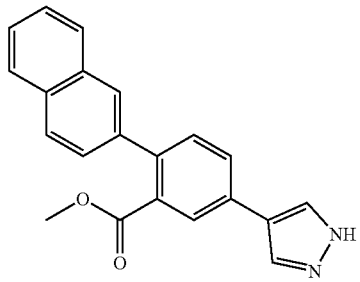 [SMILES: COC(=O)c1cc(-c2cn[nH]c2)ccc1-c1ccc2ccccc2c1]

Methyl ester 13c was prepared according to the procedure for 13a using phenyl bromide 10c (100 mg, 0.293 mmol), 4-pyrazoleboronic acid pincol ester (56.9 mg, 0.293 mmol), Cs$_2$CO$_3$ (287 mg, 0.879 mmol), and Pd(dppf)Cl$_2$.DCM (23.9 mg, 0.0293 mmol) in dioxane (2.5 mL) and water (1 mL). Purification by flash column chromatography (DCM to EtOAc) afforded 13c as a yellow solid (24.3 mg, 25% yield). R$_f$=0.41 (DCM/EtOAc 50:50 v/v). ¹H NMR (400 MHz, DMSO-d$_6$) δ 13.08 (br s, 1H), 8.38 (s, 1H), 8.06 (s, 1H), 8.02-7.85 (m, 6H), 7.59-7.51 (m, 3H), 7.43 (d, J=9.3 Hz, 1H), 3.59 (s, 3H). ¹³C NMR (101 MHz, DMSO-d$_6$) δ 168.8, 138.2, 137.9, 136.5, 133.0, 132.4, 132.0, 131.7, 131.3, 128.1, 127.9, 127.6, 127.5, 126.8, 126.5, 126.4, 126.2, 125.6, 119.9, 52.1. MS (ESI⁺) calculated for [C$_{21}$H$_{17}$N$_2$O$_2$]⁺ [M+H]⁺, 329.1; found 329.2.

Methyl 2-(phenylamino)-5-(1H-pyrazol-4-yl)benzoate (14a)

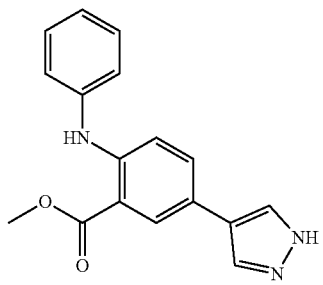 [SMILES: COC(=O)c1cc(-c2cn[nH]c2)ccc1Nc1ccccc1]

Methyl ester 14a was prepared according to the procedure for 13a using phenyl bromide 11a (139 mg, 0.454 mmol), 4-pyrazoleboronic acid pincol ester (88.1 mg, 0.454 mmol), Cs$_2$CO$_3$ (444 mg, 1.36 mmol), and Pd(dppf)Cl$_2$.DCM (37.1 mg, 0.0454 mmol) in dioxane (2.5 mL) and water (1 mL). Purification by flash column chromatography (DCM to EtOAc) afforded 14a as a yellow oil (28.0 mg, 21% yield). R$_f$=0.40 (DCM/EtOAc 50:50 v/v). ¹H NMR (400 MHz, CDCl$_3$) δ 9.44 (br s, 1H), 8.11 (s, 1H), 7.83 (s, 2H), 7.64 (s, 1H), 7.46 (d, J=8.7 Hz, 1H), 7.35 (t, J=7.6 Hz, 2H), 7.30 (d, J=8.8 Hz, 1H), 7.24 (s, 1H), 7.09 (t, J=7.3 Hz, 1H), 3.93 (s, 3H). ¹³C NMR (101 MHz, CDCl$_3$) δ 168.9, 146.6, 140.9, 131.9, 130.7, 129.6, 129.5, 128.6, 123.6, 122.4, 121.8, 114.9, 112.4, 52.0. MS (ESI⁺) calculated for [C$_{17}$H$_{16}$N$_3$O$_2$]⁺ [M+H]⁺, 294.1; found 294.1.

Methyl 2-(methyl(naphthalen-2-yl)amino)-5-(1H-pyrazol-4-yl)benzoate (14b)

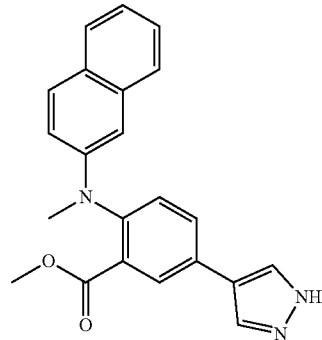 [SMILES: COC(=O)c1cc(-c2cn[nH]c2)ccc1N(C)c1ccc2ccccc2c1]

Methyl ester 14b was prepared according to the procedure for 13a using phenyl bromide 11b (47.6 mg, 0.129 mmol), 4-pyrazoleboronic acid pincol ester (24.9 mg, 0.129 mmol), Cs$_2$CO$_3$ (126 mg, 0.387 mmol), and Pd(dppf)Cl$_2$.DCM (10.5 mg, 0.0129 mmol) in dioxane (2.5 mL) and water (1 mL). Purification by flash column chromatography (DCM to EtOAc with 2% MeOH throughout) afforded 14b as a yellow oil (20.0 mg, 44% yield). R$_f$=0.56 (DCM/EtOAc/MeOH 47.5:47.5:5 v/v/v). ¹H NMR (400 MHz, CDCl$_3$) δ 7.98 (s, 1H), 7.92 (s, 2H), 7.71-7.62 (m, 3H), 7.57 (d, J=9.0 Hz, 1H), 7.40-7.30 (m, 2H), 7.22 (app t, J=7.3 Hz, 1H), 7.01 (s, 1H), 6.88 (d, J=9.0 Hz, 1H), 3.57 (s, 3H), 3.40 (s, 3H). ¹³C NMR (101 MHz, CDCl$_3$) δ 167.5, 147.0, 146.4, 134.9, 131.5, 130.5, 129.9, 129.8, 128.7, 128.6, 128.6, 127.7, 127.6, 126.5, 126.4, 126.4, 122.7, 117.8, 108.1, 52.4, 40.8. MS (ESI⁺) calculated for [C$_{22}$H$_{20}$N$_3$O$_2$]⁺ [M+H]⁺, 358.2; found 358.2.

Methyl 2-phenoxy-5-(1H-pyrazol-4-yl)benzoate (15a)

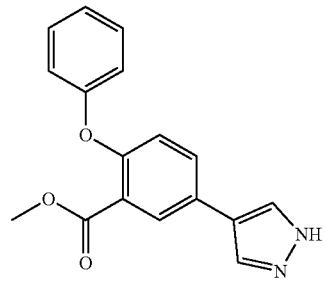 [SMILES: COC(=O)c1cc(-c2cn[nH]c2)ccc1Oc1ccccc1]

Methyl ester 15a was prepared according to the procedure for 13a using phenyl bromide 12a (105 mg, 0.307 mmol), 4-pyrazoleboronic acid pincol ester (59.5 mg, 0.307 mmol), Cs$_2$CO$_3$ (300 mg, 0.921 mmol), and Pd(dppf)Cl$_2$.DCM (25.1 mg, 0.0307 mmol) in dioxane (2.5 mL) and water (1 mL). Purification by flash column chromatography (DCM to EtOAc) afforded 15a as a brown solid (26.0 mg, 26% yield). R$_f$=0.30 (DCM/EtOAc 50:50 v/v). ¹H NMR (400 MHz, DMSO-d$_6$) δ 13.01 (br s, 1H), 8.11 (s, 2H), 8.00 (d, J=2.0

Hz, 1H), 7.82 (dd, J=8.5, 2.0 Hz, 1H), 7.36 (t, J=7.8 Hz, 2H), 7.15-7.03 (m, 2H), 6.98-6.90 (m, 2H), 3.72 (s, 3H). $^{13}$C NMR (101 MHz, DMSO-d$_6$) δ 165.5, 157.6, 152.6, 130.4, 129.9, 129.3, 127.3, 123.8, 122.9, 121.9, 119.7, 117.9, 117.3, 52.1. MS (ESI$^+$) calculated for [C$_{17}$H$_{15}$N$_2$O$_3$]$^+$ [M+H]$^+$, 295.1; found 295.1.

Methyl 5-(1H-pyrazol-4-yl)-2-(o-tolyloxy)benzoate (15b)

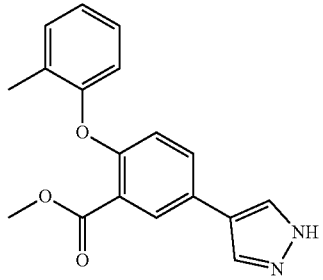 [SMILES: COC(=O)c1cc(-c2cn[nH]c2)ccc1Oc1ccccc1C]

Methyl ester 15b was prepared according to the procedure for 13a using phenyl bromide 12b (116 mg, 0.360 mmol), 4-pyrazoleboronic acid pincol ester (69.9 mg, 0.360 mmol), Cs$_2$CO$_3$ (352 mg, 1.08 mmol), and Pd(dppf)Cl$_2$.DCM (29.4 mg, 0.0360 mmol) in dioxane (2.5 mL) and water (1 mL). Purification by flash column chromatography (DCM to EtOAc with 2% MeOH throughout) afforded 15b as a brown wax (24.5 mg, 22% yield). R$_f$=0.41 (DCM/EtOAc/MeOH 47.5:47.5:5 v/v/v). $^1$H NMR (600 MHz, DMSO-d$_6$) δ 13.01 (br s, 1H), 8.08 (s, 2H), 7.99 (app t, J=1.2 Hz, 1H), 7.79-7.75 (m, 1H), 7.30 (d, J=7.2 Hz, 1H), 7.16 (app t, J=7.6 Hz, 1H), 7.05 (app t, J=7.2 Hz, 1H), 6.86 (d, J=8.7 Hz, 1H), 6.74 (d, J=7.9 Hz, 1H), 3.74 (s, 3H), 2.22 (s, 3H). $^{13}$C NMR (151 MHz, DMSO-d$_6$) δ 165.7, 154.8, 153.3, 131.4, 130.3, 128.4, 128.2, 127.4, 127.3, 123.6, 123.5, 122.7, 119.8, 119.7, 117.4, 52.1, 15.8. MS (ESI$^+$) calculated for [C$_{18}$H$_{17}$N$_2$O$_3$]$^+$ [M+H]$^+$, 309.1; found 309.2.

Methyl 5-(1H-pyrazol-4-yl)-2-(m-tolyloxy)benzoate (15c)

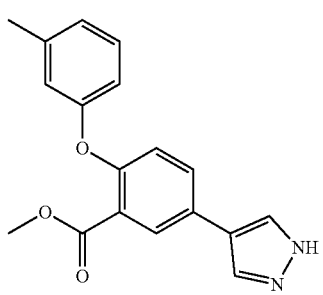 [SMILES: COC(=O)c1cc(-c2cn[nH]c2)ccc1Oc1cccc(C)c1]

Methyl ester 15c was prepared according to the procedure for 13a using phenyl bromide 12c (103 mg, 0.321 mmol), 4-pyrazoleboronic acid pincol ester (62.2 mg, 0.321 mmol), Cs$_2$CO$_3$ (314 mg, 0.962 mmol), and Pd(dppf)Cl$_2$.DCM (26.2 mg, 0.0321 mmol) in dioxane (2.5 mL) and water (1 mL). Purification by flash column chromatography (DCM to EtOAc with 2% MeOH throughout) afforded 15c as a brownish-orange wax (25.2 mg, 25% yield). R$_f$=0.45 (DCM/EtOAc/MeOH 47.5:47.5:5 v/v/v). $^1$H NMR (400 MHz, DMSO-d$_6$) δ 13.02 (br s, 1H), 8.10 (s, 2H), 7.99 (d, J=2.1 Hz, 1H), 7.81 (dd, J=8.6, 2.1 Hz, 1H), 7.23 (app t, J=7.8 Hz, 1H), 7.03 (d, J=8.5 Hz, 1H), 6.91 (d, J=7.5 Hz, 1H), 6.76 (s, 1H), 6.72 (d, J=8.2 Hz, 1H), 3.73 (s, 3H), 2.27 (s, 3H). $^{13}$C NMR (151 MHz, DMSO-d$_6$) δ 165.5, 157.5, 152.7, 139.6, 130.3, 129.6, 129.1, 127.2, 123.8, 123.7, 121.7, 119.7, 118.5, 117.9, 114.5, 52.1, 21.0. MS (ESI$^+$) calculated for [C$_{18}$H$_{17}$N$_2$O$_3$]$^+$ [M+H]$^+$, 309.1; found 309.2.

Methyl 5-(1H-pyrazol-4-yl)-2-(p-tolyloxy)benzoate (15d)

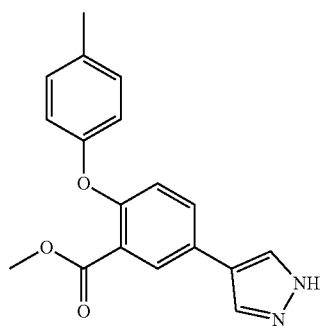 [SMILES: COC(=O)c1cc(-c2cn[nH]c2)ccc1Oc1ccc(C)cc1]

Methyl ester 15d was prepared according to the procedure for 13a using phenyl bromide 12d (103 mg, 0.321 mmol), 4-pyrazoleboronic acid pincol ester (62.2 mg, 0.321 mmol), Cs$_2$CO$_3$ (314 mg, 0.962 mmol), and Pd(dppf)Cl$_2$.DCM (26.2 mg, 0.0321 mmol) in dioxane (2.5 mL) and water (1 mL). Purification by flash column chromatography (DCM to EtOAc with 2% MeOH throughout) afforded 15d as an orange wax (21.1 mg, 21% yield). R$_f$=0.38 (DCM/EtOAc/MeOH 47.5:47.5:5 v/v/v). $^1$H NMR (400 MHz, DMSO-d$_6$) δ 13.01 (br s, 1H), 8.09 (s, 2H), 7.98 (d, J=2.1 Hz, 1H), 7.79 (dd, J=8.5, 2.2 Hz, 1H), 7.16 (d, J=8.1 Hz, 2H), 6.99 (d, J=8.5 Hz, 1H), 6.84 (d, J=8.5 Hz, 2H), 3.73 (s, 3H), 2.27 (s, 3H). $^{13}$C NMR (101 MHz, DMSO-d$_6$) δ 165.6, 155.2, 153.1, 132.0, 130.3, 130.2, 128.8, 127.2, 123.5, 121.1, 119.7, 118.2, 117.6, 52.1, 20.2. MS (ESI$^+$) calculated for [C$_{18}$H$_{17}$N$_2$O$_3$]$^+$ [M+H]$^+$, 309.1; found 309.2.

Methyl 2-(3-fluorophenoxy)-5-(1H-pyrazol-4-yl)benzoate (15e)

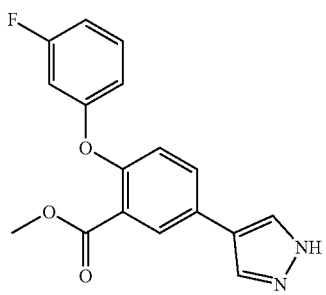 [SMILES: COC(=O)c1cc(-c2cn[nH]c2)ccc1Oc1cccc(F)c1]

Methyl ester 15e was prepared according to the procedure for 13a using phenyl bromide 12e (82.9 mg, 0.259 mmol), 4-pyrazoleboronic acid pincol ester (50.3 mg, 0.259 mmol), Cs$_2$CO$_3$ (253 mg, 0.777 mmol), and Pd(dppf)Cl$_2$.DCM (21.2 mg, 0.0259 mmol) in dioxane (2.5 mL) and water (1 mL). Purification by flash column chromatography (DCM to EtOAc with 2% MeOH throughout) afforded 15e as an off-white solid (14.9 mg, 18% yield). $R_f$=0.42 (DCM/EtOAc/MeOH 47.5:47.5:5 v/v/v). $^1$H NMR (400 MHz, DMSO-$d_6$) δ 13.02 (br s, 1H), 8.29 (s, 1H), 8.04 (s, 1H), 7.97 (s, 1H), 7.87 (d, J=6.4 Hz, 1H), 7.37 (app q, J=7.4 Hz, 1H), 7.17 (d, J=8.4 Hz, 1H), 6.92 (app t, J=9.3 Hz, 1H), 6.77 (d, J=10.6 Hz, 1H), 6.72 (d, J=7.3 Hz, 1H), 3.71 (s, 3H). $^{13}$C NMR (101 MHz, DMSO-$d_6$) δ 165.2, 162.8 (d, J=244.1 Hz), 159.3 (d, J=11.3 Hz), 151.6, 131.1 (d, J=10.0 Hz), 130.6, 130.1, 127.4, 124.0, 122.7, 119.6, 112.7 (d, J=2.9 Hz), 109.5, 109.3 (d, J=21.1 Hz), 104.5 (d, J=24.9 Hz), 52.2. MS (ESI$^+$) calculated for [$C_{17}H_{17}N_2O_3$]$^+$ [M+H]$^+$, 313.1; found 313.2.

Methyl 2-(4-fluorophenoxy)-5-(1H-pyrazol-4-yl)benzoate (15f)

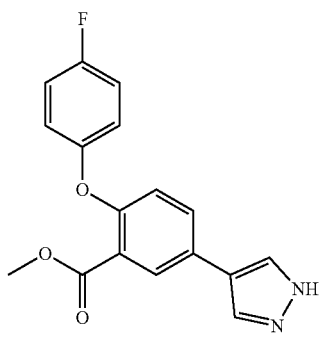 [SMILES: COC(=O)c1cc(-c2cn[nH]c2)ccc1Oc1ccc(F)cc1]

Methyl ester 15f was prepared according to the procedure for 13a using phenyl bromide 12f (105 mg, 0.321 mmol), 4-pyrazoleboronic acid pincol ester (62.4 mg, 0.321 mmol), $Cs_2CO_3$ (314 mg, 0.964 mmol), and Pd(dppf)$Cl_2$.DCM (26.2 mg, 0.0321 mmol) in dioxane (2.5 mL) and water (1 mL). Purification by flash column chromatography (DCM to EtOAc with 2% MeOH throughout) afforded 15f as a yellow oil (20.5 mg, 20% yield). $R_f$=0.40 (DCM/EtOAc/MeOH 47.5:47.5:5 v/v/v). $^1$H NMR (400 MHz, DMSO-$d_6$) δ 13.00 (br s, 1H), 8.12 (s, 2H), 8.00 (d, J=2.1 Hz, 1H), 7.82 (dd, J=8.5, 2.1 Hz, 1H), 7.19 (t, J=8.7 Hz, 2H), 7.04 (d, J=8.5 Hz, 1H), 7.01-6.94 (m, 2H), 3.74 (s, 3H). $^{13}$C NMR (151 MHz, DMSO-$d_6$) δ 165.5, 157.8 (d, J=238.7 Hz), 153.7 (d, J=1.8 Hz), 152.9, 136.1, 130.4, 129.2, 127.3, 123.6, 121.4, 119.6, 119.2 (d, J=8.4 Hz), 116.4 (d, J=23.4 Hz), 52.2. MS (ESI$^+$) calculated for [$C_{17}H_{14}FN_2O_3$]$^+$ [M+H]$^+$, 313.1; found 313.2.

Methyl 2-(naphthalen-2-yloxy)-5-(1H-pyrazol-4-yl)benzoate (15g)

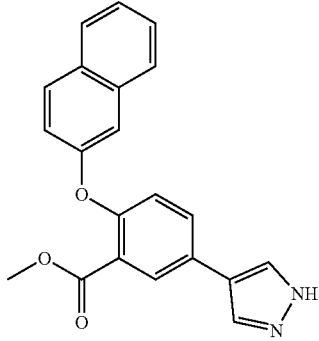 [SMILES: COC(=O)c1cc(-c2cn[nH]c2)ccc1Oc1ccc2ccccc2c1]

Methyl ester 15g was prepared according to the procedure for 13a using phenyl bromide 12g (78.3 mg, 0.219 mmol), 4-pyrazoleboronic acid pincol ester (42.5 mg, 0.219 mmol), $Cs_2CO_3$ (214 mg, 0.658 mmol), and Pd(dppf)$Cl_2$.DCM (17.9 mg, 0.0219 mmol) in dioxane (2.5 mL) and water (1 mL). Purification by flash column chromatography (DCM to EtOAc) afforded 15g as a clear oil (9.9 mg, 13% yield). $R_f$=0.35 (DCM/EtOAc 50:50 v/v). $^1$H NMR (600 MHz, CDCl$_3$) δ 8.11 (d, J=2.1 Hz, 1H), 7.91 (s, 2H), 7.84 (d, J=8.9 Hz, 1H), 7.82 (d, J=8.1 Hz, 1H), 7.67 (d, J=8.2 Hz, 1H), 7.63 (dd, J=8.5, 2.1 Hz, 1H), 7.44 (app t, J=7.4 Hz, 1H), 7.39 (app t, J=7.4 Hz, 1H), 7.29 (dd, J=8.9, 2.3 Hz, 1H), 7.21 (d, J=2.1 Hz, 1H), 7.09 (d, J=8.4 Hz, 1H), 3.81 (s, 3H). $^{13}$C NMR (151 MHz, CDCl$_3$) δ 166.3, 155.9, 154.6, 134.4, 131.4, 131.0, 130.1, 130.1, 129.2, 128.7, 127.9, 127.2, 126.7, 124.8, 123.8, 122.2, 121.4, 119.5, 112.9, 52.5. MS (ESI$^+$) calculated for [$C_{21}H_{17}N_2O_3$]$^+$ [M+H]$^+$, 345.1; found 345.1.

Methyl 2-(phenanthren-9-yloxy)-5-(1H-pyrazol-4-yl)benzoate (15j)

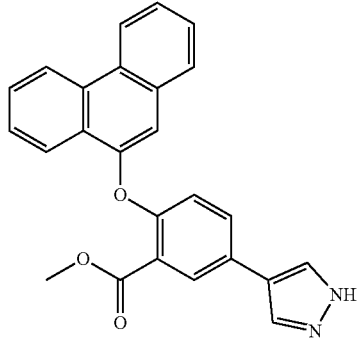 [SMILES: COC(=O)c1cc(-c2cn[nH]c2)ccc1Oc1cc2ccccc2c2ccccc12]

Methyl ester 15j was prepared according to the procedure for 13a using phenyl bromide 12j (50.0 mg, 0.123 mmol), 4-pyrazoleboronic acid pincol ester (23.8 mg, 0.123 mmol), $Cs_2CO_3$ (120 mg, 0.368 mmol), and Pd(dppf)$Cl_2$.DCM (10.0 mg, 0.0123 mmol) in dioxane (2.5 mL) and water (1 mL). Purification by flash column chromatography (DCM to EtOAc with 2% MeOH throughout) afforded 15j as a white solid (9.1 mg, 19% yield). $R_f$=0.50 (DCM/EtOAc/MeOH 47.5:47.5:5 v/v/v). $^1$H NMR (600 MHz, DMSO-$d_6$) δ 13.04 (br s, 1H), 8.90 (d, J=8.3 Hz, 1H), 8.79 (d, J=8.1 Hz, 1H), 8.36 (d, J=8.1 Hz, 1H), 8.31 (s, 1H), 8.13 (s, 1H), 8.01 (s, 1H), 7.89 (d, J=8.4 Hz, 1H), 7.83-7.78 (m, 2H), 7.75 (app t, J=7.5 Hz, 1H), 7.59 (app t, J=7.4 Hz, 1H), 7.55 (app t, J=7.5 Hz, 1H), 7.24 (d, J=8.5 Hz, 1H), 7.01 (s, 1H), 3.59 (s, 3H). $^{13}$C NMR (151 MHz, DMSO-$d_6$) δ 165.4, 152.5, 151.9, 131.8, 131.2, 130.6, 129.7, 128.8, 127.8, 127.8, 127.6, 127.2, 127.1, 126.9, 125.7, 125.5, 123.6, 123.2, 122.9, 122.3, 122.2, 119.7, 108.7, 52.1. MS (ESI$^+$) calculated for $[C_{25}H_{19}N_2O_3]^+$ [M+H]$^+$, 395.1; found 395.2.

Methyl 2-((adamantan-2-yl)oxy)-5-(1H-pyrazol-4-yl)benzoate (15k)

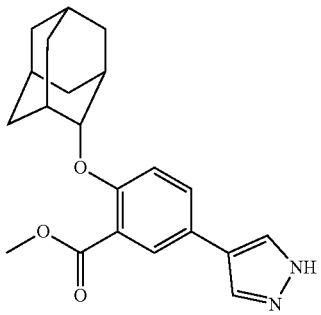 [SMILES: COC(=O)c1cc(-c2cn[nH]c2)ccc1OC1C2CC3CC(C2)CC1C3]

Methyl ester 15k was prepared according to the procedure for 13a using phenyl bromide 12k (124 mg, 0.340 mmol), 4-pyrazoleboronic acid pincol ester (66.0 mg, 0.340 mmol), Cs$_2$CO$_3$ (332 mg, 1.02 mmol), and Pd(dppf)Cl$_2$.DCM (27.8 mg, 0.0340 mmol) in dioxane (2.5 mL) and water (1 mL). Purification by flash column chromatography (DCM to EtOAc with 2% MeOH throughout) afforded 15k as a clear oil (29.4 mg, 25% yield). $R_f$=0.42 (DCM/EtOAc/MeOH 47.5:47.5:5 v/v/v). $^1$H NMR (600 MHz, DMSO-$d_6$) δ 12.90 (br s, 1H), 8.13 (s, 1H), 7.89 (s, 1H), 7.80 (d, J=2.2 Hz, 1H), 7.67 (dd, J=8.6, 2.2 Hz, 1H), 7.15 (d, J=8.8 Hz, 1H), 4.63 (app t, J=3.2 Hz, 1H), 3.81 (s, 3H), 2.13 (d, J=12.1 Hz, 2H), 2.07 (s, 2H), 1.87-1.76 (m, 6H), 1.70 (s, 2H), 1.46 (d, J=11.9 Hz, 2H). $^{13}$C NMR (151 MHz, DMSO-$d_6$) δ 166.8, 153.9, 135.8, 129.6, 127.0, 125.0, 121.8, 120.1, 115.4, 78.8, 51.8, 36.9, 35.5, 30.8, 30.8, 26.8, 26.6. MS (ESI$^+$) calculated for $[C_{21}H_{25}N_2O_3]^+$ [M+H]$^+$, 353.2; found 353.3.

Methyl 2-((1,2-dihydroacenaphthylen-4-yl)oxy)-5-(1H-pyrazol-4-yl)benzoate (15l)

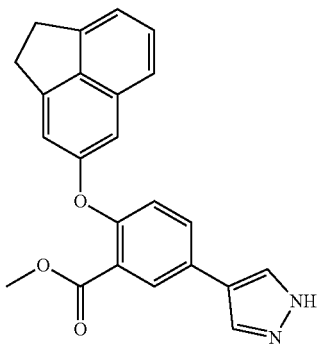 [SMILES: COC(=O)c1cc(-c2cn[nH]c2)ccc1Oc1cc2c3c(cccc3c1)CC2]

Methyl ester 15l was prepared according to the procedure for 13a using phenyl bromide 12l (10.6 mg, 0.0277 mmol), 4-pyrazoleboronic acid pincol ester (5.4 mg, 0.028 mmol), Cs$_2$CO$_3$ (27.0 mg, 0.0830 mmol), and Pd(dppf)Cl$_2$DCM (2.3 mg, 0.0028 mmol) in dioxane (1.25 mL) and water (0.5 mL). Purification by flash column chromatography (DCM to EtOAc with 2% MeOH throughout) afforded 15l as a white solid (2.7 mg, 26% yield). $R_f$=0.58 (DCM/EtOAc/MeOH 47.5:47.5:5 v/v/v). $^1$H NMR (600 MHz, DMSO-$d_6$) δ 12.99 (br s, 1H), 8.26 (s, 1H), 8.04 (d, J=1.4 Hz, 1H), 7.98 (s, 1H), 7.84 (d, J=8.5 Hz, 1H), 7.48 (d, J=8.1 Hz, 1H), 7.41 (app t, J=7.5 Hz, 1H), 7.22 (d, J=6.8 Hz, 1H), 7.12 (d, J=8.5 Hz, 1H), 7.05 (s, 1H), 6.94 (s, 1H), 3.72 (s, 3H), 3.37-3.34 (m, 4H). $^{13}$C NMR (151 MHz, DMSO-$d_6$) δ 165.5, 158.2, 152.9, 148.3, 145.5, 135.4, 131.3, 130.5, 129.3, 128.8, 127.3, 125.8, 123.9, 122.1, 121.5, 119.7, 118.1, 112.7, 107.3, 52.2, 30.2, 29.7. MS (ESI$^+$) calculated for $[C_{23}H_{19}N_2O_3]^+$ [M+H]$^+$, 371.1; found 371.1.

Methyl 5-(3-fluoro-1H-pyrazol-4-yl)-2-(naphthalen-1-yloxy)benzoate (15m)

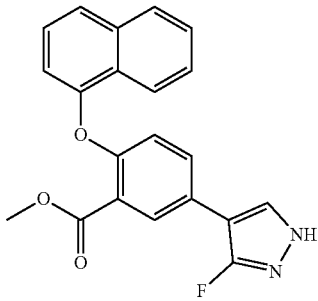 [SMILES: COC(=O)c1cc(-c2c[nH]nc2F)ccc1Oc1cccc2ccccc12]

Methyl ester 15m was prepared according to the procedure for 13a using phenyl bromide 12m (60.5 mg, 0.169 mmol), fluorinated pyrazole 16 (35.9 mg, 0.169 mmol), Cs$_2$CO$_3$ (166 mg, 0.508 mmol), and Pd(dppf)Cl$_2$.DCM (13.8 mg, 0.0169 mmol) in dioxane (2.5 mL) and water (1 mL). Purification by flash column chromatography (DCM to 30:70 DCM/EtOAc) afforded 15m as a light brown oil (15.6 mg, 24% yield). $R_f$=0.70 (DCM/EtOAc 50:50 v/v). $^1$H NMR (400 MHz, DMSO-$d_6$) δ 12.69 (br s, 1H), 8.26 (app t, J=1.9 Hz, 2H), 8.20-8.14 (m, 1H), 8.06 (d, J=2.3 Hz, 1H), 8.01-7.96 (m, 1H), 7.76 (dd, J=8.5, 2.3 Hz, 1H), 7.70 (d, J=8.3 Hz, 1H), 7.62-7.55 (m, 2H), 7.43 (app t, J=7.9 Hz, 1H), 7.08 (d, J=8.6 Hz, 1H), 6.84 (d, J=7.3 Hz, 1H), 3.65 (s, 3H). $^{13}$C NMR (101 MHz, DMSO-$d_6$) δ 165.3, 160.5 (d, J=240.5 Hz), 153.6, 152.8, 134.5, 130.9, 130.9 (d, J=5.3 Hz), 128.9, 128.0 (d, J=3.7 Hz), 127.8, 126.8, 126.4 (d, J=4.8 Hz), 126.2, 126.0, 125.5, 123.1, 121.5, 121.2, 111.9, 102.0 (d, J=17.9 Hz), 52.2. $^{19}$F NMR (376 MHz, DMSO-$d_6$) δ -135.4. MS (ESI$^+$) calculated for $[C_{21}H_{16}FN_2O_3]^+$ [M+H]$^+$, 363.1; found 363.1.

Methyl 5-(3-fluoro-1H-pyrazol-4-yl)-2-(naphthalen-2-yloxy)benzoate (15n)

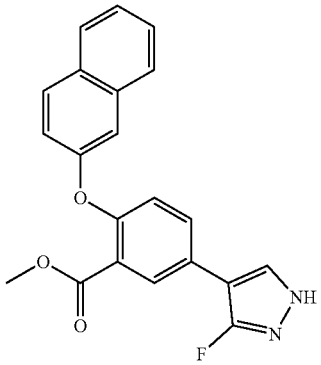 [SMILES: COC(=O)c1cc(-c2c[nH]nc2F)ccc1Oc1ccc2ccccc2c1]

Methyl ester 15n was prepared according to the procedure for 13a using phenyl bromide 12g (77.0 mg, 0.216 mmol), fluorinated pyrazole 16 (45.7 mg, 0.216 mmol), Cs$_2$CO$_3$ (211 mg, 0.647 mmol), and Pd(dppf)Cl$_2$.DCM (17.6 mg, 0.0216 mmol) in dioxane (2.5 mL) and water (1 mL). Purification by flash column chromatography (DCM to EtOAc with 2% MeOH throughout) afforded 15n as a white solid (10.5 mg, 13% yield). R$_f$=0.26 (DCM/EtOAc/MeOH 47.5:47.5:5 v/v/v). $^1$H NMR (400 MHz, CDCl$_3$) δ 9.76 (br s, 1H), 8.11 (d, J=2.3 Hz, 1H), 7.83 (app t, J=9.2 Hz, 2H), 7.71 (d, J=2.1 Hz, 1H), 7.70-7.65 (m, 2H), 7.48-7.43 (m, 1H), 7.43-7.37 (m, 1H), 7.28 (dd, J=8.9, 2.4 Hz, 1H), 7.23 (d, J=2.2 Hz, 1H), 7.09 (d, J=8.6 Hz, 1H), 3.82 (s, 3H). $^{13}$C NMR (126 MHz, CDCl$_3$) δ 166.2, 161.6 (d, J=246.2 Hz), 155.6, 154.9, 134.4, 131.3 (d, J=3.7 Hz), 130.3, 130.1, 129.5 (d, J=2.9 Hz), 127.9, 127.5, 127.3, 126.7, 125.9 (d, J=4.6 Hz), 124.9, 123.8, 122.0, 119.5, 113.2, 104.9 (d, J=17.7 Hz), 52.5. $^{19}$F NMR (376 MHz, CDCl$_3$) δ -132.8. MS (ESI$^+$) calculated for [C$_{21}$H$_{16}$FN$_2$O$_3$]$^+$ [M+H]$^+$, 363.1; found 363.1.

Methyl 2-((4-ethylnaphthalen-2-yl)oxy)-5-(3-fluoro-1H-pyrazol-4-yl)benzoate (15o)

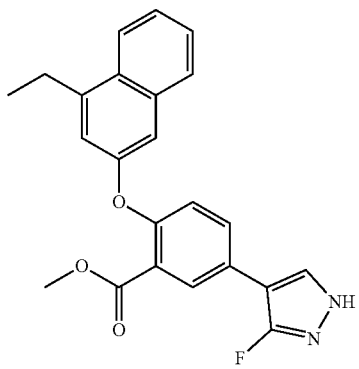 [SMILES: CCc1cc(Oc2ccc(-c3c[nH]nc3F)cc2C(=O)OC)cc2ccccc12]

Methyl ester 15o was prepared according to the procedure for 13a using phenyl bromide 12o (90.0 mg, 0.234 mmol), fluorinated pyrazole 16 (49.5 mg, 0.234 mmol), Cs$_2$CO$_3$ (228 mg, 0.701 mmol), and Pd(dppf)Cl$_2$.DCM (19.1 mg, 0.0234 mmol) in dioxane (2.5 mL) and water (1 mL). Purification by flash column chromatography (DCM to EtOAc with 2% MeOH throughout) afforded 15o as a clear oil (8.4 mg, 9% yield). R$_f$=0.73 (DCM/EtOAc/MeOH 47.5:47.5:5 v/v/v). $^1$H NMR (400 MHz, DMSO-d$_6$) δ 12.69 (br s, 1H), 8.27 (s, 1H), 8.08-8.00 (m, 2H), 7.84-7.76 (m, 2H), 7.49-7.42 (m, 2H), 7.23-7.15 (m, 2H), 7.07 (d, J=2.1 Hz, 1H), 3.71 (s, 3H), 3.08 (q, J=7.4 Hz, 2H), 1.31 (t, J=7.5 Hz, 3H). $^{13}$C NMR (151 MHz, DMSO-d$_6$) δ 165.2, 160.5 (d, J=240.9 Hz), 155.1, 152.9, 142.8, 134.4, 130.9, 130.9 (d, J=2.9 Hz), 128.9, 127.9, 127.8 (d, J=3.6 Hz), 126.6 (d, J=4.6 Hz), 126.4, 124.6, 123.7, 123.6, 122.2, 118.0, 110.3, 102.0 (d, J=17.9 Hz), 52.2, 25.0, 14.9. $^{19}$F NMR (376 MHz, DMSO-d$_6$) δ -135.3. MS (ESI$^+$) calculated for [C$_{23}$H$_{20}$FN$_2$O$_3$]$^+$ [M+H]$^+$, 391.1; found 391.1.

Methyl 2-((5-ethylnaphthalen-2-yl)oxy)-5-(3-fluoro-1H-pyrazol-4-yl)benzoate (15p)

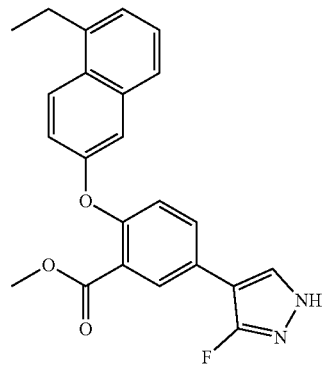 [SMILES: CCc1cccc2cc(Oc3ccc(-c4c[nH]nc4F)cc3C(=O)OC)ccc12]

Methyl ester 15p was prepared according to the procedure for 13a using phenyl bromide 12p (76.7 mg, 0.199 mmol), fluorinated pyrazole 16 (42.2 mg, 0.199 mmol), Cs$_2$CO$_3$ (195 mg, 0.597 mmol), and Pd(dppf)Cl$_2$.DCM (16.3 mg, 0.0199 mmol) in dioxane (2.5 mL) and water (1 mL). Purification by flash column chromatography (hexanes to EtOAc) afforded 15p as a clear oil (4.8 mg, 6% yield). R$_f$=0.35 (hexanes/EtOAc 50:50 v/v). $^1$H NMR (600 MHz, DMSO-d$_6$) δ 12.69 (br s, 1H), 8.28 (s, 1H), 8.11 (d, J=9.2 Hz, 1H), 8.04 (d, J=2.3 Hz, 1H), 7.81 (dd, J=8.5, 2.3 Hz, 1H), 7.65 (d, J=8.2 Hz, 1H), 7.41-7.37 (m, 1H), 7.31 (dd, J=9.1, 2.6 Hz, 1H), 7.29-7.26 (m, 2H), 7.20 (d, J=8.5 Hz, 1H), 3.72 (s, 3H), 3.06 (q, J=7.5 Hz, 2H), 1.30 (t, J=7.5 Hz, 3H). $^{13}$C NMR (151 MHz, DMSO-d$_6$) δ 165.2, 160.5 (d, J=240.8 Hz), 155.0, 153.0, 140.0, 134.5, 130.9 (d, J=3.1 Hz), 128.9, 127.9 (d, J=3.6 Hz), 127.8, 126.6 (d, J=6.1 Hz), 126.6, 126.0, 125.6, 123.8, 123.7, 122.3, 118.8, 112.9, 102.0 (d, J=17.9 Hz), 52.2, 25.3, 15.2. $^{19}$F NMR (376 MHz, DMSO-d$_6$) δ -135.3. MS (ESI$^+$) calculated for [C$_{23}$H$_{20}$FN$_2$O$_3$]$^+$ [M+H]$^+$, 391.1; found 391.1.

Methyl 2-((7-ethylnaphthalen-2-yl)oxy)-5-(3-fluoro-1H-pyrazol-4-yl)benzoate (15q)

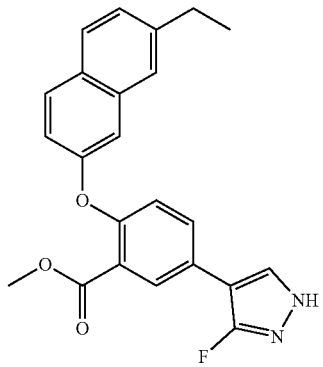 [SMILES: CCc1ccc2ccc(Oc3ccc(-c4c[nH]nc4F)cc3C(=O)OC)cc2c1]

Methyl ester 15q was prepared according to the procedure for 13a using phenyl bromide 12q (90.3 mg, 0.234 mmol), fluorinated pyrazole 16 (49.7 mg, 0.234 mmol), $Cs_2CO_3$ (229 mg, 0.703 mmol), and Pd(dppf)$Cl_2$.DCM (19.1 mg, 0.0234 mmol) in dioxane (2.5 mL) and water (1 mL). Purification by flash column chromatography (DCM to EtOAc) afforded 15q as a clear oil (15.5 mg, 17% yield). $R_f$=0.64 (DCM/EtOAc 50:50 v/v). $^1$H NMR (400 MHz, DMSO-$d_6$) δ 12.69 (br s, 1H), 8.30-8.26 (m, 1H), 8.04 (d, J=2.3 Hz, 1H), 7.89 (d, J=8.9 Hz, 1H), 7.85-7.77 (m, 2H), 7.58 (s, 1H), 7.30 (dd, J=8.4, 1.4 Hz, 1H), 7.23-7.16 (m, 3H), 3.71 (s, 3H), 2.72 (q, J=7.5 Hz, 2H), 1.23 (t, J=7.6 Hz, 3H). $^{13}$C NMR (101 MHz, DMSO-$d_6$) δ 165.2, 160.5 (d, J=240.8 Hz), 155.5, 153.0, 142.2, 134.1, 130.9 (d, J=4.2 Hz), 129.7, 128.9, 128.1, 127.9 (d, J=3.7 Hz), 127.6, 126.6 (d, J=4.8 Hz), 125.8, 124.7, 123.7, 122.2, 118.2, 111.8, 102.0 (d, J=17.7 Hz), 52.2, 28.3, 15.4. $^{19}$F NMR (376 MHz, DMSO-$d_6$) δ −135.4. MS (ESI$^+$) calculated for $[C_{23}H_{20}FN_2O_3]^+$ $[M+H]^+$, 391.1; found 391.1.

Methyl 2-((4-cyclopropylnaphthalen-2-yl)oxy)-5-(3-fluoro-1H-pyrazol-4-yl)benzoate (15r)

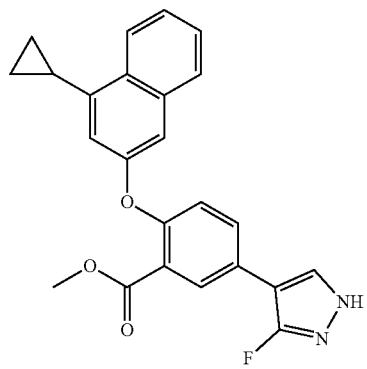 [SMILES: COC(=O)c1cc(-c2c[nH]nc2F)ccc1Oc1cc(C2CC2)c2ccccc2c1]

Methyl ester 15r was prepared according to the procedure for 13a using phenyl bromide 12r (62.0 mg, 0.156 mmol), fluorinated pyrazole 16 (33.1 mg, 0.156 mmol), $Cs_2CO_3$ (153 mg, 0.468 mmol), and Pd(dppf)$Cl_2$.DCM (12.7 mg, 0.0156 mmol) in dioxane (2.5 mL) and water (1 mL). Purification by flash column chromatography (DCM to EtOAc with 2% MeOH throughout) afforded 15r as a white solid (15.5 mg, 25% yield). $R_f$=0.69 (DCM/EtOAc/MeOH 47.5:47.5:5 v/v/v). $^1$H NMR (400 MHz, DMSO-$d_6$) δ 12.69 (br s, 1H), 8.37-8.31 (m, 1H), 8.27 (app t, J=2.2 Hz, 1H), 8.04 (d, J=2.3 Hz, 1H), 7.83-7.76 (m, 2H), 7.51-7.45 (m, 2H), 7.18 (d, J=8.6 Hz, 1H), 7.05 (d, J=2.2 Hz, 1H), 7.03 (d, J=1.9 Hz, 1H), 3.70 (s, 3H), 2.49-2.39 (m, 1H), 1.11-1.03 (m, 2H), 0.77-0.71 (m, 2H). $^{13}$C NMR (101 MHz, DMSO-$d_6$) δ 165.2, 160.5 (d, J=241.1 Hz), 155.1, 152.9, 141.9, 134.2, 130.8 (d, J=3.3 Hz), 129.5, 128.9, 127.8 (d, J=3.7 Hz), 127.7, 126.6 (d, J=6.8 Hz), 126.5, 124.6, 124.1, 123.7, 122.2, 116.1, 110.2, 102.0 (d, J=18.0 Hz), 52.2, 12.7, 6.9. $^{19}$F NMR (376 MHz, DMSO-$d_6$) δ −135.3. MS (ESI$^+$) calculated for $[C_{24}H_{20}FN_2O_3]^+$ $[M+H]^+$, 403.1; found 403.1.

Methyl 2-((4-cyclopropyl-7-ethylnaphthalen-2-yl)oxy)-5-(3-fluoro-1H-pyrazol-4-yl)benzoate (15s)

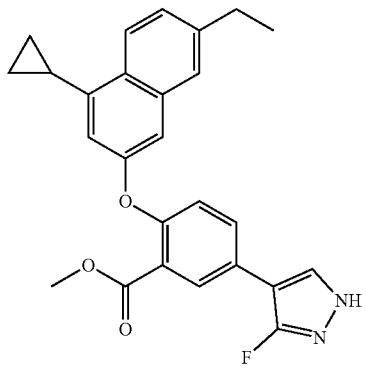 [SMILES: CCc1ccc2c(C3CC3)cc(Oc3ccc(-c4c[nH]nc4F)cc3C(=O)OC)cc2c1]

Methyl ester 15s was prepared according to the procedure for 13a using phenyl bromide 12s (48.0 mg, 0.113 mmol), fluorinated pyrazole 16 (23.9 mg, 0.113 mmol), $Cs_2CO_3$ (110 mg, 0.339 mmol), and Pd(dppf)$Cl_2$.DCM (9.2 mg, 0.011 mmol) in dioxane (2.5 mL) and water (1 mL). Purification by flash column chromatography (DCM to EtOAc) afforded 15s as a clear oil (8.4 mg, 17% yield). $R_f$=0.75 (DCM/EtOAc 50:50 v/v). $^1$H NMR (600 MHz, DMSO-$d_6$) δ 12.69 (br s, 1H), 8.27 (app t, J=2.0 Hz, 1H), 8.24 (d, J=8.6 Hz, 1H), 8.03 (d, J=2.3 Hz, 1H), 7.79 (dd, J=8.5, 2.3 Hz, 1H), 7.56 (s, 1H), 7.36 (dd, J=8.6, 1.6 Hz, 1H), 7.15 (d, J=8.6 Hz, 1H), 6.97 (d, J=2.3 Hz, 1H), 6.94 (d, J=2.0 Hz, 1H), 3.70 (s, 3H), 2.71 (q, J=7.6 Hz, 2H), 2.45-2.38 (m, 1H), 1.23 (t, J=7.6 Hz, 3H), 1.08-1.02 (m, 2H), 0.75-0.70 (m, 2H). $^{13}$C NMR (151 MHz, DMSO-$d_6$) δ 165.3, 160.5 (d, J=240.9 Hz), 155.2, 153.0, 142.1, 141.7, 134.4, 130.8 (d, J=3.0 Hz), 128.9, 128.0, 127.8 (d, J=3.6 Hz), 126.5 (d, J=4.7 Hz), 125.7, 125.4, 124.1, 123.6, 122.1, 115.2, 110.0, 102.1 (d, J=17.9 Hz), 52.2, 28.2, 15.4, 12.7, 7.0. $^{19}$F NMR (376 MHz, DMSO-$d_6$) δ −135.3. MS (ESI$^+$) calculated for $[C_{26}H_{24}FN_2O_3]^+$ $[M+H]^+$, 431.2; found 431.2.

Methyl 2-([1,1'-biphenyl]-4-yloxy)-5-(3-fluoro-1H-pyrazol-4-yl)benzoate (15t)

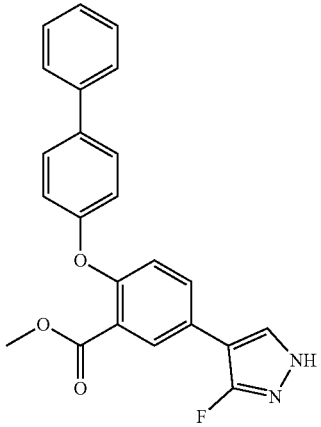 [SMILES: COC(=O)c1cc(-c2c[nH]nc2F)ccc1Oc1ccc(-c2ccccc2)cc1]

Methyl ester 15t was prepared according to the procedure for 13a using phenyl bromide 12t (96.3 mg, 0.251 mmol), fluorinated pyrazole 16 (53.3 mg, 0.251 mmol), $Cs_2CO_3$ (246 mg, 0.754 mmol), and $Pd(dppf)Cl_2 \cdot DCM$ (20.5 mg, 0.0251 mmol) in dioxane (2.5 mL) and water (1 mL). Purification by flash column chromatography (DCM to 30:70 DCM/EtOAc) afforded 15t as a brown solid (23.1 mg, 24% yield). $R_f$=0.68 (DCM/EtOAc 50:50 v/v). $^1$H NMR (400 MHz, DMSO-$d_6$) δ 12.70 (br s, 1H), 8.27 (app t, J=2.0 Hz, 1H), 8.02 (d, J=2.3 Hz, 1H), 7.81 (dd, J=8.5, 2.3 Hz, 1H), 7.69-7.61 (m, 4H), 7.49-7.41 (m, 2H), 7.38-7.30 (m, 1H), 7.19 (d, J=8.6 Hz, 1H), 7.02 (d, J=8.8 Hz, 2H), 3.75 (s, 3H). $^{13}$C NMR (101 MHz, DMSO-$d_6$) δ 165.2, 160.5 (d, J=241.0 Hz), 157.2, 152.9, 139.5, 134.9, 130.9, 130.9 (d, J=3.5 Hz), 128.9, 128.2, 127.8 (d, J=3.7 Hz), 127.1, 126.7 (d, J=4.8 Hz), 126.4, 123.8, 122.3, 117.8, 102.0 (d, J=18.1 Hz), 52.3. $^{19}$F NMR (376 MHz, DMSO-$d_6$) δ −135.4. MS (ESI$^+$) calculated for $[C_{23}H_{18}FN_2O_3]^+$ $[M+H]^+$, 389.1; found 389.1.

Methyl 2-([1,1'-biphenyl]-3-yloxy)-5-(3-fluoro-1H-pyrazol-4-yl)benzoate (15u)

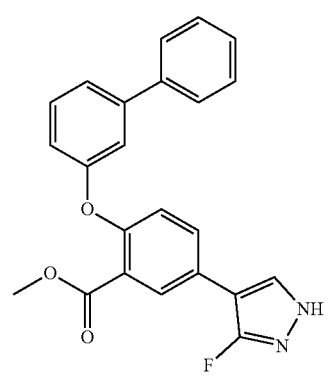 [SMILES: COC(=O)c1cc(-c2c[nH]nc2F)ccc1Oc1cccc(-c2ccccc2)c1]

Methyl ester 15u was prepared according to the procedure for 13a using phenyl bromide 12u (111 mg, 0.289 mmol), fluorinated pyrazole 16 (61.2 mg, 0.289 mmol), $Cs_2CO_3$ (282 mg, 0.867 mmol), and $Pd(dppf)Cl_2 \cdot DCM$ (20.5 mg, 0.0289 mmol) in dioxane (2.5 mL) and water (1 mL). Purification by flash column chromatography (DCM to 30:70 DCM/EtOAc) afforded 15u as a cream-colored solid (19.8 mg, 17% yield). $R_f$=0.73 (DCM/EtOAc 50:50 v/v). $^1$H NMR (400 MHz, DMSO-$d_6$) δ 12.69 (br s, 1H), 8.26 (app t, J=1.9 Hz, 1H), 8.02 (d, J=2.3 Hz, 1H), 7.79 (dd, J=8.5, 2.3 Hz, 1H), 7.63 (d, J=7.4 Hz, 2H), 7.49-7.33 (m, 5H), 7.23 (app t, J=2.0 Hz, 1H), 7.19 (d, J=8.6 Hz, 1H), 6.95-6.90 (m, 1H), 3.74 (s, 3H). $^{13}$C NMR (101 MHz, DMSO-$d_6$) δ 165.3, 160.5 (d, J=241.1 Hz), 157.9, 152.9, 142.1, 139.4, 130.8 (d, J=3.3 Hz), 130.5, 129.0, 128.9 (d, J=4.0 Hz), 127.8, 127.8 (d, J=3.8 Hz), 126.7, 123.7, 122.0, 121.5, 117.8, 116.5, 115.7, 102.0 (d, J=17.8 Hz), 52.3. $^{19}$F NMR (376 MHz, DMSO-$d_6$) δ −135.3. MS (ESI$^+$) calculated for $[C_{23}H_{18}FN_2O_3]^+$ $[M+H]^+$, 389.1; found 389.1.

Methyl 2-((3',5'-dimethyl-[1,1'-biphenyl]-3-yl)oxy)-5-(3-fluoro-1H-pyrazol-4-yl)benzoate (15v)

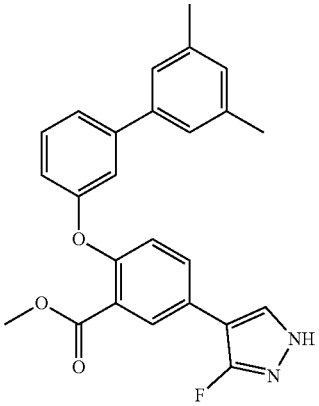 [SMILES: COC(=O)c1cc(-c2c[nH]nc2F)ccc1Oc1cccc(-c2cc(C)cc(C)c2)c1]

Methyl ester 15v was prepared according to the procedure for 13a using phenyl bromide 12v (55.0 mg, 0.134 mmol), fluorinated pyrazole 16 (28.4 mg, 0.134 mmol), $Cs_2CO_3$ (131 mg, 0.401 mmol), and $Pd(dppf)Cl_2 \cdot DCM$ (10.9 mg, 0.0134 mmol) in dioxane (2.5 mL) and water (1 mL). Purification by flash column chromatography (DCM to 50:50 DCM/EtOAc) afforded 15v as an orange solid (10.1 mg, 18% yield). $R_f$=0.73 (DCM/EtOAc 50:50 v/v). $^1$H NMR (400 MHz, DMSO-$d_6$) δ 12.67 (br s, 1H), 8.25 (app t, J=1.7 Hz, 1H), 8.00 (d, J=2.2 Hz, 1H), 7.78 (dd, J=8.6, 2.3 Hz, 1H), 7.43 (app t, J=7.8 Hz, 1H), 7.40-7.36 (m, 1H), 7.26-7.20 (m, 3H), 7.14 (d, J=8.6 Hz, 1H), 7.00 (s, 1H), 6.92-6.87 (m, 1H), 3.75 (s, 3H), 2.31 (s, 6H). $^{13}$C NMR (101 MHz, DMSO-$d_6$) δ 165.3, 160.5 (d, J=240.8 Hz), 157.6, 153.1, 142.4, 139.3, 138.0, 130.8 (d, J=3.1 Hz), 130.4, 129.2, 128.8, 127.7 (d, J=3.7 Hz), 127.7, 126.3 (d, J=4.7 Hz), 124.5, 123.5, 121.6, 116.4, 116.0, 102.0 (d, J=17.9 Hz), 52.2, 21.0. $^{19}$F NMR (376 MHz, DMSO-$d_6$) δ −135.4. MS (ESI$^+$) calculated for $[C_{25}H_{22}FN_2O_3]^+$ $[M+H]^+$, 417.2; found 417.1.

Methyl 2-((4'-ethoxy-[1,1'-biphenyl]-3-yl)oxy)-5-(3-fluoro-1H-pyrazol-4-yl)benzoate (15w)

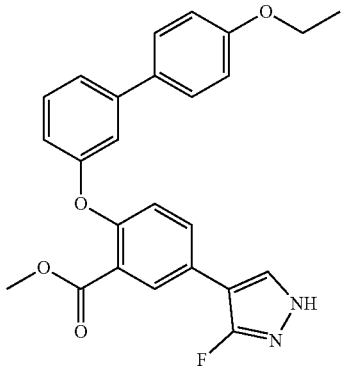 [SMILES: CCOc1ccc(-c2cccc(Oc3ccc(-c4c[nH]nc4F)cc3C(=O)OC)c2)cc1]

Methyl ester 15w was prepared according to the procedure for 13a using phenyl bromide 12w (79.8 mg, 0.187 mmol), fluorinated pyrazole 16 (39.6 mg, 0.187 mmol), Cs$_2$CO$_3$ (183 mg, 0.560 mmol), and Pd(dppf)Cl$_2$.DCM (15.3 mg, 0.0187 mmol) in dioxane (2.5 mL) and water (1 mL). Purification by flash column chromatography (DCM to EtOAc) afforded 15w as a cream-colored solid (16.0 mg, 20% yield). R$_f$=0.75 (DCM/EtOAc 50:50 v/v). $^1$H NMR (600 MHz, DMSO-d$_6$) δ 12.68 (br s, 1H), 8.26 (app t, J=1.9 Hz, 1H), 8.01 (d, J=2.4 Hz, 1H), 7.79 (dd, J=8.5, 2.4 Hz, 1H), 7.55 (d, J=8.8 Hz, 2H), 7.41 (app t, J=7.9 Hz, 1H), 7.38-7.34 (m, 1H), 7.18-7.15 (m, 2H), 6.98 (d, J=8.8 Hz, 2H), 6.86 (dd, J=8.0, 2.4 Hz, 1H), 4.05 (q, J=7.0 Hz, 2H), 3.74 (s, 3H), 1.33 (t, J=7.0 Hz, 3H). $^{13}$C NMR (151 MHz, DMSO-d$_6$) δ 165.3, 160.5 (d, J=240.9 Hz), 158.4, 157.9, 153.0, 141.8, 131.5, 130.8 (d, J=3.0 Hz), 130.4, 128.9, 127.8, 127.7 (d, J=3.6 Hz), 126.4 (d, J=4.6 Hz), 123.7, 121.9, 121.0, 115.8, 115.2, 114.8, 102.0 (d, J=17.9 Hz), 63.1, 52.2, 14.6. $^{19}$F NMR (376 MHz, DMSO-d$_6$) δ −135.3. MS (ESI$^+$) calculated for [C$_{25}$H$_{22}$FN$_2$O$_4$]$^+$ [M+H]$^+$, 433.2; found 433.2.

Methyl 5-(3-fluoro-1H-pyrazol-4-yl)-2-((4'-(3-morpholinopropoxy)-[1,1'-biphenyl]-3-yl)oxy)benzoate (15x)

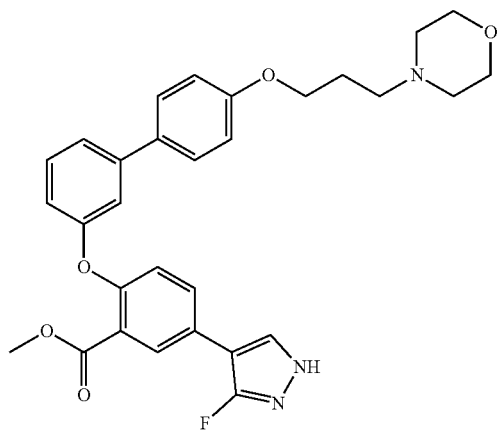 [SMILES: COC(=O)c1cc(-c2c[nH]nc2F)ccc1Oc1cccc(-c2ccc(OCCCN3CCOCC3)cc2)c1]

Methyl ester 15x was prepared according to the procedure for 13a using phenyl bromide 12x (91.5 mg, 0.174 mmol), fluorinated pyrazole 16 (36.9 mg, 0.174 mmol), Cs$_2$CO$_3$ (170 mg, 0.521 mmol), and Pd(dppf)Cl$_2$.DCM (14.2 mg, 0.0174 mmol) in dioxane (2.5 mL) and water (1 mL). Purification by flash column chromatography (DCM to EtOAc with 2% MeOH throughout) afforded 15x as a clear oil (21.4 mg, 23% yield). R$_f$=0.20 (DCM/EtOAc/MeOH 47.5:47.5:5 v/v/v). $^1$H NMR (600 MHz, DMSO-d$_6$) δ 12.71 (br s, 1H), 8.26 (s, 1H), 8.00 (d, J=2.3 Hz, 1H), 7.78 (dd, J=8.5, 2.3 Hz, 1H), 7.56 (d, J=8.8 Hz, 2H), 7.41 (app t, J=7.9 Hz, 1H), 7.39-7.34 (m, 1H), 7.20-7.14 (m, 2H), 6.99 (d, J=8.8 Hz, 2H), 6.88-6.83 (m, 1H), 4.03 (t, J=7.0 Hz, 2H), 3.74 (s, 3H), 3.57 (t, J=4.5 Hz, 4H), 2.41 (t, J=7.2 Hz, 2H), 2.36 (app s, 4H), 1.88 (app quint, J=6.5 Hz, 2H). $^{13}$C NMR (151 MHz, DMSO-d$_6$) δ 165.3, 160.5 (d, J=240.9 Hz), 158.5, 157.9, 153.0, 141.8, 131.6, 130.8 (d, J=3.1 Hz), 130.4, 128.9, 127.8, 127.7 (d, J=3.5 Hz), 126.4 (d, J=4.6 Hz), 123.7, 121.9, 121.0, 115.8, 115.2, 114.9, 102.0 (d, J=18.0 Hz), 66.2, 65.9, 54.8, 53.4, 52.2, 25.9. $^{19}$F NMR (376 MHz, DMSO-d$_6$) δ −135.4. MS (ESI$^+$) calculated for [C$_{30}$H$_{31}$FN$_3$O$_5$]$^+$ [M+H]$^+$, 532.2; found 532.2.

Synthesis of 6a-c, 7a, 7b, 8a-g, and 8j-15x 4-(1H-pyrazol-4-yl)-[1,1'-biphenyl]-2-carboxylic acid (6a)

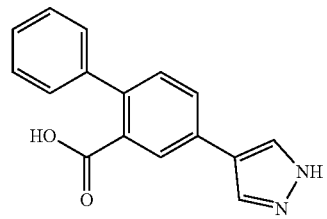 [SMILES: O=C(O)c1cc(-c2cn[nH]c2)ccc1-c1ccccc1]

A suspension of methyl ester 13a (17.3 mg, 0.0622 mmol) in EtOH (1.5 mL) and 20% (wt/wt) aqueous NaOH (1.5 mL) was stirred at room temperature for 48 hours. The reaction mixture was acidified to pH=1 with 1N HCl, diluted with EtOAc (50 mL), and washed with brine (50 mL). The organic phase was dried over anhydrous Na$_2$SO$_4$ and concentrated under reduced pressure. Purification by flash column chromatography (DCM to 99:1 EtOAc/TFA) afforded 6a as a pale yellow solid (16.4 mg, 99% yield). R$_f$=0.10 (DCM/EtOAc/TFA 49.5:49.5:1 v/v/v). $^1$H NMR (400 MHz, DMSO-d$_6$) δ 8.19 (s, 2H), 7.90 (s, 1H), 7.80 (d, J=8.1 Hz, 1H), 7.45-7.31 (m, 6H). $^{13}$C NMR (101 MHz, DMSO-d$_6$) δ 169.9, 140.6, 137.9, 133.1, 132.0, 130.9, 128.2, 128.2, 127.2, 127.1, 125.2. HRMS (ESI$^+$) calculated for [C$_{16}$H$_{13}$N$_2$O$_2$]$^+$ [M+H]$^+$, 265.0977; found 265.0978.

2-(Naphthalen-1-yl)-5-(1H-pyrazol-4-yl)benzoic acid (6b)

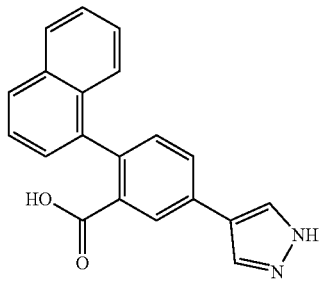 [SMILES: O=C(O)c1cc(-c2cn[nH]c2)ccc1-c1cccc2ccccc12]

Carboxylic acid 6b was prepared according to the procedure for 6a using methyl ester 13b (20.8 mg, 0.0633 mmol) in EtOH (1.5 mL) and 20% (wt/wt) aqueous NaOH (1.5 mL). Purification by flash column chromatography (DCM to 99:1 EtOAc/TFA) afforded 6b as a peach-colored solid (19.9 mg, 99% yield). $R_f$=0.12 (DCM/EtOAc/TFA 49.5:49.5:1 v/v/v). $^1$H NMR (400 MHz, DMSO-$d_6$) δ 8.23 (s, 2H), 8.11 (s, 1H), 7.97 (d, J=8.0 Hz, 1H), 7.90 (app t, J=9.2 Hz, 2H), 7.58-7.38 (m, 4H), 7.33 (app d, J=7.0 Hz, 2H). $^{13}$C NMR (101 MHz, DMSO-$d_6$) δ 168.5, 139.4, 137.2, 133.4, 133.0, 132.5, 132.1, 131.6, 128.1, 127.7, 127.2, 126.1, 126.0, 125.7, 125.6, 125.3, 125.3. HRMS (ESI$^+$) calculated for $[C_{20}H_{15}N_2O_2]^+$ [M+H]$^+$, 315.1132; found 315.1134.

2-(Naphthalen-2-yl)-5-(1H-pyrazol-4-yl)benzoic acid (6c)

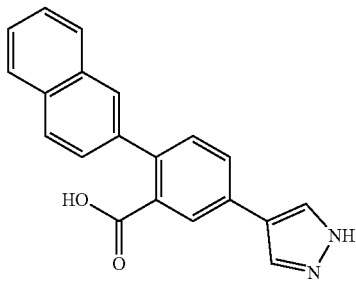 [SMILES: O=C(O)c1cc(-c2cn[nH]c2)ccc1-c1ccc2ccccc2c1]

Carboxylic acid 6c was prepared according to the procedure for 6a using methyl ester 13c (22.0 mg, 0.0670 mmol) in EtOH (1.5 mL) and 20% (wt/wt) aqueous NaOH (1.5 mL). Purification by flash column chromatography (DCM to 99:1 EtOAc/TFA) afforded 6c as a light brown solid (21.1 mg, 99% yield). $R_f$=0.13 (DCM/EtOAc/TFA 49.5:49.5:1 v/v/v). $^1$H NMR (400 MHz, DMSO-$d_6$) δ 8.22 (s, 2H), 8.02-7.82 (m, 6H), 7.59-7.46 (m, 4H). $^{13}$C NMR (101 MHz, DMSO-$d_6$) δ 169.8, 138.4, 138.1, 133.1, 132.9, 132.2, 132.0, 131.3, 131.2, 128.0, 127.5, 127.3, 127.1, 126.5, 126.3, 126.0, 125.5. HRMS (ESI$^+$) calculated for $[C_{20}H_{15}N_2O_2]^+$ [M+H]$^+$, 315.1132; found 315.1125.

2-(Phenylamino)-5-(1H-pyrazol-4-yl)benzoic acid (7a)

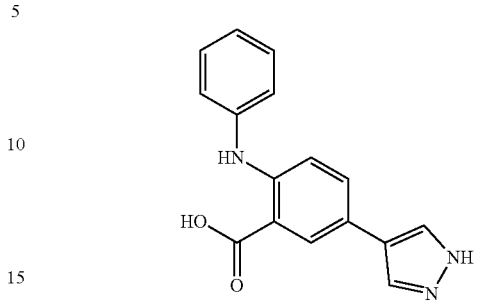

Carboxylic acid 7a was prepared according to the procedure for 6a using methyl ester 14a (28.0 mg, 0.0955 mmol) in EtOH (1.5 mL) and 20% (wt/wt) aqueous NaOH (1.5 mL). Purification by flash column chromatography (DCM to 99:1 EtOAc/TFA) afforded 7a as a mustard yellow solid (26.6 mg, 99% yield). $R_f$=0.12 (DCM/EtOAc/TFA 49.5:49.5:1 v/v/v). $^1$H NMR (400 MHz, DMSO-$d_6$) δ 9.54 (br s, 1H), 8.08 (d, J=2.1 Hz, 1H), 7.98 (s, 2H), 7.65 (dd, J=8.7, 2.1 Hz, 1H), 7.35 (t, J=7.8 Hz, 2H), 7.30-7.21 (m, 3H), 7.05 (t, J=7.3 Hz, 1H). $^{13}$C NMR (101 MHz, DMSO-$d_6$) δ 169.9, 144.8, 140.8, 131.3, 129.5, 127.9, 122.8, 122.6, 120.9, 114.7, 113.3. HRMS (ESI$^+$) calculated for $[C_{16}H_{14}N_3O_2]^+$ [M+H]$^+$, 280.1086; found 280.1083.

2-(Methyl(naphthalen-2-yl)amino)-5-(1H-pyrazol-4-yl)benzoic acid (7b)

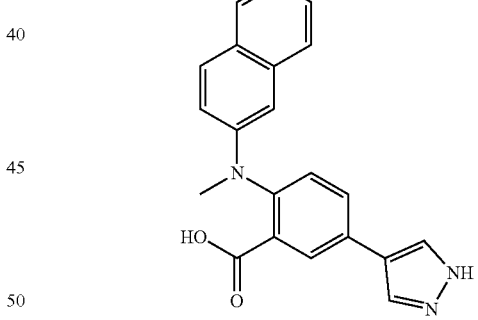

Carboxylic acid 7b was prepared according to the procedure for 6a using methyl ester 14b (19.1 mg, 0.0534 mmol) in EtOH (1.5 mL) and 20% (wt/wt) aqueous NaOH (1.5 mL). Purification by flash column chromatography (DCM to 99:1 EtOAc/TFA) afforded 7b as a yellow solid (5.3 mg, 29% yield). $R_f$=0.19 (DCM/EtOAc/TFA 49.5:49.5:1 v/v/v). $^1$H NMR (600 MHz, DMSO-$d_6$) δ 8.16 (s, 2H), 7.98 (d, J=1.5 Hz, 1H), 7.86 (dd, J=8.2, 1.6 Hz, 1H), 7.66 (app t, J=9.1 Hz, 2H), 7.60 (d, J=9.0 Hz, 1H), 7.37-7.30 (m, 2H), 7.18 (app t, J=7.4 Hz, 1H), 6.97 (d, J=1.8 Hz, 1H), 6.77 (dd, J=9.0, 2.0 Hz, 1H), 3.31 (s, 3H). $^{13}$C NMR (151 MHz, DMSO-$d_6$) δ 167.8, 146.8, 144.4, 134.6, 131.4, 130.9, 129.9, 129.6, 128.1, 127.3, 127.0, 126.8, 126.2, 126.0, 122.0, 117.1, 106.6, 40.4. HRMS (ESI$^+$) calculated for $[C_{21}H_{18}N_3O_2]^+$ [M+H]$^+$, 344.1399; found 344.1399.

2-Phenoxy-5-(1H-pyrazol-4-yl)benzoic acid (8a)

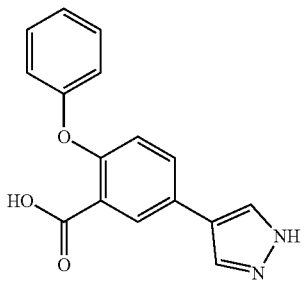 [SMILES: O=C(O)c1cc(-c2cn[nH]c2)ccc1Nc1ccccc1]

Carboxylic acid 8a was prepared according to the procedure for 6a using methyl ester 15a (23.7 mg, 0.0805 mmol) in EtOH (1.5 mL) and 20% (wt/wt) aqueous NaOH (1.5 mL). Purification by flash column chromatography (DCM to 99:1 EtOAc/TFA) afforded 8a as a brown solid (22.6 mg, 99% yield). $R_f$=0.09 (DCM/EtOAc/TFA 49.5:49.5:1 v/v/v). $^1$H NMR (400 MHz, DMSO-$d_6$) δ 8.26 (s, 2H), 8.00 (s, 1H), 7.78 (d, J=8.2 Hz, 1H), 7.34 (t, J=7.8 Hz, 2H), 7.07 (t, J=7.3 Hz, 1H), 7.02 (d, J=8.4 Hz, 1H), 6.91 (d, J=8.0 Hz, 2H). $^{13}$C NMR (101 MHz, DMSO-$d_6$) δ 166.6, 157.8, 152.4, 130.0, 129.8, 127.4, 125.3, 122.6, 121.9, 121.9, 117.2. HRMS (ESI$^+$) calculated for [$C_{16}H_{13}N_2O_3$]$^+$ [M+H]$^+$, 281.0926; found 281.0932.

5-(1H-Pyrazol-4-yl)-2-(o-tolyloxy)benzoic acid (8b)

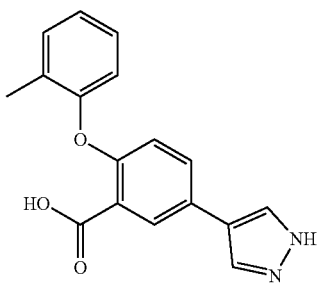 [SMILES: Cc1ccccc1Oc1ccc(-c2cn[nH]c2)cc1C(=O)O]

Carboxylic acid 8b was prepared according to the procedure for 6a using methyl ester 15b (23.2 mg, 0.0752 mmol) in EtOH (1.5 mL) and 20% (wt/wt) aqueous NaOH (1.5 mL). Purification by flash column chromatography (DCM to 99:1 EtOAc/TFA) afforded 8b as a brown solid (15.6 mg, 70% yield). $R_f$=0.24 (DCM/EtOAc/TFA 49.5:49.5:1 v/v/v). $^1$H NMR (600 MHz, DMSO-$d_6$) δ 8.11 (s, 2H), 7.98 (app t, J=1.6 Hz, 1H), 7.75-7.71 (m, 1H), 7.29 (d, J=7.4 Hz, 1H), 7.16 (app t, J=7.7 Hz, 1H), 7.04 (app t, J=7.4 Hz, 1H), 6.84 (dd, J=8.5, 1.4 Hz, 1H), 6.72 (d, J=8.0 Hz, 1H), 2.22 (s, 3H). $^{13}$C NMR (151 MHz, DMSO-$d_6$) δ 166.7, 155.1, 153.2, 131.3, 129.8, 128.3, 128.1, 127.4, 127.2, 124.2, 123.3, 119.9, 117.3, 15.8. HRMS (ESI$^+$) calculated for [$C_{17}H_{15}N_2O_3$]$^+$ [M+H]$^+$, 295.1083; found 295.1088.

5-(1H-Pyrazol-4-yl)-2-(m-tolyloxy)benzoic acid (8c)

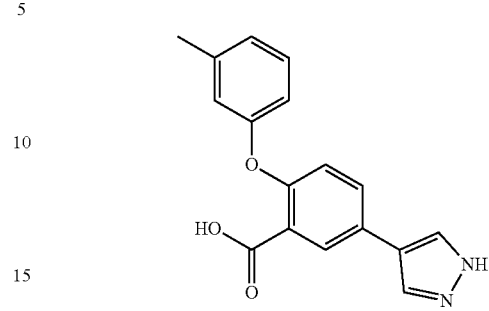

Carboxylic acid 8c was prepared according to the procedure for 6a using methyl ester 15c (24.5 mg, 0.0795 mmol) in EtOH (1.5 mL) and 20% (wt/wt) aqueous NaOH (1.5 mL). Purification by flash column chromatography (DCM to 99:1 EtOAc/TFA) afforded 8c as a brown solid (16.7 mg, 71% yield). $R_f$=0.25 (DCM/EtOAc/TFA 49.5:49.5:1 v/v/v). $^1$H NMR (400 MHz, DMSO-$d_6$) δ 8.14 (s, 2H), 7.99 (s, 1H), 7.77 (d, J=8.3 Hz, 1H), 7.22 (app t, J=7.0 Hz, 1H), 7.00 (d, J=8.8 Hz, 1H), 6.89 (d, J=7.1 Hz, 1H), 6.74 (s, 1H), 6.69 (d, J=8.2 Hz, 1H), 2.27 (s, 3H). $^{13}$C NMR (151 MHz, DMSO-$d_6$) δ 166.6, 157.8, 152.5, 139.4, 129.9, 129.5, 129.1, 127.3, 125.3, 123.3, 121.8, 117.8, 114.3, 21.0. HRMS (ESI$^+$) calculated for [$C_{17}H_{15}N_2O_3$]$^+$ [M+H]$^+$, 295.1083; found 295.1078.

5-(1H-Pyrazol-4-yl)-2-(p-tolyloxy)benzoic acid (8d)

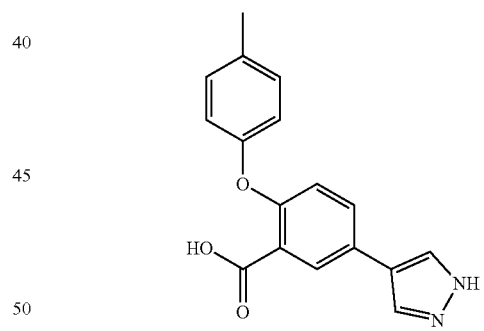

Carboxylic acid 8d was prepared according to the procedure for 6a using methyl ester 15d (19.5 mg, 0.0632 mmol) in EtOH (1.5 mL) and 20% (wt/wt) aqueous NaOH (1.5 mL). Purification by flash column chromatography (DCM to 99:1 EtOAc/TFA) afforded 8d as a brown solid (18.4 mg, 99% yield). $R_f$=0.25 (DCM/EtOAc/TFA 49.5:49.5:1 v/v/v). $^1$H NMR (400 MHz, DMSO-$d_6$) δ 8.16 (s, 2H), 7.97 (s, 1H), 7.75 (d, J=8.3 Hz, 1H), 7.15 (d, J=7.9 Hz, 2H), 6.95 (d, J=8.4 Hz, 1H), 6.82 (d, J=8.0 Hz, 2H), 2.26 (s, 3H). $^{13}$C NMR (151 MHz, DMSO-$d_6$) δ 166.7, 155.4, 152.9, 131.7, 130.2, 129.8, 128.8, 127.3, 125.0, 121.2, 117.5, 20.2. HRMS (ESI$^+$) calculated for [$C_{17}H_{15}N_2O_3$]$^+$ [M+H]$^+$, 295.1083; found 295.1082.

2-(3-Fluorophenoxy)-5-(1H-pyrazol-4-yl)benzoic acid (8e)

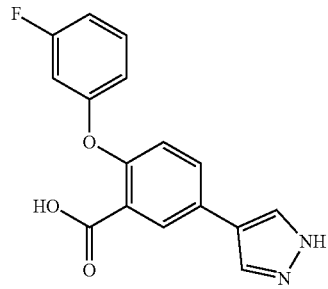 [SMILES: O=C(O)c1cc(-c2cn[nH]c2)ccc1Oc1cccc(F)c1]

Carboxylic acid 8e was prepared according to the procedure for 6a using methyl ester 15e (14.0 mg, 0.045 mmol) in EtOH (1.5 mL) and 20% (wt/wt) aqueous NaOH (1.5 mL). Purification by flash column chromatography (DCM to 99:1 EtOAc/TFA) afforded 8e as a brown solid (13.4 mg, 99% yield). $R_f$=0.24 (DCM/EtOAc/TFA 49.5:49.5:1 v/v/v). $^1$H NMR (600 MHz, DMSO-$d_6$) δ 8.20 (s, 2H), 8.03 (s, 1H), 7.83 (d, J=7.9 Hz, 1H), 7.35 (app q, J=7.1 Hz, 1H), 7.14 (d, J=7.8 Hz, 1H), 6.89 (app t, J=7.6 Hz, 1H), 6.74 (d, J=10.4 Hz, 1H), 6.69 (d, J=7.8 Hz, 1H). $^{13}$C NMR (151 MHz, DMSO-$d_6$) δ 166.3, 162.8 (d, J=243.8 Hz), 159.5 (d, J=10.9 Hz), 151.4, 131.1, 131.0 (d, J=9.9 Hz), 127.5, 125.5, 122.7, 112.6 (d, J=2.7 Hz), 109.6, 109.1 (d, J=21.0 Hz), 104.4 (d, J=25.0 Hz). HRMS (ESI$^+$) calculated for $[C_{16}H_{12}FN_2O_3]^+$ $[M+H]^+$, 299.0832; found 299.0833.

2-(4-Fluorophenoxy)-5-(1H-pyrazol-4-yl)benzoic acid (8f)

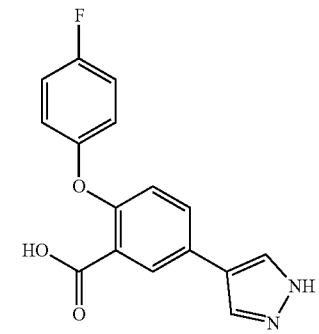 [SMILES: O=C(O)c1cc(-c2cn[nH]c2)ccc1Oc1ccc(F)cc1]

Carboxylic acid 8f was prepared according to the procedure for 6a using methyl ester 15f (19.0 mg, 0.0608 mmol) in EtOH (1.5 mL) and 20% (wt/wt) aqueous NaOH (1.5 mL). Purification by flash column chromatography (DCM to 99:1 EtOAc/TFA) afforded 8f as a brown solid (18.1 mg, 99% yield). $R_f$=0.19 (DCM/EtOAc/TFA 49.5:49.5:1 v/v/v). $^1$H NMR (600 MHz, DMSO-$d_6$) δ 8.11 (s, 2H), 7.99 (d, J=2.2 Hz, 1H), 7.78 (dd, J=8.5, 2.2 Hz, 1H), 7.18 (app t, J=8.7 Hz, 2H), 7.01 (d, J=8.5 Hz, 1H), 6.97-6.93 (m, 2H). $^{13}$C NMR (151 MHz, DMSO-$d_6$) δ 166.6, 157.7 (d, J=238.3 Hz), 153.9 (d, J=1.7 Hz), 152.7, 129.9, 129.2, 127.4, 125.1, 121.5, 119.0 (d, J=8.4 Hz), 116.3 (d, J=23.3 Hz). HRMS (ESI$^+$) calculated for $[C_{16}H_{12}FN_2O_3]^+$ $[M+H]^+$, 299.0832; found 299.0836.

2-(Naphthalen-2-yloxy)-5-(1H-pyrazol-4-yl)benzoic acid (8g)

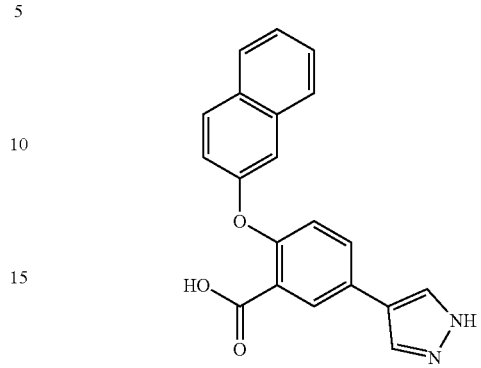

Carboxylic acid 8g was prepared according to the procedure for 6a using methyl ester 15g (9.8 mg, 0.029 mmol) in EtOH (1.5 mL) and 20% (wt/wt) aqueous NaOH (1.5 mL). Purification by flash column chromatography (DCM to 99:1 EtOAc/TFA) afforded 8g as a brown solid (9.4 mg, 99% yield). $R_f$=0.14 (DCM/EtOAc/TFA 49.5:49.5:1 v/v/v). $^1$H NMR (400 MHz, DMSO-$d_6$) δ 8.16 (s, 2H), 8.05 (d, J=1.1 Hz, 1H), 7.93 (d, J=8.9 Hz, 1H), 7.89 (d, J=7.9 Hz, 1H), 7.84 (dd, J=8.9, 1.1 Hz, 1H), 7.78 (d, J=8.0 Hz, 1H), 7.45 (app t, J=7.6 Hz, 1H), 7.40 (app t, J=6.9 Hz, 1H), 7.28 (dd, J=8.9, 1.8 Hz, 1H), 7.18 (d, J=1.4 Hz, 1H), 7.15 (d, J=8.4 Hz, 1H). $^{13}$C NMR (101 MHz, DMSO-$d_6$) δ 166.6, 156.0, 152.2, 133.9, 130.1, 129.9, 129.6, 129.3, 127.6, 127.5, 126.9, 126.6, 125.4, 124.5, 122.4, 119.0, 111.3. HRMS (ESI$^+$) calculated for $[C_{20}H_{15}N_2O_3]^+$ $[M+H]^+$, 331.1083; found 331.1082.

2-(Phenanthren-9-yloxy)-5-(1H-pyrazol-4-yl)benzoic acid (8j)

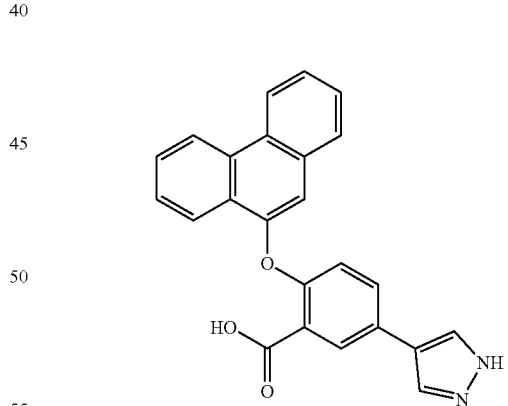

Carboxylic acid 8j was prepared according to the procedure for 6a using methyl ester 15j (9.0 mg, 0.023 mmol) in EtOH (1.5 mL) and 20% (wt/wt) aqueous NaOH (1.5 mL). Purification by flash column chromatography (DCM to 99:1 EtOAc/TFA) afforded 8j as a light brown solid (8.4 mg, 97% yield). $R_f$=0.26 (DCM/EtOAc/TFA 49.5:49.5:1 v/v/v). $^1$H NMR (600 MHz, DMSO-$d_6$) δ 8.89 (d, J=8.3 Hz, 1H), 8.79 (d, J=8.1 Hz, 1H), 8.38 (d, J=8.0 Hz, 1H), 8.18 (s, 2H), 8.11 (s, 1H), 7.86 (d, J=7.2 Hz, 1H), 7.82-7.77 (m, 2H), 7.74 (app t, J=7.4 Hz, 1H), 7.60-7.53 (m, 2H), 7.21 (d, J=8.4 Hz, 1H), 6.96 (s, 1H). $^{13}$C NMR (151 MHz, DMSO-$d_6$) δ 166.5, 152.2, 152.2, 131.8, 131.1, 130.1, 129.7, 127.8, 127.7, 127.7, 127.2, 127.0, 126.7, 125.8, 125.4, 125.2, 123.1, 122.8, 122.4, 122.3, 108.3. HRMS (ESI$^+$) calculated for $[C_{24}H_{17}N_2O_3]^+$ [M+H]$^+$, 381.1239; found 381.1240.

2-((Adamantan-2-yl)oxy)-5-(1H-pyrazol-4-yl)benzoic acid (8k)

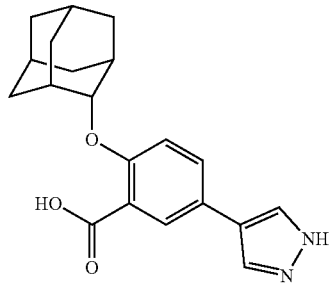 [SMILES: O=C(O)c1cc(-c2cn[nH]c2)ccc1OC1C2CC3CC(C2)CC1C3]

Carboxylic acid 8k was prepared according to the procedure for 6a using methyl ester 15k (28.8 mg, 0.0817 mmol) in EtOH (1.5 mL) and 20% (wt/wt) aqueous NaOH (1.5 mL). Purification by flash column chromatography (DCM to 99:1 EtOAc/TFA) afforded 8k as a brown solid (27.7 mg, 99% yield). $R_f$=0.30 (DCM/EtOAc/TFA 49.5:49.5:1 v/v/v). $^1$H NMR (600 MHz, DMSO-d$_6$) δ 8.00 (s, 2H), 7.78 (d, J=2.0 Hz, 1H), 7.64 (dd, J=8.6, 2.0 Hz, 1H), 7.12 (d, J=8.7 Hz, 1H), 4.62 (app t, J=3.2 Hz, 1H), 2.16 (d, J=12.0 Hz, 2H), 2.08 (s, 2H), 1.87-1.76 (m, 6H), 1.70 (s, 2H), 1.45 (d, J=11.9 Hz, 2H). $^{13}$C NMR (151 MHz, DMSO-d$_6$) δ 167.8, 153.7, 129.1, 127.0, 124.9, 123.3, 115.3, 78.8, 36.9, 35.5, 30.8, 30.8, 26.8, 26.6. HRMS (ESI$^+$) calculated for $[C_{20}H_{23}N_2O_3]^+$[M+H]$^+$, 339.1709; found 339.1706.

2-((1,2-Dihydroacenaphthylen-4-yl)oxy)-5-(1H-pyrazol-4-yl)benzoic acid (8l)

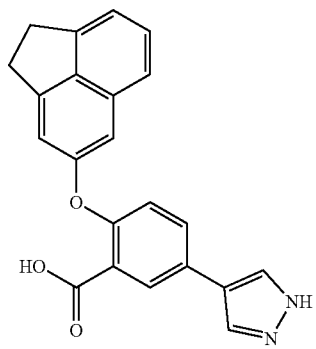 [SMILES: O=C(O)c1cc(-c2cn[nH]c2)ccc1Oc1cc2c3c(cccc3c1)CC2]

Carboxylic acid 8l was prepared according to the procedure for 6a using methyl ester 15l (2.7 mg, 0.0073 mmol) in EtOH (1.5 mL) and 20% (wt/wt) aqueous NaOH (1.5 mL). Purification by flash column chromatography (DCM to 99:1 EtOAc/TFA) afforded 8l as a white solid (2.6 mg, 99% yield). $R_f$=0.21 (DCM/EtOAc/TFA 49.5:49.5:1 v/v/v). $^1$H NMR (600 MHz, CD$_3$OD) δ 8.12 (s, 1H), 8.06 (s, 2H), 7.76 (d, J=8.4 Hz, 1H), 7.44-7.36 (m, 2H), 7.20 (d, J=6.5 Hz, 1H), 7.06-7.03 (m, 2H), 6.97 (s, 1H), 3.42-3.37 (m, 4H). $^{13}$C NMR (151 MHz, CD$_3$OD) δ 169.1, 159.4, 156.3, 149.7, 146.9, 137.3, 133.3, 131.8, 129.8 (2C), 129.5, 125.4, 122.6, 122.6, 119.2, 114.1, 109.6, 31.4, 31.0. HRMS (ESI$^+$) calculated for $[C_{22}H_{17}N_2O_3]^+$ [M+H]$^+$, 357.1239; found 357.1241.

5-(3-Fluoro-1H-pyrazol-4-yl)-2-(naphthalen-1-yloxy)benzoic acid (8m)

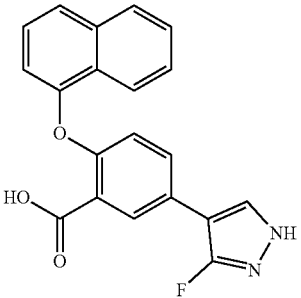 [SMILES: O=C(O)c1cc(-c2c[nH]nc2F)ccc1Oc1cccc2ccccc12]

Carboxylic acid 8m was prepared according to the procedure for 6a using methyl ester 15m (14.0 mg, 0.0386 mmol) in EtOH (1.5 mL) and 20% (wt/wt) aqueous NaOH (1.5 mL). Purification by flash column chromatography (DCM to 99:1 EtOAc/TFA) afforded 8m as a white solid (10.2 mg, 76% yield). $R_f$=0.29 (DCM/EtOAc/TFA 49.5:49.5:1 v/v/v). $^1$H NMR (600 MHz, DMSO-d$_6$) δ 13.01 (br s, 1H), 12.67 (br s, 1H), 8.25 (app t, J=1.8 Hz, 1H), 8.19 (d, J=8.0 Hz, 1H), 8.05 (d, J=2.3 Hz, 1H), 7.97 (d, J=7.6 Hz, 1H), 7.73 (dd, J=8.5, 2.3 Hz, 1H), 7.68 (d, J=8.2 Hz, 1H), 7.61-7.54 (m, 2H), 7.42 (app t, J=7.9 Hz, 1H), 7.05 (d, J=8.5 Hz, 1H), 6.79 (d, J=7.6 Hz, 1H). $^{13}$C NMR (151 MHz, DMSO-d$_6$) δ 166.4, 160.5 (d, J=240.7 Hz), 153.3, 153.1, 134.5, 130.4 (d, J=2.9 Hz), 128.8, 128.1 (d, J=3.5 Hz), 127.7, 126.8, 126.3 (d, J=4.6 Hz), 126.1, 126.1, 125.5, 124.7, 122.7, 121.6, 121.3, 111.5, 102.2 (d, J=17.9 Hz). $^{19}$F NMR (376 MHz, DMSO-d$_6$) δ −135.5. HRMS (ESI$^+$) calculated for $[C_{20}H_{14}FN_2O_3]^+$ [M+H]$^+$, 349.0988; found 349.0987.

5-(3-Fluoro-1H-pyrazol-4-yl)-2-(naphthalen-2-yloxy)benzoic acid (8n)

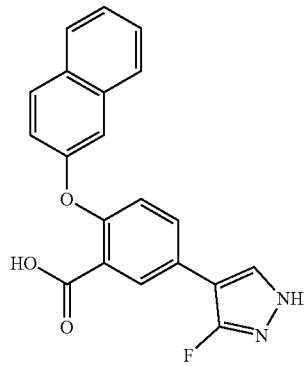 [SMILES: O=C(O)c1cc(-c2c[nH]nc2F)ccc1Oc1ccc2ccccc2c1]

Carboxylic acid 8n was prepared according to the procedure for 6a using methyl ester 15n (10.5 mg, 0.0290 mmol) in EtOH (1.5 mL) and 20% (wt/wt) aqueous NaOH (1.5 mL). Purification by flash column chromatography (DCM to 99:1 EtOAc/TFA) afforded 8n as a white solid (8.1 mg, 80% yield). $R_f$=0.21 (DCM/EtOAc/TFA 49.5:49.5:1 v/v/v). $^1$1-1NMR (600 MHz, DMSO-$d_6$) δ 13.01 (br s, 1H), 12.69 (br s, 1H), 8.28 (s, 1H), 8.05 (d, J=2.1 Hz, 1H), 7.94 (d, J=8.9 Hz, 1H), 7.90 (d, J=8.1 Hz, 1H), 7.79 (app d, J=8.3 Hz, 2H), 7.46 (app t, J=7.5 Hz, 1H), 7.41 (app t, J=7.5 Hz, 1H), 7.29 (dd, J=8.9, 2.4 Hz, 1H), 7.21 (s, 1H), 7.19 (d, J=8.5 Hz, 1H). $^{13}$C NMR (151 MHz, DMSO-$d_6$) δ 166.3, 160.5 (d, J=240.7 Hz), 155.7, 152.7, 133.9, 130.4 (d, J=3.2 Hz), 129.9, 129.4, 128.9, 128.0 (d, J=4.1 Hz), 127.6, 127.0, 126.7 (d, J=4.8 Hz), 126.6, 125.2, 124.6, 122.5, 119.1, 111.6, 102.2 (d, J=18.2 Hz). $^{19}$F NMR (376 MHz, DMSO-$d_6$) δ −135.4. HRMS (ESI$^+$) calculated for $[C_{20}H_{14}FN_2O_3]^+$ $[M+H]^+$, 349.0988; found 349.0988.

2-((4-Ethylnaphthalen-2-yl)oxy)-5-(3-fluoro-1H-pyrazol-4-yl)benzoic acid (8o)

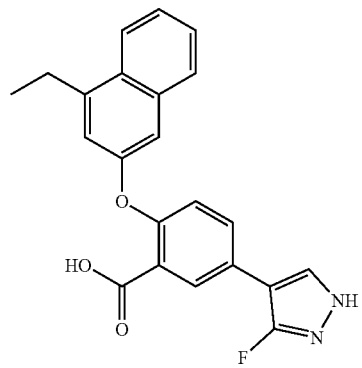 [SMILES: CCc1cc(Oc2ccc(-c3c[nH]nc3F)cc2C(=O)O)cc2ccccc12]

Carboxylic acid 8o was prepared according to the procedure for 6a using methyl ester 15o (8.1 mg, 0.021 mmol) in EtOH (1.5 mL) and 20% (wt/wt) aqueous NaOH (1.5 mL). Purification by flash column chromatography (DCM to 99:1 EtOAc/TFA) afforded 8o as a white solid (5.6 mg, 72% yield). $R_f$=0.35 (DCM/EtOAc/TFA 49.5:49.5:1 v/v/v). $^1$H NMR (600 MHz, DMSO-$d_6$) δ 12.99 (br s, 1H), 12.68 (br s, 1H), 8.27 (s, 1H), 8.07-7.99 (m, 2H), 7.81-7.74 (m, 2H), 7.49-7.41 (m, 2H), 7.21-7.15 (m, 2H), 7.03 (s, 1H), 3.08 (q, J=7.3 Hz, 2H), 1.30 (t, J=7.4 Hz, 3H). $^{13}$C NMR (151 MHz, DMSO-$d_6$) δ 166.4, 160.5 (d, J=240.9 Hz), 155.3, 152.7, 142.7, 134.5, 130.4 (d, J=2.9 Hz), 128.8, 127.9 (d, J=3.5 Hz), 127.9, 127.8, 126.5 (d, J=4.6 Hz), 126.3, 125.2, 124.5, 123.6, 122.3, 118.0, 109.9, 102.2 (d, J=17.9 Hz), 25.0, 14.9. $^{19}$F NMR (376 MHz, DMSO-$d_6$) δ −135.4. HRMS (ESI$^+$) calculated for $[C_{22}H_{18}FN_2O_3]^+$ $[M+H]^+$, 377.1301; found 377.1301.

2-((5-Ethylnaphthalen-2-yl)oxy)-5-(3-fluoro-1H-pyrazol-4-yl)benzoic acid (8p)

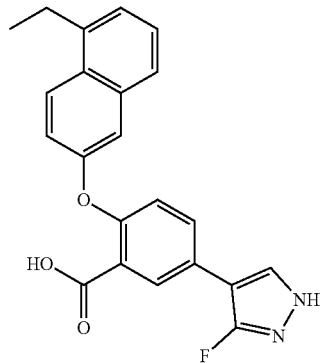 [SMILES: CCc1cccc2cc(Oc3ccc(-c4c[nH]nc4F)cc3C(=O)O)ccc12]

Carboxylic acid 8p was prepared according to the procedure for 6a using methyl ester 15p (4.5 mg, 0.012 mmol) in EtOH (1.5 mL) and 20% (wt/wt) aqueous NaOH (1.5 mL). Purification by flash column chromatography (DCM to 99:1 EtOAc/TFA) afforded 8p as a white solid (4.3 mg, 99% yield). $R_f$=0.31 (DCM/EtOAc/TFA 49.5:49.5:1 v/v/v). $^1$H NMR (600 MHz, DMSO-$d_6$) δ 13.06 (br s, 1H), 12.68 (br s, 1H), 8.28 (s, 1H), 8.10 (d, J=9.2 Hz, 1H), 8.04 (s, 1H), 7.78 (d, J=9.7 Hz, 1H), 7.63 (d, J=8.2 Hz, 1H), 7.38 (app t, J=7.6 Hz, 1H), 7.29 (dd, J=9.2, 2.0 Hz, 1H), 7.27 (d, J=7.0 Hz, 1H), 7.23 (s, 1H), 7.18 (d, J=8.5 Hz, 1H), 3.05 (q, J=7.5 Hz, 2H), 1.30 (t, J=7.5 Hz, 3H). $^{13}$C NMR (151 MHz, DMSO-$d_6$) δ 166.4, 160.5 (d, J=240.9 Hz), 155.3, 152.7, 140.0, 134.5, 130.4 (d, J=3.1 Hz), 128.9, 128.0 (d, J=3.6 Hz), 127.6, 126.6 (d, J=4.6 Hz), 126.6, 125.9, 125.5, 125.2, 123.6, 122.4, 118.8, 112.5, 102.2 (d, J=17.9 Hz), 25.2, 15.2. $^{19}$F NMR (376 MHz, DMSO-$d_6$) δ −135.4. HRMS (ESI$^+$) calculated for $[C_{22}H_{18}FN_2O_3]^+$ $[M+H]^+$, 377.1301; found 377.1301.

2-((7-Ethylnaphthalen-2-yl)oxy)-5-(3-fluoro-1H-pyrazol-4-yl)benzoic acid (8q)

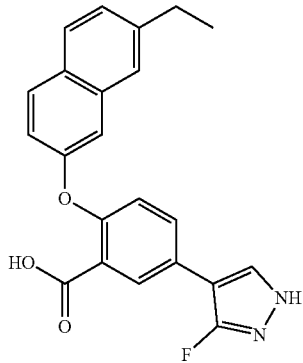 [SMILES: CCc1ccc2ccc(Oc3ccc(-c4c[nH]nc4F)cc3C(=O)O)cc2c1]

Carboxylic acid 8q was prepared according to the procedure for 6a using methyl ester 15q (15.5 mg, 0.0397 mmol) in EtOH (1.5 mL) and 20% (wt/wt) aqueous NaOH (1.5 mL). Purification by flash column chromatography (DCM to 99:1 EtOAc/TFA) afforded 8q as a white solid (10.8 mg, 72% yield). $R_f$=0.35 (DCM/EtOAc/TFA 49.5:49.5:1 v/v/v). $^1$H NMR (600 MHz, DMSO-$d_6$) δ 13.00 (br s, 1H), 12.68

(br s, 1H), 8.27 (s, 1H), 8.04 (d, J=2.2 Hz, 1H), 7.88 (d, J=8.9 Hz, 1H), 7.81 (d, J=8.4 Hz, 1H), 7.77 (dd, J=8.5, 2.2 Hz, 1H), 7.57 (s, 1H), 7.29 (d, J=8.4 Hz, 1H), 7.20 (dd, J=8.9, 2.4 Hz, 1H), 7.16 (d, J=8.5 Hz, 1H), 7.13 (d, J=2.2 Hz, 1H), 2.72 (q, J=7.6 Hz, 2H), 1.23 (t, J=7.6 Hz, 3H). $^{13}$C NMR (151 MHz, DMSO-$d_6$) δ 166.4, 160.5 (d, J=240.8 Hz), 155.8, 152.8, 142.2, 134.1, 130.4 (d, J=2.9 Hz), 129.6, 128.8, 128.0 (d, J=3.9 Hz), 127.9, 127.5, 126.6 (d, J=4.6 Hz), 125.7, 125.2, 124.6, 122.3, 118.2, 111.5, 102.2 (d, J=17.9 Hz), 28.3, 15.4. $^{19}$F NMR (376 MHz, DMSO-$d_6$) δ –135.4. HRMS (ESI$^+$) calculated for $[C_{22}H_{18}FN_2O_3]^+$ [M+H]$^+$, 377.1301; found 377.1310.

2-((4-Cyclopropylnaphthalen-2-yl)oxy)-5-(3-fluoro-1H-pyrazol-4-yl)benzoic acid (8r)

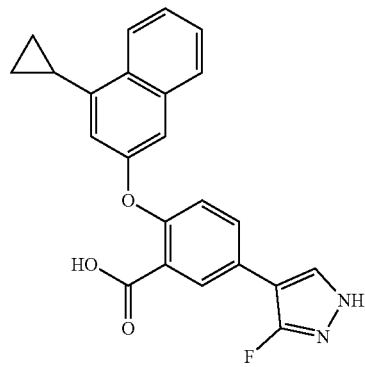

Carboxylic acid 8r was prepared according to the procedure for 6a using methyl ester 15r (15.1 mg, 0.0374 mmol) in EtOH (1.5 mL) and 20% (wt/wt) aqueous NaOH (1.5 mL). Purification by flash column chromatography (DCM to 99:1 EtOAc/TFA) afforded 8r as a sand-colored solid (12.7 mg, 87% yield). $R_f$=0.21 (DCM/EtOAc/TFA 49.5:49.5:1 v/v/v). $^1$H NMR (600 MHz, DMSO-$d_6$) δ 12.98 (br s, 1H), 12.67 (br s, 1H), 8.35-8.31 (m, 1H), 8.27 (app t, J=1.8 Hz, 1H), 8.03 (d, J=2.3 Hz, 1H), 7.80-7.75 (m, 2H), 7.50-7.45 (m, 2H), 7.16 (d, J=8.5 Hz, 1H), 7.02 (d, J=2.0 Hz, 1H), 7.00 (d, J=2.2 Hz, 1H), 2.47-2.40 (m, 1H), 1.10-1.04 (m, 2H), 0.75-0.72 (m, 2H). $^{13}$C NMR (151 MHz, DMSO-$d_6$) δ 166.4, 160.5 (d, J=240.8 Hz), 155.4, 152.7, 141.7, 134.2, 130.4 (d, J=3.0 Hz), 129.4, 128.8, 127.9 (d, J=3.5 Hz), 127.7, 126.6 (d, J=4.6 Hz), 126.5, 125.2, 124.5, 124.1, 122.3, 116.2, 109.8, 102.2 (d, J=17.8 Hz), 12.8, 6.9. $^{19}$F NMR (376 MHz, DMSO-$d_6$) δ –135.4. HRMS (ESI$^+$) calculated for $[C_{23}H_{18}FN_2O_3]^+$ [M+H]$^+$, 389.1301; found 389.1299.

2-((4-Cyclopropyl-7-ethylnaphthalen-2-yl)oxy)-5-(3-fluoro-1H-pyrazol-4-yl)benzoic acid (8s)

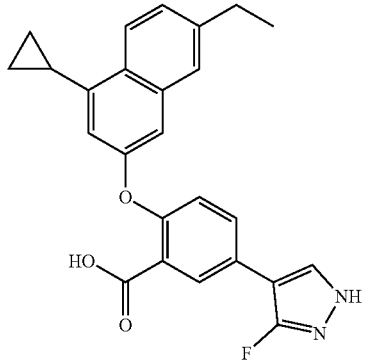 [SMILES: CCc1ccc2c(C3CC3)cc(Oc3ccc(-c4c[nH]nc4F)cc3C(=O)O)cc2c1]

Carboxylic acid 8s was prepared according to the procedure for 6a using methyl ester 15s (8.4 mg, 0.020 mmol) in EtOH (1.5 mL) and 20% (wt/wt) aqueous NaOH (1.5 mL). Purification by flash column chromatography (DCM to 99:1 EtOAc/TFA) afforded 8s as a white solid (7.3 mg, 90% yield). $R_f$=0.25 (DCM/EtOAc/TFA 49.5:49.5:1 v/v/v). $^1$H NMR (500 MHz, DMSO-$d_6$) δ 12.98 (br s, 1H), 12.67 (br s, 1H), 8.26 (s, 1H), 8.24 (d, J=8.6 Hz, 1H), 8.03 (d, J=2.1 Hz, 1H), 7.76 (dd, J=8.5, 2.1 Hz, 1H), 7.56 (s, 1H), 7.35 (dd, J=8.6, 1.8 Hz, 1H), 7.13 (d, J=8.5 Hz, 1H), 6.93 (app s, 2H), 2.72 (q, J=7.5 Hz, 2H), 2.44-2.37 (m, 1H), 1.23 (t, J=7.5 Hz, 3H), 1.08-1.03 (m, 2H), 0.74-0.69 (m, 2H). $^{13}$C NMR (151 MHz, DMSO-$d_6$) δ 166.4, 160.5 (d, J=241.0 Hz), 155.5, 152.8, 142.0, 141.5, 134.5, 130.3 (d, J=2.7 Hz), 128.8, 127.9, 127.9 (d, J=2.5 Hz), 126.5 (d, J=4.7 Hz), 125.6, 125.4, 125.2, 124.1, 122.2, 115.3, 109.7, 102.2 (d, J=17.9 Hz), 28.2, 15.4, 12.7, 6.9. $^{19}$F NMR (376 MHz, DMSO-$d_6$) δ –135.4. HRMS (ESI$^+$) calculated for $[C_{25}H_{22}FN_2O_3]^+$ [M+H]$^+$, 417.1614; found 417.1614.

2-([1,1'-Biphenyl]-4-yloxy)-5-(3-fluoro-1H-pyrazol-4-yl)benzoic acid (8t)

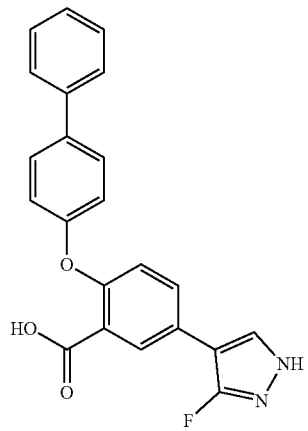 [SMILES: O=C(O)c1cc(-c2c[nH]nc2F)ccc1Oc1ccc(-c2ccccc2)cc1]

Carboxylic acid 8t was prepared according to the procedure for 6a using methyl ester 1St (22.8 mg, 0.0587 mmol) in EtOH (1.5 mL) and 20% (wt/wt) aqueous NaOH (1.5 mL). Purification by flash column chromatography (DCM to 99:1 EtOAc/TFA) afforded 8t as a white solid (18.1 mg, 82% yield). $R_f$=0.25 (DCM/EtOAc/TFA 49.5:49.5:1 v/v/v). $^1$H NMR (600 MHz, DMSO-$d_6$) δ 13.04 (br s, 1H), 12.67 (br s, 1H), 8.27 (s, 1H), 8.02 (d, J=1.8 Hz, 1H), 7.78 (dd, J=8.5, 1.9 Hz, 1H), 7.64 (d, J=8.8 Hz, 2H), 7.63 (d, J=8.2 Hz, 2H), 7.45 (t, J=7.6 Hz, 2H), 7.33 (t, J=7.3 Hz, 1H), 7.17 (d, J=8.5 Hz, 1H), 6.99 (d, J=8.5 Hz, 2H). $^{13}$C NMR (151 MHz, DMSO-$d_6$) δ 166.3, 160.5 (d, J=240.9 Hz), 157.5, 152.6, 139.6, 134.7, 130.4 (d, J=3.3 Hz), 128.9, 128.9, 128.1, 127.9 (d, J=3.8 Hz), 127.1, 126.7 (d, J=4.5 Hz), 126.4, 125.3, 122.4, 117.5, 102.1 (d, J=17.8 Hz). $^{19}$F NMR (376 MHz, DMSO-$d_6$) δ −135.4. HRMS (ESI$^+$) calculated for $[C_{22}H_{16}FN_2O_3]^+$ [M+H]$^+$, 375.1145; found 375.1145.

2-([1,1'-Biphenyl]-3-yloxy)-5-(3-fluoro-1H-pyrazol-4-yl)benzoic acid (8u)

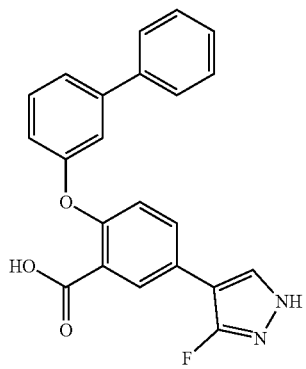 [SMILES: O=C(O)c1cc(-c2c[nH]nc2F)ccc1Oc1cccc(-c2ccccc2)c1]

Carboxylic acid 8u was prepared according to the procedure for 6a using methyl ester 15u (14.0 mg, 0.0360 mmol) in EtOH (1.5 mL) and 20% (wt/wt) aqueous NaOH (1.5 mL). Purification by flash column chromatography (DCM to 99:1 EtOAc/TFA) afforded 8u as a white solid (9.9 mg, 73% yield). $R_f$=0.36 (DCM/EtOAc/TFA 49.5:49.5:1 v/v/v). $^1$H NMR (600 MHz, DMSO-$d_6$) δ 13.03 (br s, 1H), 12.67 (br s, 1H), 8.26 (s, 1H), 8.01 (d, J=1.9 Hz, 1H), 7.76 (dd, J=8.4, 1.7 Hz, 1H), 7.62 (d, J=8.2 Hz, 2H), 7.47-7.42 (m, 3H), 7.41-7.34 (m, 2H), 7.20 (s, 1H), 7.16 (d, J=8.5 Hz, 1H), 6.90 (d, J=7.3 Hz, 1H). $^{13}$C NMR (151 MHz, DMSO-$d_6$) δ 166.4, 160.5 (d, J=239.9 Hz), 158.2, 152.7, 142.0, 139.5, 130.4, 130.3 (d, J=2.8 Hz), 129.0, 128.8, 127.8 (d, J=2.8 Hz), 127.8, 126.7, 126.5 (d, J=4.9 Hz), 125.3, 122.1, 121.2, 116.3, 115.5, 102.1 (d, J=17.9 Hz). $^{19}$F NMR (376 MHz, DMSO-$d_6$) δ −135.4. HRMS (ESI$^+$) calculated for $[C_{22}H_{16}FN_2O_3]^+$ [M+H]$^+$, 375.1145; found 375.1146.

2-((3',5'-Dimethyl-[1,1'-biphenyl]-3-yl)oxy)-5-(3-fluoro-1H-pyrazol-4-yl)benzoic acid (8v)

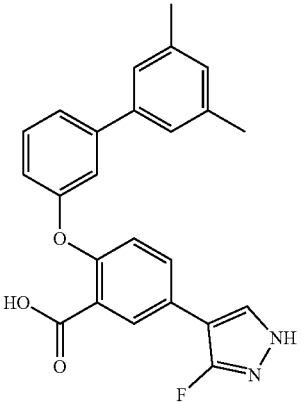 [SMILES: Cc1cc(C)cc(-c2cccc(Oc3ccc(-c4c[nH]nc4F)cc3C(=O)O)c2)c1]

Carboxylic acid 8v was prepared according to the procedure for 6a using methyl ester 15v (10.0 mg, 0.0240 mmol) in EtOH (1.5 mL) and 20% (wt/wt) aqueous NaOH (1.5 mL). Purification by flash column chromatography (DCM to 99:1 EtOAc/TFA) afforded 8v as a white solid (9.7 mg, 99% yield). $R_f$=0.34 (DCM/EtOAc/TFA 49.5:49.5:1 v/v/v). $^1$H NMR (600 MHz, DMSO-$d_6$) δ 13.04 (br s, 1H), 12.67 (br s, 1H), 8.25 (s, 1H), 8.01 (d, J=2.0 Hz, 1H), 7.75 (dd, J=8.5, 2.0 Hz, 1H), 7.41 (t, J=7.9 Hz, 1H), 7.36 (d, J=7.7 Hz, 1H), 7.22 (s, 2H), 7.20 (s, 1H), 7.12 (d, J=8.5 Hz, 1H), 7.00 (s, 1H), 6.87 (dd, J=8.0, 2.2 Hz, 1H), 2.31 (s, 6H). $^{13}$C NMR (151 MHz, DMSO-$d_6$) δ 166.4, 160.5 (d, J=240.8 Hz), 157.9, 152.9, 142.3, 139.4, 138.0, 130.3, 130.3 (d, J=2.9 Hz), 129.2, 128.8, 127.8 (d, J=3.2 Hz), 126.3 (d, J=4.5 Hz), 125.1, 124.5, 121.8, 121.3, 116.2, 115.8, 102.1 (d, J=17.9 Hz), 21.0. $^{19}$F NMR (376 MHz, DMSO-$d_6$) δ −135.4. HRMS (ESI$^+$) calculated for $[C_{24}H_{20}FN_2O_3]^+$ [M+H]$^+$, 403.1458; found 403.1463.

2-((4'-Ethoxy-[1,1'-biphenyl]-3-yl)oxy)-5-(3-fluoro-1H-pyrazol-4-yl)benzoic acid (8w)

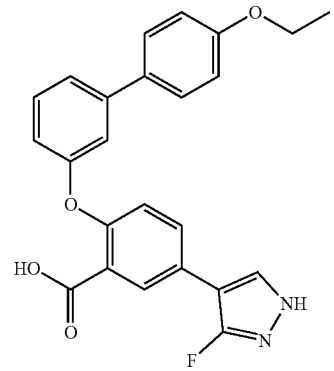 [SMILES: CCOc1ccc(-c2cccc(Oc3ccc(-c4c[nH]nc4F)cc3C(=O)O)c2)cc1]

Carboxylic acid 8w was prepared according to the procedure for 6a using methyl ester 15w (16.0 mg, 0.0370 mmol) in EtOH (1.5 mL) and 20% (wt/wt) aqueous NaOH (1.5 mL). Purification by flash column chromatography (DCM to 99:1 EtOAc/TFA) afforded 8w as a white solid (14.2 mg, 92% yield). $R_f$=0.25 (DCM/EtOAc/TFA 49.5:

49.5:1 v/v/v). $^1$H NMR (600 MHz, DMSO-d$_6$) δ 13.04 (br s, 1H), 12.66 (br s, 1H), 8.26 (s, 1H), 8.01 (d, J=1.8 Hz, 1H), 7.75 (dd, J=8.4, 1.7 Hz, 1H), 7.54 (d, J=8.5 Hz, 2H), 7.39 (app t, J=7.9 Hz, 1H), 7.34 (d, J=7.7 Hz, 1H), 7.16-7.13 (m, 2H), 6.99 (d, J=8.6 Hz, 2H), 6.83 (d, J=9.1 Hz, 1H), 4.05 (q, J=6.9 Hz, 2H), 1.33 (t, J=6.9 Hz, 3H). $^{13}$C NMR (151 MHz, DMSO-d$_6$) δ 166.4, 160.5 (d, J=241.2 Hz), 158.4, 158.2, 152.8, 141.7, 131.6, 130.3, 130.3 (d, J=3.5 Hz), 128.8, 127.8 (d, J=4.1 Hz), 127.8, 126.4 (d, J=4.6 Hz), 125.2, 122.1, 120.7, 115.6, 115.0, 114.8, 102.2 (d, J=17.8 Hz), 63.1, 14.7. $^{19}$F NMR (376 MHz, DMSO-d$_6$) δ −135.4. HRMS (ESI$^+$) calculated for [C$_{24}$H$_{20}$FN$_2$O$_4$]$^+$ [M+1-1]$^+$, 419.1407; found 419.1403.

5-(3-Fluoro-1H-pyrazol-4-yl)-2-((4'-(3-morpholinopropoxy)-[1,1'-biphenyl]-3-yl)oxy)benzoic acid (8x)

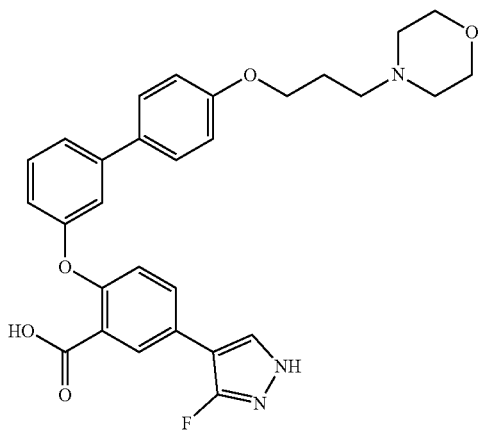 [SMILES: O=C(O)c1cc(-c2c[nH]nc2F)ccc1Oc1cccc(-c2ccc(OCCCN3CCOCC3)cc2)c1]

Carboxylic acid 8x was prepared according to the procedure for 6a using methyl ester 15x (21.0 mg, 0.0395 mmol) in EtOH (1.5 mL) and 20% (wt/wt) aqueous NaOH (1.5 mL). 8x was obtained as a light brown solid (20.2 mg, 99% yield). $^1$H NMR (600 MHz, DMSO-d$_6$) δ 12.69 (br s, 1H), 10.76 (br s, 1H), 8.26 (s, 1H), 8.01 (s, 1H), 7.75 (d, J=8.4 Hz, 1H), 7.56 (d, J=8.2 Hz, 2H), 7.40 (app t, J=7.9 Hz, 1H), 7.34 (d, J=7.5 Hz, 1H), 7.18-7.11 (m, 2H), 7.01 (d, J=8.2 Hz, 2H), 6.84 (d, J=7.7 Hz, 1H), 4.08 (t, J=5.8 Hz, 2H), 3.87-3.65 (m, 6H), 2.97 (s, 4H), 2.08 (s, 2H). $^{13}$C NMR (151 MHz, DMSO-d$_6$) δ 166.4, 160.5 (d, J=240.9 Hz), 158.2, 152.8, 141.6, 131.9, 130.3, 130.3 (d, J=3.6 Hz), 129.1, 128.8, 128.7, 127.8, 127.8 (d, J=3.5 Hz), 126.4 (d, J=4.8 Hz), 125.2, 122.0, 120.7, 115.6, 115.0, 102.1 (d, J=18.1 Hz), 68.3, 65.3, 63.9, 59.8, 29.0. $^{19}$F NMR (376 MHz, DMSO-d$_6$) δ −135.4. HRMS (ESI$^+$) calculated for [C$_{29}$H$_{29}$FN$_3$O$_5$]$^+$ [M+H]$^+$, 518.2091; found 518.2097.

Synthesis of 8h

5-Bromo-2-(naphthalen-2-yloxy)aniline (17)

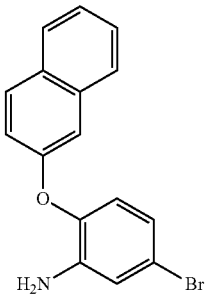 [SMILES: Nc1cc(Br)ccc1Oc1ccc2ccccc2c1]

This procedure was adapted from Maiti et al.[2] To a flame-dried vial were added 2-naphthol (400 mg, 2.77 mmol), 5-bromo-2-iodoaniline (992 mg, 3.33 mmol), copper (I) iodide (26.4 mg, 0.139 mmol), 2-picolinic acid (34.2 mg, 0.277 mmol), potassium phosphate (1.18 g, 5.55 mmol), and anhydrous DMSO (3.5 mL). The vial was sealed, degassed with N$_2$ for 7 minutes, and heated at 80° C. for 24 hours. The reaction mixture was diluted with EtOAc (100 mL) and washed with brine (100 mL). The organic phase was dried over anhydrous Na$_2$SO$_4$ and concentrated under reduced pressure. Purification by flash column chromatography (hexanes to 90:10 hexanes/EtOAc) afforded 17 as a russet-colored solid (292 mg, 33% yield). R$_f$=0.29 (hexanes/EtOAc 90:10 v/v). $^1$H NMR (600 MHz, CDCl$_3$) δ 7.84-7.79 (m, 2H), 7.68 (d, J=8.2 Hz, 1H), 7.45 (app t, J=7.5 Hz, 1H), 7.39 (app t, J=7.5 Hz, 1H), 7.26 (s, 1H), 7.21 (s, 1H), 7.00 (s, 1H), 6.84 (d, J=8.5 Hz, 1H), 6.78 (d, J=8.5 Hz, 1H), 3.90 (br s, 2H). $^{13}$C NMR (151 MHz, CDCl$_3$) δ 155.0, 142.3, 140.3, 134.4, 130.2, 130.2, 127.9, 127.2, 126.8, 124.8, 121.8, 121.5, 119.1, 118.9, 117.7, 112.0. MS (ESI$^+$) calculated for [C$_{16}$H$_{13}$BrNO]$^+$ [M+H]$^+$, 314.0; found 314.1.

(5-Bromo-2-(naphthalen-2-yloxy)phenyl)(methyl)sulfane (18)

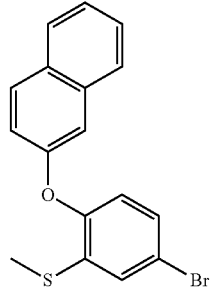 [SMILES: CSc1cc(Br)ccc1Oc1ccc2ccccc2c1]

This procedure was adapted from Hanson et al.[3] To a mixture of 17 (289 mg, 0.921 mmol) and dimethyl disulfide (2.5 mL) under N$_2$ atmosphere at 90° C. was added tert-butyl nitrite (0.18 mL, 1.4 mmol) in five equivalent portions over 10 minutes. The contents were stirred for 20 minutes at 90° C. before removal of the solvent in vacuo. Purification by flash column chromatography (hexanes to 90:10 hexanes/EtOAc) afforded 18 as a yellow oil (255 mg, 80% yield). R$_f$=0.59 (hexanes/EtOAc 90:10 v/v). $^1$H NMR (600 MHz, CDCl$_3$) δ 7.86-7.79 (m, 2H), 7.69 (d, J=8.2 Hz, 1H), 7.45 (app t, J=7.5 Hz, 1H), 7.40 (app t, J=7.5 Hz, 1H), 7.36 (s, 1H), 7.26-7.21 (m, 3H), 6.81 (d, J=8.5 Hz, 1H), 2.46 (s, 3H). $^{13}$C NMR (151 MHz, CDCl$_3$) δ 154.7, 152.5, 134.4, 133.7, 130.4, 130.2, 128.8, 128.7, 127.9, 127.3, 126.8, 124.9, 120.9, 119.3, 117.4, 113.2, 14.8.

2-(4-Bromo-2-(methylsulfonyl)phenoxy)naphthalene (19)

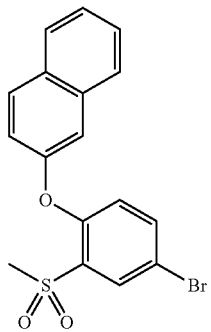 [SMILES: CS(=O)(=O)c1cc(Br)ccc1Oc1ccc2ccccc2c1]

This procedure was adapted from Hanson et al.[3] To a flask containing 18 (83.9 mg, 0.243 mmol) dissolved in acetone (1.5 mL) and water (1.5 mL) cooled to 0° C. was added oxone (179 mg, 0.292 mmol). The contents were slowly allowed to come to room temperature. After 17 hours, the reaction mixture was diluted with EtOAc (75 mL) and washed with brine (75 mL). The organic phase was dried over anhydrous Na$_2$SO$_4$ and concentrated under reduced pressure. Purification by flash column chromatography (hexanes to 70:30 hexanes/EtOAc) afforded 19 as a clear oil (14.9 mg, 16% yield). R$_f$=0.43 (hexanes/EtOAc 75:25 v/v). $^1$H NMR (400 MHz, CDCl$_3$) δ 8.22 (d, J=2.4 Hz, 1H), 7.91 (d, J=8.9 Hz, 1H), 7.87 (d, J=7.7 Hz, 1H), 7.77 (d, J=7.7 Hz, 1H), 7.61 (dd, J=8.7, 2.3 Hz, 1H), 7.55-7.47 (m, 3H), 7.27 (dd, J=9.2, 2.3 Hz, 1H), 6.85 (d, J=8.8 Hz, 1H), 3.36 (s, 3H). $^{13}$C NMR (101 MHz, CDCl$_3$) δ 155.1, 152.8, 138.2, 134.3, 132.5, 132.4, 131.3, 130.8, 128.0, 127.6, 127.2, 126.0, 120.5, 119.9, 116.7, 115.6, 43.6. MS (ESI$^+$) calculated for [C$_{17}$H$_{14}$BrO$_3$S]$^+$ [M+H]$^+$, 377.0; found 377.0.

4-(3-(Methylsulfonyl)-4-(naphthalen-2-yloxy)phenyl)-1H-pyrazole (8h)

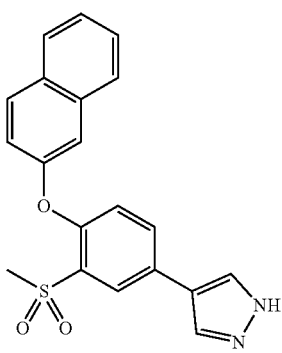 [SMILES: CS(=O)(=O)c1cc(-c2cn[nH]c2)ccc1Oc1ccc2ccccc2c1]

Methyl sulfone 8h was prepared according to the procedure for 13a using phenyl bromide 19 (14.9 mg, 0.0395 mmol), 4-pyrazoleboronic acid pincol ester (7.7 mg, 0.040 mmol), Cs$_2$CO$_3$ (38.6 mg, 0.118 mmol), and Pd(dppf)Cl$_2$.DCM (3.2 mg, 0.0040 mmol) in dioxane (1.5 mL) and water (0.6 mL). Purification by flash column chromatography (hexanes to EtOAc with 2% MeOH throughout) afforded 8h as a white solid (4.4 mg, 30% yield). R$_f$=0.28 (hexanes/EtOAc/MeOH 47.5:47.5:5 v/v/v). $^1$H NMR (400 MHz, CDCl$_3$) δ 8.20 (s, 1H), 7.92-7.85 (m, 4H), 7.77 (d, J=7.9 Hz, 1H), 7.64 (d, J=8.4 Hz, 1H), 7.54-7.45 (m, 3H), 7.32 (d, J=8.9 Hz, 1H), 7.00 (d, J=8.5 Hz, 1H), 3.38 (s, 3H). $^{13}$C NMR (101 MHz, CDCl$_3$) δ 154.2, 153.4, 134.3, 132.3, 131.5, 131.5, 131.4, 131.1, 130.6, 128.4, 128.0, 127.5, 127.1, 126.6, 125.7, 120.0, 119.8, 116.2, 43.6. HRMS (ESI$^+$) calculated for [C$_{20}$H$_{17}$N$_2$O$_3$S]$^+$ [M+H]$^+$, 365.0960; found 365.0959.

Synthesis of 8i

5-Bromo-2-hydroxybenzenesulfonamide (20)

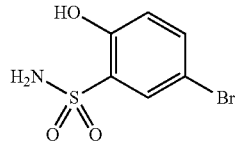 [SMILES: NS(=O)(=O)c1cc(Br)ccc1O]

To a suspension of 5-bromo-2-methoxybenzenesulfonamide (300 mg, 1.13 mmol) in anhydrous DCM (6 mL) cooled to −78° C. was added boron tribromide (1M in DCM, 2.0 mL, 2.0 mmol) dropwise. The mixture was stirred at −78° C. for 1 hour, then at room temperature for 2 hours. After quenching at −78° C. with MeOH (1 mL), the reaction mixture was diluted with EtOAc (100 mL) and washed with brine (100 mL). The organic phase was dried over anhydrous Na$_2$SO$_4$ and concentrated under reduced pressure. Purification by flash column chromatography (DCM to EtOAc) afforded 20 as a white solid (218 mg, 77% yield). R$_f$=0.38 (DCM/EtOAc 50:50 v/v). $^1$H NMR (400 MHz, DMSO-d$_6$) δ 10.98 (br s, 1H), 7.71 (d, J=2.0 Hz, 1H), 7.57 (dd, J=8.7, 2.0 Hz, 1H), 7.12 (br s, 2H), 6.95 (d, J=8.7 Hz, 1H). $^{13}$C NMR (101 MHz, DMSO-d$_6$) δ 154.1, 135.8, 131.3, 129.6, 119.3, 108.9. MS (ESI$^+$) calculated for [C$_6$H$_7$BrNO$_3$S]$^+$ [M+H]$^+$, 251.9; found 251.9.

5-Bromo-2-(naphthalen-2-yloxy)benzenesulfonamide (21)

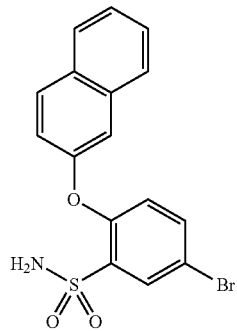 [SMILES: NS(=O)(=O)c1cc(Br)ccc1Oc1ccc2ccccc2c1]

Phenyl bromide 21 was prepared according to the procedure for 17 using phenol 20 (213 mg, 0.846 mmol), 2-iodonaphthalene (181 mg, 0.711 mmol), copper (I) iodide (8.1 mg, 0.042 mmol), 2-picolinic acid (10.4 mg, 0.0846 mmol), and potassium phosphate (359 mg, 1.69 mmol) in anhydrous DMSO (2 mL). Purification by flash column chromatography (hexanes to EtOAc) afforded 21 as a fuschia oil (99.2 mg, 37% yield). $R_f$=0.18 (hexanes/EtOAc 50:50 v/v). $^1$H NMR (400 MHz, DMSO-$d_6$) δ 11.30 (br s, 1H), 10.34 (br s, 1H), 7.82-7.75 (m, 3H), 7.72 (d, J=7.9 Hz, 1H), 7.55-7.53 (m, 1H), 7.51 (dd, J=8.8, 2.5 Hz, 1H), 7.43 (app t, J=7.1 Hz, 1H), 7.38 (app t, J=7.3 Hz, 1H), 7.34 (dd, J=8.7, 1.8 Hz, 1H), 6.87 (d, J=8.7 Hz, 1H). $^{13}$C NMR (101 MHz, DMSO-$d_6$) δ 154.8, 137.2, 135.4, 133.2, 131.9, 129.8, 128.8, 127.5, 127.0, 126.6, 126.5, 124.9, 120.0, 119.5, 115.2, 109.0. MS (ESI$^+$) calculated for $[C_{16}H_{13}BrNO_3S]^+$ $[M+H]^+$, 378.0; found 378.0.

2-(Naphthalen-2-yloxy)-5-(1H-pyrazol-4-yl)benzenesulfonamide (8i)

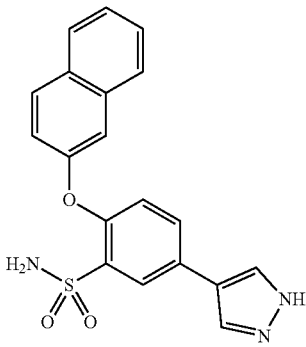 [SMILES: NS(=O)(=O)c1cc(-c2cn[nH]c2)ccc1Oc1ccc2ccccc2c1]

Sulfonamide 8i was prepared according to the procedure for 13a using phenyl bromide 21 (90.0 mg, 0.238 mmol), 4-pyrazoleboronic acid pincol ester (46.2 mg, 0.238 mmol), $Cs_2CO_3$ (233 mg, 0.714 mmol), and Pd(dppf)$Cl_2$·DCM (19.4 mg, 0.0238 mmol) in dioxane (2.5 mL) and water (1 mL). Purification by flash column chromatography (DCM to EtOAc with 2% MeOH throughout) afforded 8i as a white solid (13.1 mg, 15% yield). $R_f$=0.31 (DCM/EtOAc/MeOH 47.5:47.5:5 v/v/v). $^1$H NMR (400 MHz, DMSO-$d_6$) δ 12.89 (br s, 1H), 10.79 (br s, 1H), 10.22 (br s, 1H), 8.10 (s, 1H), 7.91 (d, J=2.2 Hz, 1H), 7.78 (s, 1H), 7.76-7.71 (m, 2H), 7.69 (d, J=8.2 Hz, 1H), 7.59-7.53 (m, 2H), 7.42-7.30 (m, 3H), 6.88 (d, J=8.5 Hz, 1H). $^{13}$C NMR (151 MHz, DMSO-$d_6$) δ 153.5, 135.8, 133.2, 131.5, 129.6, 128.6, 127.4, 127.0, 126.5, 126.3, 125.0, 124.8, 124.6, 123.8, 119.9, 119.9, 117.5, 114.5. HRMS (ESI$^+$) calculated for $[C_{19}H_{16}N_3O_3S]^+$ $[M+H]^+$, 366.0912; found 366.0912.

Synthesis of Fluorinated Pyrazole 16

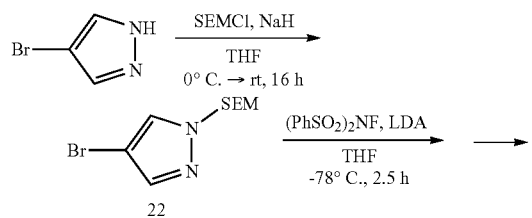

4-Bromo-1-((2-(trimethylsilyl)ethoxy)methyl)-1H-pyrazole (22)

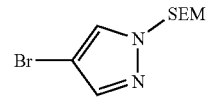

To a solution of 4-bromopyrazole (4.00 g, 27.2 mmol) in anhydrous THF (25 mL) cooled to 0° C. was added NaH (60% dispersion in mineral oil, 1.63 g, 40.8 mmol) in four equivalent portions. The contents were stirred at 0° C. for 30 minutes, and then 2-(trimethylsilyl)ethoxymethyl chloride (5.06 mL, 28.6 mmol) was added slowly. The reaction was stirred at room temperature for 16 hours, diluted with diethyl ether (200 mL), and washed with brine (100 mL). The organic phase was dried over anhydrous $Na_2SO_4$ and concentrated under reduced pressure to afford 22 as a clear oil (7.50 g, 99% yield). $^1$H NMR (400 MHz, CDCl$_3$) δ 7.59 (s, 1H), 7.49 (s, 1H), 5.38 (s, 2H), 3.55 (t, J=8.1 Hz, 2H), 0.90 (t, J=8.5 Hz, 2H), −0.02 (s, 9H). $^{13}$C NMR (101 MHz, CDCl$_3$) δ 140.5, 129.6, 94.8, 80.8, 67.1, 17.9, −1.3.

4-Bromo-3-fluoro-1-((2-(trimethylsilyl)ethoxy)methyl)-1H-pyrazole (23)

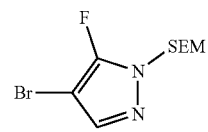

This procedure was adapted from Albrecht et al.[4] To a solution of bromopyrazole 22 (4.50 g, 16.2 mmol) in anhydrous THF (30 mL) cooled to −78° C. was slowly added lithium diisopropylamide (2M in THF, 12.2 mL, 24.3 mmol). The contents were stirred at −78° C. for 1.5 hours, and then N-fluorobenzenesulfonimide (dissolved in 15 mL anhydrous THF, 7.68 g, 24.3 mmol) was added followed by a THF rinse (15 mL). The mixture was stirred at −78° C. for 1 hour before quenching with saturated $NH_4Cl$ (30 mL). The solvent was removed in vacuo, and the residue was dissolved in EtOAc (200 mL) and washed with brine (100 mL). The organic phase was dried over anhydrous $Na_2SO_4$ and concentrated under reduced pressure. Purification by flash column chromatography (hexanes to 95:5 hexanes/EtOAc)

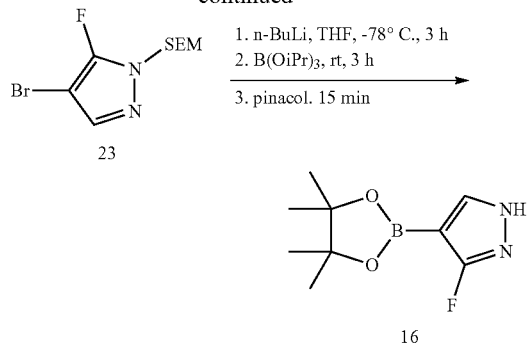

4-Bromo-1-((2-(trimethylsilyl)ethoxy)methyl)-1H-pyrazole (22)

afforded 23 as a white solid (814 mg, 17% yield). $R_f$=0.41 (hexanes/EtOAc 90:10 v/v). $^1$H NMR (400 MHz, CDCl$_3$) δ 7.40 (d, J=2.2 Hz, 1H), 5.35 (s, 2H), 3.61 (t, J=8.2 Hz, 2H), 0.91 (t, J=8.2 Hz, 2H), −0.01 (s, 9H). $^{13}$C NMR (101 MHz, CDCl$_3$) δ 151.4 (d, J=277.4), 139.5 (d, J=6.8 Hz), 76.5 (d, J=1.3 Hz), 74.1 (d, J=17.8 Hz), 67.2, 17.6, −1.5. $^{19}$F NMR (376 MHz, DMSO-d$_6$) δ −136.4.

3-Fluoro-4-(4,4,5,5-tetramethyl-1,3,2-dioxaborolan-2-yl)-1H-pyrazole (16)

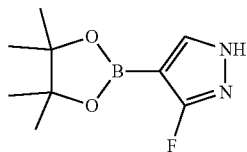

To a slurry of n-BuLi (2.5 M in hexanes, 3.30 mL, 8.26 mmol) in anhydrous THF (3 mL) cooled to −78° C. was added bromopyrazole 23 (dissolved in 4 mL anhydrous THF, 813 mg, 2.75 mmol) dropwise, followed by a THF rinse (4 mL). The contents were stirred for 1 hour at −78° C., then at room temperature for 2 hours. The reaction was cooled back to −78° C. for the addition of triisopropylborate (0.76 mL, 3.3 mmol), after which, it was returned to room temperature for 3 hours. Pinacol (dissolved in 6 mL anhydrous THF, 439 mg, 3.72 mmol) was added dropwise. After stirring for 15 minutes, the reaction mixture was quenched with glacial AcOH (0.5 mL) and filtered through a plug of celite. The filtrate was diluted in EtOAc (100 mL) and washed with brine (100 mL). The organic phase was dried over anhydrous Na$_2$SO$_4$ and concentrated under reduced pressure. Purification by flash column chromatography (hexanes to 50:50 hexanes/EtOAc) afforded 16 as a pale yellow solid (226 mg, 39% yield). $R_f$=0.45 (hexanes/EtOAc 50:50 v/v). $^1$H NMR (500 MHz, DMSO-d$_6$) δ 12.63 (br s, 1H), 7.84 (s, 1H), 1.25 (s, 12H). $^{13}$C NMR (126 MHz, DMSO-d$_6$) δ 156.0 (d, J=244.7), 137.5, 83.0, 24.5. $^{19}$F NMR (470 MHz, DMSO-d$_6$) δ −128.2. MS (ESI$^+$) calculated for [C$_9$H$_{15}$BFN$_2$O$_2$]$^+$ [M+H]$^+$, 213.1; found 213.1.

Synthesis of Acenaphthyl Intermediate 28

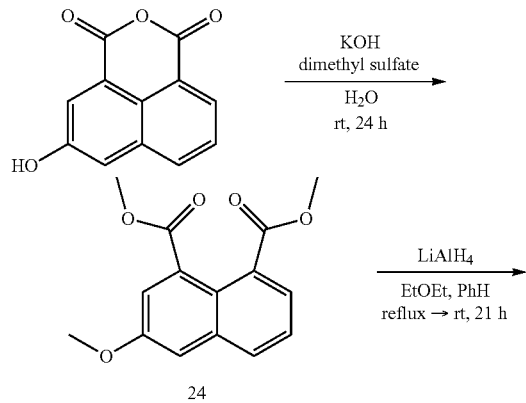

Dimethyl naphthalene-1,8-dicarboxylate (24)

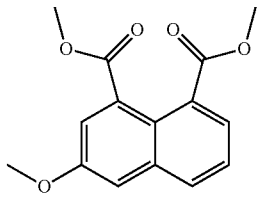

This procedure was adapted from Brown et al.[5] To a suspension of 3-hydroxy-1,8-naphthalic anhydride (5.00 g, 23.3 mmol) in water (20 mL) was added KOH (dissolved in 20 mL water, 4.32 g, 77.0 mmol). Dimethyl sulfate (11.1 mL, 117 mmol) was added dropwise, and the mixture was stirred at room temperature for 6 hours. Additional portions of KOH (dissolved in 100 mL water, 5.63 g, 23.3 mmol) and dimethyl sulfate (11.1 mL, 117 mmol) were added all at once, and the reaction was stirred at room temperature for 18 hours. The reaction mixture was filtered through a pad of celite. The filtrate was diluted in diethyl ether (250 mL) and washed with brine (100 mL). The organic phase was dried over anhydrous Na$_2$SO$_4$ and concentrated under reduced pressure to afford 24 as a yellow gel (6.40 g, 99% yield). $R_f$=0.55 (hexanes/EtOAc 50:50 v/v). $^1$H NMR (400 MHz, DMSO-d$_6$) δ 8.11 (dd, J=8.2, 0.9 Hz, 1H), 7.77 (dd, J=7.1, 1.1 Hz, 1H), 7.66 (d, J=2.7 Hz, 1H), 7.60 (app t, J=8.1 Hz, 1H), 7.55 (d, J=2.7 Hz, 1H), 3.93 (s, 3H), 3.81 (s, 3H), 3.80 (s, 3H). $^{13}$C NMR (101 MHz, DMSO-d$_6$) δ 168.5, 167.9, 156.1, 135.7, 131.5, 131.0, 129.3, 127.5, 126.1, 122.0, 121.7, 110.6, 55.8, 52.2, 52.0. MS (ESI$^+$) calculated for [C$_{14}$H$_{11}$O$_4$]$^+$ [M−OCH$_3$]$^+$, 243.1; found 243.1.

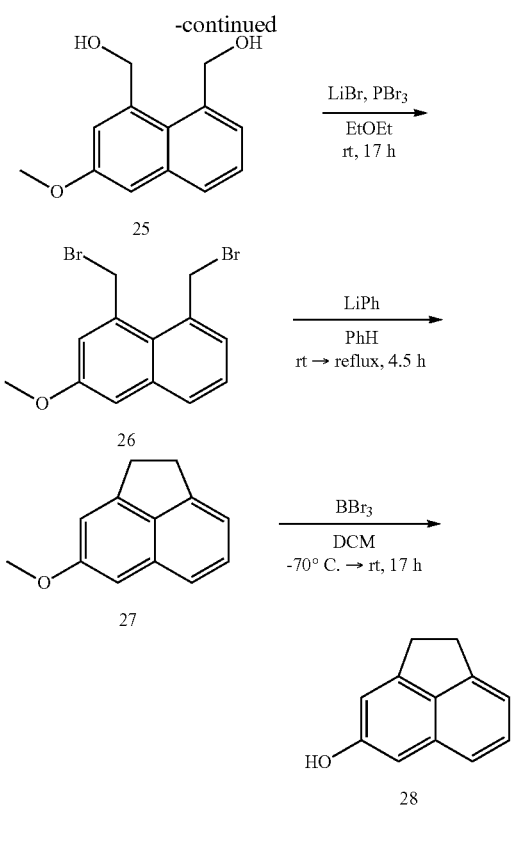

(3-Methoxynaphthalene-1,8-diyl)dimethanol (25)

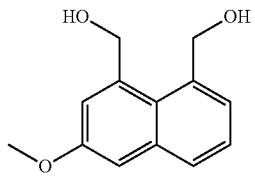 [SMILES: COc1cc(CO)c2c(CO)cccc2c1]

This procedure was adapted from Brown et al.[5] To a suspension of diester 24 (6.43 g, 23.4 mmol) in anhydrous diethyl ether (120 mL) and anhydrous benzene (11 mL) was slowly added lithium aluminium hydride (2.63 g, 70.3 mmol). Once frothing subsided, the walls of the flask were washed with more diethyl ether (15 mL), and the contents were heated at reflux for 5 hours and then at room temperature for 16 hours. The reaction was quenched with water (2 mL), a solution of 5M aqueous NaOH (2 mL), and an additional portion of water (6 mL). The contents were stirred for 15 minutes. A few scoops of $MgSO_4$ were added, and then the mixture was stirred for another 15 minutes. The contents were filtered, and the solid was collected and dried to afford 25 as a white solid (2.95 g, 58% yield). $R_f$=0.32 (hexanes/EtOAc 40:60 v/v). $^1$H NMR (600 MHz, DMSO-$d_6$) δ 7.76 (d, J=7.9 Hz, 1H), 7.43 (d, J=6.5 Hz, 1H), 7.38 (app t, J=7.5 Hz, 1H), 7.32 (d, J=2.4 Hz, 1H), 7.25 (d, J=2.5 Hz, 1H), 5.31 (app t, J=5.5 Hz, 1H), 5.24 (t, J=5.4 Hz, 1H), 5.08 (d, J=5.5 Hz, 2H), 4.98 (d, J=5.4 Hz, 2H), 3.87 (s, 3H). $^{13}$C NMR (151 MHz, DMSO-$d_6$) δ 155.9, 140.9, 138.4, 136.7, 128.1, 126.0, 125.3, 125.3, 119.3, 106.5, 63.8, 62.9, 55.0. MS (ESI$^+$) calculated for $[C_{13}H_{13}O_2]^+$ [M-OH]$^+$, 201.1; found 201.1.

1,8-Bis(bromomethyl)-3-methoxynaphthalene (26)

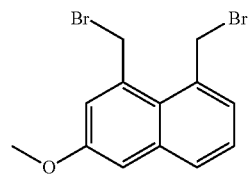 [SMILES: COc1cc(CBr)c2c(CBr)cccc2c1]

This procedure was adapted from Brown et al.[5] To a suspension of diol 25 (2.95 g, 13.5 mmol) and LiBr (705 mg, 8.11 mmol) in anhydrous diethyl ether (140 mL) under $N_2$ atmosphere at 0° C. was slowly added phosphorus tribromide (3.20 mL, 33.8 mmol). The contents were stirred at room temperature for 17 hours, then quenched at 0° C. with water (4 mL). The reaction mixture was diluted with diethyl ether (250 mL) and washed with brine (100 mL). The organic phase was dried over anhydrous $Na_2SO_4$ and concentrated under reduced pressure to afford 26 as an orange solid (4.56 g, 98% yield). $R_f$=0.66 (hexanes/EtOAc 75:25 v/v). $^1$H NMR (400 MHz, CDCl$_3$) δ 7.77 (d, J=7.9 Hz, 1H), 7.49-7.44 (m, 1H), 7.40 (app t, J=7.5 Hz, 1H), 7.29 (s, 1H), 7.18 (s, 1H), 5.25 (s, 2H), 5.23 (s, 2H), 3.92 (s, 3H). $^{13}$C NMR (101 MHz, CDCl$_3$) δ 156.5, 137.9, 135.2, 133.6, 130.9, 130.8, 126.3, 125.2, 124.5, 109.7, 55.5, 37.4, 36.7. MS (ESI$^+$) calculated for $[C_{13}H_{13}Br_2O]^+$ [M+H]$^+$, 342.9; found 342.9.

4-Methoxy-1,2-dihydroacenaphthylene (27)

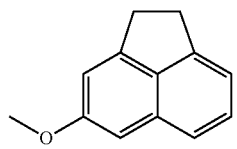

To a solution of dibromide 26 (678 mg, 1.97 mmol) in anhydrous benzene (40 mL) was added phenyllithium (1.8 M in di-n-butyl ether, 1.20 mL, 2.17 mmol) dropwise. The reaction was stirred at room temperature for 1 hour and then heated at reflux for 3.5 hours. The solvent was removed in vacuo, and the residue was dissolved in EtOAc (100 mL) and washed with brine (100 mL). The organic phase was dried over anhydrous $Na_2SO_4$ and concentrated under reduced pressure. Purification by flash column chromatography (hexanes to 90:10 hexanes/EtOAc) afforded 27 as a yellow solid (274 mg, 75% yield). $R_f$=0.67 (hexanes/EtOAc 90:10 v/v). $^1$H NMR (400 MHz, CDCl$_3$) δ 7.47 (d, J=8.1 Hz, 1H), 7.40 (app t, J=6.9 Hz, 1H), 7.14 (d, J=6.8 Hz, 1H), 6.94 (s, 1H), 6.91 (s, 1H), 3.91 (s, 3H), 3.41-3.32 (m, 4H). $^{13}$C NMR (101 MHz, CDCl$_3$) δ 160.5, 147.9, 145.7, 135.2, 132.2, 128.6, 121.3, 117.3, 112.2, 101.0, 55.7, 30.8, 30.2. MS (ESI$^+$) calculated for $[C_{13}H_{13}O]^+$ [M+H]$^+$, 185.1; found 185.1.

1,2-Dihydroacenaphthylen-4-ol (28)

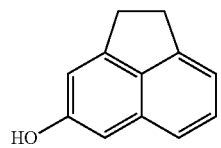 [SMILES: Oc1cc2c3c(cccc3c1)CC2]

Alcohol 28 was prepared according to the procedure for 20 using methyl ether 27 (831 mg, 4.51 mmol) and boron tribromide (1M in DCM, 8.11 mL, 8.11 mmol) in anhydrous DCM (31 mL). Purification by flash column chromatography (hexanes to 75:25 hexanes/EtOAc) afforded 28 as a cream-colored solid (534 mg, 70% yield). $R_f$=0.45 (hexanes/EtOAc 75:25 v/v). $^1$H NMR (600 MHz, CDCl$_3$) δ 7.43-7.37 (m, 2H), 7.13 (d, J=7.4 Hz, 1H), 6.91-6.88 (m, 2H), 4.93 (s, 1H), 3.40-3.37 (m, 2H), 3.36-3.33 (m, 2H). $^{13}$C NMR (151 MHz, CDCl$_3$) δ 156.0, 148.7, 145.9, 135.1, 132.3, 128.8, 121.0, 117.2, 111.3, 104.6, 30.8, 30.3. MS (ESI$^+$) calculated for $[C_{12}H_{11}O]^+$ [M+H]$^+$, 171.1; found 171.1.

Synthesis of Naphthol Intermediates 31o and 31s

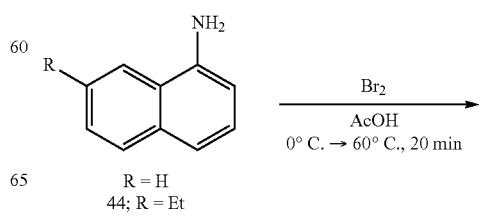

2,4-dibromo-7-ethylnaphthalen-1-amine (29s)

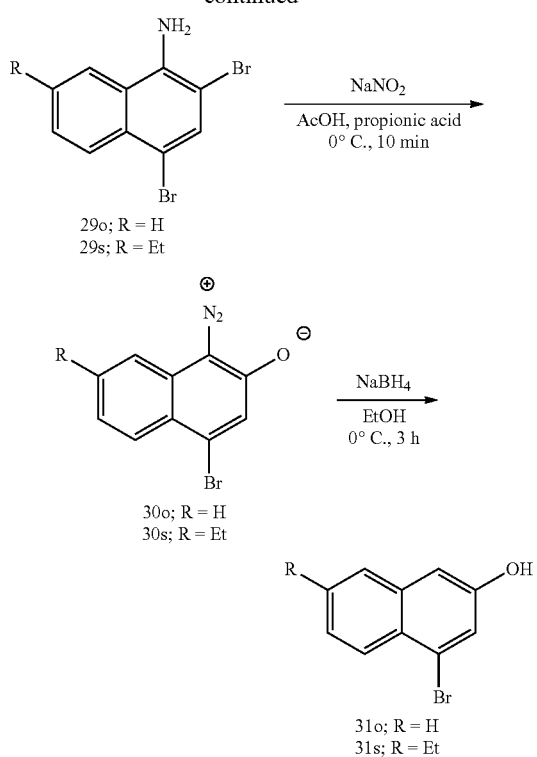

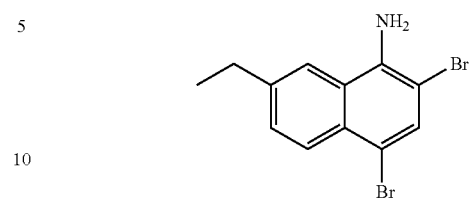

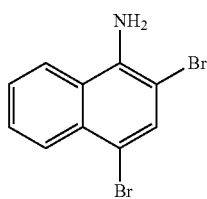 [SMILES: Nc1c(Br)cc(Br)c2ccccc12]

2,4-Dibromonaphthalen-1-amine (29o)

This procedure was adapted from MacLean et al.[6] To a solution of 1-naphthylamine (5.00 g, 34.9 mmol) in glacial AcOH (15 mL) cooled to 0° C. was slowly added bromine (dissolved in 25 mL glacial AcOH, 3.96 mL, 76.8 mmol). The reaction was stirred at 0° C. for 5 minutes, then at 60° C. for another 15 minutes. The mixture was cooled to room temperature. The precipitate was collected by suction filtration and washed with AcOH (50 mL). The purple solid was suspended in water (70 mL) and stirred, adding NaOH until the solution tested alkaline. The mixture was cooled to 0° C., and the precipitate was collected by filtration and washed with water until the filtrate ran clear. The solid was air dried overnight to afford 29o as a purple solid (9.47 g, 90% yield). $^1$H NMR (400 MHz, CDCl$_3$) δ 8.17 (d, J=8.9 Hz, 1H), 7.83-7.77 (m, 2H), 7.62-7.57 (m, 1H), 7.56-7.50 (m, 1H), 4.65 (br s, 2H). $^{13}$C NMR (101 MHz, CDCl$_3$) δ 139.7, 132.8, 131.5, 128.2, 127.5, 126.6, 124.5, 121.5, 111.0, 103.5. MS (ESI$^+$) calculated for [C$_{10}$H$_8$Br$_2$N]$^+$ [M+H]$^+$, 301.9; found 301.9.

Dibromide 29s was prepared according to the procedure for 29o using aminonaphthalene 44 (1.10 g, 6.42 mmol) and bromine (0.73 mL, 14 mmol) in glacial AcOH (28 mL). Purification by filtration afforded 29s as a brown solid (1.80 g, 85% yield). R$_f$=0.38 (hexanes/EtOAc 90:10 v/v). $^1$H NMR (600 MHz, CDCl$_3$) δ 8.08 (d, J=8.6 Hz, 1H), 7.73 (s, 1H), 7.56 (s, 1H), 7.46 (d, J=8.6 Hz, 1H), 4.61 (br s, 2H), 2.85 (q, J=7.6 Hz, 2H), 1.33 (t, J=7.6 Hz, 3H). $^{13}$C NMR (151 MHz, CDCl$_3$) δ 143.0, 139.3, 131.8, 130.0, 128.6, 128.2, 124.8, 119.5, 111.1, 103.7, 29.3, 15.8. MS (ESI$^+$) calculated for [C$_{12}$H$_{12}$Br$_2$N]$^+$[M+H]$^+$, 329.9; found 329.9.

4-bromo-1-diazonionaphthalen-2-olate (30o)

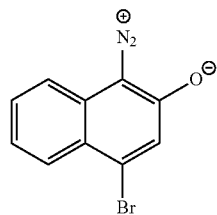

This procedure was adapted from MacLean et al.[6] To a solution of dibromide 29o (9.47 g, 31.4 mmol) in glacial AcOH (160 mL) and propionic acid (30 mL) cooled to 0° C. was added NaNO$_2$ (2.28 g, 31.4 mmol) in four equivalent portions. The reaction was stirred for 10 minutes. Water (160 mL) was added, and the mixture was filtered quickly. The filtrate was diluted with more water (1 L), and the product was allowed to precipitate overnight. Filtration afforded 30o as a brown solid (4.96 g, 63% yield). $^1$H NMR (600 MHz, DMSO-d$_6$) δ 7.99 (d, J=8.1 Hz, 1H), 7.69-7.63 (m, 2H), 7.45-7.40 (m, 1H), 7.20 (s, 1H). $^{13}$C NMR (151 MHz, DMSO-d$_6$) δ 176.0, 137.1, 130.9, 129.3, 129.2, 126.9, 125.3, 123.5, 121.3, 78.3. MS (ESI$^+$) calculated for [C$_{10}$H$_6$BrN$_2$O]$^+$ [M+H]$^+$, 249.0; found 248.9.

4-bromo-1-diazonio-7-ethylnaphthalen-2-olate (30s)

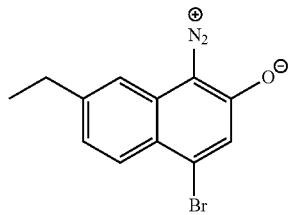

Zwitterion 30s was prepared according to the procedure for 30o using dibromide 29s (1.80 g, 5.48 mmol) and NaNO$_2$ (397 mg, 5.75 mmol) in glacial AcOH (25 mL) and propionic acid (5 mL). Purification by filtration afforded 30s as a brown solid (1.02 g, 67% yield). R$_f$=0.38 (hexanes/EtOAc 90:10 v/v). $^1$H NMR (400 MHz, CDCl$_3$) δ 7.98 (d, J=8.3 Hz, 1H), 7.20 (d, J=8.3 Hz, 1H), 7.10 (s, 1H), 7.06 (s, 1H), 2.78 (q, J=7.6 Hz, 2H), 1.30 (t, J=7.6 Hz, 3H). $^{13}$C NMR (101 MHz, CDCl$_3$) δ 166.2, 148.0, 138.7, 130.6, 129.1, 126.9, 125.8, 123.2, 118.8, 110.2, 29.1, 15.5. MS (ESI$^+$) calculated for [C$_{12}$H$_{10}$BrN$_2$O]$^+$ [M+H]$^+$, 277.0; found 277.0.

4-Bromonaphthalen-2-ol (31o)

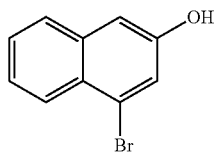 [SMILES: Oc1cc(Br)c2ccccc2c1]

This procedure was adapted from MacLean et al.[6] To a suspension of zwitterion 30o (4.96 g, 19.9 mmol) in EtOH (100 mL) cooled to 0° C. was slowly added sodium borohydride (791 mg, 20.9 mmol). After 3 hours at 0° C., the mixture was poured into 300 mL of ice water. Once the ice melted, the product was extracted with EtOAc (150 mL). The organic phase was dried over anhydrous Na$_2$SO$_4$ and concentrated under reduced pressure to afford 31o as a black solid (4.37 g, 98% yield). R$_f$=0.46 (hexanes/EtOAc 75:25 v/v). $^1$H NMR (400 MHz, DMSO-d$_6$) δ 10.11 (br s, 1H), 7.97 (d, J=8.3 Hz, 1H), 7.76 (d, J=8.0 Hz, 1H), 7.51-7.45 (m, 2H), 7.44-7.38 (m, 1H), 7.20 (d, J=1.7 Hz, 1H). $^{13}$C NMR (151 MHz, DMSO-d$_6$) δ 155.1, 135.3, 127.2, 126.9, 126.0, 125.8, 124.5, 122.4, 122.2, 109.3. MS (ESI$^+$) calculated for [C$_{10}$H$_8$BrO]$^+$ [M+H]$^+$, 223.0; found 223.0.

4-Bromo-7-ethylnaphthalen-2-ol (31s)

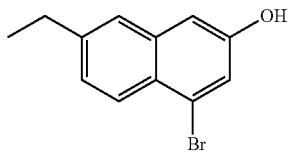

Naphthol 31s was prepared according to the procedure for 31o using zwitterion 30s (1.02 g, 3.68 mmol) and sodium borohydride (146 mg, 3.87 mmol) in EtOH (25 mL). Purification by flash column chromatography (hexanes to 75:25 hexanes/EtOAc) afforded 31s as a purple solid (404 mg, 44% yield). R$_f$=0.50 (hexanes/EtOAc 75:25 v/v). $^1$H NMR (400 MHz, CDCl$_3$) δ 8.04 (d, J=8.7 Hz, 1H), 7.44 (s, 1H), 7.38 (d, J=2.3 Hz, 1H), 7.29 (d, J=8.6 Hz, 1H), 7.07 (d, J=2.1 Hz, 1H), 4.94 (br s, 1H), 2.80 (q, J=7.6 Hz, 2H), 1.31 (t, J=7.6 Hz, 3H). $^{13}$C NMR (101 MHz, CDCl$_3$) δ 153.1, 143.7, 135.6, 127.1, 126.4, 126.3, 124.7, 123.6, 121.1, 109.5, 29.0, 15.5. MS (ESI$^-$) calculated for [C$_{12}$H$_{10}$BrO]$^-$ [M−H]$^-$, 249.0; found 249.0.

Synthesis of Naphthol Intermediates 34o-q

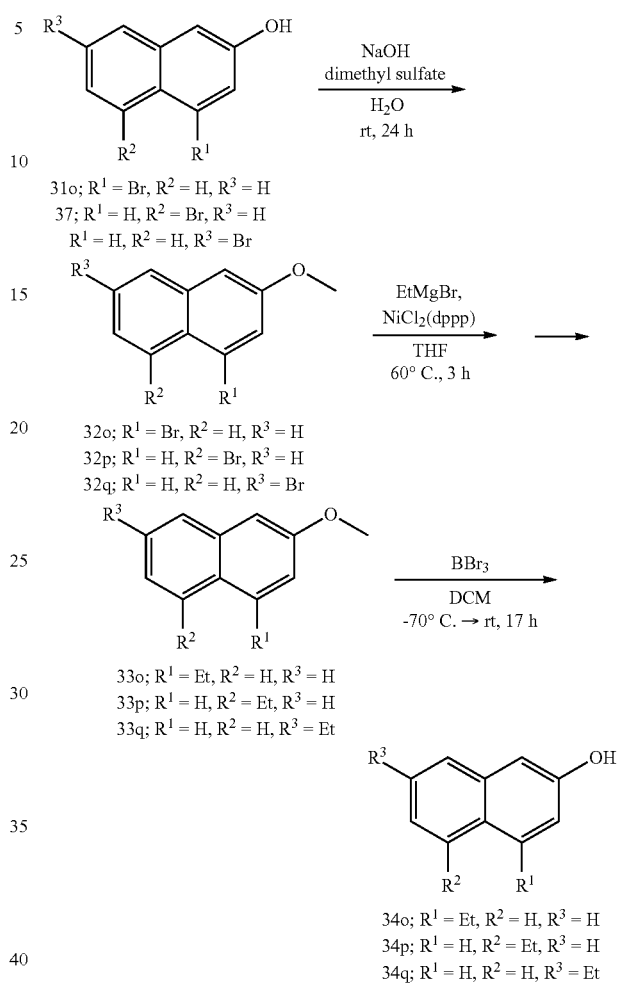

1-Bromo-3-methoxynaphthalene (32o)

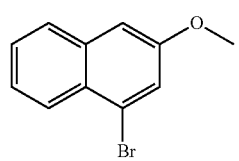

To a suspension of naphthol 31o (1.77 g, 7.93 mmol) in water (20 mL) at room temperature was added NaOH (dissolved in 50 mL water, 634 mg, 15.9 mmol). The contents were stirred until all solids were dissolved before the dropwise addition of dimethyl sulfate (1.50 mL, 15.9 mmol). After 24 hours of stirring, the reaction mixture was washed with diethyl ether (125 mL). The organic phase was dried over anhydrous Na$_2$SO$_4$ and concentrated under reduced pressure. Purification by flash column chromatography (hexanes to 90:10 hexanes/EtOAc) afforded 32o as a white solid (766 mg, 41% yield). R$_f$=0.48 (hexanes/EtOAc 90:10 v/v). $^1$H NMR (400 MHz, CDCl$_3$) δ 8.14 (d, J=8.1 Hz, 1H), 7.72 (d, J=7.7 Hz, 1H), 7.50 (d, J=2.3 Hz, 1H), 7.49-7.41 (m, 2H), 7.12 (d, J=2.1 Hz, 1H), 3.92 (s, 3H). $^{13}$C NMR (101 MHz, CDCl$_3$) δ 157.3, 135.3, 127.8, 127.3, 127.3, 127.1, 125.1, 123.6, 122.8, 106.2, 55.7.

1-Bromo-6-methoxynaphthalene (32p)

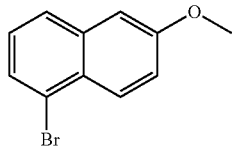

Methyl ether 32p was prepared according to the procedure for 32o using naphthol 37 (1.74 g, 7.80 mmol), NaOH (dissolved in 50 mL water, 624 mg, 15.6 mmol), and dimethyl sulfate (1.48 mL, 15.6 mmol) in water (20 mL). Purification by flash column chromatography (hexanes to 90:10 hexanes/EtOAc) afforded 32p as a white solid (1.38 g, 74% yield). R$_f$=0.49 (hexanes/EtOAc 90:10 v/v). $^1$H NMR (400 MHz, CDCl$_3$) δ 8.14 (d, J=9.2 Hz, 1H), 7.69 (d, J=8.2 Hz, 1H), 7.62 (d, J=7.4 Hz, 1H), 7.30-7.23 (m, 2H), 7.13 (d, J=2.2 Hz, 1H), 3.94 (s, 3H). $^{13}$C NMR (101 MHz, CDCl$_3$) δ 158.3, 136.0, 128.9, 127.8, 127.6, 126.9, 126.9, 122.8, 120.1, 106.2, 55.6.

2-Bromo-7-methoxynaphthalene (32q)

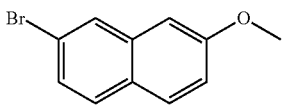

Methyl ether 32q was prepared according to the procedure for 32o using 2-bromo-7-hydroxynaphthylene (482 mg, 2.16 mmol), NaOH (dissolved in 12 mL water, 173 mg, 2.16 mmol), and dimethyl sulfate (0.41 mL, 4.3 mmol) in water (5 mL). 32q was obtained as a yellow solid (504 mg, 98% yield) and used in the next step without purification. R$_f$=0.66 (hexanes/EtOAc 90:10 v/v). $^1$H NMR (400 MHz, CDCl$_3$) δ 7.90 (s, 1H), 7.70 (d, J=8.8 Hz, 1H), 7.62 (d, J=8.6 Hz, 1H), 7.40 (dd, J=8.6, 1.4 Hz, 1H), 7.15 (dd, J=8.9, 2.3 Hz, 1H), 7.03 (d, J=1.7 Hz, 1H), 3.92 (s, 3H). $^{13}$C NMR (151 MHz, CDCl$_3$) δ 158.5, 136.0, 129.5, 129.4, 128.9, 127.5, 127.0, 120.7, 119.3, 105.1, 55.5.

1-Ethyl-3-methoxynaphthalene (33o)

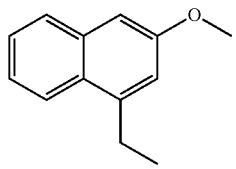

Magnesium turnings (139 mg, 5.72 mmol) were sealed in a vial and stirred vigorously at 90° C. under vacuum for 1 hour. The magnesium was flushed with N$_2$ and brought to room temperature. Anhydrous THF (1 mL) was added, followed by a few drops of bromoethane to initiate the Grignard reaction. The contents were diluted with more anhydrous THF (8 mL), and bromoethane (0.30 mL, 4.1 mmol) was added dropwise over 30 minutes. The mixture was stirred until almost all the magnesium was consumed (about 30 minutes). The Grignard solution was then transferred to a separate vial containing naphthyl bromide 32o (646 mg, 2.72 mmol) and NiCl$_2$(dppp) (73.8 mg, 0.136 mmol) under N$_2$ atmosphere, and the mixture was heated at 60° C. for 3 hours. The reaction was quenched with MeOH (2 mL), and the solvent was removed in vacuo. The residue was dissolved in EtOAc (125 mL) and washed with brine (100 mL). The organic layer was dried over anhydrous Na$_2$SO$_4$ and concentrated under reduced pressure. Purification by flash column chromatography (hexanes to 95:5 hexanes/EtOAc) afforded 33o as a yellow oil (401 mg, 79% yield). R$_f$=0.47 (hexanes/EtOAc 95:5 v/v). $^1$H NMR (400 MHz, CDCl$_3$) δ 7.97 (d, J=8.3 Hz, 1H), 7.75 (d, J=8.1 Hz, 1H), 7.47-7.41 (m, 1H), 7.40-7.34 (m, 1H), 7.05-7.98 (m, 2H), 3.92 (s, 3H), 3.08 (q, J=7.5 Hz, 2H), 1.38 (t, J=7.5 Hz, 3H). $^{13}$C NMR (101 MHz, CDCl$_3$) δ 157.4, 142.3, 135.3, 127.7, 127.7, 126.2, 123.8, 123.6, 117.8, 104.1, 55.3, 25.8, 14.8. MS (ESI$^+$) calculated for [C$_{13}$H$_{15}$O]$^+$ [M+H]$^+$, 187.1; found 187.1.

1-Ethyl-6-methoxynaphthalene (33p)

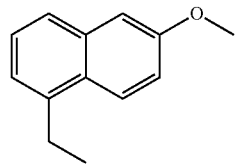

Methyl ether 33p was prepared according to the procedure for 33o using naphthyl bromide 32p (500 mg, 2.11 mmol), NiCl$_2$(dppp) (57.2 mg, 0.105 mmol), bromoethane (0.24 mL, 3.2 mmol), and magnesium turnings (108 mg, 4.43 mmol) in anhydrous THF (8 mL). Purification by flash column chromatography (hexanes to 95:5 hexanes/EtOAc) afforded 33p as a clear oil (328 mg, 84% yield). R$_f$=0.54 (hexanes/EtOAc 95:5 v/v). $^1$H NMR (400 MHz, CDCl$_3$) δ 7.97 (d, J=8.9 Hz, 1H), 7.61 (d, J=8.2 Hz, 1H), 7.37 (app t, J=7.6 Hz, 1H), 7.22-7.15 (m, 3H), 3.93 (s, 3H), 3.08 (q, J=7.5 Hz, 2H), 1.37 (t, J=7.5 Hz, 3H). $^{13}$C NMR (400 MHz, CDCl$_3$) δ 157.3, 140.5, 135.2, 127.3, 126.5, 125.5, 125.4, 122.9, 118.4, 106.8, 55.4, 26.1, 15.3. MS (ESI$^+$) calculated for [C$_{13}$H$_{15}$O]$^+$ [M+H]$^+$, 187.1; found 187.1.

2-Ethyl-7-methoxynaphthalene (33q)

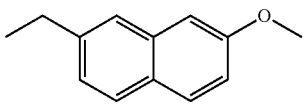

Methyl ether 33q was prepared according to the procedure for 33o using naphthyl bromide 32q (600 mg, 2.53 mmol), NiCl$_2$(dppp) (68.6 mg, 0.127 mmol), bromoethane (0.28 mL, 3.8 mmol), and magnesium turnings (129 mg, 5.31 mmol) in anhydrous THF (9 mL). Purification by flash column chromatography (hexanes to 95:5 hexanes/EtOAc) afforded 33q as a white solid (378 mg, 80% yield). R$_f$=0.42

(hexanes/EtOAc 95:5 v/v). $^1$H NMR (400 MHz, CDCl$_3$) δ 7.70 (app s, 1H), 7.68 (s, 1H), 7.53 (s, 1H), 7.21 (dd, J=8.3, 1.6 Hz, 1H), 7.10-7.06 (m, 2H), 3.92 (s, 3H), 2.80 (q, J=7.6 Hz, 2H), 1.32 (t, J=7.6 Hz, 3H). $^{13}$C NMR (101 MHz, CDCl$_3$) δ 157.9, 142.5, 135.0, 129.2, 127.7, 127.6, 124.9, 124.7, 117.9, 105.6, 55.4, 29.2, 15.7. MS (ESI$^+$) calculated for [C$_{13}$H$_{15}$O]$^+$ [M+H]$^+$, 187.1; found 187.1.

4-Ethylnaphthalen-2-ol (34o)

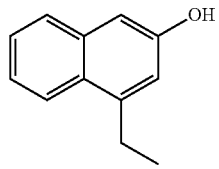

Naphthol 34o was prepared according to the procedure for 20 using methyl ether 33o (393 mg, 2.11 mmol) and boron tribromide (1M in DCM, 4.22 mL, 4.22 mmol) in anhydrous DCM (10 mL). Purification by flash column chromatography (hexanes to 75:25 hexanes/EtOAc) afforded 34o as an orange solid (304 mg, 83% yield). R$_f$=0.56 (hexanes/EtOAc 75:25 v/v). $^1$H NMR (400 MHz, CDCl$_3$) δ 7.97 (d, J=8.4 Hz, 1H), 7.69 (d, J=7.9 Hz, 1H), 7.45-7.40 (m, 1H), 7.39-7.33 (m, 1H), 7.01 (d, J=2.4 Hz, 1H), 6.99 (d, J=2.4 Hz, 1H), 4.84 (br s, 1H), 3.08 (q, J=7.5 Hz, 2H), 1.38 (t, J=7.5 Hz, 3H). $^{13}$C NMR (101 MHz, CDCl$_3$) δ 153.1, 143.0, 135.3, 127.6, 127.4, 126.3, 123.9, 123.6, 116.8, 107.8, 25.8, 14.9. MS (ESI$^+$) calculated for [C$_{12}$H$_{13}$O]$^+$ [M+H]$^+$, 173.1; found 173.1.

5-ethylnaphthalen-2-ol (34p)

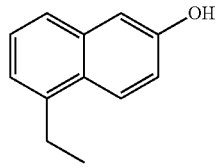

Naphthol 34p was prepared according to the procedure for 20 using methyl ether 33p (319 mg, 1.71 mmol) and boron tribromide (1M in DCM, 3.43 mL, 3.43 mmol) in anhydrous DCM (10 mL). Purification by flash column chromatography (hexanes to 75:25 hexanes/EtOAc) afforded 34p as a dark yellow oil (269 mg, 91% yield). R$_f$=0.48 (hexanes/EtOAc 75:25 v/v). $^1$H NMR (400 MHz, CDCl$_3$) δ 7.98 (d, J=9.0 Hz, 1H), 7.55 (d, J=8.2 Hz, 1H), 7.36 (app t, J=7.6 Hz, 1H), 7.20 (d, J=7.0 Hz, 1H), 7.16 (d, J=2.2 Hz, 1H), 7.13 (dd, J=9.0, 2.5 Hz, 1H), 4.92 (br s, 1H), 3.08 (q, J=7.5 Hz, 2H), 1.37 (t, J=7.5 Hz, 3H). $^{13}$C NMR (101 MHz, CDCl$_3$) δ 153.1, 140.6, 135.3, 127.4, 126.7, 126.0, 125.1, 122.9, 117.4, 110.5, 26.1, 15.2. MS (ESI$^+$) calculated for [C$_{12}$H$_{13}$O]$^+$ [M+H]$^+$, 173.1; found 173.1.

7-Ethylnaphthalen-2-ol (34q)

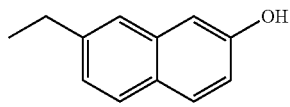

Naphthol 34q was prepared according to the procedure for 20 using methyl ether 33q (375 mg, 2.02 mmol) and boron tribromide (1M in DCM, 4.03 mL, 4.03 mmol) in anhydrous DCM (17 mL). Purification by flash column chromatography (hexanes to 75:25 hexanes/EtOAc) afforded 34q as a peach-colored solid (286 mg, 82% yield). R$_f$=0.53 (hexanes/EtOAc 75:25 v/v). $^1$H NMR (400 MHz, CDCl$_3$) δ 7.71 (d, J=6.2 Hz, 1H), 7.69 (d, J=5.8 Hz, 1H), 7.47 (s, 1H), 7.20 (dd, J=8.4, 1.6 Hz, 1H), 7.09 (d, J=2.4 Hz, 1H), 7.03 (dd, J=8.8, 2.5 Hz, 1H), 4.83 (br s, 1H), 2.78 (q, J=7.6 Hz, 2H), 1.32 (t, J=7.6 Hz, 3H). $^{13}$C NMR (101 MHz, CDCl$_3$) δ 153.5, 142.7, 135.0, 129.7, 127.8, 127.6, 125.1, 124.3, 116.9, 109.3, 29.2, 15.6. MS (ESI$^+$) calculated for [C$_{12}$H$_{13}$O]$^+$ [M+H]$^+$, 173.1; found 173.1.

Synthesis of Naphthol Intermediate 37

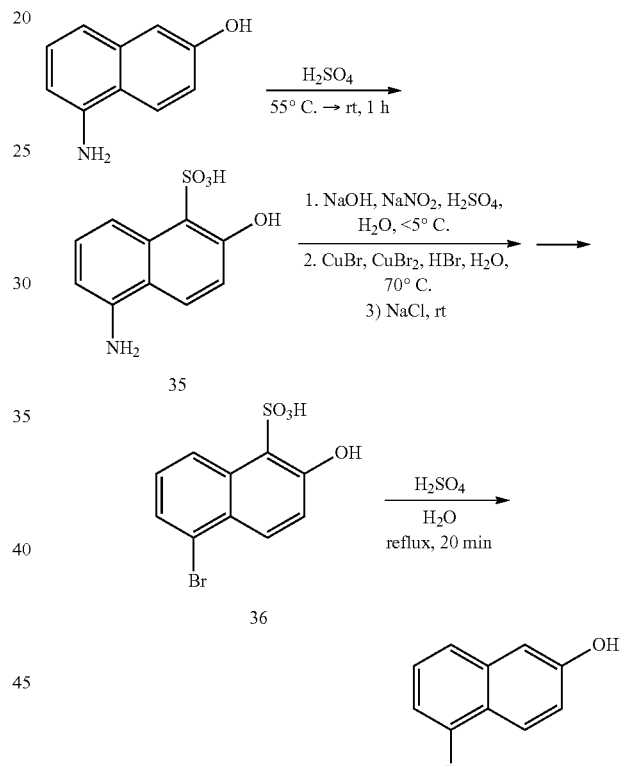

5-Amino-2-hydroxynaphthalene-1-sulfonic acid (35)

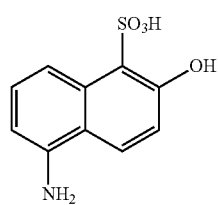 [SMILES: Nc1cccc2c(S(=O)(=O)O)c(O)ccc12]

This procedure was adapted from Everett et al.[7] A flask containing 5-amino-2-naphthol (3.00 g, 18.8 mmol) was heated to 55° C. before the addition of fuming $H_2SO_4$ (10 mL). The mixture was stirred for 1 hour, removed from the heat, covered, and allowed to sit at room temperature overnight. The contents were suspended in water (125 mL) and filtered. The solid was then taken up in acetone (70 mL), filtered again, washed with more acetone (10 mL), and air-dried to afford 35 as a white solid (3.74 g, 83% yield). $^1$H NMR (600 MHz, DMSO-$d_6$) δ 12.19 (br s, 1H), 9.96 (br s, 2H), 8.67 (d, J=8.8 Hz, 1H), 7.87 (d, J=9.3 Hz, 1H), 7.49 (dd, J=8.7, 7.5 Hz, 1H), 7.31 (d, J=7.2 Hz, 1H), 7.24 (d, J=9.2 Hz, 1H). $^{13}$C NMR (151 MHz, DMSO-$d_6$) δ 152.9, 131.7, 128.6, 126.0, 125.7, 124.8, 121.9, 120.9, 120.4, 116.8. MS (ESI$^+$) calculated for $[C_{10}H_{10}NO_4S]^+$ $[M+H]^+$, 240.0; found 240.0.

5-Bromo-2-hydroxynaphthalene-1-sulfonic acid (36)

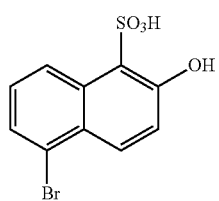 [SMILES: O=S(=O)(O)c1c(O)ccc2c(Br)cccc12]

This procedure was adapted from Everett et al.[7] To a flask containing fuming $H_2SO_4$ (2.75 mL, 51.6 mmol) and water (7.5 mL) cooled to 0° C. was added a solution of sulfonic acid 35 (3.74 g, 15.6 mmol), NaOH (644 mg, 16.1 mmol), and $NaNO_2$ (1.07 g, 15.5 mmol) in water (30 mL) dropwise without allowing the temperature to exceed 5° C. The brownish-yellow precipitate was filtered and washed with ice water. The moist filter cake was then added to a flask containing CuBr (2.27 g, 15.8 mmol), $CuBr_2$ (3.51 g, 15.7 mmol), and HBr (3.67 mL, 71.9 mmol) dissolved in water (75 mL). The walls of the flask were washed with more water (25 mL), and the mixture was heated at 70° C. for 1 hour before filtering. To the filtrate was added NaCl (65 g, 1.1 mol), and the mixture was stirred at room temperature overnight. The precipitate was collected by suction filtration and air-dried to afford 36 as a sand-colored solid (3.76 g, 79% yield). $^1$H NMR (400 MHz, DMSO-$d_6$) δ 12.17 (br s, 1H), 8.71 (d, J=8.7 Hz, 1H), 8.05 (d, J=9.2 Hz, 1H), 7.65 (d, J=7.4 Hz, 1H), 7.36 (dd, J=8.6, 7.6 Hz, 1H), 7.19 (d, J=9.2 Hz, 1H). $^{13}$C NMR (101 MHz, DMSO-$d_6$) δ 152.9, 132.2, 129.6, 126.9, 126.0, 125.7, 121.7, 121.7, 121.2. MS (ESI$^-$) calculated for $[C_{10}H_6BrO_4S]^-$ $[M-H]^-$, 300.9; found 300.9.

5-Bromonaphthalen-2-ol (37)

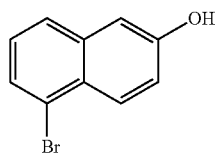 [SMILES: Oc1ccc2c(Br)cccc2c1]

This procedure was adapted from Everett et al.[7] A suspension of sulfonic acid 36 (3.76 g, 12.4 mmol) in 20% (wt/wt) aqueous $H_2SO_4$ (75 mL) was heated at reflux for 20 minutes. After cooling to room temperature, the reaction mixture was extracted with diethyl ether (125 mL). The organic phase was washed with brine (75 mL), dried over anhydrous $Na_2SO_4$, and concentrated under reduced pressure. Purification by flash column chromatography (hexanes to 50:50 hexanes/EtOAc) afforded 37 as a brown solid (1.74 g, 63% yield). $R_f$=0.81 (hexanes/EtOAc 50:50 v/v). $^1$H NMR (400 MHz, CDCl$_3$) δ 8.16 (d, J=9.1 Hz, 1H), 7.66-7.60 (m, 2H), 7.28-7.23 (m, 1H), 7.20 (dd, J=9.1, 2.5 Hz, 1H), 7.16 (d, J=2.5 Hz, 1H), 4.96 (s, 1H). $^{13}$C NMR (400 MHz, CDCl$_3$) δ 154.1, 136.0, 129.5, 127.9, 127.7, 127.1, 126.5, 122.9, 119.1, 110.0. MS (ESI$^+$) calculated for $[C_{10}H_8BrO]^+$ $[M+H]^+$, 223.0; found 223.0.

Synthesis of Naphthol Intermediates 40r and 40s

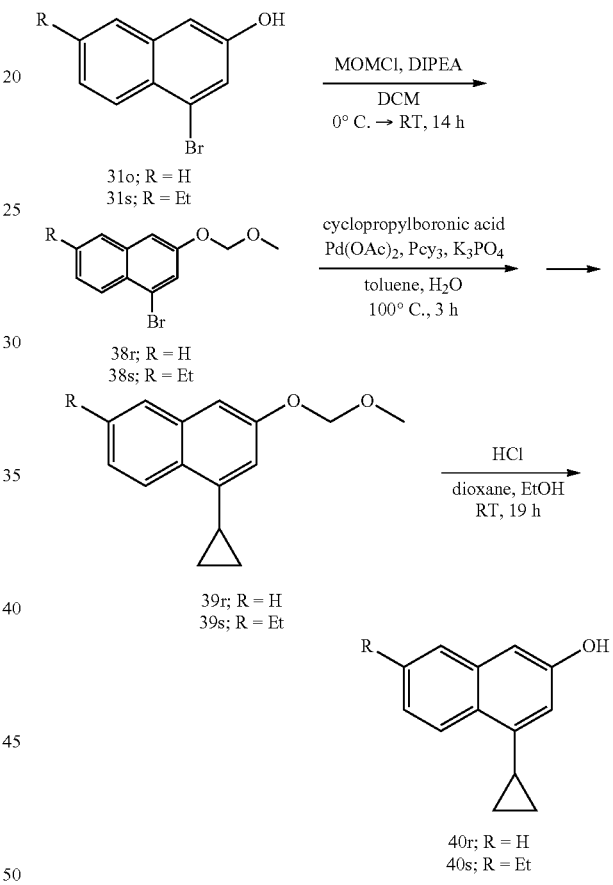

1-Bromo-3-(methoxymethoxy)naphthalene (38r)

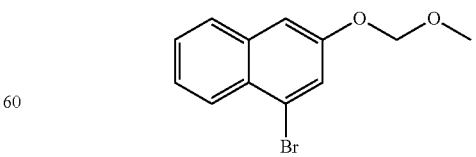

To a solution of naphthol 310 (542 mg, 2.43 mmol) and diisopropylethylamine (0.47 mL, 2.7 mmol) in anhydrous DCM (12 mL) cooled to 0° C. was slowly added chloromethyl methyl ether (0.20 mL, 2.7 mmol). The solution was warmed to room temperature and stirred for 14 hours. The reaction mixture was diluted with EtOAc (100 mL) and washed with brine (100 mL). The organic phase was dried over anhydrous Na$_2$SO$_4$ and concentrated under reduced pressure. Purification by flash column chromatography (hexanes to 75:25 hexanes/EtOAc) afforded 38r as a yellow oil (528 mg, 81% yield). R$_f$=0.62 (hexanes/EtOAc 75:25 v/v). $^1$H NMR (400 MHz, CDCl$_3$) δ 8.16-8.13 (m, 1H), 7.75-7.71 (m, 1H), 7.58 (d, J=2.3 Hz, 1H), 7.51-7.43 (m, 2H), 7.39 (d, J=2.2 Hz, 1H), 5.28 (s, 2H), 3.52 (s, 3H). $^{13}$C NMR (101 MHz, CDCl$_3$) δ 154.7, 135.2, 128.3, 127.6, 127.3, 127.0, 125.5, 123.5, 123.2, 110.3, 94.8, 56.3.

1-Bromo-6-ethyl-3-(methoxymethoxy)naphthalene (38s)

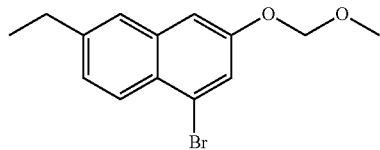 [SMILES: CCc1ccc2c(Br)cc(OCOC)cc2c1]

Naphthyl bromide 38s was prepared according to the procedure for 38r using naphthol 31s (404 mg, 1.61 mmol), diisopropylethylamine (0.31 mL, 1.8 mmol), and chloromethyl methyl ether (0.13 mL, 1.8 mmol) in anhydrous DCM (9 mL). Purification by flash column chromatography (hexanes to 75:25 hexanes/EtOAc) afforded 38s as a purple oil (412 mg, 87% yield). R$_f$=0.72 (hexanes/EtOAc 75:25 v/v). $^1$H NMR (400 MHz, CDCl$_3$) δ 8.05 (d, J=8.6 Hz, 1H), 7.54-7.48 (m, 2H), 7.35-7.30 (m, 2H), 5.27 (s, 2H), 3.51 (s, 3H), 2.80 (q, J=7.6 Hz, 2H), 1.31 (t, J=7.6 Hz, 3H). $^{13}$C NMR (101 MHz, CDCl$_3$) δ 154.7, 143.4, 135.4, 127.0, 126.8, 126.8, 125.4, 123.2, 122.2, 110.0, 94.8, 56.3, 28.9, 15.5.

1-Cyclopropyl-3-(methoxymethoxy)naphthalene (39r)

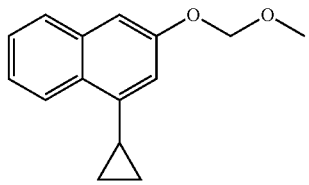 [SMILES: COCOc1cc(C2CC2)c2ccccc2c1]

A mixture of naphthyl bromide 38r (521 mg, 1.95 mmol), cyclopropylboronic acid (218 mg, 2.53 mmol), K$_3$PO$_4$ (1.45 g, 6.82 mmol), tricyclohexylphosphine (54.6 mg, 0.195 mmol), toluene (9 mL), and water (0.6 mL) in a vial was degassed with N$_2$ for 7 minutes. Pd(OAc)$_2$ (21.9 mg, 0.0974 mmol) was added, the vial was sealed, and the contents were heated at 100° C. for 3 hours. The reaction mixture was then diluted with EtOAc (100 mL) and washed with brine (100 mL). The organic phase was dried over anhydrous Na$_2$SO$_4$ and concentrated under reduced pressure. Purification by flash column chromatography (hexanes to 95:5 hexanes/EtOAc) afforded 39r as a yellow oil (396 mg, 89% yield). R$_f$=0.37 (hexanes/EtOAc 95:5 v/v). $^1$H NMR (400 MHz, CDCl$_3$) δ 8.32 (d, J=8.1 Hz, 1H), 7.75 (d, J=7.7 Hz, 1H), 7.48-7.39 (m, 2H), 7.26 (s, 1H), 7.00 (d, J=2.3 Hz, 1H), 5.29 (s, 2H), 3.52 (s, 3H), 2.38-2.29 (m, 1H), 1.10-1.04 (m, 2H), 0.81-0.75 (m, 2H). $^{13}$C NMR (101 MHz, CDCl$_3$) δ 154.8, 141.5, 134.9, 129.8, 127.8, 126.3, 124.4, 124.0, 117.1, 108.3, 94.6, 56.2, 13.3, 6.7. MS (ESI$^+$) calculated for [C$_{15}$H$_{17}$O$_2$]$^+$ [M+H]$^+$, 229.1; found 229.1.

1-Cyclopropyl-6-ethyl-3-(methoxymethoxy)naphthalene (39s)

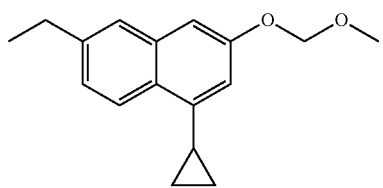 [SMILES: CCc1ccc2c(C3CC3)cc(OCOC)cc2c1]

Cyclopropylnaphthalene 39s was prepared according to the procedure for 39r using naphthyl bromide 38s (408 mg, 1.38 mmol), cyclopropylboronic acid (154 mg, 1.80 mmol), K$_3$PO$_4$ (1.03 g, 4.84 mmol), tricyclohexylphosphine (38.8 mg, 0.138 mmol), and Pd(OAc)$_2$ (15.5 mg, 0.0691 mmol) in toluene (6 mL) and water (0.4 mL). Purification by flash column chromatography (hexanes to 95:5 hexanes/EtOAc) afforded 39s as a brown oil (277 mg, 78% yield). R$_f$=0.39 (hexanes/EtOAc 95:5 v/v). $^1$H NMR (400 MHz, CDCl$_3$) δ 8.23 (d, J=8.6 Hz, 1H), 7.54 (s, 1H), 7.29 (dd, J=8.6, 1.4 Hz, 1H), 7.20 (d, J=1.8 Hz, 1H), 6.94-6.90 (m, 1H), 5.27 (s, 2H), 3.51 (s, 3H), 2.80 (q, J=7.6 Hz, 2H), 2.36-2.28 (m, 1H), 1.32 (t, J=7.6 Hz, 3H), 1.08-1.02 (m, 2H), 0.79-0.74 (m, 2H). $^{13}$C NMR (101 MHz, CDCl$_3$) δ 154.9, 142.3, 141.3, 135.2, 128.2, 125.6, 125.2, 124.4, 116.1, 108.0, 94.6, 56.2, 29.1, 15.7, 13.3, 6.7. MS (ESI$^+$) calculated for [C$_{17}$H$_{21}$O$_2$]$^+$ [M+H]$^+$, 257.1; found 257.1.

4-Cyclopropylnaphthalen-2-ol (40r)

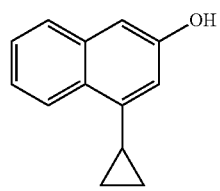 [SMILES: Oc1cc(C2CC2)c2ccccc2c1]

To a solution of protected naphthylene 39r (392 mg, 1.72 mmol) in EtOH (4 mL) was added an emulsion of concentrated HCl (0.15 mL) in dioxane (3.85 mL). The mixture was stirred at room temperature for 2 hours before the addition of another portion of concentrated HCl (0.15 mL). The contents were stirred for 17 more hours, diluted with diethyl ether (100 mL) and washed with brine (100 mL). The organic phase was dried over anhydrous Na$_2$SO$_4$ and concentrated under reduced pressure to afford 40r as a red oil (316 mg, 99% yield). R$_f$=0.53 (hexanes/EtOAc 75:25 v/v). $^1$H NMR (400 MHz, CDCl$_3$) δ 8.31 (d, J=8.3 Hz, 1H), 7.68 (d, J=8.1 Hz, 1H), 7.47-7.42 (m, 1H), 7.42-7.36 (m, 1H), 7.00 (d, J=2.2 Hz, 1H), 6.89 (d, J=2.1 Hz, 1H), 4.99 (br s, 1H), 2.39-2.29 (m, 1H), 1.11-1.03 (m, 2H), 0.81-0.72 (m, 2H). $^{13}$C NMR (101 MHz, CDCl$_3$) δ 153.1, 142.0, 135.1, 129.2, 127.1, 126.5, 124.6, 123.6, 115.8, 107.9, 13.3, 6.8. MS (ESI$^+$) calculated for [C$_{13}$H$_{13}$O]$^+$ [M+H]$^+$, 185.1; found 185.1.

4-Cyclopropyl-7-ethylnaphthalen-2-ol (40s)

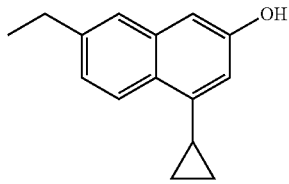 [SMILES: CCc1ccc2c(C3CC3)cc(O)cc2c1]

Naphthol 40s was prepared according to the procedure for 40r using protected naphthalene 39s (275 mg, 1.07 mmol) and concentrated HCl (0.18 mL) in EtOH (5 mL) and dioxane (4.91 mL). Purification by flash column chromatography (hexanes to 75:25 hexanes/EtOAc) afforded 40s as a yellow oil (181 mg, 65% yield). $R_f$=0.48 (hexanes/EtOAc 75:25 v/v). $^1$H NMR (400 MHz, CDCl$_3$) δ 8.22 (d, J=8.6 Hz, 1H), 7.47 (s, 1H), 7.30-7.24 (m, 1H), 6.95 (s, 1H), 6.82 (s, 1H), 4.79 (s, 1H), 2.79 (q, J=7.5 Hz, 2H), 2.37-2.28 (m, 1H), 1.33 (t, J=7.6 Hz, 3H), 1.09-1.02 (m, 2H), 0.79-0.73 (m, 2H). $^{13}$C NMR (151 MHz, CDCl$_3$) δ 153.2, 142.5, 141.8, 135.3, 127.7, 124.9, 124.8, 124.5, 114.9, 107.6, 29.1, 15.7, 13.3, 6.7. MS (ESI$^+$) calculated for [C$_{15}$H$_{17}$O]$^+$ [M+H]$^+$, 213.1; found 213.1.

Synthesis of Naphthylamine Intermediate 44

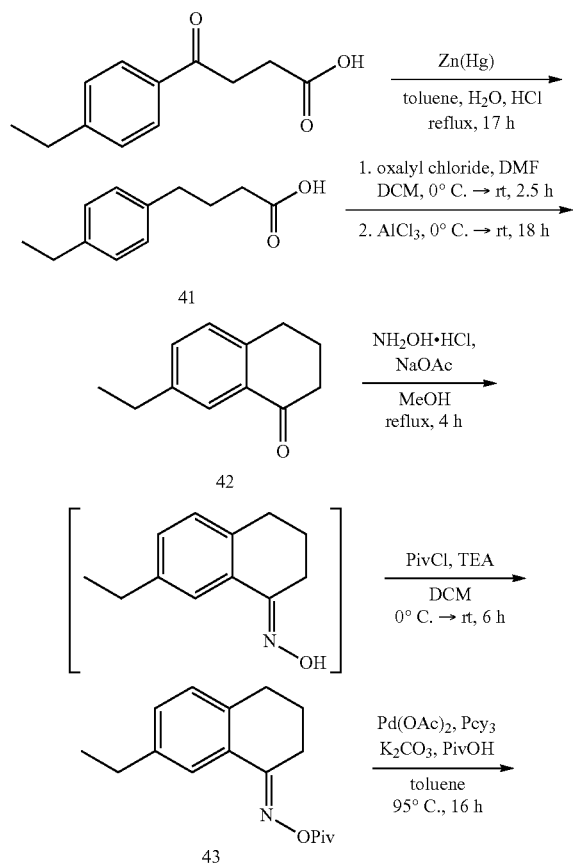

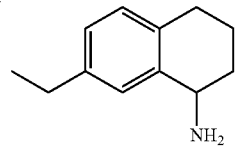

4-(4-Ethylphenyl)butanoic acid (41)

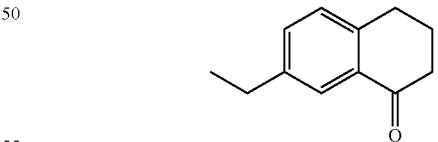

To a solution of mercuric chloride (666 mg, 2.45 mmol) in water (7 mL) and concentrated HCl (20 mL) was slowly added zinc (6.66 g, 102 mmol). After bubbling subsided, additional portions of mercuric chloride (666 mg, 2.45 mmol) and zinc (6.66 g, 102 mmol) were added. The contents were stirred for 30 minutes at room temperature. The liquid was decanted, and the solid amalgam was washed twice with water. A solution of 4-(4-ethylphenyl)-4-oxobutyric acid (3.00 g, 14.5 mmol) in toluene (7.5 mL), water (15 mL), and concentrated HCl (15 mL) was then added to the mercury-zinc amalgam. The mixture was heated at reflux for 17 hours, then filtered. The filtrate was diluted with EtOAc (200 mL) and washed with brine (100 mL). The organic phase was dried over anhydrous Na$_2$SO$_4$ and concentrated under reduced pressure. Purification by flash column chromatography (DCM to 25:75 DCM/EtOAc) afforded 41 as a white solid (2.04 g, 73% yield). $R_f$=0.27 (DCM/EtOAc 50:50 v/v). $^1$H NMR (400 MHz, DMSO-d$_6$) δ 12.03 (br s, 1H), 7.11 (d, J=8.2 Hz, 2H), 7.08 (d, J=8.2 Hz, 2H), 2.60-2.48 (m, 4H), 2.20 (t, J=7.4 Hz, 2H), 1.77 (app quint, J=7.5 Hz, 2H), 1.16 (t, J=7.6 Hz, 3H). $^{13}$C NMR (101 MHz, DMSO-d$_6$) δ 174.3, 141.1, 138.7, 128.2, 127.7, 34.0, 33.1, 27.8, 26.4, 15.7. MS (ESI$^+$) calculated for [C$_{12}$H$_{15}$O]$^+$ [M-OH]$^+$, 175.1; found 175.1.

7-ethyl-3,4-dihydronaphthalen-1(2H)-one (42)

To a solution of carboxylic acid 41 (1.91 g, 9.93 mmol) and anhydrous DMF (7 drops) in anhydrous DCM (30 mL) cooled to 0° C. was added oxalyl chloride (1.68 mL, 19.9 mmol) dropwise. The contents were stirred at 0° C. for 1 hour, then at room temperature for 1.5 hours. The mixture was cooled to 0° C., and aluminium chloride (2.65 g, 19.9 mmol) was added. The reaction was returned to room temperature, stirred for 18 hours, and quenched at 0° C. with 1N aqueous HCl (7 mL). The reaction mixture was diluted with EtOAc (200 mL) and washed with brine (100 mL). The organic phase was dried over anhydrous Na$_2$SO$_4$ and concentrated under reduced pressure. Purification by flash column chromatography (hexanes to 90:10 hexanes/EtOAc) afforded 42 as a pale yellow oil (1.45 g, 84% yield). $R_f$=0.40 (hexanes/EtOAc 90:10 v/v). $^1$H NMR (400 MHz, CDCl$_3$) δ 7.88 (s, 1H), 7.32 (d, J=9.1 Hz, 1H), 7.17 (d, J=7.8 Hz, 1H), 2.93 (t, J=6.1 Hz, 2H), 2.71-2.62 (m, 4H), 2.12 (app quint, J=6.4 Hz, 2H), 1.24 (t, J=7.6 Hz, 3H). $^{13}$C NMR (101 MHz, CDCl$_3$) δ 198.8, 142.9, 142.0, 133.4, 132.6, 128.9, 126.3, 39.4, 29.5, 28.6, 23.6, 15.7. MS (ESI$^+$) calculated for [C$_{12}$H$_{15}$O]$^+$ [M+H]$^+$, 175.1; found 175.1.

7-Ethyl-3,4-dihydronaphthalen-1(2H)-one O-pivaloyl oxime (43)

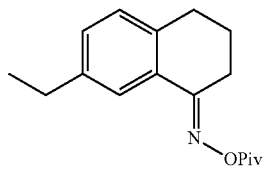

This procedure was adapted from Hong et al.[8] To a solution of tetralone 42 (1.41 g, 8.08 mmol) in MeOH (25 mL) was added hydroxylamine hydrochloride (673 mg, 9.69 mmol) and NaOAc (1.59 g, 19.4 mmol). The contents were heated at reflux for 4 hours, monitoring formation of the oxime by mass spectrometry. The solvent was then removed in vacuo. The residue was dissolved in EtOAc (200 mL) and washed with brine (100 mL). The organic phase was dried over anhydrous Na$_2$SO$_4$ and concentrated under reduced pressure to afford the oxime intermediate, which was dissolved in anhydrous DCM (40 mL) and cooled to 0° C. Triethylamine (3.38 mL, 24.2 mmol) was added to the solution, followed by the dropwise addition of pivaloyl chloride (1.99 mL, 16.2 mmol). The mixture was stirred at room temperature for 6 hours, then diluted with EtOAc (150 mL) and washed with brine (75 mL). The organic phase was dried over anhydrous Na$_2$SO$_4$ and concentrated under reduced pressure. Purification by flash column chromatography (hexanes to 90:10 hexanes/EtOAc) afforded 43 as a cream-colored solid (2.20 g, 99% yield). $R_f$=0.50 (hexanes/EtOAc 90:10 v/v). $^1$H NMR (400 MHz, CDCl$_3$) δ 8.02 (s, 1H), 7.19 (d, J=7.8 Hz, 1H), 7.09 (d, J=7.8 Hz, 1H), 2.85 (t, J=6.6 Hz, 2H), 2.75 (t, J=5.7 Hz, 2H), 2.63 (q, J=7.6 Hz, 2H), 1.88 (app quint, J=6.4 Hz, 2H), 1.34 (s, 9H), 1.22 (t, J=8.1 Hz, 3H). $^{13}$C NMR (101 MHz, CDCl$_3$) δ 175.4, 162.5, 142.8, 138.4, 130.7, 128.9, 128.7, 125.0, 39.1, 29.4, 28.7, 27.5, 25.8, 21.6, 15.9. MS (ESI$^+$) calculated for [C$_{17}$H$_{24}$NO$_2$]$^+$ [M+H]$^+$, 274.2; found 274.2.

7-ethylnaphthalen-1-amine (44)

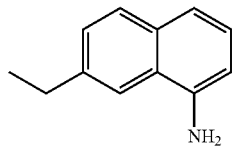

A mixture of protected oxime 43 (2.20 g, 8.05 mmol), Pd(OAc)$_2$ (181 mg, 0.805 mmol), tricyclohexylphosphine (451 mg, 1.61 mmol), K$_2$CO$_3$ (4.45 g, 32.2 mmol), pivalic acid (247 mg, 2.41 mmol), and anhydrous toluene (40 mL) were degassed with N$_2$ for 7 minutes and heated at 95° C. for 16 hours. The reaction mixture was filtered through a pad of basic alumina. The filtrate was diluted with EtOAc (200 mL) and washed with brine (100 mL). The organic phase was dried over anhydrous Na$_2$SO$_4$ and concentrated under reduced pressure. Purification by flash column chromatography (hexanes to 75:25 hexanes/EtOAc) afforded 44 as a deep red oil (1.10 g, 80% yield). $R_f$=0.21 (hexanes/EtOAc 90:10 v/v). $^1$H NMR (400 MHz, CDCl$_3$) δ 7.74 (d, J=8.4 Hz, 1H), 7.60 (s, 1H), 7.34 (dd, J=8.4, 1.4 Hz, 1H), 7.30 (d, J=8.1 Hz, 1H), 7.23 (t, J=8.0 Hz, 1H), 6.77 (d, J=7.2 Hz, 1H), 4.12 (br s, 2H), 2.84 (q, J=7.6 Hz, 2H), 1.34 (t, J=7.6 Hz, 3H). $^{13}$C NMR (101 MHz, CDCl$_3$) δ 141.7, 141.0, 133.0, 128.7, 127.1, 125.5, 124.0, 119.0, 118.8, 110.0, 29.5, 15.9. MS (ESI$^+$) calculated for [C$_{12}$H$_{14}$N]$^+$ [M+H]$^+$, 172.1; found 172.1.

Synthesis of Biphenyl Intermediates 45v and 45w

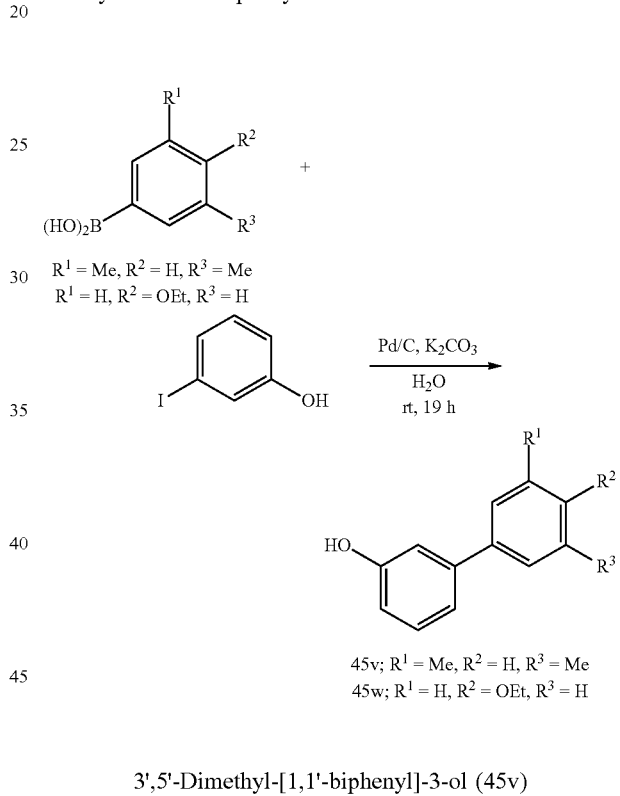

45v; R$^1$ = Me, R$^2$ = H, R$^3$ = Me
45w; R$^1$ = H, R$^2$ = OEt, R$^3$ = H

3',5'-Dimethyl-[1,1'-biphenyl]-3-ol (45v)

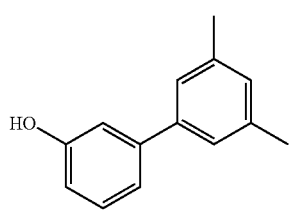

A mixture of 3-iodophenol (502 mg, 2.28 mmol), 3,5-dimethylbenzeneboronic acid (342 mg, 2.28 mmol), K$_2$CO$_3$ (1.26 g, 9.13 mmol), Pd (10% by weight on carbon, 48.6 mg, 0.0456 mmol), and water (15 mL) in a sealed vial was degassed with N$_2$ for 7 minutes and heated at 80° C. for 2.5 hours. The reaction mixture was diluted with EtOAc (125 mL) and washed with brine (100 mL). The organic phase was dried over anhydrous Na$_2$SO$_4$ and concentrated under reduced pressure. Purification by flash column chromatography (hexanes to 75:25 hexanes/EtOAc) afforded 45v as a clear oil (452 mg, 99% yield). R$_f$=0.46 (hexanes/EtOAc 75:25 v/v). $^1$H NMR (400 MHz, CDCl$_3$) δ 7.29 (app t, J=7.9 Hz, 1H), 7.19 (s, 2H), 7.18-7.14 (m, 1H), 7.05 (app t, J=2.0 Hz, 1H), 7.00 (s, 1H), 6.80 (dd, J=8.0, 2.5 Hz, 1H), 4.77 (br s, 1H), 2.38 (s, 6H). $^{13}$C NMR (101 MHz, CDCl$_3$) δ 155.9, 143.4, 140.9, 138.4, 130.0, 129.3, 125.2, 120.0, 114.2, 114.1, 21.5. MS (ESI$^+$) calculated for [C$_{14}$H$_{15}$O]$^+$ [M+H]$^+$, 199.1; found 199.1.

4'-Ethoxy-[1,1'-biphenyl]-3-ol (45w)

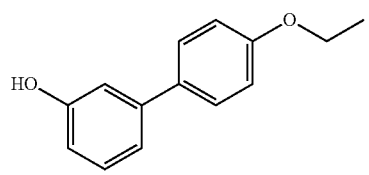 [SMILES: CCOc1ccc(-c2cccc(O)c2)cc1]

Phenol 45w was prepared according to the procedure for 45v using 3-iodophenol (510 mg, 2.32 mmol), 4-ethoxyphenylboronic acid (385 mg, 2.32 mmol), K$_2$CO$_3$ (1.28 g, 9.27 mmol), and Pd (10% by weight on carbon, 49.3 mg, 0.0464 mmol) in water (15 mL). Purification by flash column chromatography (hexanes to 75:25 hexanes/EtOAc) afforded 45w as a white solid (454 mg, 91% yield). R$_f$=0.36 (hexanes/EtOAc 75:25 v/v). $^1$H NMR (400 MHz, CDCl$_3$) δ 7.52-7.47 (m, 2H), 7.29 (d, J=7.9 Hz, 1H), 7.13 (d, J=7.7 Hz, 1H), 7.02 (app t, J=2.1 Hz, 1H), 6.98-6.93 (m, 2H), 6.77 (dd, J=8.4, 2.1 Hz, 1H), 4.82 (br s, 1H), 4.08 (q, J=7.0 Hz, 2H), 1.44 (t, J=7.0 Hz, 3H). $^{13}$C NMR (101 MHz, CDCl$_3$) δ 158.8, 156.0, 142.8, 133.2, 130.1, 128.2, 119.5, 114.9, 113.8, 113.7, 63.7, 15.0. MS (ESI$^+$) calculated for [C$_{14}$H$_{15}$O$_2$]$^+$ [M+H]$^+$, 215.1; found 215.1.

Synthesis of Biphenyl Intermediate 48

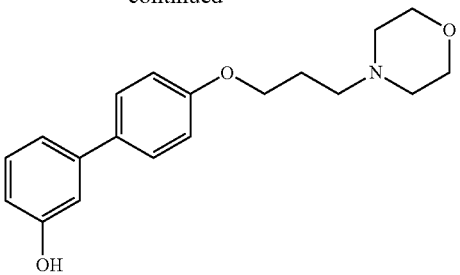

48

4-(3-bromopropyl)morpholine (46)

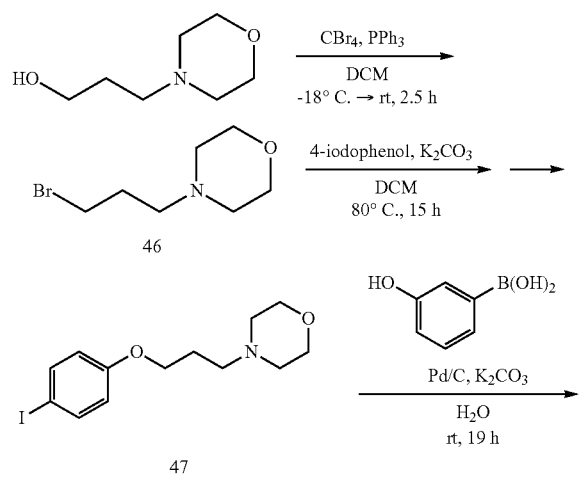

To a solution of 3-morpholinopropanol (1.20 g, 8.26 mmol) in anhydrous DCM (40 mL) cooled to −18° C. was added tetrabromomethane (2.74 g, 8.26 mmol) in four equivalent portions. The mixture was stirred at −18° C. for 15 minutes before the addition of triphenylphosphine (2.17 g, 8.26 mmol) in four equivalent portions. The reaction was brought to room temperature and stirred for 2.5 hours. Water (40 mL) was added, and the mixture was stirred vigorously for a few minutes. The layers were allowed to separate, and the organic phase was washed with 1N HCl (50 mL). The acid layer was neutralized with 1N NaOH (50 mL), and then washed with EtOAc (100 mL). The organic phase was dried over anhydrous Na$_2$SO$_4$ and concentrated under reduced pressure to afford 46 as a white solid (1.09 g, 63% yield). R$_f$=0.14 (hexanes/EtOAc 50:50 v/v). $^1$H NMR (400 MHz, CDCl$_3$) δ 3.71 (t, J=4.5 Hz, 4H), 3.47 (t, J=6.6 Hz, 2H), 2.53-2.41 (m, 6H), 2.03 (app quint, J=6.8 Hz, 2H). $^{13}$C NMR (101 MHz, CDCl$_3$) δ 67.1, 57.0, 53.8, 31.7, 29.7. MS (ESI$^+$) calculated for [C$_7$H$_{15}$BrNO]$^+$ [M+H]$^+$, 208.0; found 208.0.

4-(3-(4-Iodophenoxy)propyl)morpholine (47)

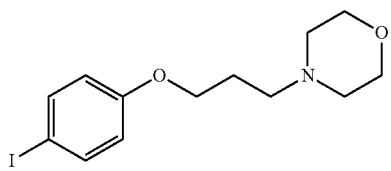 [SMILES: Ic1ccc(OCCCN2CCOCC2)cc1]

To a solution of bromide 46 (810 mg, 3.89 mmol) and 4-iodophenol (779 mg, 3.54 mmol) in anhydrous DMF (7 mL) was added K$_2$CO$_3$ (731 mg, 5.31 mmol). The contents were heated at 80° C. for 15 hours. The reaction mixture was diluted with EtOAc (100 mL) and washed with brine (100 mL). The organic phase was dried over anhydrous Na$_2$SO$_4$ and concentrated under reduced pressure. Purification by flash column chromatography (85:15 hexanes/EtOAc to EtOAc) afforded 47 as a white solid (1.07 g, 87% yield). R$_f$=0.13 (hexanes/EtOAc 50:50 v/v). $^1$H NMR (400 MHz, CDCl$_3$) δ 7.54 (d, J=8.3 Hz, 2H), 6.68 (d, J=8.3 Hz, 2H), 3.99 (t, J=6.3 Hz, 2H), 3.72 (t, J=4.3 Hz, 4H), 2.50 (t, J=7.3 Hz, 2H), 2.48-2.43 (m, 4H), 1.95 (app quint, J=6.6 Hz, 2H). $^{13}$C NMR (101 MHz, CDCl$_3$) δ 159.0, 138.3, 117.1, 82.7, 67.2, 66.4, 55.6, 53.9, 26.5. MS (ESI$^+$) calculated for [C$_{13}$H$_{19}$INO$_2$]$^+$ [M+H]$^+$, 348.0; found 348.0.

4'-(3-Morphohnopropoxy)-[1,1'-biphenyl]-3-ol (48)

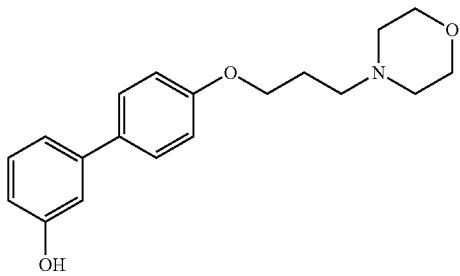 [SMILES: Oc1cccc(-c2ccc(OCCCN3CCOCC3)cc2)c1]

Phenol 48 was prepared according to the procedure for 45v using phenyl iodide 47 (1.07 g, 3.08 mmol), 3-hydroxybenzeneboronic acid (425 mg, 3.08 mmol), K$_2$CO$_3$ (1.70 g, 12.3 mmol), and Pd (10% by weight on carbon, 65.6 mg, 0.0616 mmol) in water (30 mL). Purification by flash column chromatography (DCM to EtOAc with 2% MeOH throughout) afforded 48 as a white solid (671 mg, 70% yield). R$_f$=0.24 (DCM/EtOAc/MeOH 47.5:47.5:5 v/v/v). $^1$H NMR (400 MHz, DMSO-d$_6$) δ 9.44 (br s, 1H), 7.51 (d, J=8.6 Hz, 2H), 7.21 (app t, J=7.8 Hz, 1H), 7.05-6.93 (m, 4H), 6.70 (dd, J=8.1, 1.5 Hz, 1H), 4.04 (t, J=6.5 Hz, 2H), 3.58 (t, J=4.3 Hz, 4H), 2.49-2.24 (m, 6H), 1.89 (app quint, J=6.5 Hz, 2H). $^{13}$C NMR (101 MHz, DMSO-d$_6$) δ 158.2, 157.7, 141.3, 132.6, 129.8, 127.6, 116.9, 114.8, 113.7, 113.0, 66.2, 65.8, 54.8, 53.3, 25.8. MS (ESI$^+$) calculated for [C$_{19}$H$_{24}$NO$_3$]$^+$ [M+H]$^+$, 314.2; found 314.1.

In order to facilitate further study of the in vitro and in vivo biology of MIF, series of potent MIF tautomerase inhibitors have been pursued. Starting from a 113-µM docking hit, a novel series, which features a pyrazole instead of a phenol, was optimized to yield compounds with K$_i$ values as low as 60-70 nM. The optimization was greatly facilitated by molecular modeling and the ability to obtain multiple high-resolution crystal structures, which guided the effective selection and placement of substituents. Recognition of the potential benefit of addition of a fluorine in the pyrazole ring also provided an essential boost along with a synthetic challenge.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (6), or a salt, solvate, stereoisomer, or tautomer thereof, or any mixtures thereof:

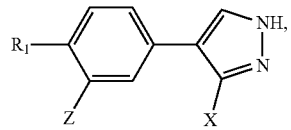

(6)

wherein:
R$_1$ is selected from the group consisting of phenyl and naphthyl;
Z is selected from the group consisting of —C(=O)OR, —S(=O)R, —S(=O)$_2$R, and —S(=O)$_2$NRR;
X is selected from the group consisting of H, C$_1$-C$_3$ alkyl, and halogen;
wherein the phenyl or naphthyl is independently optionally substituted with at least one group independently selected from the group consisting of halogen, —OH, —C(=O)OR, C$_1$-C$_6$ alkyl, C$_1$-C$_6$ haloalkyl, C$_1$-C$_6$ alkoxy, C$_1$-C$_6$ haloalkoxy, C$_3$-C$_6$ cycloalkyl, C$_3$-C$_6$ cycloalkoxy, C$_3$-C$_6$ halocycloalkyl, C$_3$-C$_6$ halocycloalkoxy, -(CH$_2$)$_{1-6}$NRR, -O(CH$_2$)$_{1-6}$NRR, -(CH$_2$)$_{1-6}$NR(C$_1$-C$_6$ acyl), -O(CH$_2$)$_{1-6}$NR(C$_1$-C$_6$ acyl), -(CH$_2$)$_{1-6}$OR, -O(CH$_2$)$_{1-6}$OR, -(CH$_2$)$_{1-6}$C(=O)OR, -O(CH$_2$)$_{1-6}$C(=O)OR, -(CH$_2$)$_{1-6}$OR, -O(CH$_2$)$_{1-6}$OR, -(OCH$_2$CH$_2$)$_{1-6}$NRR, and -(OCH$_2$CH$_2$)$_{1-6}$C(=O)OR;
wherein each occurrence of R is independently selected from the group consisting of H and C$_1$-C$_6$ alkyl, or two R groups combine with the N atom to which they are both bound to form a 3-8 membered heterocyclyl or heteroaryl group.

2. A compound selected from the group consisting of:

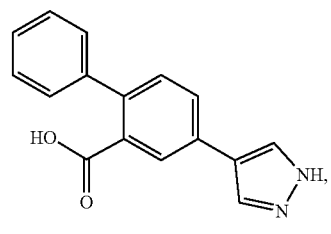

6a 4-(1H-pyrazol-4-yl)-
[1,1'biphenyl]-2-carboxylic acid;

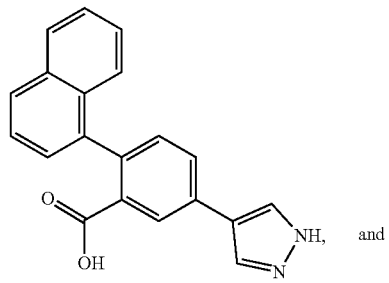

6b and 2-(Naphthalen-1-yl)-5-
(1H-pyrazol-4-yl)benzoic acid;

-continued

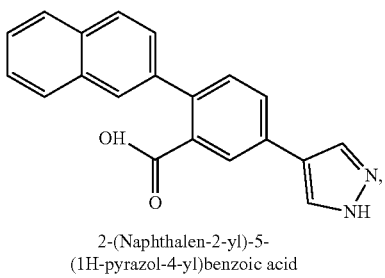

2-(Naphthalen-2-yl)-5-(1H-pyrazol-4-yl)benzoic acid or a salt, solvate, stereoisomer, or tautomer thereof, or any mixtures thereof.

3. A pharmaceutical composition comprising the compound of claim 1 and at least one pharmaceutically acceptable excipient.

4. A method of treating or ameliorating an inflammatory disease, a neurological disorder, or cancer in a subject in need thereof, the method comprising administering to the subject an effective amount of the compound of claim 1, wherein the inflammatory disease is rheumatoid arthritis, Crohn's disease, or inflammatory bowel syndrome, wherein the neurological disorder is schizophrenia, and wherein the cancer is colorectal cancer, lung cancer, breast cancer, or prostate cancer.

5. A method of inhibiting macrophage migration inhibitory factor in a subject in need thereof, the method comprising administering to the subject an effective amount of the compound of claim 1.

6. A compound of formula (7) or formula (8), or a salt, solvate, stereoisomer, or tautomer thereof, or any mixtures thereof:

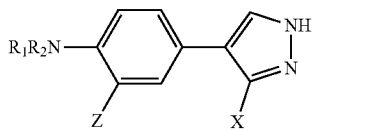

or

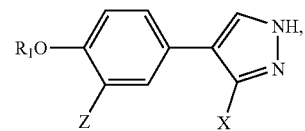

wherein:
  in the compound of formula (7), $R_1$ is selected from the group consisting of H, $C_1$-$C_6$ alkyl, phenyl, naphthyl, tetrahydronaphthyl, phenanthryl, bicyclic heteroaryl, 1,2-dihydroacenaphthyl, acenaphthyl, adamantyl, (heteroaryl)-phenyl, and biphenyl;
  in the compound of formula (8), $R_1$ is selected from the group consisting of H, $C_1$-$C_6$ alkyl, phenyl, naphthyl, tetrahydronaphthyl, phenanthryl, bicyclic heteroaryl, 1,2-dihydroacenaphthyl, acenaphthyl, adamantyl, (heteroaryl)-phenyl, and biphenyl, methylphenyl, methoxyphenyl, fluorophenyl, ethylnapthyl, cyclopropylnaphthyl, methylbiphenyl, ethoxybiphenyl, and N-morpholinopropoxybiphenyl;
  $R_2$ is selected from the group consisting of H and $C_1$-$C_6$ alkyl;

Z is selected from the group consisting of —C(=O) OR, —S(=O)R, —S(=O)$_2$R, and —S(=O)2NRR;
  X is selected from the group consisting of H, $C_1$-$C_3$ alkyl, and halogen;
    wherein the phenyl, naphthyl, tetrahydronaphthyl, phenanthryl, bicyclic heteroaryl, 1,2-dihydroacenaphthyl, acenaphthyl, adamantyl, (heteroaryl)-phenyl, or biphenyl is independently optionally substituted with at least one group independently selected from the group consisting of halogen, —OH, —C(=O)OR, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_3$-$C_6$ halocycloalkyl, $C_3$-$C_6$ halocycloalkoxy, -(CH$_2$)$_{1-6}$NRR, -O(CH$_2$)$_{1-6}$NRR, -(CH$_2$)$_{1-6}$NR(C$_1$-C$_6$ acyl), -O(CH$_2$)$_{1-6}$NR(C$_1$-C$_6$ acyl), -(CH$_2$)$_{1-6}$OR, -O(CH$_2$)$_{1-6}$OR, -(CH$_2$)$_{1-6}$C(=O)OR, -O(CH$_2$)$_{1-6}$C(=O)OR, -(CH$_2$)$_{1-6}$OR, -O(CH$_2$)$_{1-6}$OR, -(OCH$_2$CH$_2$)$_{1-6}$NRR, and -(OCH$_2$CH$_2$)$_{1-6}$C(=O)OR;
    wherein each occurrence of R is independently selected from the group consisting of H and $C_1$-$C_6$ alkyl, or two R groups combine with the N atom to which they are both bound to form a 3-8 membered heterocyclyl or heteroaryl group.

7. The compound of claim 6, which is a compound of formula (7):

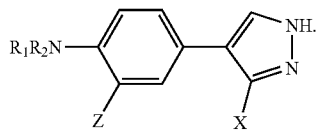

8. The compound of claim 7, wherein $R_1$ is selected from the group consisting of phenyl and naphthyl.

9. The compound of claim 7, wherein $R_2$ is methyl.

10. A compound selected from the group consisting of:

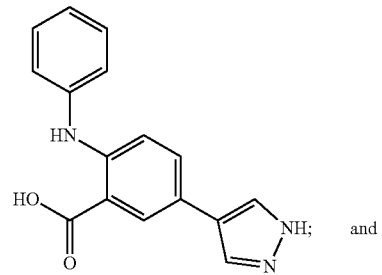

2-(Phenylamino)-5-(1H-pyrazol-4-yl)benzoic acid and

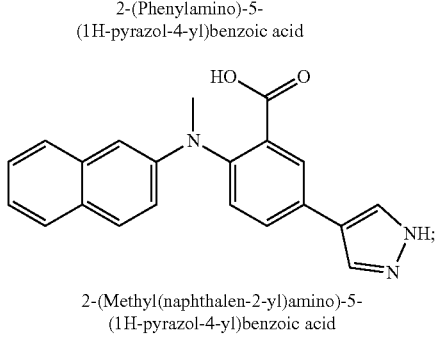

2-(Methyl(naphthalen-2-yl)amino)-5-(1H-pyrazol-4-yl)benzoic acid or a salt, solvate, stereoisomer, or tautomer thereof, or any mixtures thereof.

11. The compound of claim 6, which is a compound of formula (8):

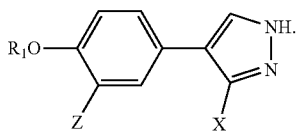

8

12. The compound of claim 11, wherein $R_1$ is selected from the group consisting of methylphenyl, methoxyphenyl, fluorophenyl, ethylnapthyl, cyclopropylnaphthyl, methylbiphenyl, ethoxybiphenyl, and N-morpholinopropoxybiphenyl.

13. The compound of claim 11, wherein X is fluorine.

14. A compound selected from the group consisting of:

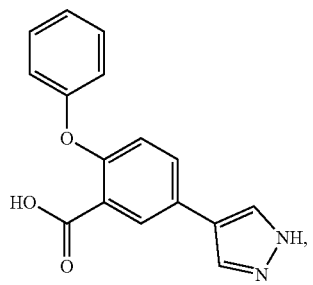

8a

2-Phenoxy-5-(1H-pyrazol-4-yl)benzoic acid;

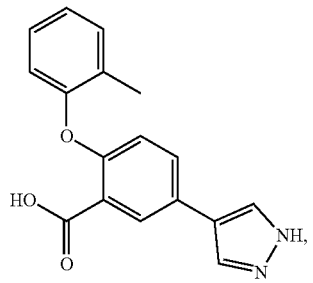

8b 5-(1H-Pyrazol-4-yl)-2-(o-tolyloxy)benzoic acid;

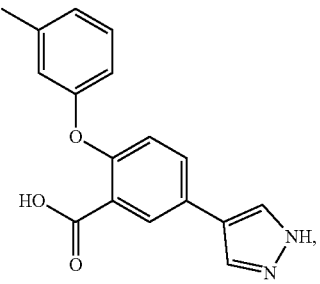

8c 5-(1H-Pyrazol-4-yl)-2-(m-tolyloxy)benzoic acid;

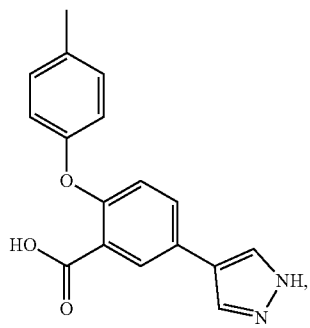

8d 5-(1H-Pyrazol-4-yl)-2-(p-tolyloxy)benzoic acid;

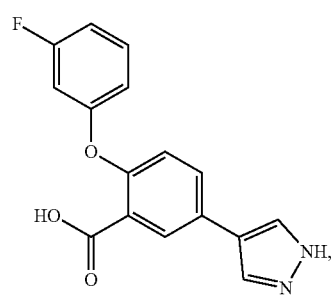

8e 2-(3-Fluorophenoxy)-5-(1H-pyrazol-4-yl)benzoic acid;

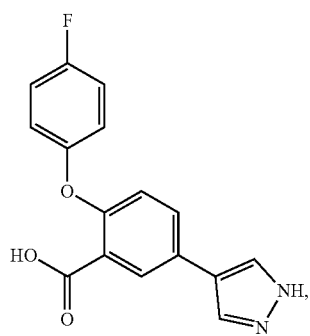

8f 2-(4-Fluorophenoxy)-5-(1H-pyrazol-4-yl)benzoic acid;

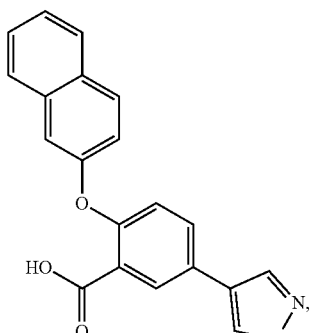

8g 2-(Naphthalen-2-yloxy)-5-(1H-pyrazol-4-yl)benzoic acid;

-continued

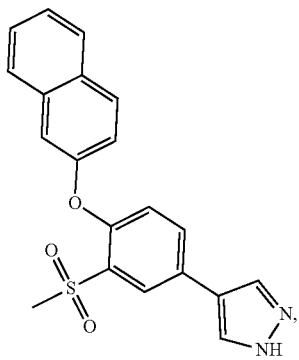

4-(3-(Methylsulfonyl)-4-(naphthalen-2-yloxy)phenyl)-1H-pyrazole;

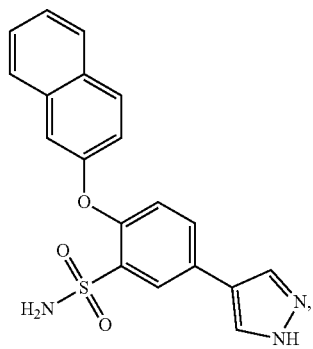

2-(Naphthalen-2-yloxy)-5-(1H-pyrazol-4-yl)benzenesulfonamide;

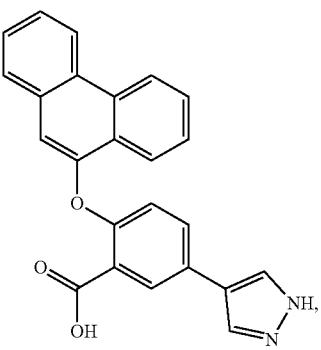

2-(Phenanthren-9-yloxy)-5-(1H-pyrazol-4-yl)benzoic acid;

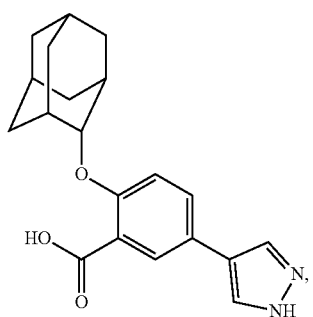

2-((Adamantan-2-yl)oxy)-5-(1H-pyrazol-4-yl)benzoic acid;

-continued

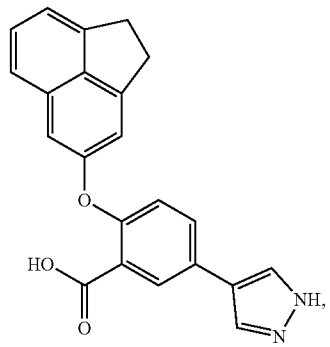

2-((1,2-Dihydroacenaphthylen-4-yl)oxy)-5-(1H-pyrazol-4-yl)benzoic acid;

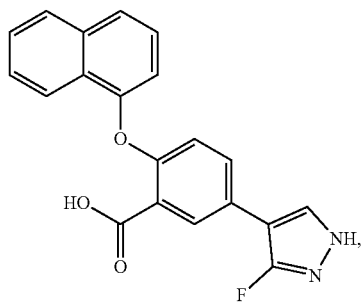

5-(3-Fluoro-1H-pyrazol-4-yl)-2-(naphthalen-1-yloxy)benzoic acid;

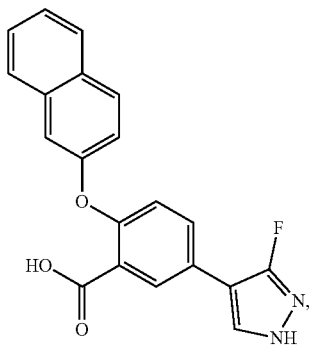

5-(3-Fluoro-1H-pyrazol-4-yl)-2-(naphthalen-2-yloxy)benzoic acid;

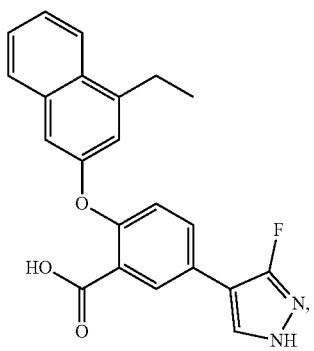

2-((Ethylnaphthalen-2-yl)oxy)-5-(3-fluoro-1H-pyrazol-4-yl)benzoic acid;

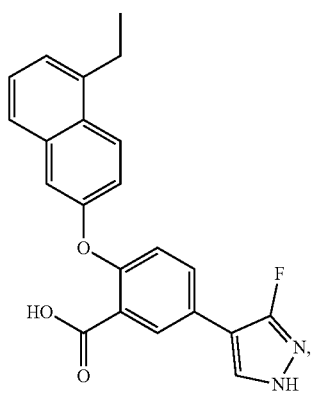
2-((5-Ethylnaphthalen-2-yl)oxy)-5-
(3-fluoro-1H-pyrazol-4-yl)benzoic acid;
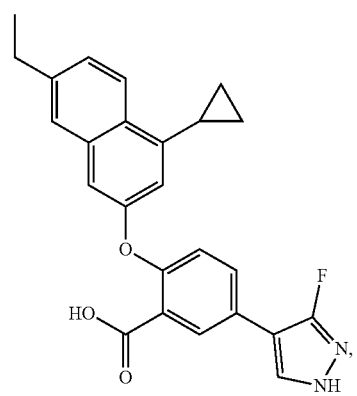
2-((4-Cyclopropyl-7-ethylnaphthalen-2-yl)oxy)-5-
(3-fluoro-1H-pyrazol-4-yl)benzoic acid;
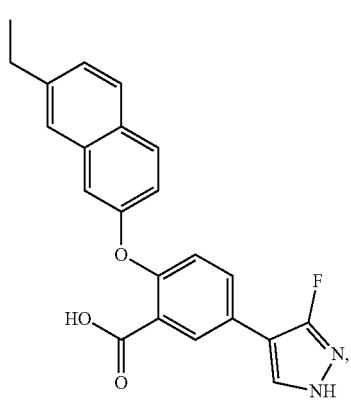
2-((7-Ethylnaphthalen-2-yl)oxy)-5-
(3-fluoro-1H-pyrazol-4-yl)benzoic acid;
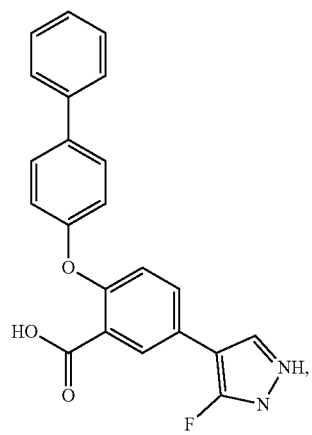
2-([1,1'-Biphenyl]-4-yloxy)-5-
(3-fluoro-1H-pyrazol-4-yl)benzoic acid;
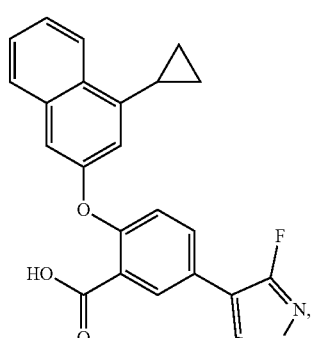
2-((4-Cyclopropylnaphthalen-2-yl)oxy)-5-
(3-fluoro-1H-pyrazol-4-yl)benzoic acid;
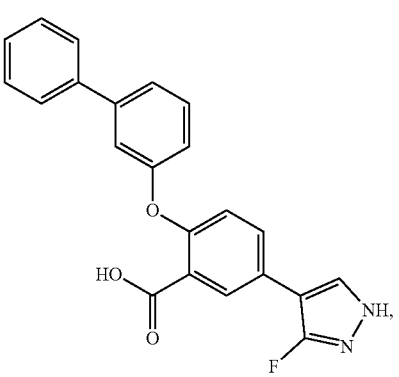
2-([1,1'-Biphenyl]-3-yloxy)-5-
(3-fluoro-1H-pyrazol-4-yl)benzoic acid;

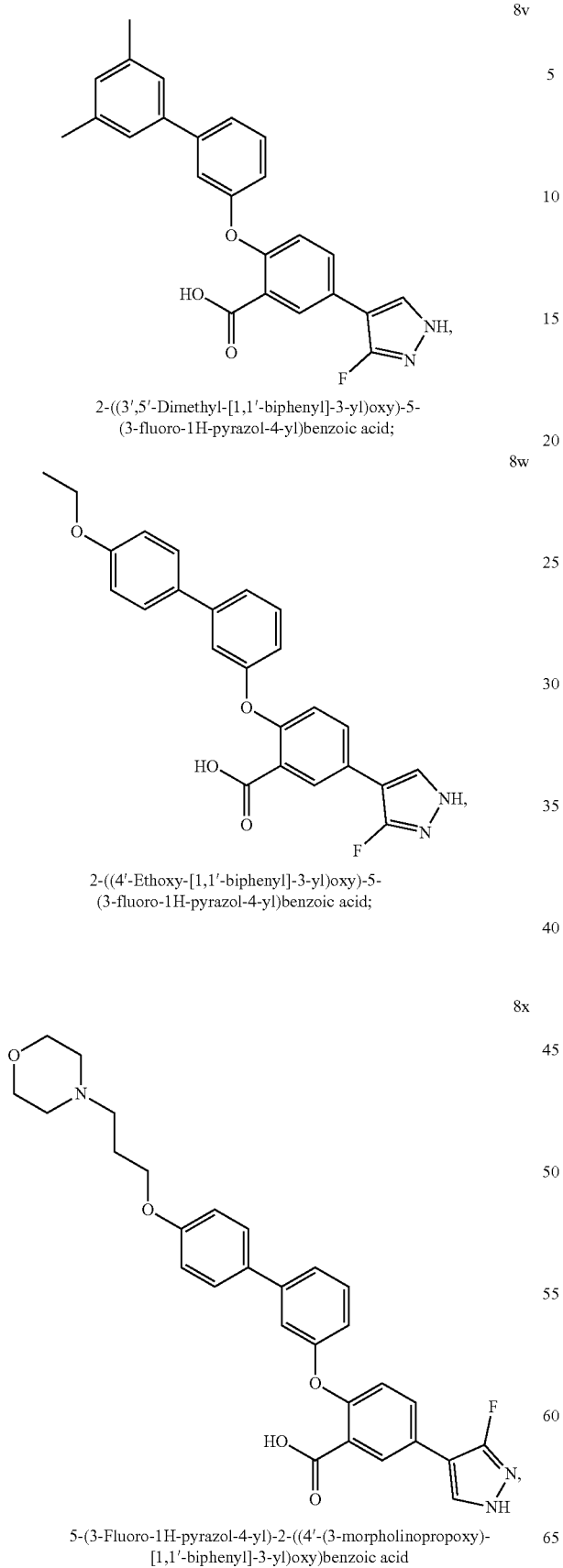
2-((3',5'-Dimethyl-[1,1'-biphenyl]-3-yl)oxy)-5-(3-fluoro-1H-pyrazol-4-yl)benzoic acid;
2-((4'-Ethoxy-[1,1'-biphenyl]-3-yl)oxy)-5-(3-fluoro-1H-pyrazol-4-yl)benzoic acid;
5-(3-Fluoro-1H-pyrazol-4-yl)-2-((4'-(3-morpholinopropoxy)-[1,1'-biphenyl]-3-yl)oxy)benzoic acid
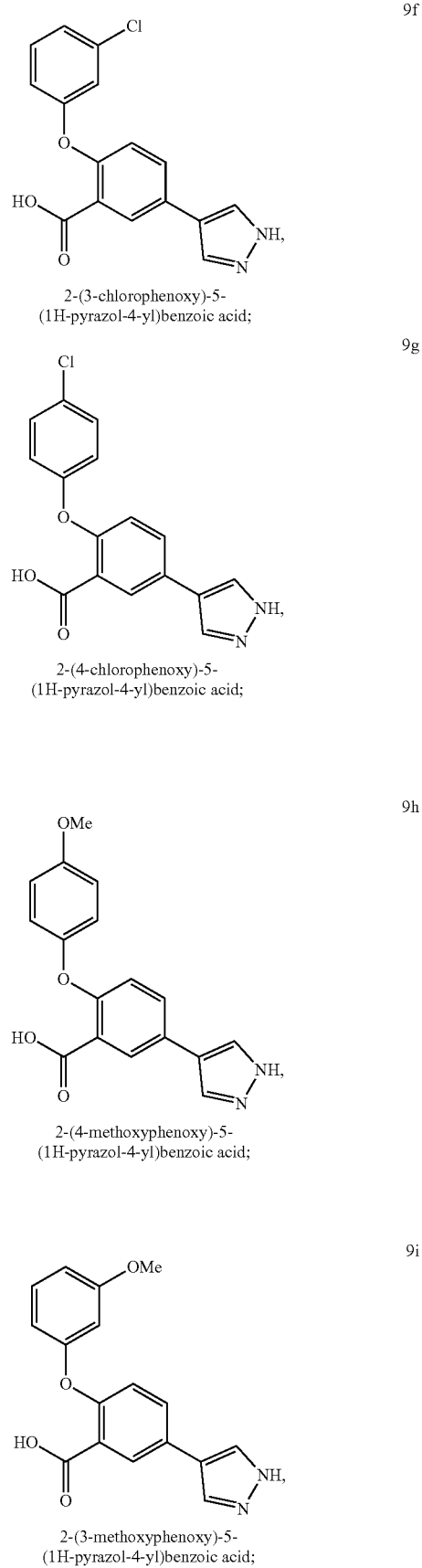
2-(3-chlorophenoxy)-5-(1H-pyrazol-4-yl)benzoic acid;
2-(4-chlorophenoxy)-5-(1H-pyrazol-4-yl)benzoic acid;
2-(4-methoxyphenoxy)-5-(1H-pyrazol-4-yl)benzoic acid;
2-(3-methoxyphenoxy)-5-(1H-pyrazol-4-yl)benzoic acid;

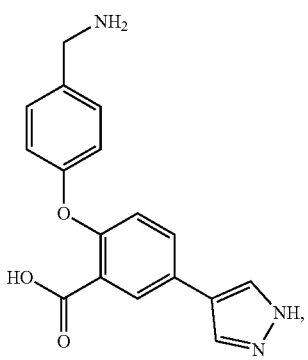
2-(4-(aminomethyl)phenoxy)-5-
(1H-pyrazol-4-yl)benzoic acid;
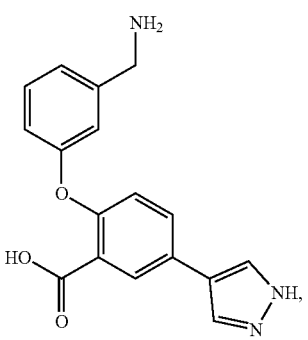
2-(3-(aminomethyl)phenoxy)-5-
(1H-pyrazol-4-yl)benzoic;
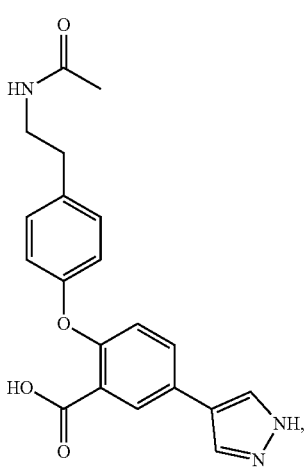
2-(4-(2-acetamidoethyl)phenoxy)-5-
(1H-pyrazol-4-yl)benzoic acid;
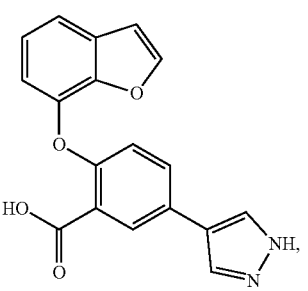
2-(benzofuran-7-yloxy)-5-
(1H-pyrazol-4-yl)benzoic acid;
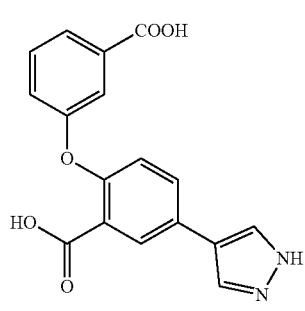
2-(3-carboxyphenoxy)-5-
(1H-pyrazol-4-yl)benzoic acid;
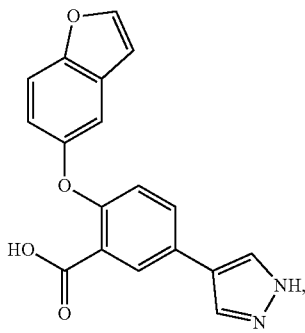
2-(benzofuran-5-yloxy)-5-
(1H-pyrazol-4-yl)benzoic acid;
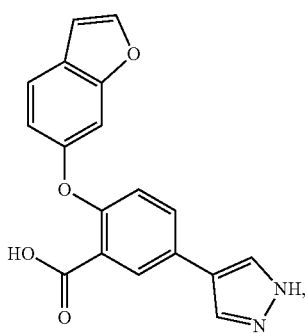
2-(benzofuran-6-yloxy)-5-
(1H-pyrazol-4-yl)benzoic acid;
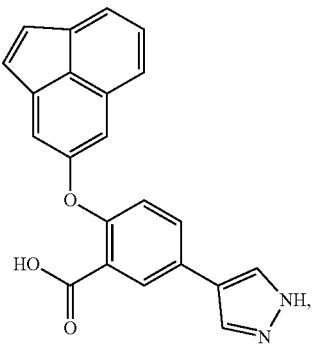
2-(acenaphthylen-4-yloxy)-5-
(1H-pyrazol-4-yl)benzoic acid;

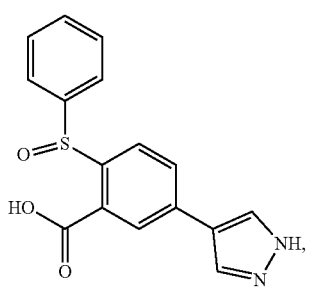

2-(phenylsulfinyl)-5-
(1H-pyrazol-4-yl)benzoic acid;

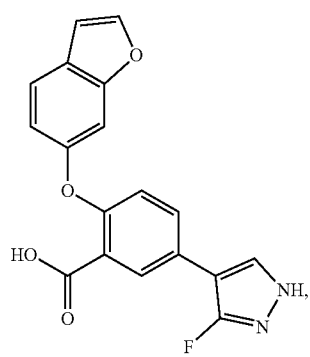

2-(benzofuran-6-yloxy)-5-
(3-fluoro-1H-pyrazol-4-yl)benzoic acid;

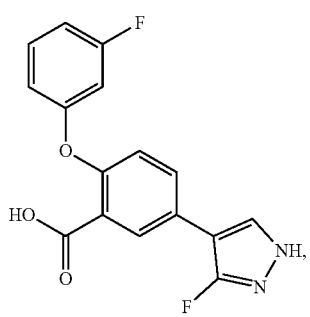

5-(3-fluoro-1H-pyrazol-4-yl)-2-
(3-fluorophenoxy)benzoic acid;

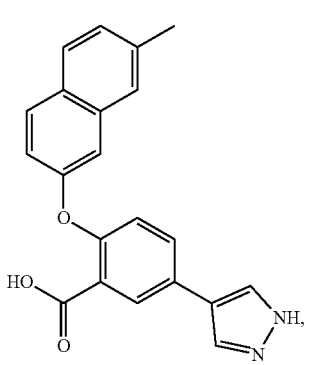

2-((7-methylnaphthalen-2-yl)oxy)-5-
(1H-pyrazol-4-yl)benzoic acid;

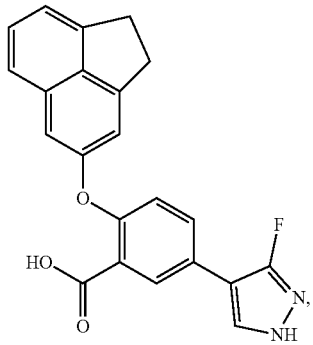

2-((1,2-dihydroacenaphthylen-4-yl)oxy)-5-
(3-fluoro-1H-pyrazol-4-yl)benzoic acid;

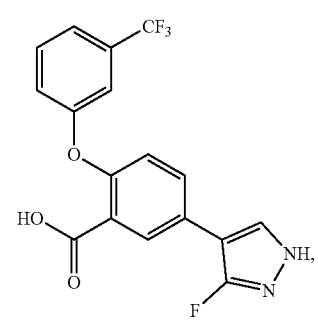

5-(3-fluoro-1H-pyrazol-4-yl)-2-
(3-trifluoromethyl)phenoxy)benzoic acid;

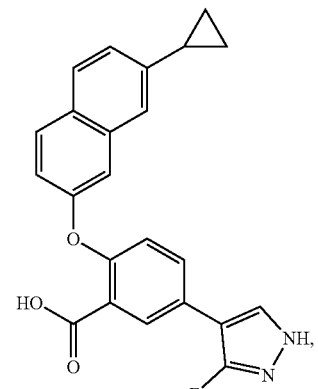

2-((7-cyclopropylnaphthalen-2-yl)oxy)-5-
(3-flouro-1H-pyrazol-4-yl)benzoic acid;

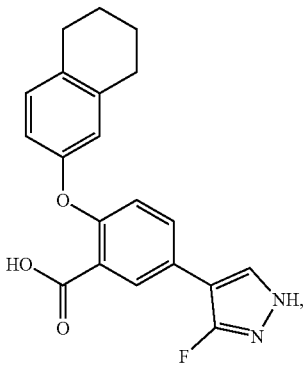

5-(3-fluoro-1H-pyrazol-4-yl)-2-
((5,6,7,8-tetrahydronaphthalen-2-yl)benzoic acid;

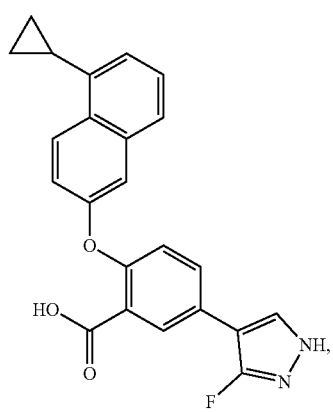

2-((5-cyclopropylnaphthalen-2-yl)oxy)-5-
(3-fluoro-1H-pyrazol-4-yl)benzoic acid;

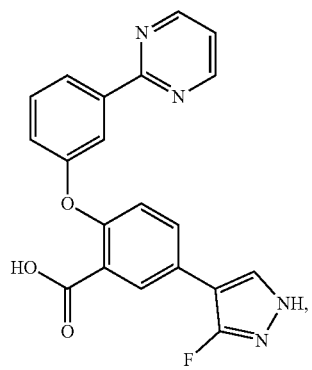

5-(3-fluoro-1H-pyrazol-4-yl)-2-
(3-(pyrimidin-2-yl)phenoxy)benzoic acid;

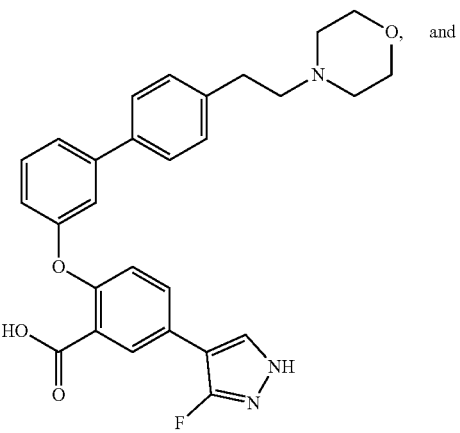

5-(3-fluoro-1H-pyrazol-4-yl)-2-((4'-(2-morpholinoethyl)-
[1,1'-biphenyl]-3-yl)oxy)benzoic acid;

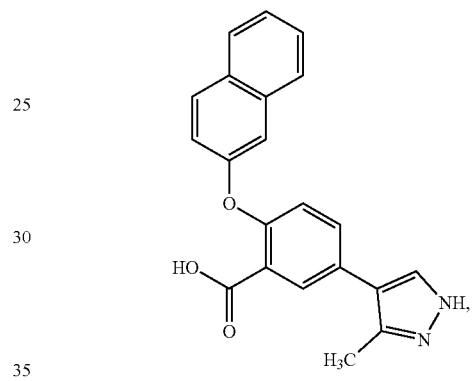

5-(3-methyl-1H-pyrazol-4-yl)-2-
(naphthalen-2-yloxy)benzoic acid;

or a salt, solvate, stereoisomer, or tautomer thereof, or any mixtures thereof.

15. A pharmaceutical composition comprising the compound of claim 6 and at least one pharmaceutically acceptable excipient.

16. A method of treating or ameliorating an inflammatory disease, a neurological disorder, or cancer in a subject in need thereof, the method comprising administering to the subject an effective amount of the compound of claim 6,
wherein the inflammatory disease is rheumatoid arthritis, Crohn's disease, or inflammatory bowel syndrome,
wherein the neurological disorder is schizophrenia, and
wherein the cancer is colorectal cancer, lung cancer, breast cancer, or prostate cancer.

17. A method of inhibiting macrophage migration inhibitory factor in a subject in need thereof, the method comprising administering to the subject an effective amount of the compound of claim 6.

* * * * *